(12) United States Patent
Hugueney et al.

(10) Patent No.: US 9,556,424 B2
(45) Date of Patent: Jan. 31, 2017

(54) 1-DEOXY-D-XYLULOSE 5-PHOSPHATE SYNTHASE ALLELES RESPONSIBLE FOR ENHANCED TERPENE BIOSYNTHESIS

(75) Inventors: Phlippe Hugueney, March-Hugstetten (DE); Eric Duchene, Strasbourg (FR); Didier Merdinoglu, Colmar (FR)

(73) Assignee: GENOPLANTE-VALOR, Paris (FR)

( * ) Notice: Subject to any disclaimer, the term of this patent is extended or adjusted under 35 U.S.C. 154(b) by 675 days.

(21) Appl. No.: 13/880,488

(22) PCT Filed: Oct. 20, 2011

(86) PCT No.: PCT/EP2011/005283
§ 371 (c)(1),
(2), (4) Date: Jun. 18, 2013

(87) PCT Pub. No.: WO2012/052171
PCT Pub. Date: Apr. 26, 2012

(65) Prior Publication Data
US 2013/0276166 A1    Oct. 17, 2013

(30) Foreign Application Priority Data

Oct. 20, 2010  (EP) .................................. 10013809
May 10, 2011  (EP) .................................. 11003842

(51) Int. Cl.
*C12N 9/88*         (2006.01)
*C12P 5/00*         (2006.01)
*A01H 5/08*         (2006.01)
*C12N 9/10*         (2006.01)
*C12N 15/82*        (2006.01)

(52) U.S. Cl.
CPC ............... *C12N 9/88* (2013.01); *A01H 5/0812* (2013.01); *C12N 9/1022* (2013.01); *C12N 15/8209* (2013.01); *C12N 15/8243* (2013.01); *C12N 15/8274* (2013.01); *C12P 5/007* (2013.01); *C12Y 202/01007* (2013.01); *Y02P 20/52* (2015.11)

(58) Field of Classification Search
CPC .......... A01H 5/0812; A01H 5/00; C12N 9/10; C12N 15/82
See application file for complete search history.

(56) References Cited

FOREIGN PATENT DOCUMENTS

| EP | WO 00/04491 | * | 8/2000 | ............. C12N 15/54 |
|----|-------------|---|--------|--------------------------|
| GB | WO 00/44912 | * | 8/2000 | ............. C12N 15/54 |
| GB | 2 430 200 A |   | 3/2007 |                          |

(Continued)

OTHER PUBLICATIONS

Xiang, S., et al. "Crystal structure of 1-deoxy-D-xylulose 5-phosphate synthase, a crucial enzyme for isoprenoids biosynthesis." Journal of Biological Chemistry 282.4 (2007): 2676-2682.*

(Continued)

*Primary Examiner* — Russell Kallis
*Assistant Examiner* — Fan Weihua
(74) *Attorney, Agent, or Firm* — Young & Thompson

(57) ABSTRACT

A method of enhancement of the 1-deoxy-D-xylulose 5-phosphate synthase (DXS) activity of plants or bacteria to increase terpenes production in cells, an enhanced DXS sequence likely to be obtained by this method, a method of enhancement of production of terpenes in a host cell containing the enhanced DXS enzyme, and transgenic bacterium or plants that express this polypeptide are described.

14 Claims, 29 Drawing Sheets

(56) References Cited

FOREIGN PATENT DOCUMENTS

| WO | 99/11757 A1 | 3/1999 |
| WO | 00/44912 A1 | 8/2000 |

OTHER PUBLICATIONS

Emanuelli, Francesco, et al. 2010, "A candidate gene association study on muscat flavor in grapevine (*Vitis vinifera* L.)." BMC Plant Biology 10: 241.*

Xiang S., et al, 2007, "Crystal structure of 1-deoxy-D-xylulose 5-phosphate synthase, a crucial enzyme for isoprenoids biosynthesis." J. Biol. Chem. 282:2676-2682.*

Lange et al.: "A family of transketolases that directs isoprenoid biosynthesis via a mevalonate-independent pathway", FASEB Journal, Fed. of American Soc. for Experimental Biology, US, vol. 95, Mar. 1, 1998 (Mar. 1, 1998), pp. 2100-2104, XP002116672, ISSN: 0892-6638 abstract; figure 4.

Kuzuyama Tomohisa et al.: "Cloning and Characterization of 1-Deoxy-D-Xylulose 5-Phosphate Synthase From *Streptomyces* Sp. Strain CL190, Which Uses Both the Mevalonate and Nonmevalonate Pathways for Isopentenyl Diphosphate Biosynthesis", Journal of Bacteriology, American Society for Microbiology, Washington, DC; US, vol. 182, No. 4, Feb. 1, 2000 (Feb. 1, 2000), pp. 891-897, XP009081766, ISSN: 0021-9193, DOI: 10.1128/B.182.4.891-897.2000.

Duchene Eric et al.: "A grapevine (*Vitis vinifera* L.) deoxy-d-xylulose synthase gene colocates with a major quantitative trait loci for terpenol content", Theoretical and Applied Genetics, vol. 118, No. 3, Feb. 2009 (Feb. 2009), pp. 541-552, XP02620521, ISSN: 0040-5752, DOI: 10.1007/s00122-008-0919-8 abstract.

Juri Battilana et al.: "The 1-doxy-d-xylulose 5-phosphate synthase gene co-localizes with a major QTL affecting monoterpene content in grapevine", Theoretical and Applied Genetics; International Journal of Plant Breeding Research, vol. 118, No. 4, Nov. 27, 2008 (Nov. 27, 2008), pp. 653-669, XP019698334, Springer, Berlin, DE ISSN: 1432-2242 abstract.

Xiang Song et al.: "Crystal structure of 1-deoxy-d-xylulose 5-phosphate synthase, a crucial enzyme for isoprenoids biosynthesis", Journal of Biological Chemistry, vol. 282. No. 4. Jan. 2007 (Jan. 2007), pp. 2676-2682, XP002620522, ISSN: 0021-9258, DOI:10.1074/jbc.m610135200, abstract.

Jaillon Olivier et al.: "The grapevine genome sequence suggests ancestral hexaploidization in major angiosperm phyla", Nature (London), vol. 449. No. 7161, Sep. 2007 (Sep. 2007), pp. 463-467-Methods, XP002620523, ISSN: 0028-0836. DOI: 10.1038/nature.06148, abstract; sequence D7T6L3.

Paetzold Heike et al.: "The Isogene 1-Deoxy-D-Xylulose 5-Phosphate Synthase 2 Controls Isoprenoid Profiles, Precursor Pathway Allocation, and Density of Tomato Trichomes", Molecular Plant, vol. 3. No. 5. Sep. 2010 (Sep. 2010), pp. 904-916. XP002620524, the whole document.

Munoz-Bertomeu Jesus et al.: "Up-regulation of I-deoxy-D-xylulose-5-phosphate synthase enhances production of essential oils in transgenic spike lavender", Plant Physiology (Rockville), vol. 142. No. 3. Nov. 2006 (Nov. 2006), pp. 890-900. XP002620525, ISSN: 0032-0889. DOI: 10.1104/pp.I06.086355 abstract.

International Search Report, dated Feb. 29, 2012, from corresponding PCT application.

* cited by examiner

MoDXS1 (SEQ ID N°8)

ATGGCTCTCTGTACGCTCTCATTTCCTGCCCATTTTAGCCAGGCTGCTGCTTCAAATCCTCAGAGACTTACTCCTCAGTGTTCC
CATTTGTTCTTGGGGGTGGATTTGCAGTGCCAATCCCAGCAAAGGAGTAAGGCCAGGAAAAGGCCAAATGGGGTTTGTGCATCA
CTTTCGGATAGGGAGGAGTATCATTCCCAGAGACCACCAACTCCTCTCCTGGACACTATCAATTATCCAATTCACATGAAAAAT
CTGTCTGTCAAGGAGCTGAAACAACTCGCAGATGAACTAAGGTCTGATGTTGTCTTCAATGTTTCCAAAACTGGGGGTCACTTG
GGCTCCAGCCTCGGGGTTGTGGAGCTCACTGTGGCTCTTCATTATGTCTTCAATGCCCCTCAAGACAGGATACTATGGGATGTT
GGTCATCAGTCTTACCCACACAAAATTCTAACTGGGAGAAGAGATCAAATGCATACCATGAGGCAAACAGATGGGTTAGCGGGA
TTCACCAAGCGCTCGGAGAGTGAATATGACTGCTTTGGAACCGGCCACAGTTCTACTACCATCTCAGCAGGCTTGGGAATGGCG
GTCGGCCGGGATCTAAAAGGAAAAAACAACAACGTCATTGCTGTCATAGGTGATGGAGCCATGACTGCAGGGCAAGCTTATGAA
GCAATGAACAATGCTGGTTACCTGGATTCTGACATGATTGTTATCCTTAATGACAACAAGCAGGTTTCTTTACCCACTGCTACT
CTAGATGGGCCCATACCACCTGTAGGAGCTTTGAGCAGTGCTCTTAGTAGGTTACAATCAAACAGACCTCTTAGAGAATTACGA
GAGGTTGCCAAGGGCGTTACCAAACAGATTGGCGGACCGATGCATGAATTGGCTGCAAAAGTTGATGAATATGCTCGTGGGATG
ATCAGTGGTTCTGGATCAACACTTTTTGAAGAGCTTGGACTCTATTATATAGGTCCTGTTGATGGCCACAACATAGATGACCTT
GTTGCCATTCTCAAGGAGGTTAAGAGTACCAAGACAACAGGTCCAGTTCTGATCCATGTTGTCACAGAGAAAGGCCGCGGATAT
CCATATGCTGAGAAAGCTGCAGATAAGTACCATGGAGTGACCAAGTTCGATCCTGCTACTGGAAAACAATTCAAATCCAGTGCT
CCTACTCAGTCCTACACAACATATTTTGCAGAGGCTTTGATTGCAGAAGCAGAGGTGGACAAGGATATTGTTGCAATTCATGCA
GCAATGGGGGGTGGAACGGGCTTGAATCTCTTCCATCGCCGGTTCCCCACACGATGCTTTGATGTTGGGATAGCAGAACAGCAT
GCTGTTACCTTTGCTGCTGGTCTAGCCTGTGAAGGCATTAAACCTTTTTGTGCAATCTACTCATCTTTCATGCAGAGAGCTTAT
GACCAGGTGGTGCATGATGTAGATTTGCAGAAGCTGCCAGTGAAATTTGCAATGGACAGAGCTGGGCTGGTTGGAGCAGATGGC
CCAACACATTGTGGAGCTTTTGATGTCGCTTTCATGGCTTGCCTTCCAAACATGGTGGTGATGGCTCCTGCTGATGAGGCTGAG
CTTTTTTCACATGGTGGCCACAGCTGCTGCCATAGATGACAGGCCCAGTTGTTTCCGGTACCCAAGAGGAAATGGGGTGGGTGTT
GAACTGCCACCAGGGAACAAAGGCATTCCTATTGAGGTTGGAAGGGGCCGAATATTGATTGAGGGGGAGAGAGTTGCACTCTTG
GGCTATGGAACAGCAGTACAGAGCTGTTTGGTTGCGTCTTCTTTGCTGGAACAACATGGCTTACGAATAACAGTCGCAGATGCC
CGCTTCTGCAAACCATTGGACCATGCTCTTATTCGTAGCCTAGCAAAATCACATGAAGTTTTGATTACAGTAGAAGAAGGGTCA
ATTGGTGGTTTTGGGTCTCATGTTGCTCAGTTTTTGGCCCTTAATGGTCTTCTTGATGGCACAACAAAGTGGAGTCCCATGGTT
CTTCCTGATCGGTACATAGACCATGGAGCGCCAGCGGACCAGTTGGCCATGGCGGGTCTGACACCATCTCATATTGCAGCAACA
GTATTCAATATACTTGGACAAACAAGGGAGGCCCTGGAGATCATGTTATAG

Figure 1

MoDXS2 (SEQ ID N°9)

```
ATGGCTCTCTGTACGCTCTCATTTCCTGCCCATTTTAGCCAGGCTGCTGCTTCAAATCCTCAGAGACTTACTCCTCAGTGTTC
CCATTTGTTCTTGGGGGTGGATTTGCAGTGCCAATCCCAGCAAAGGAGTAAGGCCAGGAAAAGGCCAAATGGGGTTTGTGCAT
CACTTTCGGATAGGGAGGAGTATCATTCCCAGAGACCACCAACTCCTCTCCTGGACACTATCAATTATCCAATTCACATGAAA
AATCTGTCTGTCAAGGAGCTGAAACAACTCGCAGATGAACTAAGGTCTGATGTTGTCTTCAATGTTTCCAAAACTGGGGGTCA
CTTGGGCTCCAGCCTCGGGGTTGTGGAGCTCACTGTGGCTCTTCATTATGTCTTCAATGCCCCTCAAGACAGGATACTATGGG
ATGTTGGTCATCAGTCTTACCCACACAAAATTCTAACTGGGAGAAGAGATCAAATGCATACCATGAGGCAAACAGATGGGTTA
GCGGGATTCACCAAGCGCTCGGAGAGTGAATATGACTGCTTTGGAACCGGCCACAGTTCTACTACCATCTCAGCAGGCTTGGG
AATGGCGGTCGGCCGGGATCTAAAAGGAAAAAACAACAACGTCATTGCTGTCATAGGTGATGGAGCCATGACTGCAGGGCAAG
CTTATGAAGCAATGAACAATGCTGGTTACCTGGATTCTGACATGATTGTTATCCTTAATGACAACAAGCAGGTTTCTTTACCC
ACTGCTACTCTAGATGGGCCCATACCACCTGTAGGAGCTTTGAGCAGTGCTCTTAGTAGGTTACAATCAAACAGACCTCTTAG
AGAATTACGAGAGGTTGCCAATGGCGTTACCAAACAGATTGGCGGACCGATGCATGAATTGGCTGCAAAAGTTGATGAATATG
CTCGTGGGATGATCAGTGGTTCTGGATCAACACTTTTTGAAGAGCTTGGACTCTATTATATAGGTCCTGTTGATGGCCACAAC
ATAGATGACCTTGTTGCCATTCTCAAGGAGGTTAAGAGTACCAAGACAACAGGTCCAGTTCTGATCCATGTTGTCACAGAGAA
AGGCCGCGGATATCCATATGCTGAGAAAGCTGCAGATAAGTACCATGGAGTGACCAAGTTCGATCCTGCTACTGGAAAACAAT
TCAAATCCAGTGCTCCTACTCAGTCCTACACAACATATTTTGCAGAGGCTTTGATTGCAGAAGCAGAGGTGGACAAGGATATT
GTTGCAATTCATGCAGCAATGGGGGGTGGAACGGGCTTGAATCTCTTCCATCGCCGGTTCCCCACACGATGCTTTGATGTTGG
GATAGCAGAACAGCATGCTGTTACCTTTGCTGCTGGTCTAGCCTGTGAAGGCATTAAACCTTTTTGTGCAATCTACTCATCTT
TCATGCAGAGAGCTTATGACCAGGTGGTGCATGATGTAGATTTGCAGAAGCTGCCAGTGAAATTTGCAATGGACAGAGCTGGG
CTGGTTGGAGCAGATGGCCCAACACATTGTGGAGCTTTTGATGTCGCTTTCATGGCTTGCCTTCCAAACATGGTGGTGATGGC
TCCTGCTGATGAGGCTGAGCTTTTTCACATGGTGGCCACAGCTGCTGCCATAGATGACAGGCCCAGTTGTTTCCGGTACCCAA
GAGGGAAATGGGGTGGGTATTGAACTGCCACCAGGGAACAAAGGCATTCCTATTGAGGTTGGAAGGGGCCGAATATTGATTGAG
GGGGAGAGAGTTGCACTCTTGGGCTATGGAACAGCAGTACAGAGCTGTTTGGTTGCGTCTTCTTTGCTGGAACAACATGGCTT
ACGAATAACAGTCGCAGATGCCCGCTTCTGCAAACCATTGGACCATGCTCTTATTCGTAGCCTAGCAAAATCACATGAAGTTT
TGATTACAGTAGAAGAAGGGTCAATTGGTGGTTTTGGGTCTCATGTTGCTCAGTTTTTGGCCCTTAATGGTCTTCTTGATGGC
ACAACAAAGTGGAGTCCCATGGTTCTTCCTGATCGGTACATAGACCATGGAGCGCCAGCGGACCAGTTGGCCATGGCGGGTCT
GACACCATCTCATATTGCAGCAACAGTATTCAATATACTTGGACAAACAAGGGAGGCCCTGGAGATCATGTTATAG
```

GwDXS2 (SEQ ID N°10)

```
ATGGCTCTCTGTACGCTCTCATTTCCTGCCCATTTTAGCCAGGCTGCTGCTTCAAATCCTCAGAGACTTACTCCTCAGTGTTC
CCATTTGTTCTTGGGGGTGGATTTGCAGTGCCAATCCCAGCAAAGGAGTAAGGCCAGGAAAAGGCCAAATGGGGTTTGTGCAT
CACTTTCGGATAGGGAGGAGTATCATTCCCAGAGACCACCAACTCCTCTCCTGGACACTATCAATTATCCAATTCACATGAAA
AATCTGTCTGTCAAGGAGCTGAAACAACTCGCAGATGAACTAAGGTCTGATGTTGTCTTCAATGTTTCCAAAACTGGGGGTCA
CTTGGGCTCCAGCCTCGGGGTTGTGGAGCTCACTGTGGCTCTTCATTATGTCTTCAATGCCCCTCAAGACAGGATACTATGGG
ATGTTGGTCATCAGTCTTACCCACACAAAATTCTAACTGGGAGAAGAGATCAAATGCATACCATGAGGCAAACAGATGGGTTA
GCGGGATTCACCAAGCGCTCGGAGAGTGAATATGACTGCTTTGGAACCGGCCACAGTTCTACTACCATCTCAGCAGGCTTGGG
AATGGCGGTCGGCCGGGATCTAAAAGGAAAAAACAACAACGTCATTGCTGTCATAGGTGATGGAGCCATGACTGCAGGGCAAG
CTTATGAAGCAATGAACAATGCTGGTTACCTGGATTCTGACATGATTGTTATCCTTAATGACAACAAGCAGGTTTCTTTACCC
ACTGCTACTCTAGATGGGCCCATACCACCTGTAGGAGCTTTGAGCAGTGCTCTTAGTAGGTTACAATCAAACAGACCTCTTAG
AGAATTACGAGAGGTTGCCAAGGGCGTTACCAAACAGATTGGCGGACCGATGCATGAATTGGCTGCAAAAGTTGATGAATATG
CTTGTGGGATGATCAGTGGTTCTGGATCAACACTTTTTGAAGAGCTTGGACTCTATTATATAGGTCCTGTTGATGGCCACAAC
ATAGATGACCTTGTTGCCATTCTCAAGGAGGTTAAGAGTACCAAGACAACAGGTCCAGTTCTGATCCATGTTGTCACAGAGAA
AGGCCGCGGATATCCATATGCTGAGAAAGCTGCAGATAAGTACCATGGAGTGACCAAGTTCGATCCTGCTACTGGAAAACAAT
TCAAATCCAGTGCTCCTACTCAGTCCTACACAACATATTTTGCAGAGGCTTTGATTGCAGAAGCAGAGGTGGACAAGGATATT
GTTGCAATTCATGCAGCAATGGGGGGTGGAACGGGCTTGAATCTCTTCCATCGCCGGTTCCCCACACGATGCTTTGATGTTGG
GATAGCAGAACAGCATGCTGTTACCTTTGCTGCTGGTCTAGCCTGTGAAGGCATTAAACCTTTTTGTGCAATCTACTCATCTT
TCATGCAGAGAGCTTATGACCAGGTGGTGCATGATGTAGATTTGCAGAAGCTGCCAGTGAAATTTGCAATGGACAGAGCTGGG
CTGGTTGGAGCAGATGGCCCAACACATTGTGGAGCTTTTGATGTCGCTTTCATGGCTTGCCTTCCAAACATGGTGGTGATGGC
TCCTGCTGATGAGGCTGAGCTTTTTCACATGGTGGCCACAGCTGCTGCCATAGATGACAGGCCCAGTTGTTTCCGGTACCCAA
GAGGGAAATGGGGTGGGTGTTGAACTGCCACCAGGGAACAAAGGCATTCCTATTGAGGTTGGAAGGGGCCGAATATTGATTGAG
GGGGAGAGAGTTGCACTCTTGGGCTATGGAACAGCAGTACAGAGCTGTTTGGTTGCGTCTTCTTTGCTGGAACAACATGGCTT
ACGAATAACAGTCGCAGATGCCCGCTTCTGCAAACCATTGGACCATGCTCTTATTCGTAGCCTAGCAAAATCACATGAAGTTT
TGATTACAGTAGAAGAAGGGTCAATTGGTGGTTTTGGGTCTCATGTTGCTCAGTTTTTGGCCCTTAATGGTCTTCTTGATGGC
ACAACAAAGTGGAGTCCCATGGTTCTTCCTGATCGGTACATAGACCATGGAGCGCCAGCGGACCAGTTGGCCATGGCGGGTCT
GACACCATCTCATATTGCAGCAACAGTATTCAATATACTTGGACAAACAAGGGAGGCCCTGGAGATCATGTTATAG
```

Figure 1 (continuation)

```
           1        10        20        30        40        50        60
           |        |         |         |         |         |         |
Consensus  MALCTLSPPAEFSQAAASNPQRLTPQCSHLFLGVDLQCQSQQRSKARKRPNGVCASLSDR Gw_DXS2    ............................................................
Mo_DXS1    ............................................................
Mo_DXS2    ............................................................

70        80        90        100       110       120
                    |         |         |         |         |         |
Consensus  EEYHSQRPPTPLLDTINYPIHMKHLSVRELEQLADELRSDVVFNVSKTGGHLGSSLGVVE Gw_DXS2    ............................................................
Mo_DXS1    ............................................................
Mo_DXS2    ............................................................

130       140       150       160       170       180
                    |         |         |         |         |         |
Consensus  LTVALHYVFNAPQDRILWDVGHQSYPHKILTGRRDQMHTKRQTDGLAGFTKRSESEYDCF Gw_DXS2    ............................................................
Mo_DXS1    ............................................................
Mo_DXS2    ............................................................

190       200       210       220       230       240
                    |         |         |         |         |         |
Consensus  GTGHSSTTISAGLGHAVGRDLKGKNNRVIAVIGDGAMTAGQAYEAMNNAGYLSDRIVIL Gw_DXS2    ............................................................
Mo_DXS1    ............................................................
Mo_DXS2    ............................................................

250       260       270       280       290       300
                    |         |         |         |         |         |
Consensus  NDNKQVSLPTATLDGPIPPVGALSSALSRLQSNRPLRELREVAKGVTKQIGGPMHELAAK Gw_DXS2    .............................................R..............
Mo_DXS1    .............................................K..............
Mo_DXS2    .............................................N..............

310       320       330       340       350       360
                    |         |         |         |         |         |
Consensus  VDEYAKGMISGSGSTLFEELGLYYIGPVDGHNIDDLVAILKEVKSTKTTGPVLIHVVTEK Gw_DXS2    .....C......................................................
Mo_DXS1    .....R......................................................
Mo_DXS2    .....R......................................................

370       380       390       400       410       420
                    |         |         |         |         |         |
Consensus  GRGYPYAEKAADKYHGVFKFDPATGKQFKSSAPTQSYTTYFAEALIAEASVDKDIVAIHA Gw_DXS2    ............................................................
Mo_DXS1    ............................................................
Mo_DXS2    ............................................................

430       440       450       460       470       480
                    |         |         |         |         |         |
Consensus  AMGGGTGLNLFERRFPTRCFDVGIAEQHAVTFAAGLACEGIKPFCAIYSSFMQRAYDQVV Gw_DXS2    ............................................................
Mo_DXS1    ............................................................
Mo_DXS2    ............................................................

490       500       510       520       530       540
                    |         |         |         |         |         |
Consensus  HDVDLQKLPVKFAMDRAGLVGADGPTHCGAFDVAFMACLPNMVVMAPADEAELFHMVATA Gw_DXS2    ............................................................
Mo_DXS1    ............................................................
Mo_DXS2    ............................................................

550       560       570       580       590       600
                    |         |         |         |         |         |
Consensus  AAIDDRPSCFRYPRGNGVGKELPPGNKGIPIKVGKGRILIEGERVALLGYGTAVQSCLVA Gw_DXS2    .........V..................................................
Mo_DXS1    .........V..................................................
Mo_DXS2    .........I..................................................

610       620       630       640       650       660
                    |         |         |         |         |         |
Consensus  SSLLEQHGLRITVADARPCKPLDHALIRSLAKSHEVLITVEEGSIGGFGSHVAQFLALNG Gw_DXS2    ............................................................
Mo_DXS1    ............................................................
Mo_DXS2    ............................................................

670       680       690       700       710    737
                    |         |         |         |         |        |
Consensus  LLDGTTKWSPHVLPDRYIDHGAPADQLAMAGLTPSHIAATVFNILGQTREALRIML*

Gw_DXS2    ............................................................
Mo_DXS1    ............................................................
Mo_DXS2    ............................................................
```

Figure 2

```
                                  1         10        20        30        40        50
Consensus                         MAXXXXXXPXXXXXXXXXXXBXXXXXXXXSXXXXXXXLXXXXXXXXXXX
Mo_DXS1                           ..LCTLSF.AHFSQA--AASNPQRLTPQC.HLFLGVD.QCQ-SQQRSKA-
Mo_DXS2                           ..LCTLSF.AHFSQA--AASNPQRLTPQC.HLFLGVD.QCQ-SQQRSKA-
Gw_DXS2                           ..LCTLSF.AHFSQA--AASNPQRLTPQC.HLFLGVD.QCQ-SQQRSKA-
Arabidopsis thaliana              ..SSAFAF.SYIITKGGLSTDSCKSTSLS.SRSLVTD.PSPCLKPNNNSH
Capsicum annuum                   ..LCAYAF.GILNRTVAVASDASKPTPLF.EWIHGTD.QFQFHQKLTQV-
Catharanthus roseus
Glycine max                                                      KLLPLP.HSQWG--.HFLAHAHRLHQM
Narcissus pseudonarcissus
Nicotiana tabacum                 ..LCNYAV.GILNRT--VASDYSKQSPLF.ELFHGTD.QYQFQHKLTRV-
Oryza sativa
                                           60        70        80        90        100
Consensus                         XXRXXXXVXASXXXXXXXXXXXXPXXPJXDTXNXPXHMKNLSXXXLXQLXXE
Mo_DXS1                           RK.PNG.C...LSDREEYHSQR.PT.LL..I.Y.I......VKE.K..AD.
Mo_DXS2                           RK.PNG.C...LSDREEYHSQR.PT.LL..I.Y.I......VKE.K..AD.
Gw_DXS2                           RK.PNG.C...LSDREEYHSQR.PT.LL..I.Y.I......VKE.K..AD.
Arabidopsis thaliana              SN.RAK.C...LAEKGEYYSNR.PT.LL..I.Y.I......VKE.K..SD.
Capsicum annuum                   KK.SRT.Q...LSESCEYYTQR.PT.IV..I.Y.I......LKE.K..AD.
Catharanthus roseus                         DFSGEK.PT.LL..I.Y.V......AHD.E..AA.
Glycine max                       KK.PCG.Y...LSESGEYYSHR.PT.LL..V.Y.I......AKE.K..AD.
Narcissus pseudonarcissus                   YSGEK.AV.LL..I.D.A......TQD.E..AS.
Nicotiana tabacum                 KK.SRG.Q...LSEKGEYYAQR.PT.LL..I.Y.I......VKE.K..AE.
Oryza sativa                      A...GAWKIDYSGEK.AT.LL..V.Y.V......TPE.E..AA.
                                           110       120       130       140       150
Consensus                         LRXXXXXXXVXXTGGHLXXSLGVVXLXVXLHXXFBXPXDXIJWDVGHQXYX
Mo_DXS1                           ..SDVVFN.SK.....GS.....E.T.A..YV.NA.Q.R.L......S.P
Mo_DXS2                           ..SDVVFN.SK.....GS.....E.T.A..YV.NA.Q.R.L......S.P
Gw_DXS2                           ..SDVVFN.SK.....GS.....E.T.A..YV.NA.Q.R.L......S.P
Arabidopsis thaliana              ..SDVIFN.SK.....GS.....E.T.A..YI.NT.Q.K.L......S.P
Capsicum annuum                   ..SDTIFN.SK.....GS.....E.T.A..YV.NA.Q.R.L......S.P
Catharanthus roseus               ..AEIVYS.AK.....SA.....D.T.A..HV.NT.E.R.I......A.P
Glycine max                       ..SDVIFS.SR.....GS.....E.T.A..YV.NA.Q.K.L......S.P
Narcissus pseudonarcissus         ..LDIVHS.SK.....SA.....D.T.V..HV.DT.D.R.I......A.A
Nicotiana tabacum                 ..SDTIFN.SK.....GS.....E.T.A..YV.NT.Q.R.L......S.P
Oryza sativa                      ..AEIVHT.SK.....SS.....E.A.A..HV.DT.E.K.I......A.P
                                           160       170       180       190       200
Consensus                         HKILTGRRXXMXTXRQTXGLXGFXKRXESXXDXFGXGHSSTXISAXLGHA
Mo_DXS1                           ........DQ.H.M...D..A..T..S..EY.C..T.....T...G....
Mo_DXS2                           ........DQ.H.M...D..A..T..S..EY.C..T.....T...G....
Gw_DXS2                           ........DQ.H.M...D..A..T..S..EY.C..T.....T...G....
Arabidopsis thaliana              ........GK.P.M...N..S..T..G..EH.C..T.....T...G....
Capsicum annuum                   ........EK.S.L...N..A..T..S..EY.C..T.....T...G....
Catharanthus roseus               ........SK.H.I...S..A..P..D..IY.A..A.....S...G....
Glycine max                       ........DQ.H.M...N..S..T..G..EF.C..T.....T...G....
Narcissus pseudonarcissus         ........SR.H.L...S..A..P..D..VH.A..A.....S...G....
Nicotiana tabacum                 ........GK.S.L...D..A..T..S..EY.C..T.....T...G....
Oryza sativa                      ........SR.H.I...S..A..P..D..AH.A..A.....S...A....
                                           210       220       230       240       250
Consensus                         VXRDJXGXXNXVXXVIGDGXMTAGQAYEAMNNXGXLDXBXIVXLNDNXQV
Mo_DXS1                           .G..LK.KN.N.IA.....A............A.Y..SDM..I....K..
Mo_DXS2                           .G..LK.KN.N.IA.....A............A.Y..SDM..I....K..
Gw_DXS2                           .G..LK.KN.N.IA.....A............A.Y..SDM..I....K..
Arabidopsis thaliana              .G..LK.KN.N.VA.....A............A.Y..SDM..I....K..
Capsicum annuum                   .G..LK.RN.N.IA.....A............A.Y..SDM..I....R..
Catharanthus roseus               .A..IL.KN.N.IS.....A............A.F..ANL..V....K..
Glycine max                       .G..LK.RK.N.VA.....A............A.Y..SDM..I....K..
Narcissus pseudonarcissus         .A..LL.KS.H.IS.....V............V.Y..SNL..V....K..
Nicotiana tabacum                 .G..LK.KN.N.IA.....A............A.Y..SDM..I....R..
Oryza sativa                      .A..LL.KK.H.IS.....A............S.Y..SNM..V....K..
                                           260       270       280       290       300
Consensus                         SLPTATLBGPXXPVGALSXALXXLQXXXXXRXLREXAXXXTKXIGXXXHZ
Mo_DXS1                           .......D..IP......S..SR..SNRPL.E...V.KGV..Q..GPM.E
Mo_DXS2                           .......D..IP......S..SR..SNRPL.E...V.NGV..Q..GPM.E
Gw_DXS2                           .......D..IP......S..SR..SNRPL.E...V.KGV..Q..GPM.E
Arabidopsis thaliana              .......D..SP......S..SR..SNPAL.E...V.KGM..Q..GPM.Q
Capsicum annuum                   .......D..VP......S..SR..SNRPL.E...V.KGV..Q..GPM.E
Catharanthus roseus               .......D..AT......S..SK..ASPKF.Q...A.KSI..Q..PQA.E
Glycine max                       .......D..IP......S..SR..SNRPL.E...V.KGV..R..GPM.E
Narcissus pseudonarcissus         .......N..AT......G..AK..ASAKF.Q...A.KCI..Q..GQA.E
Nicotiana tabacum                 .......D..AP......R..SR..SNRPL.E...V.KGV..Q..GPM.E
Oryza sativa                      .......D..AT......K..TK..SSTKL.R...A.KTV..Q..GQA.E
```

Figure 3

```
                          310         320         330         340         350
Consensus            XAAKVDXYAXGMXSXXGXXLFEELGLYYIGPVDGHXXXDLXXIXXXVXXX
Mo_DXS1              L.....E..R..I.GS.ST..................NID..VA.LKE.KST
Mo_DXS2              L.....E..R..I.GS.ST..................NID..VA.LKE.KST
Gw_DXS2              L.....E..C..I.GS.ST..................NID..VA.LKE.KST
Arabidopsis thaliana L.....V..R..I.GT.SS..................NID..VA.LKE.KST
Capsicum annuum      L.....E..R..I.GS.ST..................NID..IS.LKE.RST
Catharanthus roseus  V.....E..R..L.AT.ST..................SIE..VT.PQK.KAM
Glycine max          L.....E..R..I.GS.SS..................NID..VA.LNE.KST
Narcissus pseudonarcissus V.....E..R..I.AS.AS..................NVE..VA.FKK.KAM
Nicotiana tabacum    L.....E..R..I.GS.ST..................NID..IS.LKE.RST
Oryza sativa         V.....E..R..V.AS.ST..................SVD..VA.FNK.KSM 360         370         380         390         400
Consensus            XXXGPVLXHXXTEKGXGYPXAEXAXDXXHGVXKFDPXTGXQFKXXXXTXS
Mo_DXS1              KTT....I.VV....R...Y..K.A.KY...T....A..K...SSAP.Q.
Mo_DXS2              KTT....I.VV....R...Y..K.A.KY...T....A..K...SSAP.Q.
Gw_DXS2              KTT....I.VV....R...Y..K.A.KY...T....A..K...SSAP.Q.
Arabidopsis thaliana RTT....I.VV....R...Y..R.D.KY...V....A..R...TTNE.Q.
Capsicum annuum      KTT....I.VV....R...Y..R.A.KY...A....A..K...GSAK.Q.
Catharanthus roseus  PAP....I.IV....K...P..V.A.KM...V....K..K...SKSP.L.
Glycine max          KTT....I.VI....R...Y..K.A.KY...T....P..K...SKAT.Q.
Narcissus pseudonarcissus PSP....V.IV....K...P..A.A.KM...V....K..K...TKFP.L.
Nicotiana tabacum    KTT....I.VI....R...Y..R.A.KY...A....A..K...VSAK.Q.
Oryza sativa         PAP....V.IV....K...P..A.A.RM...V....T..R...SKCS.L.

410         420         430         440         450
Consensus            YTXYFAEXLXXEAEXDXXXXXIHAAMGGGTGXNXFXXXXFPXRCFDVGIAE
Mo_DXS1              ..T.....A.IA...V.KDIVA.........L.L.HRR..T.........
Mo_DXS2              ..T.....A.IA...V.KDIVA.........L.L.HRR..T.........
Gw_DXS2              ..T.....A.IA...V.KDIVA.........L.L.HRR..T.........
Arabidopsis thaliana ..T.....A.VA...V.KDVVA.........L.L.QRR..T.........
Capsicum annuum      ..T.....A.IA...A.KDIVA.........M.L.LRR..T.........
Catharanthus roseus  ..Q.....S.IK...I.NKIIA.........L.Y.QKR..D.........
Glycine max          ..T.....A.IA...A.KDVVA.........M.L.HRR..T.........
Narcissus pseudonarcissus ..Q.....S.VK...V.EKIVA.........L.F.QKK..D.........
Nicotiana tabacum    ..T.....A.IA...A.KDIVA.........M.I.HRR..N.........
Oryza sativa         ..Q.....A.IR...A.DKVVG.........L.Y.HKR..E.........

460         470         480         490         500
Consensus            QHAVTFAAGLAXEGJKPFCAIYSSFXQRXYDQVVHDVDLQKLPVXFAKDR
Mo_DXS1              ..............C..I..........M..A...........K...K..M..
Mo_DXS2              ..............C..I..........M..A...........K...K..M..
Gw_DXS2              ..............C..I..........M..A...........K...K..M..
Arabidopsis thaliana ..............C..L..........M..A...........K...R..M..
Capsicum annuum      ..............C..L..........M..A...........K...R..M..
Catharanthus roseus  ..............T..L..........L..G...........K...R..M..
Glycine max          ..............C..L..........M..A...........K...R..M..
Narcissus pseudonarcissus ..............T..L..........L..G...........K...R..L..
Nicotiana tabacum    ..............C..L..........L..A...........K...R..M..
Oryza sativa         ..............A..L..........L..G...........R...R..M..

510         520         530         540         550
Consensus            AGLVGADGPTHCGXFDVXXMACLPNMXVMAPXDEXXLXXXXVATAXXIBDR
Mo_DXS1              .............A...AF........V....A..AE.FHM....AA.D..
Mo_DXS2              .............A...AF........V....A..AE.FHM....AA.D..
Gw_DXS2              .............A...AF........V....A..AE.FHM....AA.D..
Arabidopsis thaliana .............A...TF........I....S..AD.FNM....VA.D..
Capsicum annuum      .............A...TF........V....S..AE.FHI....AA.D..
Catharanthus roseus  .............A...AY........I....S..AE.MHM....AK.D..
Glycine max          .............S...TF........V....S..AD.FHM....AA.N..
Narcissus pseudonarcissus .............A...TY........I....S..AE.MHM....AA.D..
Nicotiana tabacum    .............A...TF........S...TE.FHM....AA.D..
Oryza sativa         .............A...AY........V....A..AE.MHM....AA.D..

560         570         580         590         600
Consensus            PXCFRXPRGNGXGXXLPXXXKGXPJEXGXGRXLXXGXXVAJLGYGXXVQX
Mo_DXS1              .S...Y......V.VE..PGN..I.I.V.R..I.IE.ER..L....TA..S
Mo_DXS2              .S...Y......V.IE..PGN..I.I.V.R..I.IE.ER..L....TA..S
Gw_DXS2              .S...Y......V.VE..PGN..I.I.V.R..I.IE.ER..L....TA..S
Arabidopsis thaliana .S...Y......I.VA..PGN..V.I.K..I.KE.ER..L....SA..S
Capsicum annuum      .S...Y......I.VE..AGN..I.L.V.K..I.VE.ER..L....SA..N
Catharanthus roseus  .C...F......I.VA..PNN..T.L.I.K..I.VE.SR..I....SI..Q
Glycine max          .S...Y......I.VQ..TGN..T.L.I.K..I.IE.ER..L....SA..N
Narcissus pseudonarcissus .S...F......V.VA..SDY..T.L.I.K..I.ME.DK..I....SI..S
Nicotiana tabacum    .S...Y......I.VE..VGN..T.L.V.K..I.VE.ER..L....SA..N
Oryza sativa         .S...F......I.AV..PNH..T.L.V.K..V.VG.NR..L....TM..A
```

Figure 3 (continuation)

```
                                   610         620         630         640         650
Consensus                    CXXAXXXXXXXXXXXTVADXXFCKPLDXXLIXXLXXXHEXLXTVEXGSIG
Mo_DXS1                      .LV.SSLLEQHGLRI....AR......HA..RS.AKS..V.I...E....
Mo_DXS2                      .LV.SSLLEQHGLRI....AR......HA..RS.AKS..V.I...E....
Gw_DXS2                      .LV.SSLLEQHGLRI....AR......HA..RS.AKS..V.I...E....
Arabidopsis thaliana         .LG.AVMLEERGLNV....AR......RA..RS.AKS..V.I...E....
Capsicum annuum              .LA.ASVLESRGLQV....AR......RA..RS.AKS..V.V...K....
Catharanthus roseus          .LG.AEMLKSHNVSP....AK......GD..KT.AKE..I.I...E....
Glycine max                  .LA.ASLVECHGLRL....AR......RS..RS.AKS..V.I...E....
Narcissus pseudonarcissus    .LK.AGSLRERGISA....GR......SE..RR.VNE..I.I...E....
Nicotiana tabacum            .LA.AAVLVTRGLQV....AR......GA..RS.AKS..V.I...E....
Oryza sativa                 .MK.AEALKEHGIYV....AR......TG..RE.AAE..V.V...E....

660         670         680         690         700
Consensus                    GFXSHVXXXXXLXGJLDGXXKXXXXXLPDRYIDHGXPXDQJXXAGLXXXH
Mo_DXS1                      ..G...AQFLA.N.L...TT.WSPMV.........A.A..LAM...TPS.
Mo_DXS2                      ..G...AQFLA.N.L...TT.WSPMV.........A.A..LAM...TPS.
Gw_DXS2                      ..G...AQFLA.N.L...TT.WSPMV.........A.A..LAM...TPS.
Arabidopsis thaliana         ..G...VQFLA.D.L...KL.WRPMV.........A.A..LAE...MPS.
Capsicum annuum              ..G...VQFMA.D.L...KL.WRPIV.........S.A..LAE...TPS.
Catharanthus roseus          ..G...THFLS.T.I...PI.VRSLF.........A.V..IEE...SSR.
Glycine max                  ..G...AQFMA.D.L...KL.WRPIV.........S.A..LSL...TPS.
Narcissus pseudonarcissus    ..A...SHFLS.N.L...HL.LRSMV.........A.K..IEE...SSK.
Nicotiana tabacum            ..G...AQFMA.D.L...KL.WRPIV.........S.A..LAE...TPS.
Oryza sativa                 ..G...AHYLS.S.L...PL.LRSMF.........A.V..LEE...TPR.

710       721
Consensus                    IXXTXXXXJXXXXEAXXXML*
Mo_DXS1                      .AA.VFNILGQTR..LEI...
Mo_DXS2                      .AA.VFNILGQTR..LEI...
Gw_DXS2                      .AA.VFNILGQTR..LEI...
Arabidopsis thaliana         .AA.ALNLIGAPR..LF*
Capsicum annuum              .AA.VFNILGQTR..LEV.
Catharanthus roseus          .CA.ILSLLGKPK..LKL
Glycine max                  .AA.VFNVLRQTR..LEV.
Narcissus pseudonarcissus    .AG.VLSLLGRPM..FQL
Nicotiana tabacum            .AA.VFNILGQTR..LEV.
Oryza sativa                 .AA.VLSLLGRPL..LQL
```

Figure 3 (continuation)

MO_DXS1 (SEQ ID N°3)

MALCTLSFPAHFSQAAASNPQRLTPQCSHLFLGVDLQCQSQQRSKARKRPNGVCASLSDREEYHSQRPPTPLLDT
INYPIHMKNLSVKELKQLADELRSDVVFNVSKTGGHLGSSLGVVELTVALHYVFNAPQDRILWDVGHQSYPHKIL
TGRRDQMHTMRQTDGLAGFTKRSESEYDCFGTGHSSTTISAGLGMAVGRDLKGKNNNVIAVIGDGAMTAGQAYEA
MNNAGYLDSDMIVILNDNKQVSLPTATLDGPIPPVGALSSALSRLQSNRPLRELREVAKGVTKQIGGPMHELAAK
VDEYARGMISGSGSTLFEELGLYYIGPVDGHNIDDLVAILKEVKSTKTTGPVLIHVVTEKGRGYPYAEKAADKYH
GVTKFDPATGKQFKSSAPTQSYTTYFAEALIAEAEVDKDIVAIHAAMGGGTGLNLFHRRFPTRCFDVGIAEQHAV
TFAAGLACEGIKPFCAIYSSFMQRAYDQVVHDVDLQKLPVKFAMDRAGLVGADGPTHCGAFDVAFMACLPNMVVM
APADEAELFHMVATAAAIDDRPSCFRYPRGNGVGVELPPGNKGIPIEVGRGRILIEGERVALLGYGTAVQSCLVA
SSLLEQHGLRITVADARFCKPLDHALIRSLAKSHEVLITVEEGSIGGFGSHVAQFLALNGLLDGTTKWSPMVLPD
RYIDHGAPADQLAMAGLTPSHIAATVFNILGQTREALEIML

MO_DXS2 (SEQ ID N°4)

MALCTLSFPAHFSQAAASNPQRLTPQCSHLFLGVDLQCQSQQRSKARKRPNGVCASLSDREEYHSQRPPTPLLDT
INYPIHMKNLSVKELKQLADELRSDVVFNVSKTGGHLGSSLGVVELTVALHYVFNAPQDRILWDVGHQSYPHKIL
TGRRDQMHTMRQTDGLAGFTKRSESEYDCFGTGHSSTTISAGLGMAVGRDLKGKNNNVIAVIGDGAMTAGQAYEA
MNNAGYLDSDMIVILNDNKQVSLPTATLDGPIPPVGALSSALSRLQSNRPLRELREVANGVTKQIGGPMHELAAK
VDEYARGMISGSGSTLFEELGLYYIGPVDGHNIDDLVAILKEVKSTKTTGPVLIHVVTEKGRGYPYAEKAADKYH
GVTKFDPATGKQFKSSAPTQSYTTYFAEALIAEAEVDKDIVAIHAAMGGGTGLNLFHRRFPTRCFDVGIAEQHAV
TFAAGLACEGIKPFCAIYSSFMQRAYDQVVHDVDLQKLPVKFAMDRAGLVGADGPTHCGAFDVAFMACLPNMVVM
APADEAELFHMVATAAAIDDRPSCFRYPRGNGVGIELPPGNKGIPIEVGRGRILIEGERVALLGYGTAVQSCLVA
SSLLEQHGLRITVADARFCKPLDHALIRSLAKSHEVLITVEEGSIGGFGSHVAQFLALNGLLDGTTKWSPMVLPD
RYIDHGAPADQLAMAGLTPSHIAATVFNILGQTREALEIML

GW_DXS2 (SEQ ID N°6)

MALCTLSFPAHFSQAAASNPQRLTPQCSHLFLGVDLQCQSQQRSKARKRPNGVCASLSDREEYHSQRPPTPLLDT
INYPIHMKNLSVKELKQLADELRSDVVFNVSKTGGHLGSSLGVVELTVALHYVFNAPQDRILWDVGHQSYPHKIL
TGRRDQMHTMRQTDGLAGFTKRSESEYDCFGTGHSSTTISAGLGMAVGRDLKGKNNNVIAVIGDGAMTAGQAYEA
MNNAGYLDSDMIVILNDNKQVSLPTATLDGPIPPVGALSSALSRLQSNRPLRELREVAKGVTKQIGGPMHELAAK
VDEYACGMISGSGSTLFEELGLYYIGPVDGHNIDDLVAILKEVKSTKTTGPVLIHVVTEKGRGYPYAEKAADKYH
GVTKFDPATGKQFKSSAPTQSYTTYFAEALIAEAEVDKDIVAIHAAMGGGTGLNLFHRRFPTRCFDVGIAEQHAV
TFAAGLACEGIKPFCAIYSSFMQRAYDQVVHDVDLQKLPVKFAMDRAGLVGADGPTHCGAFDVAFMACLPNMVVM
APADEAELFHMVATAAAIDDRPSCFRYPRGNGVGVELPPGNKGIPIEVGRGRILIEGERVALLGYGTAVQSCLVA
SSLLEQHGLRITVADARFCKPLDHALIRSLAKSHEVLITVEEGSIGGFGSHVAQFLALNGLLDGTTKWSPMVLPD
RYIDHGAPADQLAMAGLTPSHIAATVFNILGQTREALEIML

Figure 8

Truncated MO_DXS2 (SEQ ID N°5)

VCASLSDREEYHSQRPPTPLLDTINYPIHMKNLSVKELKQLADELRSDVVFNVSKTGGHLGSSLGVVELTVALHY
VFNAPQDRILWDVGHQSYPHKILTGRRDQMHTMRQTDGLAGFTKRSESEYDCFGTGHSSTTISAGLGMAVGRDLK
GKNNNVIAVIGDGAMTAGQAYEAMNNAGYLDSDMIVILNDNKQVSLPTATLDGPIPPVGALSSALSRLQSNRPLR
ELREVANGVTKQIGGPMHELAAKVDEYARGMISGSGSTLFEELGLYYIGPVDGHNIDDLVAILKEVKSTKTTGPV
LIHVVTEKGRGYPYAEKAADKYHGVTKFDPATGKQFKSSAPTQSYTTYFAEALIAEAEVDKDIVAIHAAMGGGTG
LNLFHRRFPTRCFDVGIAEQHAVTFAAGLACEGIKPFCAIYSSFMQRAYDQVVHDVDLQKLPVKFAMDRAGLVGA
DGPTHCGAFDVAFMACLPNMVVMAPADEAELFHMVATAAAIDDRPSCFRYPRGNGVGIELPPGNKGIPIEVGRGR
ILIEGERVALLGYGTAVQSCLVASSLLEQHGLRITVADARFCKPLDHALIRSLAKSHEVLITVEEGSIGGFGSHV
AQFLALNGLLDGTTKWSPMVLPDRYIDHGAPADQLAMAGLTPSHIAATVFNILGQTREALEIML

Truncated GW_DXS2 (SEQ ID N°7)

VCASLSDREEYHSQRPPTPLLDTINYPIHMKNLSVKELKQLADELRSDVVFNVSKTGGHLGSSLGVVELTVALHY
VFNAPQDRILWDVGHQSYPHKILTGRRDQMHTMRQTDGLAGFTKRSESEYDCFGTGHSSTTISAGLGMAVGRDLK
GKNNNVIAVIGDGAMTAGQAYEAMNNAGYLDSDMIVILNDNKQVSLPTATLDGPIPPVGALSSALSRLQSNRPLR
ELREVAKGVTKQIGGPMHELAAKVDEYACGMISGSGSTLFEELGLYYIGPVDGHNIDDLVAILKEVKSTKTTGPV
LIHVVTEKGRGYPYAEKAADKYHGVTKFDPATGKQFKSSAPTQSYTTYFAEALIAEAEVDKDIVAIHAAMGGGTG
LNLFHRRFPTRCFDVGIAEQHAVTFAAGLACEGIKPFCAIYSSFMQRAYDQVVHDVDLQKLPVKFAMDRAGLVGA
DGPTHCGAFDVAFMACLPNMVVMAPADEAELFHMVATAAAIDDRPSCFRYPRGNGVGVELPPGNKGIPIEVGRGR
ILIEGERVALLGYGTAVQSCLVASSLLEQHGLRITVADARFCKPLDHALIRSLAKSHEVLITVEEGSIGGFGSHV
AQFLALNGLLDGTTKWSPMVLPDRYIDHGAPADQLAMAGLTPSHIAATVFNILGQTREALEIML

Figure 8 (continuation)

*E.coli* DXS (SEQ ID N°13)

```
ATGAGTTTTGATATTGCCAAATACCCGACCCTGGCACTGGTCGACTCCACCCAGGAGTTACGACTGTT
GCCGAAAGAGAGTTTACCGAAACTCTGCGACGAACTGCGCCGCTATTTACTCGACAGCGTGAGCCGTT
CCAGCGGGCACTTCGCCTCCGGGCTGGGCACGGTCGAACTGACCGTGGCGCTGCACTATGTCTACAAC
ACCCCGTTTGACCAATTGATTTGGGATGTGGGCATCAGGCTTATCCGCATAAAATTTTGACCGGACG
CCGCGACAAAATCGGCACCATCCGTCAGAAAGGCGGTCTGCACCCGTTCCCGTGGCGCGGCGAAAGCG
AATATGACGTATTAAGCGTCGGGCATTCATCAACCTCCATCAGTGCCGGAATTGGTATTGCGGTTGCT
GCCGAAAAGAAGGCAAAAATCGCCGCACCGTCTGTGTCATTGGCGATGGCGCGATTACCGCAGGCAT
GGCGTTTGAAGCGATGAATCACGCGGGCGATATCCGTCCTGATATGCTGGTGATTCTCAACGACAATG
AAATGTCGATTTCCGAAAATGTCGGCGCGCTCAACAACCATCTGGCACAGCTGCTTTCCGGTAAGCTT
TACTCTTCACTGCGCGAAGGCGGGAAAAAAGTTTTCTCTGGCGTGCCGCCAATTAAAGAGCTGCTCAA
ACGCACCGAAGAACATATTAAAGGCATGGTAGTGCCTGGCACGTTGTTTGAAGAGCTGGGCTTTAACT
ACATCGGCCCGGTGGACGGTCACGATGTGCTGGGGCTTATCACCACGCTAAAGAACATGCGCGACCTG
AAAGGCCCGCAGTTCCTGCATATCATGACCAAAAAAGGTCGTGGTTATGAACCGGCAGAAAAAGACCC
GATCACTTTCCACGCCGTGCCTAAATTTGATCCCTCCAGCGGTTGTTTGCCGAAAAGTAGCGGCGGTT
TGCCGAGCTATTCAAAAATCTTTGGCGACTGGTTGTGCGAAACGGCAGCGAAAGACAACAAGCTGATG
GCGATTACTCCGGCGATGCGTGAAGGTTCCGGCATGGTCGAGTTTTCACGTAAATTCCCGGATCGCTA
CTTCGACGTGGCAATTGCCGAGCAACACGCGGTGACCTTTGCTGCGGGTCTGGCGATTGGTGGGTACA
AACCCATTGTCGCGATTTACTCCACTTTCCTGCAACGCGCCTATGATCAGGTGCTGCATGACGTGGCG
ATTCAAAAGCTTCCGGTCCTGTTCGCCATCGACCGCGCGGGCATTGTTGGTGCTGACGGTCAAACCCA
TCAGGGTGCTTTTGATCTCTCTTACCTGCGCTGCATACCGGAAATGGTCATTATGACCCCGAGCGATG
AAAACGAATGTCGCCAGATGCTCTATACCGGCTATCACTATAACGATGGCCCGTCAGCGGTGCGCTAC
CCGCGTGGCAACGCGGTCGGCGTGGAACTGACGCCGCTGGAAAAACTACCAATTGGCAAAGGCATTGT
GAAGCGTCGTGGCGAGAAACTGGCGATCCTTAACTTTGGTACGCTGATGCCAGAAGCGGCGAAAGTCG
CCGAATCGCTGAACGCCACGCTGGTCGATATGCGTTTTGTGAAACCGCTTGATGAAGCGTTAATTCTG
GAAATGGCCGCCAGCCATGAAGCGCTGGTCACCGTAGAAGAAAACGCCATTATGGGCGGCGCAGGCAG
CGGCGTGAACGAAGTGCTGATGGCCCATCGTAAACCAGTACCCGTGCTGAACATTGGCCTGCCGGACT
TCTTTATTCCGCAAGGAACTCAGGAAGAAATGCGCGCCGAACTCGGCCTCGATGCCGCTGGTATGGAA
GCCAAAATCAAGGCCTGGCTGGCATAA
```

Figure 9

**Truncated *E.coli* DXS (SEQ ID N°14)**

```
ATGAGTTTTGATATTGCCAAATACCCGACCCTGGCACTGGTCGACTCCACCCAGGAGTTACGACTGTT
GCCGAAAGAGAGTTTACCGAAACTCTGCGACGAACTGCGCCGCTATTTACTCGACAGCGTGAGCCGTT
CCAGCGGGCACTTCGCCTCCGGGCTGGGCACGGTCGAACTGACCGTGGCGCTGCACTATGTCTACAAC
ACCCCGTTTGACCAATTGATTTGGGATGTGGGGCATCAGGCTTATCCGCATAAAATTTTGACCGGACG
CCGCGACAAAATCGGCACCATCCGTCAGAAAGGCGGTCTGCACCCGTTCCCGTGGCGCGGCGAAAGCG
AATATGACGTATTAAGCGTCGGGCATTCATCAACCTCCATCAGTGCCGGAATTGGTATTGCGGTTGCT
GCCGAAAAAGAAGGCAAAAATCGCCGCACCGTCTGTGTCATTGGCGATGGCGCGATTACCGCAGGCAT
GGCGTTTGAAGCGATGAATCACGCGGGCGATATCCGTCCTGATATGCTGGTGATTCTCAACGACAATG
AAATGTCGATTTCCGAAAATGTCGGCGCGCTCAACAACCATCTGGCACAGCTGCTTTCCGGTAAGCTT
TACTCTTCACTGCGCGAAGGCGGGAACAAAGTTTTCTCTG.ATTTTAATTCAATACCCGACCCTGGCA
CTGGTCGACTCCCCCAGGAGTTACGACTGTTGCCGAAAGAGAGTTTACCGAAACTCTGCGACGAACTG
CGCCGCTATTTACTCGACAGCGTGAGCCGTTCCAGCGGGCACTTCGCCTCCGGGCTGGGCACGGTCGA
ACTGACCGTGGCGCTGCACTATGTCTACAACACCCCGTTTGACCAATTGATTTGGGATGTGGGGCATC
AGGCTTATCCGCATAAAATTTTGACCGGACGCCGCGACAAAATCGGCACCATCCGTCAGAAAGGCGGT
CTGCACCCGTTCCCGTGGCGCGGCGAAAGCGAATATGACGTATTAAGCGTCGGGCATTCATCAACCTC
CATCAGTGCCGGAATTGGTATTGCGGTTGCTGCCGAAAAAGAAGGCAAAAATCGCCGCACCGTCTGTG
TCATTGGCGATGGCGCGATTACCGCAGGCATGGCGTTTGAAGCGATGAATCACGCGGGCGATATCCGT
CCTGATATGCTGGTGATTCTCAACGACAATGAAATGTCGATTTCCGAAAATGTCGGCGCGCTCAACAA
CCATCTGGCACAGCTGCTTTCCGGTAAGCTTTACTCTTCACTGCGCGAAGGCGGGAACAAAGTTTTCT
CTGCGTGCCGCCAATTAAAGAGCTGCTCAAACGCACCGAAGAACATATTAAAGGCATGGTAGTGCCTG
GCACGTTGTTTGAAGAGCTGGGCTTTAACTACATCGGCCCGGTGGACGGTCACGATGTGCTGGGGCTT
ATCACCACGCTAAAGAACATGCGCGACCTGAAAGGCCCGCAGTTCCTGCATATCATGACCAAAAAAGG
TCGTGGTTATGAACCGGCAGAAAAAGACCCGATCACTTTCCACGCCGTGCCTAAATTTGATCCCTCCA
GCGGTTGTTTGCCGAAAAGTAGCGGCGGTTTGCCGAGCTATTCAAAAATCTTTGGCGACTGGTTGTGC
GAAACGGCAGCGAAAGACAACAAGCTGATGGCGATTACTCCGGCGATGCGTGAAGGTTCCGGCATGGT
CGAGTTTTCACGTAAATTCCCGGATCGCTACTTCGACGTGGCAATTGCCGAGCAACACGCGGTGACCT
TGCTGCGGGTCTGGCGATTGGTGGGTACAAACCCATTGTCGCGATTTACTCCACTTTCCTGCAACGC
GCCTATGATCAGGTGCTGCATGACGTGGCGATTCAAAAGCTTCCGGTCCTGTTCGCCATCGACCGCGC
GGGCATTGTTGGTGCTGACGGTCAAACCCATCAGGGTGCTTTTGATCTCTCTTACCTGCGCTGCATAC
CGGAAATGGTCATTATGACCCCGAGCGATGAAAACGAATGTCGCCAGATGCTCTATACCGGCTATCAC
TATAACGATGGCCCGTCAGCGGTGCGCTACCCGCGTGGCAACGCGGTCGGCGTGGAACTGACGCCGCT
GGAAAAACTACCAATTGGCAAAGGCATTGTGAAGCGTCGTGGCGAGAAACTGGCGATCCTTAACTTTG
GTACGCTGATGCCAGAAGCGGCGAAAGTCGCCGAATCGCTGAACGCCACGCTGGTCGATATGCGTTTT
GTGAAACCGCTTGATGAAGCGTTAATTCTGGAAATGGCCGCCAGCCATGAAGCGCTGGTCACCGTAGA
AGAAAACGCCATTATGGGCGGCGCAGGCAGCGGCGTGAACGAAGTGCTGATGGCCCATCGTAAACCAG
TACCCGTGCTGAACATTGGCCTGCCGGACTTCTTTATTCCGCAAGGAACTCAGGAAGAAATGCGCGCC
GAACTCGGCCTCGATGCCGCTGGTATGGAAGCCAAAATCAAGGCCTGGCTGGCATAA
```

Figure 9 (continuation)

E.coli DXS-K213N (SEQ ID N°15)

```
ATGAGTTTTGATATTGCCAAATACCCGACCCTGGCACTGGTCGACTCCACCCAGGAGTTACGACTGTT
GCCGAAAGAGAGTTTACCGAAACTCTGCGACGAACTGCGCCGCTATTTACTCGACAGCGTGAGCCGTT
CCAGCGGGCACTTCGCCTCCGGGCTGGGCACGGTCGAACTGACCGTGGCGCTGCACTATGTCTACAAC
ACCCCGTTTGACCAATTGATTTGGGATGTGGGGCATCAGGCTTATCCGCATAAAATTTTGACCGGACG
CCGCGACAAAATCGGCACCATCCGTCAGAAAGGCGGTCTGCACCCGTTCCCGTGGCGCGGCGAAAGCG
AATATGACGTATTAAGCGTCGGGCATTCATCAACCTCCATCAGTGCCGGAATTGGTATTGCGGTTGCT
GCCGAAAAAGAAGGCAAAAATCGCCGCACCGTCTGTGTCATTGGCGATGGCGCGATTACCGCAGGCAT
GGCGTTTGAAGCGATGAATCACGCGGGCGATATCCGTCCTGATATGCTGGTGATTCTCAACGACAATG
AAATGTCGATTTCCGAAAATGTCGGCGCGCTCAACAACCATCTGGCACAGCTGCTTTCCGGTAAGCTT
TACTCTTCACTGCGCGAAGGCGGGAACAAAGTTTTCTCTGGCGTGCCGCCAATTAAAGAGCTGCTCAA
ACGCACCGAAGAACATATTAAAGGCATGGTAGTGCCTGGCACGTTGTTTGAAGAGCTGGGCTTTAACT
ACATCGGCCCGGTGGACGGTCACGATGTGCTGGGGCTTATCACCACGCTAAAGAACATGCGCGACCTG
AAAGGCCCGCAGTTCCTGCATATCATGACCAAAAAAGGTCGTGGTTATGAACCGGCAGAAAAAGACCC
GATCACTTTCCACGCCGTGCCTAAATTTGATCCCTCCAGCGGTTGTTTGCCGAAAAGTAGCGGCGGTT
TGCCGAGCTATTCAAAAATCTTTGGCGACTGGTTGTGCGAAACGGCAGCGAAAGACAACAAGCTGATG
GCGATTACTCCGGCGATGCGTGAAGGTTCCGGCATGGTCGAGTTTTCACGTAAATTCCCGGATCGCTA
CTTCGACGTGGCAATTGCCGAGCAACACGCGGTGACCTTTGCTGCGGGTCTGGCGATTGGTGGGTACA
AACCCATTGTCGCGATTTACTCCACTTTCCTGCAACGCGCCTATGATCAGGTGCTGCATGACGTGGCG
ATTCAAAAGCTTCCGGTCCTGTTCGCCATCGACCGCGCGGGCATTGTTGGTGCTGACGGTCAAACCCA
TCAGGGTGCTTTTGATCTCTCTTACCTGCGCTGCATACCGGAAATGGTCATTATGACCCCGAGCGATG
AAAACGAATGTCGCCAGATGCTCTATACCGGCTATCACTATAACGATGGCCCGTCAGCGGTGCGCTAC
CCGCGTGGCAACGCGGTCGGCGTGGAACTGACGCCGCTGGAAAAAACTACCAATTGGCAAAGGCATTGT
GAAGCGTCGTGGCGAGAAACTGGCGATCCTTAACTTTGGTACGCTGATGCCAGAAGCGGCGAAAGTCG
CCGAATCGCTGAACGCCACGCTGGTCGATATGCGTTTTGTGAAACCGCTTGATGAAGCGTTAATTCTG
GAAATGGCCGCCAGCCATGAAGCGCTGGTCACCGTAGAAGAAAACGCCATTATGGGCGGCGCAGGCAG
CGGCGTGAACGAAGTGCTGATGGCCCATCGTAAACCAGTACCCGTGCTGAACATTGGCCTGCCGGACT
TCTTTATTCCGCAAGGAACTCAGGAAGAAATGCGCGCCGAACTCGGCCTCGATGCCGCTGGTATGGAA
GCCAAAATCAAGGCCTGGCTGGCATAA
```

Figure 9 (continuation)

*E.coli* DXS-K234C (SEQ ID N°16)

```
ATGAGTTTTGATATTGCCAAATACCCGACCCTGGCACTGGTCGACTCCACCCAGGAGTTACGACTGTT
GCCGAAAGAGAGTTTACCGAAACTCTGCGACGAACTGCGCCGCTATTTACTCGACAGCGTGAGCCGTT
CCAGCGGGCACTTCGCCTCCGGGCTGGGCACGGTCGAACTGACCGTGGCGCTGCACTATGTCTACAAC
ACCCCGTTTGACCAATTGATTTGGGATGTGGGGCATCAGGCTTATCCGCATAAAATTTTGACCGGACG
CCGCGACAAAATCGGCACCATCCGTCAGAAAGGCGGTCTGCACCCGTTCCCGTGGCGCGGCGAAAGCG
AATATGACGTATTAAGCGTCGGGCATTCATCAACCTCCATCAGTGCCGGAATTGGTATTGCGGTTGCT
GCCGAAAAAGAAGGCAAAAATCGCCGCACCGTCTGTGTCATTGGCGATGGCGCGATTACCGCAGGCAT
GGCGTTTGAAGCGATGAATCACGCGGGCGATATCCGTCCTGATATGCTGGTGATTCTCAACGACAATG
AAATGTCGATTTCCGAAAATGTCGGCGCGCTCAACAACCATCTGGCACAGCTGCTTTCCGGTAAGCTT
TACTCTTCACTGCGCGAAGGCGGGAAAAAAGTTTTCTCTGGCGTGCCGCCAATTAAAGAGCTGCTCAA
ACGCACCGAAGAACATATTTGCGGCATGGTAGTGCCTGGCACGTTGTTTGAAGAGCTGGGCTTTAACT
ACATCGGCCCGGTGGACGGTCACGATGTGCTGGGGCTTATCACCACGCTAAAGAACATGCGCGACCTG
AAAGGCCCGCAGTTCCTGCATATCATGACCAAAAAAGGTCGTGGTTATGAACCGGCAGAAAAAGACCC
GATCACTTTCCACGCCGTGCCTAAATTTGATCCCTCCAGCGGTTGTTTGCCGAAAAGTAGCGGCGGTT
TGCCGAGCTATTCAAAAATCTTTGGCGACTGGTTGTGCGAAACGGCAGCGAAAGACAACAAGCTGATG
GCGATTACTCCGGCGATGCGTGAAGGTTCCGGCATGGTCGAGTTTTCACGTAAATTCCCGGATCGCTA
CTTCGACGTGGCAATTGCCGAGCAACACGCGGTGACCTTTGCTGCGGGTCTGGCGATTGGTGGGTACA
AACCCATTGTCGCGATTTACTCCACTTTCCTGCAACGCGCCTATGATCAGGTGCTGCATGACGTGGCG
ATTCAAAAGCTTCCGGTCCTGTTCGCCATCGACCGCGCGGGCATTGTTGGTGCTGACGGTCAAACCCA
TCAGGGTGCTTTTGATCTCTCTTACCTGCGCTGCATACCGGAAATGGTCATTATGACCCCGAGCGATG
AAAACGAATGTCGCCAGATGCTCTATACCGGCTATCACTATAACGATGGCCCGTCAGCGGTGCGCTAC
CCGCGTGGCAACGCGGTCGGCGTGGAACTGACGCCGCTGGAAAAACTACCAATTGGCAAAGGCATTGT
GAAGCGTCGTGGCGAGAAACTGGCGATCCTTAACTTTGGTACGCTGATGCCAGAAGCGGCGAAAGTCG
CCGAATCGCTGAACGCCACGCTGGTCGATATGCGTTTTGTGAAACCGCTTGATGAAGCGTTAATTCTG
GAAATGGCCGCCAGCCATGAAGCGCTGGTCACCGTAGAAGAAACGCCATTATGGGCGGCGCAGGCAG
CGGCGTGAACGAAGTGCTGATGGCCCATCGTAAACCAGTACCCGTGCTGAACATTGGCCTGCCGGACT
TCTTTATTCCGCAAGGAACTCAGGAAGAAATGCGCGCCGAACTCGGCCTCGATGCCGCTGGTATGGAA
GCCAAAATCAAGGCCTGGCTGGCATAA
```

Figure 9 (continuation)

```
MO_DXS1    MALCTLSFPAHFSQAAASNPQRLTPQCSHLFLGVDLQCQSQQRSKARKRPNGVCASLSDR
MO_DXS2    MALCTLSFPAHFSQAAASNPQRLTPQCSHLFLGVDLQCQSQQRSKARKRPNGVCASLSDR
GW_DXS2    MALCTLSFPAHFSQAAASNPQRLTPQCSHLFLGVDLQCQSQQRSKARKRPNGVCASLSDR
Ecoli_DXS  ------------------------------------------------------------

MO_DXS1    EEYHSQRPPTPLLDTINYPIHMKNLSVKELKQLADELRSDVVFNVSKTGGHLGSSLGVVE
MO_DXS2    EEYHSQRPPTPLLDTINYPIHMKNLSVKELKQLADELRSDVVFNVSKTGGHLGSSLGVVE
GW_DXS2    EEYHSQRPPTPLLDTINYPIHMKNLSVKELKQLADELRSDVVFNVSKTGGHLGSSLGVVE
Ecoli_DXS  --MSFDIAKYPTLALVDSTQELRLLPKESLPKLCDELRRYLLDSVSRSSGHFASGLGTVE MO_DXS1    LTVALHYVFNAPQDRILWDVGHQSYPHKILTGRRDQMHTMRQTDGLAGFTKRSESEYDCF
MO_DXS2    LTVALHYVFNAPQDRILWDVGHQSYPHKILTGRRDQMHTMRQTDGLAGFTKRSESEYDCF
GW_DXS2    LTVALHYVFNAPQDRILWDVGHQSYPHKILTGRRDQMHTMRQTDGLAGFTKRSESEYDCF
Ecoli_DXS  LTVALHYVYNTPFDQLIWDVGHQAYPHKILTGRRDKIGTIRQKGGLHPFPWRGESEYDVL MO_DXS1    GTGHSSTTISAGLGMAVGRDLKGKNNNVIAVIGDGAMTAGQAYEAMNNAGYLDSDMIVIL
MO_DXS2    GTGHSSTTISAGLGMAVGRDLKGKNNNVIAVIGDGAMTAGQAYEAMNNAGYLDSDMIVIL
GW_DXS2    GTGHSSTTISAGLGMAVGRDLKGKNNNVIAVIGDGAMTAGQAYEAMNNAGYLDSDMIVIL
Ecoli_DXS  SVGHSSTSISAGIGIAVAAEKEGKNRRTVCVIGDGAITAGMAFEAMNHAGDIRPDMLVIL MO_DXS1    NDNKQVSLPTATLDGPIPPVGALSSALSRLQSNRPLRELREVAKGVTKQIGGPMHELAAK
MO_DXS2    NDNKQVSLPTATLDGPIPPVGALSSALSRLQSNRPLRELREVANGVTKQIGGPMHELAAK
GW_DXS2    NDNKQVSLPTATLDGPIPPVGALSSALSRLQSNRPLRELREVAKGVTKQIGGPMHELAAK
Ecoli_DXS  NDN-EMSIS--------ENVGALNNHLAQLLSGKLYSSLREGGKKVFSGVP-PIKELLKR MO_DXS1    VDEYARGMISGSGSTLFEELGLYYIGPVDGHNIDDLVAILKEVKSTKTTGPVLIHVVTEK
MO_DXS2    VDEYARGMISGSGSTLFEELGLYYIGPVDGHNIDDLVAILKEVKSTKTTGPVLIHVVTEK
GW_DXS2    VDEYACGMISGSGSTLFEELGLYYIGPVDGHNIDDLVAILKEVKSTKTTGPVLIHVVTEK
Ecoli_DXS  TEEHIKGMVV--PGTLFEELGFNYIGPVDGHDVLGLITTLKNMRDLK--GPQFLHIMTKK MO_DXS1    GRGYPYAEKAADKYHGVTKFDPATGKQFKSSAPTQSYTTYFAEALIAEAEVDKDIVAIHA
MO_DXS2    GRGYPYAEKAADKYHGVTKFDPATGKQFKSSAPTQSYTTYFAEALIAEAEVDKDIVAIHA
GW_DXS2    GRGYPYAEKAADKYHGVTKFDPATGKQFKSSAPTQSYTTYFAEALIAEAEVDKDIVAIHA
Ecoli_DXS  GRGYEPAEKDPITFHAVPKFDPSSGCLPKSSGGLPSYSKIFGDWLCETAAKDNKLMAITP MO_DXS1    AMGGGTGLNLFHRRFPTRCFDVGIAEQHAVTFAAGLACEGIKPFCAIYSSFMQRAYDQVV
MO_DXS2    AMGGGTGLNLFHRRFPTRCFDVGIAEQHAVTFAAGLACEGIKPFCAIYSSFMQRAYDQVV
GW_DXS2    AMGGGTGLNLFHRRFPTRCFDVGIAEQHAVTFAAGLACEGIKPFCAIYSSFMQRAYDQVV
Ecoli_DXS  AMREGSGMVEFSRKFPDRYFDVAIAEQHAVTFAAGLAIGGYKPIVAIYSTFLQRAYDQVL MO_DXS1    HDVDLQKLPVKFAMDRAGLVGADGPTHCGAFDVAFMACLPNMVVMAPADEAELFHMVATA
MO_DXS2    HDVDLQKLPVKFAMDRAGLVGADGPTHCGAFDVAFMACLPNMVVMAPADEAELFHMVATA
GW_DXS2    HDVDLQKLPVKFAMDRAGLVGADGPTHCGAFDVAFMACLPNMVVMAPADEAELFHMVATA
Ecoli_DXS  HDVAIQKLPVLFAIDRAGIVGADGQTHQGAFDLSYLRCIPEMVIMTPSDENECRQMLYTG MO_DXS1    AAIDDRPSCFRYPRGNGVGVELPPGNKGIPIEVGRGRILIEGERVALLGYTAVQSCLVA
MO_DXS2    AAIDDRPSCFRYPRGNGVGIELPPGNKGIPIEVGRGRILIEGERVALLGYTAVQSCLVA
GW_DXS2    AAIDDRPSCFRYPRGNGVGVELPPGNKGIPIEVGRGRILIEGERVALLGYTAVQSCLVA
Ecoli_DXS  YHYNDGPSAVRYPRGNAVGVELTPLEK---LPIGKGIVKRRGEKLAILNFGTLMPE---A MO_DXS1    SSLLEQHGLRITVADARFCKPLDHALIRSLAKSHEVLITVEEGSI-GGFGSHVAQFLALN
MO_DXS2    SSLLEQHGLRITVADARFCKPLDHALIRSLAKSHEVLITVEEGSI-GGFGSHVAQFLALN
GW_DXS2    SSLLEQHGLRITVADARFCKPLDHALIRSLAKSHEVLITVEEGSI-GGFGSHVAQFLALN
Ecoli_DXS  AKVAES--LNATLVDMRFVKPLDEALILEMAASHEALVTVEENAIMGGAGSGVNEVLMAH MO_DXS1    GLLDGTTKWSPMVLPDRYIDHGAPADQLAMAGLTPSHIAATVFNILGQTREALEIML*
MO_DXS2    GLLDGTTKWSPMVLPDRYIDHGAPADQLAMAGLTPSHIAATVFNILGQTREALEIML*
GW_DXS2    GLLDGTTKWSPMVLPDRYIDHGAPADQLAMAGLTPSHIAATVFNILGQTREALEIML*
Ecoli_DXS  ---RKPVPVLNIGLPDFFIPQGTQEEMRAELGLDAAGMEAKIKAWLA*----------
```

Figure 10

*E.coli*_DXS (SEQ ID N°17)

MSFDIAKYPTLALVDSTQELRLLPKESLPKLCDELRRYLLDSVSRSSGHFASGLGTVELTVALHYVYN
TPFDQLIWDVGHQAYPHKILTGRRDKIGTIRQKGGLHPFPWRGESEYDVLSVGHSSTSISAGIGIAVA
AEKEGKNRRTVCVIGDGAITAGMAFEAMNHAGDIRPDMLVILNDNEMSISENVGALNNHLAQLLSGKL
YSSLREGGKKVFSGVPPIKELLKRTEEHIKGMVVPGTLFEELGFNYIGPVDGHDVLGLITTLKNMRDL
KGPQFLHIMTKKGRGYEPAEKDPITFHAVPKFDPSSGCLPKSSGGLPSYSKIFGDWLCETAAKDNKLM
AITPAMREGSGMVEFSRKFPDRYFDVAIAEQHAVTFAAGLAIGGYKPIVAIYSTFLQRAYDQVLHDVA
IQKLPVLFAIDRAGIVGADGQTHQGAFDLSYLRCIPEMVIMTPSDENECRQMLYTGYHYNDGPSAVRY
PRGNAVGVELTPLEKLPIGKGIVKRRGEKLAILNFGTLMPEAAKVAESLNATLVDMRFVKPLDEALIL
EMAASHEALVTVEENAIMGGAGSGVNEVLMAHRKPVPVLNIGLPDFFIPQGTQEEMRAELGLDAAGME
AKIKAWLA*

*E.coli*_DXS-K213N (SEQ ID N°19)

MSFDIAKYPTLALVDSTQELRLLPKESLPKLCDELRRYLLDSVSRSSGHFASGLGTVELTVALHYVYN
TPFDQLIWDVGHQAYPHKILTGRRDKIGTIRQKGGLHPFPWRGESEYDVLSVGHSSTSISAGIGIAVA
AEKEGKNRRTVCVIGDGAITAGMAFEAMNHAGDIRPDMLVILNDNEMSISENVGALNNHLAQLLSGKL
YSSLREGGNKVFSGVPPIKELLKRTEEHIKGMVVPGTLFEELGFNYIGPVDGHDVLGLITTLKNMRDL
KGPQFLHIMTKKGRGYEPAEKDPITFHAVPKFDPSSGCLPKSSGGLPSYSKIFGDWLCETAAKDNKLM
AITPAMREGSGMVEFSRKFPDRYFDVAIAEQHAVTFAAGLAIGGYKPIVAIYSTFLQRAYDQVLHDVA
IQKLPVLFAIDRAGIVGADGQTHQGAFDLSYLRCIPEMVIMTPSDENECRQMLYTGYHYNDGPSAVRY
PRGNAVGVELTPLEKLPIGKGIVKRRGEKLAILNFGTLMPEAAKVAESLNATLVDMRFVKPLDEALIL
EMAASHEALVTVEENAIMGGAGSGVNEVLMAHRKPVPVLNIGLPDFFIPQGTQEEMRAELGLDAAGME
AKIKAWLA*

*E.coli*_DXS-K234C (SEQ ID N°20)

MSFDIAKYPTLALVDSTQELRLLPKESLPKLCDELRRYLLDSVSRSSGHFASGLGTVELTVALHYVYN
TPFDQLIWDVGHQAYPHKILTGRRDKIGTIRQKGGLHPFPWRGESEYDVLSVGHSSTSISAGIGIAVA
AEKEGKNRRTVCVIGDGAITAGMAFEAMNHAGDIRPDMLVILNDNEMSISENVGALNNHLAQLLSGKL
YSSLREGGKKVFSGVPPIKELLKRTEEHICGMVVPGTLFEELGFNYIGPVDGHDVLGLITTLKNMRDL
KGPQFLHIMTKKGRGYEPAEKDPITFHAVPKFDPSSGCLPKSSGGLPSYSKIFGDWLCETAAKDNKLM
AITPAMREGSGMVEFSRKFPDRYFDVAIAEQHAVTFAAGLAIGGYKPIVAIYSTFLQRAYDQVLHDVA
IQKLPVLFAIDRAGIVGADGQTHQGAFDLSYLRCIPEMVIMTPSDENECRQMLYTGYHYNDGPSAVRY
PRGNAVGVELTPLEKLPIGKGIVKRRGEKLAILNFGTLMPEAAKVAESLNATLVDMRFVKPLDEALIL
EMAASHEALVTVEENAIMGGAGSGVNEVLMAHRKPVPVLNIGLPDFFIPQGTQEEMRAELGLDAAGME
AKIKAWLA*

Truncated *E.coli*_DXS (SEQ ID N°18)

MSFDIAKYPTLALVDSTQELRLLPKESLPKLCDELRRYLLDSVSRSSGHFASGLGTVELTVALHYVYN
TPFDQLIWDVGHQAYPHKILTGRRDKIGTIRQKGGLHPFPWRGESEYDVLSVGHSSTSISAGIGIAVA
AEKEGKNRRTVCVIGDGAITAGMAFEAMNHAGDIRPDMLVILNDNEMSISENVGALNNHLAQLLSGKL
YSSLREGGNKVFSGF*

Figure 13

Consensus of bacterial DXS sequence (SEQ ID N°22)

```
M.....KYPTLA.......LR.LP...LP.L.BELR..LL..VS.SSGHFASGLG.VELTVA.HYVY.TPFD...
WDVGHQAYPHKILTGRRD.I..IRQK.G.HPFPWR.ES..D.L.VGHSSTSISAGJG.A.AA..E...R...CVI
GDGAITAGMAFEAM.HAGDI..D.LV.LNDN.MSISENVG.LNN.LAQJLSGK.Y..LRE.GK......PPIK.L
...TEEHJKGM.VP.TLFEELGFNYIGPVDGHDV..L..TL.NMR.LK.PQ.LH.MTKKG.GY.PAE.DPI..HA
VPKFD...G.LPK......P..S..FG.WL.E.AA.D..LMA.TPAMREGSGM..FS...P..YFDVAIAEQH..
TFAAGLA.G.Y.P.VAIYSTFLQRAYDQ.JHD.AIQ.LPV.F..DR.GJVGADGQTHQG.FDL...RC.P.M..M
.PSDENECR.ML.TG.H...GP..VRYPRG........PL...PJGKG...R.G...AJL.FGTL...A...A..
.NAT.VDMRFVKPLD..L....A..H....T.EE.A..GGAGSGVNE..M......VLNJGL.D.F...G.Q.E
......L...G........A
```

Figure 14

**Consensus of bacterial DXS sequences including *Deinococcus radiodurans*
(SEQ ID N°21)**

```
M........P.L.........L..L....LP.L..ELR..J....S....H.AS.LG.V.J..A.HYV...P.D...
.DVGHQAY.HKILTGRRD....I....G...F....ES..D.J.VGH.STSJ...JG.A.A...Z........VI
GDG.JT.GMA..A....GD.....L..LNDN.MSISENVG..N.....J...K........GK........PJ..
.............P.....F....G..Y.GPVDGHBV..L...L....L..P..LH..T.KG.G...AE.DPI.
.H...KFD...G.........S..FG....E.A..D......TPAMREGSG...FS...P..Y.DV.IAE.
...T.AAG.A.....P.VAIYSTFLQRAYDQ.JHD.AIZ.L.V.F..DR.GJVGADG.TH.G.FDL...R..P..
....P.D..E.R.ML........GP...RYPRG..............G.......G....JL..G.....A...
A........VB.RFVKPLD...............T.E.....GG.G..V.E..........V..JGJ.D.F....
...........J................
```

Figure 15

| Organism | Sequence |
|---|---|
| Escherichia coli | SVGHSSTSISAGIGIAVAAEKEGKNRRTVCVIGDGAITAGMAFEAMNHAGDIRPDMLVIL |
| Shigella dysenteriae | SVGHSSTSISAGIGIAVAAEKEGKNRRTVCVIGDGAITAGMAFEAMNHAGDIRPDMLVVL |
| Citrobacter sp. | SVGHSSTSISAGIGIAVAAEKEGKERRTVCVIGDGAITAGMAFEAMNHAGDIRPDMLVIL |
| Salmonella enterica | SVGHSSTSISAGIGIAVAAREGKDRRTVCVIGDGAITAGMAFEAMNHAGDIRPDMLVIL |
| Enterobacter sp. | SVGHSSTSISAGIGIAVAAEKENKQRRTVCVIGDGAITAGMAFEAMNHAGDIKPDMLVIL |
| Cronobacter sakazakii | SVGHSSTSISAGIGIAVAAAREEKNRPTVCVIGDGAITAGMAFEAMNHAGDIRPDMLVIL |
| Klebsiella pneumoniae | SVGHSSTSISAGIGVAIAAAEDKQRRAVCVIGDGAITAGMAFEAMNHAGDIKPDLLVVL |
| Yersinia pseudotuberculosis | SVGHSSTSISAGLGMAVAAEREGKGRRTVCVIGDGAITAGMAFEAMSHAGDIHSDMLVIL |
| Yersinia pestis | SVGHSSTSISAGLGMAVAAEREGKGRRTVCVIGDGAITAGMAFEAMSHAGDIHSDMLVIL |
| Erwinia sp. | NVGHSSTSISAGLGMAVAADKEAQGRRTACVIGDGAITAGMAFEAMNHAGDIKADLLVVL |
| Pantoea ananatis | SVGHSSTSISAGLGMAAAAEREGKGRRTACVIGDGAITAGMAFEAMNHAGDIKSDMLVIL |
| Dickeya dadantii | SVGHSSTSISAGLGMAVAAEREGLGRRTVCVIGDGAITAGMAFEAMNHAGDIKPDMLVVL |
| Pectobacterium atrosepticum | SVGHSSTSISAGLGMAVAAEREGKGRKTVCVIGDGAITAGMAFEAMNHAGDIKSDLLVIL |
| Xenorhabdus nematophila | CVGHSSTSISAGLGMAIAAEREGKGRKTVCVIGDGAITAGMAFEAMNHAGDIDPDMLVIL |
| Rahnella sp. | SVGHSSTSISAGLGMAVAAEREGKGRRTVCVIGDGAITAGMAFEAMNHAGDIKPDMLVIL |
| Serratia odorifera | SVGHSSTSISAGLGMAVAAEREGKNRRTVCVIGDGAITAGMAFEAMNHAGDINPDMLVVL |
| Deinococcus radiodurans | TVGHASTSLANALGMALARDAQGKDFHVAAVIGDGSLTGGMALAALNTIGDMGRKMLIVL |
| Escherichia coli | NDNEMSISENVGALNNHLAQLLSGKLYSSLREGGKKVFSGVP-PIKELLKRTEEHIKGMV |
| Shigella dysenteriae | NDNEMSISENVGALNNHLAQLLSGKLYSSLREGGKKVFSGVP-PIKELLKRTEEHIKGMV |
| Citrobacter sp. | NDNEMSISENVGALNNHLAQLLSGKLYSSLREGGKKVFSGVP-PIKELLLKRTEEHIKGMV |
| Salmonella enterica | NDNEMSISENVGALNNHLAQLLSGKLYSSLREGGKKVFSGVP-PIKELLKRTEEHIKGMV |
| Enterobacter sp. | NDNEMSISENVGALNNHLAQLLSGKLYSTLREGGKRVFSGVP-PIKELLKRTEEHIKGMV |
| Cronobacter sakazakii | NDNEMSISENVGALNNHLAQLLSGKLYSTLREGGKRVFSNVP-PIKELLKRTEEHIKGMV |
| Klebsiella pneumoniae | NDNEMSISENVGALNNHLAQLLSGKLYSTLREGGKRVFSGVP-PIKELLKRTEEHIKGMV |
| Yersinia pseudotuberculosis | NDNEMSISENVGGLNNHLAQLLSGKLYASLREGGKKAFSALP-PIKDLLKRTEEHLKGMV |
| Yersinia pestis | NDNGMSISENVGGLNNHLAQLLSGKLYASLREGGKKAFSALP-PIKDLLKRTEEHLKGMV |
| Erwinia sp. | NDNEMSISENVGALNNKRLAQILSGKTYSRLRESGKKVLDGLP-PIKELVKRTEEHLKGMV |
| Pantoea ananatis | NDNEMSISENVGALNNHRLAQILSGKTYARLREGGKRVLTGLP-PIKELVKRTEEHLKGMV |
| Dickeya dadantii | NDNEMSISENVGALNNHLAQLLSGKLYSTLREGGKKVLSGLP-PIKELVKRTEEHLKGMV |
| Pectobacterium atrosepticum | NDNEMSISENVGALNNHLAQLLSGKLYASLREGGKKVLSGLP-PIKELVKRTEEHLKGMV |
| Xenorhabdus nematophila | NDNEMSISENVGALNNHLAQLLSGKLYTTLREGGKKVFSNLP-PIKELVKRTEEHLKGMV |
| Rahnella sp. | NDNEMSISENVGALNNHLAQLLSGKLYSRLREGGKKVLSGLP-PIKELVRRTEEHLKGMM |
| Serratia odorifera | NDNEMSISENVGALNNHLAQLLSGKLYSTLREGGKRVLSGLP-PIKELVKRTEEHLKGMV |
| Deinococcus radiodurans | NDNEMSISENVGAMNKFMRGLQVQKWFQEGEGAGKKAVEAVSKPLADFMSRAKNSTRHFF |

Figure 16 (continuation)

```
Escherichia coli             VPGTL--FEELGFNYIGPVDGHDVLGLITTLKNMRDLKGPQFLHIMTKKGRGYEPAEKDP
Shigella dysenteriae         VPGTL--FEELGFNYIGPVDGHDVLGLITTLKNMRDLKGPQFLHIMTKKGRGYEPAEKDP
Citrobacter sp.              VPGTL--FEELGFNYIGPVDGHDVLGLITTLKNMRDLKGPQFLHIMTKKGRGYEPAEKDP
Salmonella enterica          VPGTL--FEELGFNYIGPVDGHDVMGLISTLKNMRDLKGPQFLHIMTKKGRGYEPAEKDP
Enterobacter sp.             VPGTL--FEELGFNYIGPVDGHDVLGLVTTLKNMRDLKGPQFLHIMTKKGRGYEPAEKDP
Cronobacter sakazakii        VPGTL--FEELGFNYIGPVDGHDVLGLVNTLKNMRDLKGPQFLHIMTKKGRGYEPAEKDP
Klebsiella pneumoniae        VPGTL--FEELGFNYIGPVDGHDVLGLVSTLKNMRDLKGPQFLHIMTKKGRGYEPAEKDP
Yersinia pseudotuberculosis  VPSTL--FEELGFNYIGPVDGHDVHTLTQTLKNMRDLKGPQLLHIMTKKGKGYAPAEKDP
Yersinia pestis              VPSTL--FEELGFNYIGPVDGHDVHTLTQTLKNMRDLKSPQLLHIMTKKGKGYAPAEKDP
Erwinia sp.                  VPGTL--FEELGFNYIGPVDGHDVLALVHTLRNMRALKGPQFLHVMTKKGKGYAPAEKDP
Pantoea ananatis             VPGTL--FEELGFNYIGPVDGHDVLFLVNTLSNMRSLKGPQFLHIMTKKGKGYAPAEQDP
Dickeya dadantii             VPGTL--FEELGFNYIGPVDGHDVQSLVHTLKNMRSLKGPQLLHIMTKKGKGYAPAEQDP
Pectobacterium atrosepticum  VPGTL--FEELGFNYIGPVDGHDVQALSHTLKNMRELKGPQLLHIMTKKGKGYAPAEKDP
Xenorhabdus nematophila      VPGTL--FEELGFNYIGPVDGHDVLALTQTLKNMRDLKGPQLLHIMTKKGKGYAPAEKDP
Rahnella sp.                 VPGTL--FEELGFNYIGPVDGHDVVALAQTLKNMRDLKGPLVATLKNMRDLKGPIVATLKNMRDLKGPIVATLKNMRDLKGPIVATLKNMRDLKGPIVATL
Serratia odorifera           VPGTL--FEELGFNYIGPVDGHDVQGLVATLKNMRDLKGPIVATLKNMRDLKGPIVATLKNMRDLKGPIVATLKNMRDLKGPIVATLKNMRDLKGPIVATL
Deinococcus radiodurans      DPASVNPFAAMGVRYVGPVDGHNVQELVWLLERLVDLDGPTILHIVTTKGKLSYAEADP Escherichia coli             ITFHAVPKFDPSSGCLPKSSGG-LPSYSKIFGDWLCETAAKDNKLMAITPAMREGSGMVE
Shigella dysenteriae         ITFHAVPKFDPSSGCLPKSSGG-LPSYSKIFGDWLCETAAKDNKLMAITPAMREGSGMVE
Citrobacter sp.              ITFHAVPKFDPSSGCLPKSSGG-LPSYSKIFGDWLCETAAKDNKLMAITPAMREGSGMVE
Salmonella enterica          ITFHAVPKFDPSSGCLPKSSGG-LPGYSKIFGDWLCETAAKDSKLMAITPAMREGSGMVE
Enterobacter sp.             ITFHAVPKFDPTSGCLPKSSGG-MPSYSKIFGDWLCETAAKDNKLMAVTPAMREGSGMVE
Cronobacter sakazakii        ITFHAVPKFDPESGTLPKSSGG-QPSYSKIFGDWLCETAAKDDKLMAITPAMREGSGMVE
Klebsiella pneumoniae        ITFHAVPKFDHTSGVLPKSSGG-LPSYSKIFGDWLCETAAKDNKLMAITPAMREGSGMVE
Yersinia pseudotuberculosis  IGWHAVPKFDPASGTLPKSQSS-LPTYSKIFGEWLCETAAKDSKLMAVTPAMREGSGMVR
Yersinia pestis              IGWHAVPKFDPASGTLPKSQSS-LPTYSKIFGEWLCETAAKDSKLMAVTPAMREGSGMVR
Erwinia sp.                  ISWHAVPKFDPASGLLPKSAEG-LPSYSKIFGQWLSETAAVDDKLMAVTPAMREGSGMVS
Pantoea ananatis             ITWHAVPKFDVASGELPKSAEG-LPSYSKIFGNWLCEMAAHDTKLMAITPAMREGSGMVG
Dickeya dadantii             ISWHAVPKFDPASGTLPKNKEA-LPTYSAVFGEWLKETAAADSRLMAITPAMREGSGMVS
Pectobacterium atrosepticum  ISWHAVPKFDPASGTLPKSREGAQPTYSKIFGQWLQETAAKDSKLMAITPAMREGSGMLQ
Xenorhabdus nematophila      ISWHAVPKFDPTTGSLPKSADT-RPTFSKIFGDWLCEEAAQDKKLMAITPAMREGSGMVR
Rahnella sp.                 ISFHAVPKFDPASGTLPKSKEG-LPTYSKIFGDWLCETAAKDSKLMAVTPAMREGSGMVR
Serratia odorifera           ISFHAVPKFDPASGTLPKSAGG-QPSYSKIFGDWLCETAAKDSSLMAITPAMREGSGMVQ
Deinococcus radiodurans      IYWHGPAKFDPATGEYVPSSAY---SWSAAFGEAVTEWAKTDPRTFVVTPAMREGSGLVE
```

Figure 16 (continuation)

| Organism | Sequence |
|---|---|
| Escherichia coli | FSRKFPDRYFDVAIAEQHAVTFAAGLAIGGYKPIVAIYSTFLQRAYDQVLHDVAIQKLPV |
| Shigella dysenteriae | FSRKFPDRYFDVAIAEQHAVTFAAGLAIGGYKPIVAIYSTFLQRAYDQVLHDVAIQKLPV |
| Citrobacter sp. | FSRKFPDRYFDVAIAEQHAVTFAAGLAIGGYKPVVAIYSTFLQRAYDQVLHDVAIQKLPV |
| Salmonella enterica | FSRKFPDQYFDVAIAEQHAVTFAAGLAIGGYKPIVAIYSTFLQRAYDQVIHDVAIQKLPV |
| Enterobacter sp. | FSKKYPDQYFDVAIAEQHAVTFAAGLAIGGYKPIVAIYSTFLQRAYDQVIHDVAIQKLPV |
| Cronobacter sakazakii | FSRKYPAQYFDVAIAEQHAVTFAAGLAIGGYKPVVAIYSTFLQRAYDQVIHDVAIQKLPV |
| Klebsiella pneumoniae | FSRKKFPDRYFDVAIAEQHAVTFAAGLAIGDYKPVVAIYSTFLQRAYDQVIHDVAIQKLPV |
| Yersinia pseudotuberculosis | FSREYPQQYFDVAIAEQ

```
           Escherichia coli    RYPRGNAVGVELTPLEKLPIGKGIVKRRGEKLAILNFGTLMPEAAKVAESL-NATLVDMR
       Shigella dysenteriae    RYPRGNAVGVELTPLEKLPIGKGIVKRRGEKLAILNFGTLMPEAAKVAESL-NATLVDMR
            Citrobacter sp.    RYPRGNAVGVELTPLEQLPIGKGIVKRHGEKVAILNFGTLMPEAAQVAESL-NATLVDMR
        Salmonella enterica    RYPRGNAQGVALTPLEKLPIGKGLVKRHGEKLAILNFGTLMPEAAKVAEAL-NATLVDMR
           Enterobacter sp.    RYPRGNAVGVELEPLTKMPIGKGIVKRHGEKLAILNFGTLMPEAAKVAESM-NATLVDMR
      Cronobacter sakazakii    RYPRGNALGVTLEPLQKLPIGKGVVKRHGEKVALLNFGTLLPEATQAAEAL-NATLVDMR
      Klebsiella pneumoniae    RYPRGSGTGATLEPLASLPIGKGVVKRQGEKIAILNFGTLLPEAAAVADKL-NATLVDMR
Yersinia pseudotuberculosis    RYPRGNGTGAVLEPLEMLPIGKGVLRREGEKIAILCFGTLLAQAQLAAENL-NATLVDMR
           Yersinia pestis     RYPRGNGTSAVLEPLEMLPIGKGVLRREGEKIAILCFGTLLAQAQLAAENL-NATLVDMR
               Erwinia sp.     RYPRGTGTGAPFEPLAALPLGKGVIKRQGEKLAILNFGTLLPQAAVTAEAM-NATLVDMR
           Pantoea ananatis    RYPRGTGTGAALTPLQSLPLGKGVVKRQGEKLAILNFGTLLPEASKVAEAL-NATLVDMR
           Dickeya dadantii    RYPRGNVLGVELTPLETLPIGKGVVKRQGEKIAILNFGTLLPEAQQVADAL-NATLVDMR
Pectobacterium atrosepticum    RYPRGNGTGTELTPLSELPIGKGVVRRQGKTVAILNFGTLLPEAQAVAEKL-NATLVDMR
    Xenorhabdus nematophila    RYPRGAGTGAELQPLETLPIGKGVLRRQGEKIAILNFGTLLPYALQAAETL-NATVVDMR
              Rahnella sp.     RYPRGNGTGATSEPLASLPIGKGVVRREGEKVAILNFGTLLPEALAAAEKR-NATVVDMR
        Serratia odorifera     RYPRGNGTGAQLEPLGALPIGKGVVRREGEKVAILNFGTLLPEAAQVAEAL-NATLVDMR
    Deinococcus radiodurans    RYPRGNTAQVPAGTWPDLKWGEWERLKGGDDVVILAGGKALDYALKAAEDLPGVGVVNAR Escherichia coli    FVKPLDEALILEMAASHEALVTVEENAIMGGAGSGVNEVLMAHRKPVPVLNIGLPDFFIP
       Shigella dysenteriae    FVKPLDDALILEMAASHEALVTVEENAIMGGAGSGVNEVLMAHRKPVPVLNIGLPDFFIP
            Citrobacter sp.    FVKPLDETLILEMAAQHEVLVTIEENAIMGGAGSGVNEVLMAHRKPVPVLNIGLPDFFIP
        Salmonella enterica    FVKPLDDTLILEMAAQHDALVTLEENAIMGGAGSGVNEVLMAHRKPVPVLNIGLPDFFIP
           Enterobacter sp.    FVKPLDETLILEMASRHEVLITLEENAIMGGAGSGVNEVLMANRKPIPVLNLGLPDRFIP
      Cronobacter sakazakii    FVKPLDEALIMELAGRHEALVTIEENAVMGGAGSGVNEVLMAKRKPVPVLNIGLPDHFIP
      Klebsiella pneumoniae    FVKPLDTALILQLAGEHDALVTLEENAIMGGAGSGVNEVLMAHRRAVPVLNIGLPDYFIP
Yersinia pseudotuberculosis    FVKPLDEELVLEMAAKHQVLVTVEENAIMGGAGSGVNELLMAKRRWVPVLNIGLPDLFVP
           Yersinia pestis     FVKPLDEELVLEMAAKHQVLVTVEENAIMGGAGSGVNELLMAKRRWVPVLNIGLPDLFVP
               Erwinia sp.     FVKPLDEALVLELAAQHQALVTLEEGAIKGGAGSGVNELLMAKRKPVPVLNIGLPDEFIP
           Pantoea ananatis    FVKPLDTSLIAELAASHESLITLEEGAIKGGAGSGVNEFVMAKRLGVPVLNIGLPDEFIP
           Dickeya dadantii    FVKPLDEALVASLAASHDVLVTLEENAVMGGAGSGVNEYLMANRLPVPVLNLGLPDIFIP
Pectobacterium atrosepticum    FVKPLDEALLEELAQSHSTFVTLEENAVMGGAGSGVNEFLMAKRLAVSVLNIGLPDVFIP
    Xenorhabdus nematophila    FVKPLDKELTLEMAASHDLLVTLEENAIMGGAGSGVNEFLMQEKRLVPVLNLGLPDYFIP
              Rahnella sp.     FVKPLDEALIQELASSHEVLVTLEENAIMGGAGSGVNELLMSRRILVPVLNIGLADSFVP
        Serratia odorifera     FVKPLDEQLVLELAASHEVLVTLEENAIMGGAGSGVNELLMAKRRAVPVLNIGLPDSFVS
    Deinococcus radiodurans    FVKPLDEEMLREVGGRARALITVEDNTVVGGFGGAVLEALNSMNLHPTVRVLGIPDEFQE
```

Figure 16 (continuation)

Escherichia coli                QGTQEEMRAELGLDAAGMEAKIKAWLA*------
Shigella dysenteriae            QGTQEEMRAELGLDAAGMEAKIKAWLA-------
Citrobacter sp.                 QGTQDEARADLGLNAAGIETKIKAWLA-------
Salmonella enterica             QGTQEEARAELGLDAAGIEAKIKAWQA-------
Enterobacter sp.                QGTQDEARAEIGLDAAGIEAKIRTWLA-------
Cronobacter sakazakii           QGTQDEARAEIGLTASGIEQRVRDWLA-------
Klebsiella pneumoniae           QGTQEEIRADLGLDAAGIEAKIRDWLA-------
Yersinia pseudotuberculosis     QGEQDEMRSELGLDAAGIQRQIEAWLA-------
Yersinia pestis                 QGEQDEMRSELGLDAAGIQRQIEAWLA-------
Erwinia sp.                     QGTQEEIRSDYQLDANGIRQQITDWLA-------
Pantoea ananatis                PGTQEEMRHDYQLDIDGIQQQISRWLA-------
Dickeya dadantii                QGSQAEIRTELSLDAAGIERRIRNWLA-------
Pectobacterium atrosepticum     QGSQEEIRVDIGLDAAGIERRITQWM-------
Xenorhabdus nematophila         QGTQQELHADLGLDAAGIKNRIEKYLA-------
Rahnella sp.                    QGTQDEIRHDIGLDAEGIDRQITDWLA-------
Serratia odorifera              QGSQEEVRVDLGLDAAGIRRQIEAWLA-------
Deinococcus radiodurans         HATAESVHARAGIDAPAIRTVLAELGVDVPIEV Figure 16 (continuation)

Consensus of plant DXS sequence (SEQ ID N°23)

TPLLDT.NYP.H.KN....ZL.QL..ELR......VS.TGGHL..SLGVVELTVA.HY.F..P.D..JWDVGHQ.Y.HKI.TGRR..M.T.R.T.GL.GFTKR.ESE.D.FG.GHS
ST.ISA.LGMA.GRD.K...N.V.VIGDGA.T.G.A.EAMN.A..LD.BMIVILNDN.QVSLPT.......PVGA......JQ....LRELRE.AKG.TKQJ........AK.
D.YARGMISG..S.LFEELGLYYIGP.DGHNJDDL..L.V...T.GPVL.HV.TEKG.GY..AE...DK.HGV.KFDP.TG.Q.......YT.YFA..L..EA..D....A
.HAAM.GGTGL.F...P.R.FDVGIAEQHAVTF.AGLACEGJ.PFC.IYS.F.QR.YDQ..HDV.LQ.LPV.FAMDRAG.VGADG.THCGAFD....A.LP.M..MAP.BEA.L
..MVAT..AIDD.PSCF.PRGNG.G..L........KG.FJE.G.G...ZG..V.L..YG..V...A...LZ......TV.DARFCKPLD..L.R..A..H.V....EEG.
.GGF..HV..FL.L.G.LDG..K..PM..PD..I.HG...DQ...AGL...HIA......JG.......A.........

Figure 17

```
                          1         10        20        30        40        50        60
                          |         |         |         |         |         |         |
             Vitis vinifera    ------------------------------------------MALCTLSFPAHFSQAAASNPQRLTPQCSHLFLG
      Arabidopsis thaliana    ------------------------MASSAFAFPSYIITKGGLSTDSCKSTSLSSSRSLVTD
           Pinus densiflora   ------------------------------------MASSAVIQSNANQLSSMGFAFSSGSLCH
 Chlamydomonas reinhardtii    ----------------------------------------------ARGVRSAAPTRQRRAEA
         Dunaliella salina    MFLPAKLPSCKGWLENSRTTSQHPAGTRPLVAARKPSARRDRQTTARTRAEPGVPSTPAG Vitis vinifera    VDLQCQSQQRSKARKRPNGVCASLSDREEVHSQRPPTPLLDTINYPIHMKNLSVKELKQL
      Arabidopsis thaliana    LPSPCLKPNNNSHSNRRAKVCASLAEKGEYYSNRPPTPLLDTINYPIHMKNLSVKELKQL
           Pinus densiflora   QIKPAKLESKKLGRRVGKAYASALSDQGEYYSEKPPTPLLDTINYPIHMKNLSIRELKQL
 Chlamydomonas reinhardtii    ---SVNAPRAGPAGSYSGEWDKLSVEEIDEWRGVGPKTPLLDTVNYPVHLKNFNNEQLKQL
         Dunaliella salina    ---LVAQEELDDPYYDGTYTRLSFEEIDAWDTQGLPTPLLDTVNYPVHIKNFNMPQLRQL Vitis vinifera    ADELRSDVVFNVSKTGGHLGSSLGVVELTVALHYVFNAPQDRILWDVGHQSYPHKILTGR
      Arabidopsis thaliana    SDELRSDVIFNVSKTGGHLGSSLGVVELTVALHYIFNTPQDKILWDVGHQSYPHKILTGR
           Pinus densiflora   SNELRSDIFEVSRTGGHLGSSLGVVELTVALHYVFDAPEDKILWDVGHQAYPHKILTGR
 Chlamydomonas reinhardtii    CKELRSDIVHTVSRTGGHLSSLGVVELTVAMHYVFNTPEDKIIWDVGHQAYGHKILTGR
         Dunaliella salina    CKELRAEIVHGVSKTGGHLSASLGVVELTVAMHYVFSAPDDKFIWDVGHQAYVHKIMTGR Vitis vinifera    RDQMHTMRQTDGLAGFTKRSESEYDCFGTGHSSTTISAGLGMAVGRDLKGKNNNVIAVIG
      Arabidopsis thaliana    RGKMFTMRQTNGLSGFTKRGESEHDCFGTGHSSTTISAGLGMAVGRDLKGKNNNVVAVIG
           Pinus densiflora   RDKMPTLRQTNGLSGFTKRSESEYDCFGAGHSSTISAGLGMAAGRDLKGKNNHVISVIG
 Chlamydomonas reinhardtii    RKGMATIRQTNGLSGFTKRDESEYDPFGAGHSSTSISAALGMAVGRDVKGKKNSVIAVIG
         Dunaliella salina    RDKMQTIRKTGGLSGFTKRAESEYDPFGAGHSSTSISAGLGMAVGRDTKNRNNQVVAVIG Vitis vinifera    DGAMTAGQAYEAMNNAGYLDSDMIVILNDNKQVSLPTATLDGPIPPVGALSSALSRLQSN
      Arabidopsis thaliana    DGAMTAGQAYEAMNNAGYLDSDMIVILNDNKQVSLPTATLDGPSPPVGALSSALSRLQSN
           Pinus densiflora   DGAMTAGQAFEAMNNARYLDSNMIVILNDNKQVSLPTANLDGPIPPVGALS----KLQSS
 Chlamydomonas reinhardtii    DGAITGGMAYEAMNHAGFLDKNMIVILNDNQQVSLPTQYNNKNQDPVGALSAIARLQAN
         Dunaliella salina    DGAITGGMAYEAMNHAGFLDKNMIVILNDNQQVSLPTQYNSKNQAPVGAMAGTLARIQAN Vitis vinifera    RPLRELREVAKGVTKQIGGPMHELAAKVDEYARGMISGSGSTLFEELGLYYIGPVDGHNI
      Arabidopsis thaliana    PAIRELREVAKGMTKQIGGPMHQLAAKVDVYARGMISGTGSSLFEELGLYYIGPVDGHNI
           Pinus densiflora   KPLRELREVAKGVTKQLGAPMHELAAKVDEYARGMISGSRSTLFEELGLYYIGPVDGHNI
 Chlamydomonas reinhardtii    RPLRELREIAKGVTKQLPDVVQKATAKIDEYARGMISGTGSTLFEELGLYYIGPVDGHNL
         Dunaliella salina    RPLRELREVAKGMTKQLPTAVQNATAKIDEYARGMISGTGSTLFEELGLYYIGPLDGHNL
```

Figure 18

| | |
|---|---|
| Vitis vinifera | DDLVAILKEVKSTKTTGPVLIHVVTEKGRGYPYAEKAADKYHGVTKFDPATGKQFKSSAP |
| Arabidopsis thaliana | DDLVAILKEVKSTRTTGPVLIHVVTEKGRGYPYAERADDKYHGVVKFDPATGRQFKTTNE |
| Pinus densiflora | DDLLTILRDVKATHTTGPVLIHVVTEKGRGYPYAERAADKYHGVVKFDPATGKQFKGKAP |
| Chlamydomonas reinhardtii | DDLIAVLSEVRSAETVGPVLVHVVTEKGRGYLPAETAQDKMHGVVKFDPRTGKQVQAKTK |
| Dunaliella salina | DDLISVLSEVRSAETIGPVLIHVITEKGHGYEPAEASQDKMRGVVKFDPKTGKQFASKPK |
| | |
| Vitis vinifera | TQSYTTYFAEALIAEAEVDKDIVAIHAAMGGGTGLNLFHRRFPTRCFDVGIAEQHAVTFA |
| Arabidopsis thaliana | TQSYTTYFAEALVAEAEVDKDVVAIHAAMGGGTGLNLFQRRFPTRCFDVGIAEQHAVTFA |
| Pinus densiflora | TQTYTTYFAEALISEAEADKNIVAVHAAMGGGTGLNMFSKRFPTRCFDVGIAEQHAVTFA |
| Chlamydomonas reinhardtii | AMSYTNYFADALTAEAERDSRIVAVHAAMAGGTGLYRFEKKFPDRTFDVGIAEQHAVTFA |
| Dunaliella salina | TMSYTNYFADSLIAEAKRDSRIMAIHAAMAGGTGLTRFENALPDRVFDVGIAEQHAVTFS |
| | |
| Vitis vinifera | AGLACEGIKPFCAIYSSFMQRAYDQVVHDVDLQKLPVKFAMDRAGLVGADGPTHCGAFDV |
| Arabidopsis thaliana | AGLACEGLKPFCAIYSSFMQRAYDQVVHDVDLQKLPVRFAMDRAGLVGADGPTHCGAFDV |
| Pinus densiflora | AGLACEGLKPFCAIYSSFLQRAYDQVIHDVDLQNLPVRFAMDRAGLVGADGPTHCGAFDV |
| Chlamydomonas reinhardtii | AGLACEGLVPFCTIYSTFMQRGYDQIVHDVSLQKLPVRFPRGNGLGLDLAAYGISKDLKG |
| Dunaliella salina | AGLACEGLVFCTIYSTFLQRGYDQVVHDVALQNLPVRFAMDRAGMVGADGATHCGAFDI |
| | |
| Vitis vinifera | AFMACLPNMVVMAPADEAELFHMVATAAAIDDRPSCFRYPRGNGVGVELPPGN-----KG |
| Arabidopsis thaliana | TFMACLPNMIVMAPSDEADLFNMVATAVAIDDRPSCFRYPRGNGIGVALPP-G-N---KG |
| Pinus densiflora | TYLACLPNMVVMAPSNEAELFHMVATAAAIDDRPSCFGFPRGNGVGAQLPPGN-----KG |
| Chlamydomonas reinhardtii | TFMASLPHMITMAPSNEAELINMVATCAAIDDAPSCFRFPRGNGLGLDLAAYGISKDLKG |
| Dunaliella salina | TYMASLPNMVCMAPSNEAELINMVATAAAIDDRPSCFRFPRGNGIGVLEAAGIK-DMKG |
| | |
| Vitis vinifera | IPIEVGRGRILIEGERVALLGYGTAVQSCLVASSLLEQHGLRITVADARFCKPLDHALIR |
| Arabidopsis thaliana | VPIEIGKGRILKEGERVALLGYGSAVQSCLGAAVMLEERGLNVTVADARFCKPLDRALIR |
| Pinus densiflora | VPLEIGKGRILVEGDRVALLGYGTVVQNCLAASALLEEQDLSVTVADARFCKPLDRDLVR |
| Chlamydomonas reinhardtii | VPLEVGKGVPRQGKDVCLVAYGSSVNEALAAADMLERDGVSTTVIDARFCKPLDTKLIR |
| Dunaliella salina | TPLEIGKGVVRRQGTDVCLLAYGSSVNEAMAAAEALQLDGVSATVIDARFCKPLDTDLIR |
| | |
| Vitis vinifera | SLAKSHEVLITVFEEGSIGGFGSSHVAQFLALNGLLDGTTKWSPMVLPDRYIDHGAPADQLA |
| Arabidopsis thaliana | SLAKSHEVLITVEEGSIGGFGSSHVVQFLALDGLLDGKLKWRPMVLPDRYIDHGAPADQLA |
| Pinus densiflora | SLAREHEVLIVEEGTIGGFGSSHVAHFLALDGFLDGKLKWRPMVLPDHYIEHGAPSDQMI |
| Chlamydomonas reinhardtii | SAAKEHPVMITEEGSVGGFAAHVMQFLALEGLLDGGLKFRPMTLPDRYIDHGDYRDQLA |
| Dunaliella salina | KAAQEHPVMVSIEEGAIGGFAAHVMQFLITLEGLLDGGLKFRPMCMDRFIEHGDYRDQLN |

Figure 18 (continuation)

```
Vitis vinifera              MAGLTPSHIAATVFNILGQTREALEIML*-------
Arabidopsis thaliana        EAGLMPSHIAATAINLIGAPREALF*----------
Pinus densiflora            EAGLTASHIAASVLNMLGRTREALQVMS--------
Chlamydomonas reinhardtii   MAGLTSQHIASTAITTLGRAKDAAKFSISALQA----
Dunaliella salina           LAGLTPGHIAGTALQILGRKAGAAKYAISNTGLVAA
```

Figure 18 (continuation)

1-DEOXY-D-XYLULOSE 5-PHOSPHATE SYNTHASE ALLELES RESPONSIBLE FOR ENHANCED TERPENE BIOSYNTHESIS

BACKGROUND OF THE INVENTION

Field of the Invention

This invention relates to a new polypeptide having an enhanced 1-deoxy-D-xylulose 5-phosphate synthase (DXS) activity compared to typical plant or bacteria DXS proteins. This polypeptide is responsible for a massive accumulation of terpenes in cells.

The invention also relates to transgenic plants, bacteria or yeast that express this polypeptide, and are capable of a greatly enhanced accumulation of terpenes, in comparison to plants, bacteria or yeast expressing a typical DXS gene.

The invention also relates to a method of production of terpenes by culturing transgenic plants, bacteria or yeast that express this polypeptide.

Finally the invention relates to transgenic plants that express this polypeptide, and are resistant to clomazone.

Description of the Related Art

Isoprenoids (also known as terpenoids or terpenes) are considered to be the largest family of natural products occurring in nature, with over 29 000 individual compounds identified to date. Chemically, they are extremely diverse in their structure and complexity. Isoprenoids are involved in numerous fundamental biological functions and therefore, they are essential for the normal growth and developmental processes in all living organisms. For instance, isoprenoids include eukaryotic membrane stabilizers (sterols), animal and plant hormones (steroids, retinoids, gibberellins and abscisic acid), pigments for photosynthesis (carotenoids and phytol side chain of chlorophyll), and carriers for electron transport (menaquinone, plastoquinone and ubiquinone).

Consequently, isoprenoids are a large, diverse group of complex natural products with considerable commercial interest. Isoprenoids are today mostly extracted from plants or chemically synthesized to be used as pharmaceuticals (e.g. taxol, bisabolol, and artemisinin), animal feed supplements and food colorants (various carotenoids such as lycopene and β-carotene) or flavors and fragrances (e.g. menthol, patchoulol, and nootkatone).

Isoprenoids are classified into groups according to the number of carbons they contain; the major groups of interest are monoterpenes ($C_{10}$), sesquiterpenes ($C_{15}$), diterpenes ($C_{20}$), and triterpenes ($C_{30}$).

All isoprenoids are synthesized via a common metabolic precursor, isopentenyl diphosphate (IPP; $C_5$). It was previously assumed that IPP was synthesized exclusively from mevalonate by the so-called <<mevalonate pathway>>. However, more recent investigations have shown that in eubacteria, green algae, and plants, IPP is also synthesized by a different pathway, designated the 2-C-methyl-b-erythritol-4-phosphate (MEP) pathway. Therefore, plants possess both the mevalonate and the MEP pathways, responsible respectively for the biosynthesis of IPP in the cytosol and in plastids.

The first intermediate of the MEP pathway is 1-deoxyxylulose-5-phosphate (DXP), whose biosynthesis from glyceraldehyde-3-phosphate (63P) and pyruvate is catalyzed by the thiamine-dependent enzyme 1-deoxyxylulose-5-phosphate synthase (DXS). DXS has been shown to catalyze a rate-limiting step in the formation of isoprenoids in bacteria and in plants. Indeed, in *Arabidopsis thaliana* and tomato (*Lycopersicon esculentum*), the over-expression of DXS resulted in elevated levels of plastid-derived isoprenoids like carotenoids. This is also the case in aromatic plants such as spike lavender (*Lavandula latifolia*), where the over-expression of DX5 led to a substantial increase in essential oil production.

Terpenoids are involved in aromas and fragrances of many plant-derived products, and, among them, monoterpenols contribute strongly to the aroma profiles of table grapes and wines. Floral flavors described as rose or lily of the valley, are related to the presence of molecules such as linalool, geraniol, nerol, alpha-terpineol or citronellol. The highest concentrations of these molecules are found in varieties of the "Muscat" group or in Gewurztraminer, leading to very characteristic aromas in these varieties. Floral flavors have appeared spontaneously in genotypes not related to the Muscat group.

DEFICIENCIES IN THE PRIOR ART

Certain diterpenoids have been commercially exploited, particularly in the pharmaceutical sector. This is true in particular for diterpenoids from the taxane class, paclitaxel and docetaxel, used in the treatment of breast and ovarian cancer. Paclitaxel is a natural molecule extracted from the yew (*Taxus* sp.), while docetaxel is a semi-synthetic molecule, derived from a paclitaxel precursor, 10-deacetyl baccatin III (or 10-DAB III), also extracted from yew. Most of the paclitaxel biosynthetic genes of yew have been described. These molecules are costly to produce due to the relatively low abundance of 10-DAB III and especially of paclitaxel in yew extracts, and due to the absence of a synthetic method that can be scaled up industrially, on account of the structural complexity of the molecules.

Thus there is a high demand for methods for producing terpenes of interest at a lower cost, but also for producing terpene derivatives that are not yet easily accessible to synthesis.

The chemical industry, which produces organic molecules by traditional chemical processes, is increasingly turning to production processes utilizing microbial cell factories. The key drivers for this development towards green chemistry are that such so-called "biotechnological processes" are more environmentally friendly, that many compounds produced by microorganisms are too complex to be obtained by organic synthesis and that the microbial cell factory represents an unlimited supply of the particular compound. Currently, isoprenoids are produced at large scale by extraction from plants or by chemical synthesis. The major drawbacks of both of these methods are low yields and high costs. A third option is to produce the desired isoprenoids by in vitro enzymatic conversion, but this approach is limited by the availability of precursors, and therefore in most cases not economically viable.

Metabolic engineering of microorganisms for isoprenoid production may lead to production of large amounts of isoprenoids from cheap carbon sources in fermentation processes, and thereby solve many of the current problems in industrial isoprenoid production, whilst allowing for biotechnological exploitation of the large diversity found in the isoprenoid group of natural compounds.

A number of isoprenoid products have been produced by genetically engineered microorganisms, including limonene, carotenoids, epi-cedrol, taxadiene, and others. In order to enhance isoprenoid production in *Escherichia coli*, the genes dxs (encoding DXP synthase), dxr (DXP reductoisomerase) and idi (IPP isomerase) have been overexpressed with good results for several of the above-mentioned isoprenoid products (reviewed in MAURY et al, 2005). A further increase in amorphadiene production by *E. coli* has been obtained by expressing the mevalonate pathway from *Saccharomyces cerevisiae* in an amorphadiene producing strain of *E. coli*. Some isoprenoid compounds have also been produced in yeasts, including epi-cedrol in *S. cerevisiae*, lycopene and beta-carotene in *S. cerevisiae* and *Candida utilis*. In several cases, isoprenoid production in yeast has been shown to be enhanced by overexpression of HMG1 (encoding HMG-COA reductase) (reviewed in MAURY et al, 2005).

In spite of the background depicted above, there is still a need for further processes for producing terpenes and terpenoids and, in particular, for ways of accumulating terpenes in microorganisms with higher yields and in a less costly and time intensive manner than in the prior known methods. It is therefore an objective of the present invention to provide a method for producing terpenes or terpenoids that fulfils this need.

It is a particular objective of the present invention to produce a microorganism that accumulates and/or secretes high amounts of terpenes to the surrounding medium. The production of terpenes by such a microorganism is preferably stable over time.

Furthermore, an objective of the present invention is to engineer plants with enhanced isoprenoid production with an aim to purify the isoprenoid component, as a means of increasing the nutritional value of food crops, or to enhance the fitness of the plant itself by increasing resistance to herbivores, pests or pathogens The present invention seeks to overcome these and other drawbacks inherent in the prior art by providing transgenic plants, bacteria or yeast that express one of these two genes, and are capable of a greatly enhanced accumulation of terpenes, in comparison to plants, bacteria or yeast expressing a typical dxs gene.

BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

The FIG. 1 shows the nucleotide sequence of cDNAs corresponding to different DX5 alleles in *V. vinifera* cv Muscat Ottonel (MO) (MODXS1, SEQ ID No8, and MODXS2, SEQ ID No9) and Gewurztraminer (GW) (GWDXS2, SEQ ID No10). Positions corresponding to SNPs indicated in bold letters.

The FIG. 2 shows the comparison of the proteins corresponding to the different DX5 alleles in MO and GW with the associated consensus sequence corresponding to SEQ ID No2.

The FIG. 3 shows the consensus sequence (by which the sequence SEQ ID No1 was obtained) resulting from the comparison of DX5 proteins from different plant species:
First Line: Consensus
$2^{nd}$ line: Mo_DXS1
$3^{rd}$ line: Mo_DXS2
$4^{th}$ line: GW_DXS2
$5^{th}$ line: *Arabidopsis thaliana*
$6^{th}$ line: *Capsicum annuum*
$7^{th}$ line: *Catharanthus roseus*
$8^{th}$ line: *Glycine max*
$9^{th}$ line: *Narcissus pseudonarcissus*
$10^{th}$ line: *Nicotiana tabacum*
$11^{th}$ line: *Oryza sativa*

Figure 4:
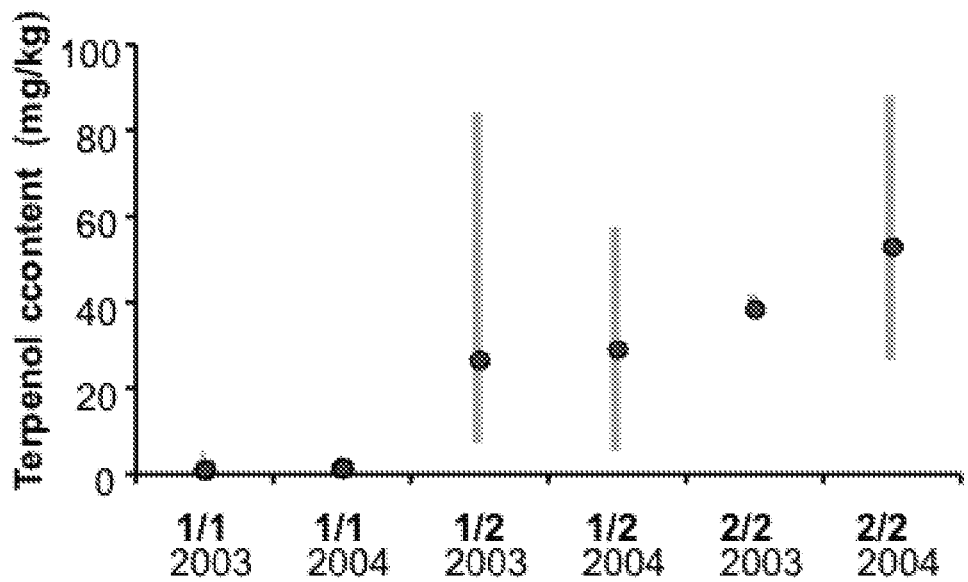

The FIG. 4 shows the Terpenol content (pool of 5 major terpenols: geraniol, linalol, citronellol, nerol, alpha-terpineol) in grape berry skins and DXS genotype in a Muscat Ottonel progeny (years 2003 and 2004) (1: MoDXS1; 2: MoDXS2).

Figure 5:
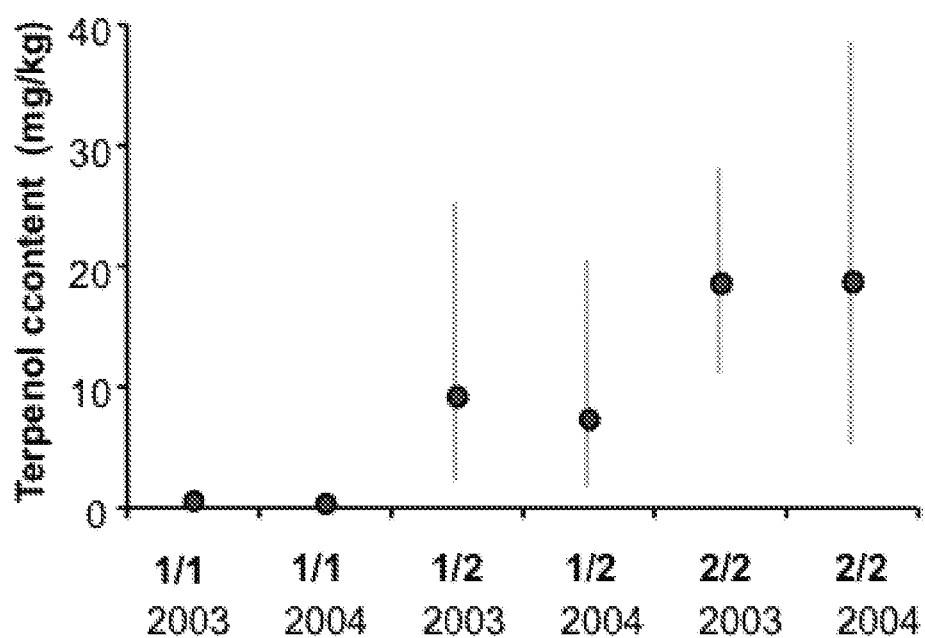

The FIG. 5 shows the Terpenol content (pool of 5 major terpenols: geraniol, linalol, citronellol, nerol, alpha-terpineol) in grape berry skins and DXS genotype in a Gewurztraminer progeny (years 2004 and 2005) (1: GwDXS1=MoDXS1; and 2: GwDXS2).

Figure 6:
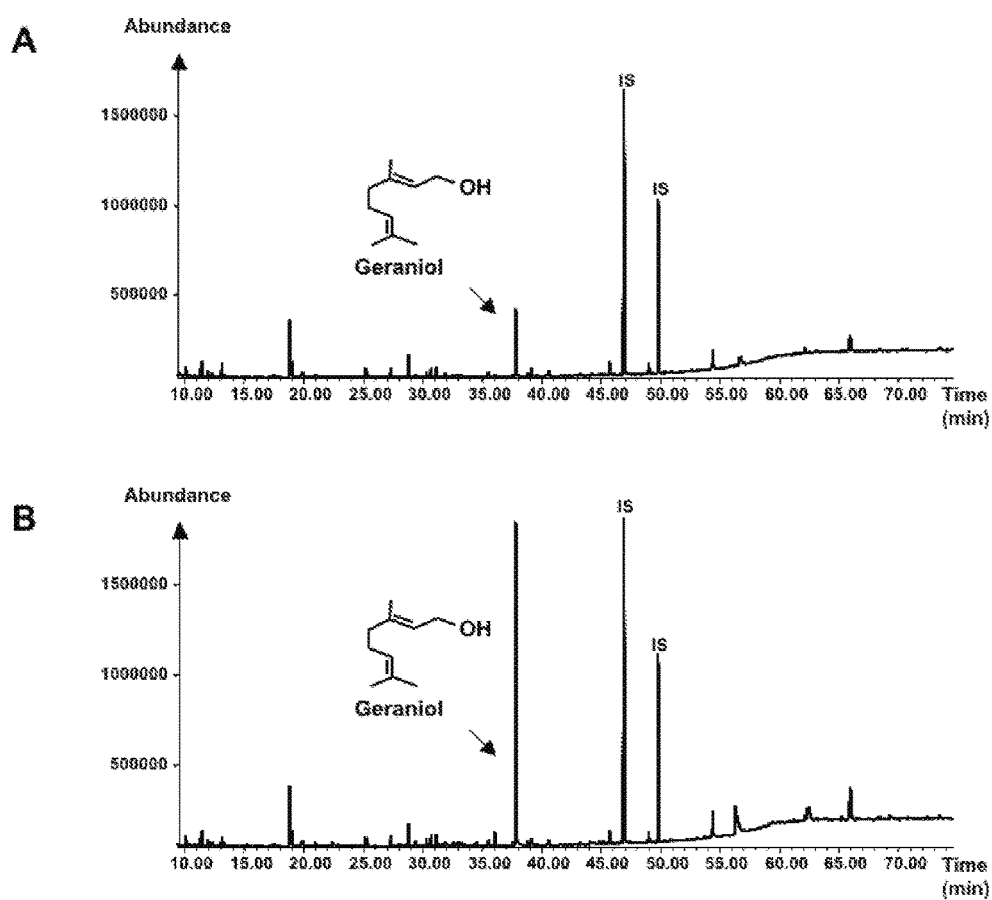
Figure 7:
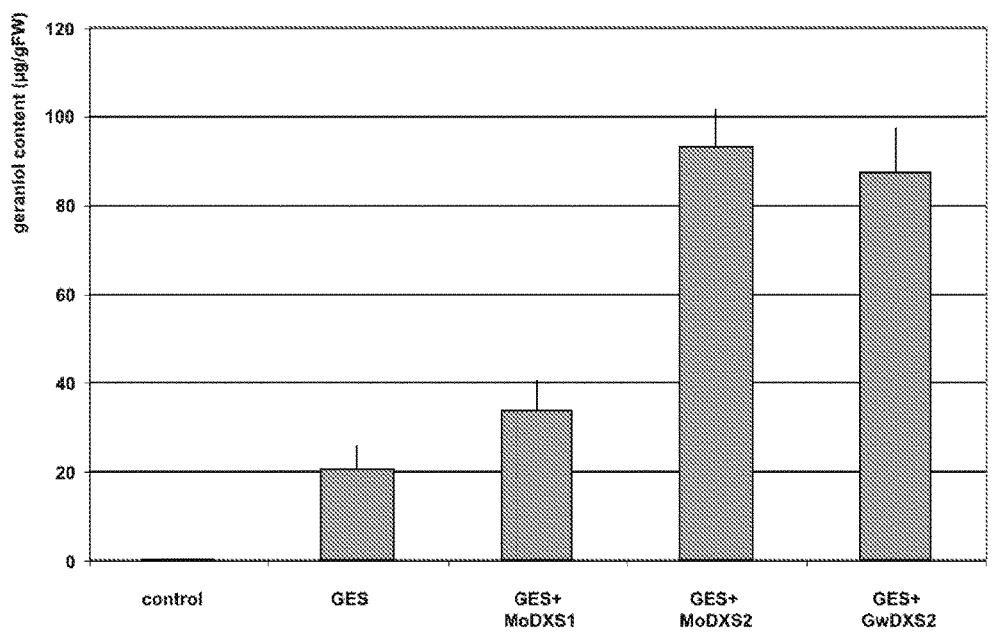

The FIG. 6 shows GC-MS analysis of terpenes produced in tobacco leaves co-expressing DXS alleles from grapevine and geraniol synthase (GES) from basil. A: Analysis of tobacco leaves co-expressing MoDXS1 and GES. B: Analysis of tobacco leaves co-expressing MoDXS2 and GES The FIG. 7 shows the In planta geraniol biosynthesis, following transient co-expression of GES and DXS alleles in tobacco leaves. Untransformed tobacco leaves (control), leaves expressing GES alone and leaves co-expressing GES and DXX alleles were analysed using GC-MS, 4 days post *Agrobacterium*-mediated transformation. For each condition, geraniol amounts are means (±standard errors) of 9 independent experiments.

The FIG. 8 shows the amino acid sequence of MODXS1 (SEQ ID No3), MODXS2 (SEQ ID No4), truncated MODXS2 with DXS activity (SEQ ID No5) and GWDXS2 (SEQ ID No6), truncated GWDXS2 with DXS activity (SEQ ID No7).

The FIG. 9 shows the nucleotide sequence of the wild type DXS gene from *E. coli* (*Ecoli* DXS), the sequence of the gene encoding the truncated form of the DXS protein (truncated *Ecoli* DXS) and the sequence of the genes encoding the DXS protein harbouring the K213→N and the R306→C mutations (*Ecoli* DXS-K213N and *Ecoli* DXS-K234C, respectively).

The FIG. 10 shows the comparison of the proteins corresponding to the different DXS alleles in *V. vinifera* cv Muscat Ottonel (MO) (MODXS1, SEQ ID No8, and MODXS2, SEQ ID No9) and Gewurztraminer (GW) (GWDXS2, SEQ ID No10) with the DXS protein from *Escherichia coli* (Lois et al., 1998). The amino acids corresponding to the SNPs in MODXS2 and GWDXS2 and the corresponding amino acids in the DXS from *E. coli* are indicated in bold letters.

Figure 11:
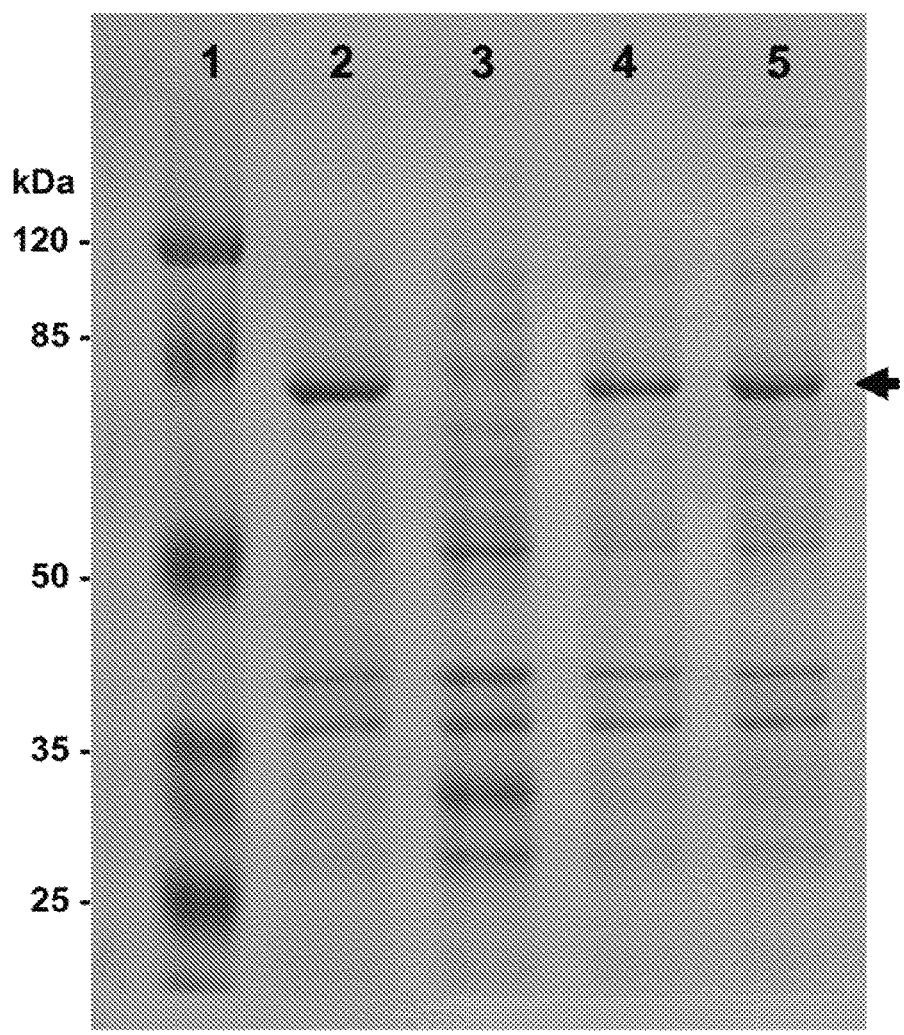

The FIG. 11 shows a sodium dodecyl sulfate polyacrylamide gel electrophoresis (SDS-PAGE) analysis of recombinant DXS expressed in the *E. coli* strain BL21-Gold(DE3) pLysS.

Lane 1: molecular weight marker.
Lane 2: BL21-Gold(DE3)pLysS transformed with the plasmid pHGWA-*Ecoli*DXS.
Lane 3: BL21-Gold(DE3)pLysS transformed with the plasmid pHGWA-Truncated*Ecoli*DXS.
Lane 4: BL21-Gold(DE3)pLysS transformed with the plasmids pHGWA-*Ecoli*DXS-K213N. Lane 5: BL21-Gold (DE3)pLysS transformed with the plasmids pHGWA-*Ecoli*DXS-K234C. DXS expression was induced with 1 mM IPTG for 24 h at 28° C.

The arrow indicates the position of the DXS protein and the molecular weight of the markers are indicated.

Figure 12:
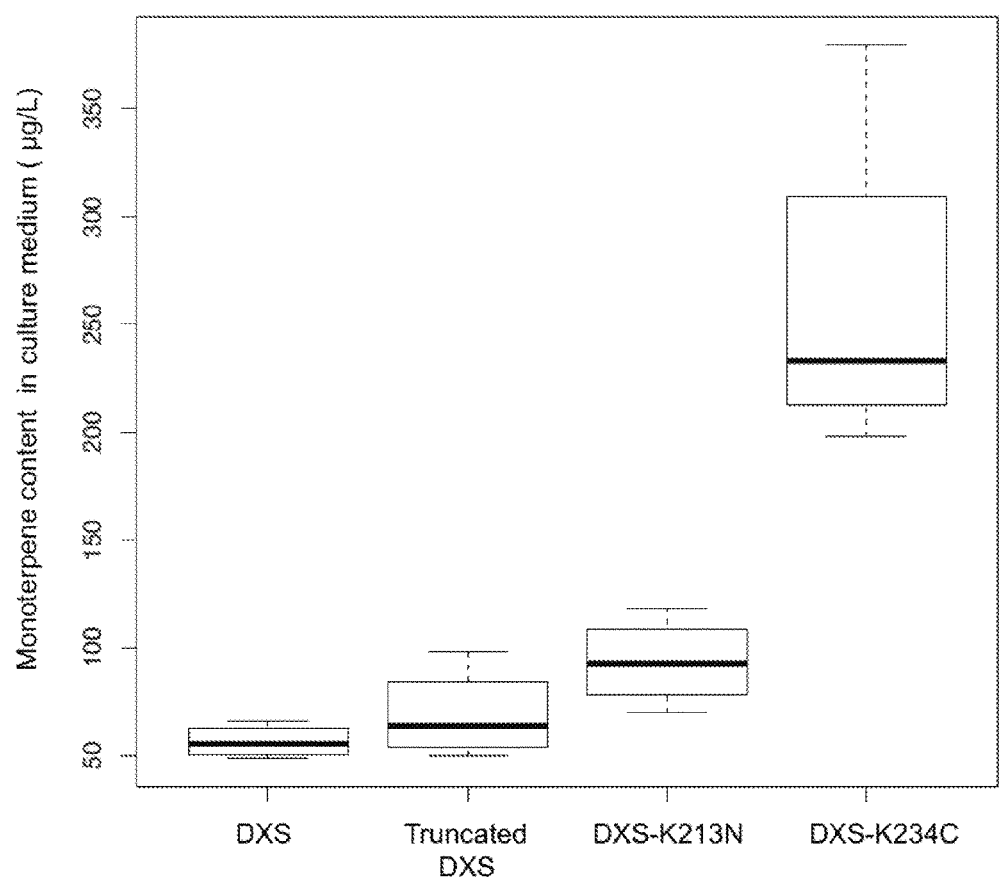

The FIG. 12 shows a box plot presenting monoterpene contents in culture medium of *E. coli* transformed with different DXS constructs: wild type *Ecoli*DXS, Truncated*Ecoli*DXS, *Ecoli*DXS-K213N, *Ecoli*DXS-K234C. Monoterpene contents represent the sum of the two major monoterpenes accumulated in *E. coli* cultures: geraniol and geranyl acetate. The data correspond to the results of 4 independent experiments. For each construct, the bold bar represents the median, the limits of the box are the 1$^{st}$ and the 4$^{th}$ quartiles and the bars out of the box indicate the extreme values.

The FIG. 13 shows the amino acids sequence of *E. coli* DXS, *E. coli* DXS-K213N, *E. coli* DXS-K234C and Truncated *E. coli* DXS.

The FIG. 14 shows the consensus of bacterial DXS sequence (conserved amino acids are indicated, dots represent non-conserved amino acids). Amino acids corresponding to K213 and K234 in the DXS protein from *E. coli* are shaded.

The FIG. 15 shows the consensus of bacterial DXS sequences including *Deinococcus radiodurans* (conserved amino acids are indicated, dots represent non-conserved amino acids).

Figure 16:
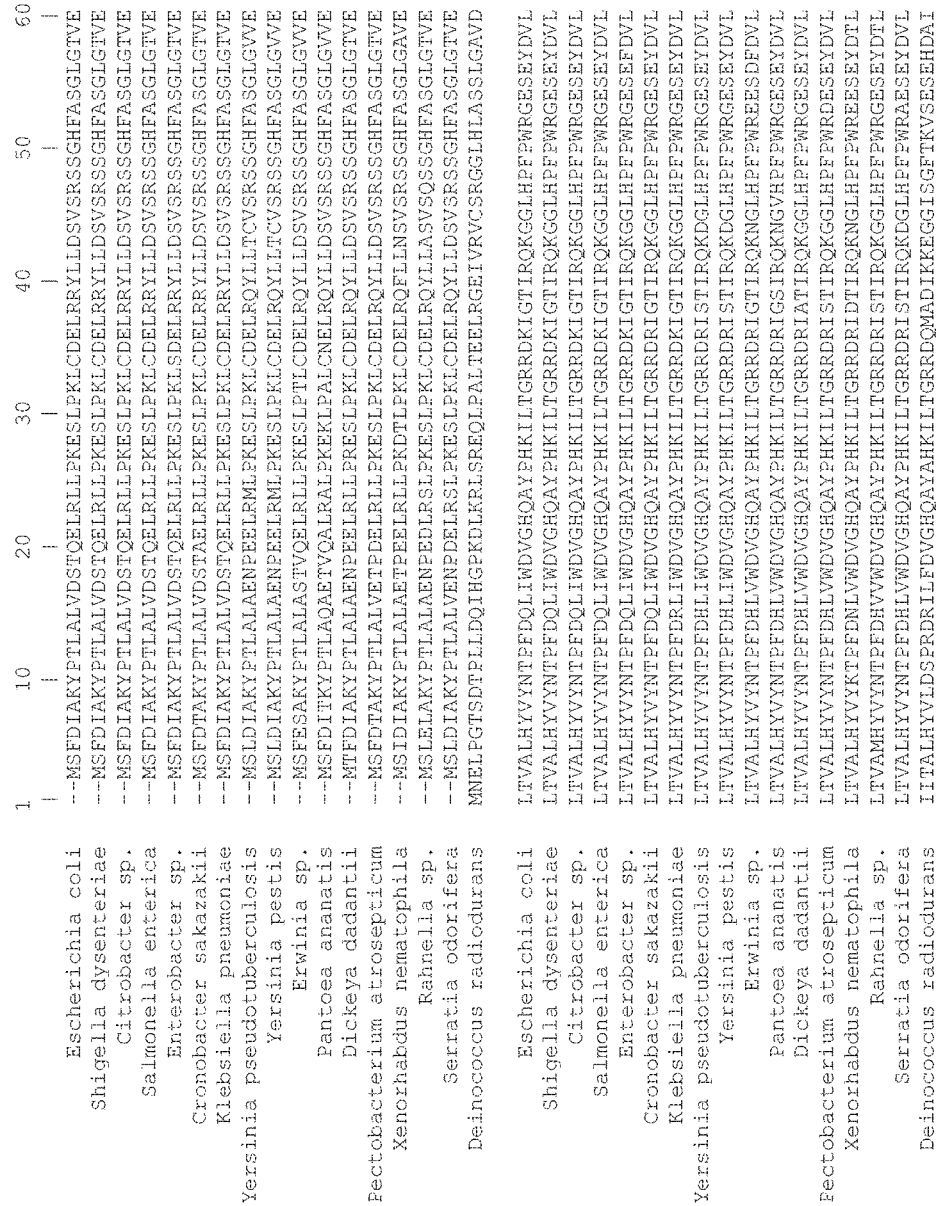

The FIG. 16 shows the amino acids sequence of DXS proteins from *Escherichia coli, Shigella dysenteriae, Citrobacter* sp., *Salmonella enterica, Enterobacter* sp., *Cronobacter sakazakii, Klebsiella pneumonia, Yersinia pseudotuberculosis, Yersinia pestis, Erwinia* sp., *Pantoea ananatis, Dickeya dadantii, Pectobacterium atrosepticum, Xenorhabdus nematophila, Rahnella* sp., *Serratia odorifera* and *Deinococcus radiodurans*.

The FIG. 17 shows the consensus of plant DXS sequence (conserved amino acids are indicated, dots represent non-conserved amino acids). Amino acids corresponding to K284 and R306 in the DXS protein from *V. vinifera* are shaded.

The FIG. 18 shows the amino acids sequence of DXS proteins from *Vitis vinifera, Arabidopsis thaliana, Pinus densiflora, Chlamydomonas reinhardtii* and *Dunaliella salina*.

DETAILED DESCRIPTION OF THE INVENTION

A first object of the invention relates to a method of enhancement of the 1-deoxy-D-xylulose 5-phosphate synthase (DXS) activity of plants or bacteria to increase terpenes production comprising the steps of:
a) Determining at least one mutation site, preferably two, on the polypeptide having a DXS activity of a plant or a bacteria by doing a sequence comparison between a reference sequence selected in the group comprising SEQ ID No2, SEQ ID No4, SEQ ID No6, SEQ ID No19, SEQ ID No20, SEQ ID No21, SEQ ID No22 and SEQ ID No23 and the sequence of said plant or bacteria;
b) Proceeding to the mutation on the at least one mutation sites, preferably on two mutation sites;
c) Obtaining a polypeptide having an enhanced DXS activity compared to the typical DXS.

The step (a) of determination of mutation site(s) can be done by proceeding to a sequence comparison. The sequence of plant or bacteria to mute can be optimally aligned with a reference sequence selected from the group comprising SEQ ID No2, SEQ ID No4, SEQ ID No6, SEQ ID No19, SEQ ID No20, SEQ ID No21, SEQ ID No22 and SEQ ID No23.

Preferably, the reference sequence is selected from the group comprising SEQ ID No4, SEQ ID No6, SEQ ID No19 and SEQ ID No20.

More preferably, SEQ ID No4 or SEQ ID No6 are used as reference sequences for determining a mutation site on a plant polypeptide and SEQ ID No19 or SEQ ID No20 are used as reference sequences for determining a mutation site on a bacteria polypeptide.

As an example, the amino acids corresponding to K284 and R306 in the DXS from *Vitis vinifera* can be identified in a DXS protein from another organism using a multiple sequence alignment computer program, such as ClustalW (Thompson et al., 1994) or MUSCLE (Edgar, 2004).

As used herein, the terms "enhancement of DXS activity" and "enhanced DXS" refer to a modified DXS according to the present invention that permit to increase terpenes production and/or accumulation in a host cell, for example plant, bacteria or yeast, transformed by this modified DXS in comparison to a host cell expressing a typical DXS gene.

The expression "typical DXS gene" as used herein is the gene appearing at high frequency, for example the wild type of DXS MoDXS1, also known as SEQ ID No8.

As used herein, the term "mutation" corresponds to any modification in the sequence of the original nucleic acid sequence. These mutations comprise small-scale mutations, or large scale mutations. Small scale mutations are those affecting a gene in one or a few nucleotides, including point mutations, insertions or deletions of one or more extra nucleotides in the DNA. Point mutations can be silent, missense and nonsense mutation. Large scale mutation in the genomic structure, such as gene duplications, deletions, or mutations whose effect is to juxtapose previously separate pieces of DNA, potentially bringing together separate genes to form functionally distinct fusion genes. These last mutations include chromosomal translocations, interstitial deletions, chromosomal inversions and loss of heterozygosity.

Preferably, the present mutation is a point mutation. Point mutations are individual substitutions, deletions or additions which alter, add or delete a single amino acid or a small percentage of amino acids (typically less than 5%, more typically less than 4%, 2% or 1%, or less).

As used herein, the term "mutation site" refers to the locus of the polynucleotide represented by one or several nucleotide that is subject to a mutation as described previously.

The methods for proceeding to said mutations are well known to the man of the art. For example, site-directed mutagenesis can be performed using the QuikChange kit (Stratagene, La Jolla, Calif.)

Site-directed mutagenesis methods have also been described by Zoller & Smith (1982) "Oligonucleotide-directed mutagenesis using M13-derived vectors: an efficient and general procedure for the production of point mutations in any DNA fragment" Nucleic Acids Res. 10:6487-6500

As used herein, the expression "increase terpenes production" means that the amount of terpene produced and/or accumulated in a host cell, for example plant, bacteria or yeast, transformed by this modified DXS is higher than the amount of terpene produced and/or accumulated in a host cell expressing the typical DXS gene.

Preferably, terpene production according to the present invention is increased by a factor ten.

As an example, the mutation K234→C introduced in the polynucleotide encoding the DXS enzyme of *E. coli* permits to increase the terpene production by at least a factor ten.

A second object of the invention relates to a polypeptide of plant or bacteria, having an enhanced DXS activity compared to the typical DXS of said plant or bacteria, likely to be obtained by the method of the present invention.

A third object of the invention relates to an isolated polypeptide having a DXS activity, which comprises a sequence having at least 90% identity with the sequence SEQ ID No21 or fragments thereof, wherein the amino acid at position 213 of SEQ ID No21 is an asparagine and/or the amino acid at position 234 of SEQ ID No21 is a cysteine.

SEQ ID No21 is a consensus of bacterial DXS sequences including *Deinococcus radiodurans*, which has often been characterized in the literature.

In a preferred embodiment, the isolated polypeptide of the invention has the sequence SEQ ID No22 or fragments thereof, wherein the amino acid at position 213 of SEQ ID No22 is an asparagine and/or the amino acid at position 234 of SEQ ID No22 is a cysteine.

SEQ ID No22 is a consensus of bacterial DXS sequences characterized in that it is similar to SEQ ID No21 except that it doesn't encompass the DXS sequence of *D. radiodurans*.

In a more preferred embodiment, the polypeptide of the invention comprises the sequence SEQ ID No19.

In a more preferred embodiment, the polypeptide of the invention comprises the sequence SEQ ID No20.

A fourth object of the invention relates to an isolated polypeptide having a deoxy-D-xylulose synthase (DXS) activity, which comprises a sequence having at least 90% identity with the sequence SEQ ID No1 or fragments thereof, wherein the amino acid at position 310 of SEQ ID No1 is a cysteine and/or the amino acid at position 288 of SEQ ID No1 is an asparagine.

As used herein, the terms "amino acid" and "amino acids" refer to all naturally occurring L-α-amino acids or their residues. The amino acids are identified by either the single-letter or three-letter designations (Asp D aspartic acid; Ile I isoleucine; Thr T threonine; Leu L leucine; Ser 5 serine; Tyr Y tyrosine; Glu E glutamic acid; Phe F phenylalanine; Pro P proline; His H histidine; Gly G glycine; Lys K lysine; Ala A alanine; Arg R arginine; Cys C cysteine; Trp W tryptophan; Val V valine; Gln Q glutamine; Met M methionine; Asn N asparagine).

It will also be understood that natural amino acids may be also replaced by chemically modified amino acids. Typically, such chemically modified amino acids enable to increase the polypeptide half life.

The term "1-deoxy-D-xylulose 5-phosphate synthase" (abbreviated as "DXS") is used herein to mean an enzyme capable of catalyzing a transketolase-type condensation involving pyruvate and glyceraldehyde-3-phosphate (GAP) to form 1-deoxy-D-xylulose-5-phosphate. Said enzymatic activity can be simply determined using a radiolabelled substrate as described by Lois et al. (1998). The enzyme reaction mixture consists of 50 mM Tris-HCl pH=7.5, 2.5 mM MgCl2, 1 mM thiamin diphosphate, 5 mM 2-mercaptoethanol, 0.2 mM [2-14C]pyruvate (15.9 mCi/mmol, NEN), 50 mM pyruvate, 50 mM DL-glyceraldehyde 3-phosphate in a final volume of 50 μL. After incubation for 2 h at 37° C., the reactions are stopped by heating at 80° C. for 3 min. After centrifugation at 13,000 g for 5 min, 10 μL of the supernatant (2-5 ml) are loaded onto a TLC plate (silica gel 60, Merck). Labeled D-1-deoxyxylulose 5-phosphate is separated from [2-14C]pyruvate by using n-propyl alcohol/ethyl acetate/H2O (6:1:3) as solvent and quantified by autoradiography or scintillation counting. Alternatively, a fluorimetric assay of 1-deoxy-D-xylulose 5-phosphate synthase can be used, as described by Querol et al. (2001).

Preferably, the isolated polypeptide of the invention comprises a sequence having at least 90% amino acids sequence identity with the polypeptide sequence SEQ ID No2 or fragments thereof, wherein the amino acid at position 306 of SEQ ID No2 is a cysteine and/or the amino acid at position 284 of SEQ ID No2 is an asparagine.

Still preferably, the polypeptide of the invention has an enzymatic activity, which is at least 50% superior as compared to the polypeptide SEQ ID No3, preferably at least 70%, and most preferably at least 100% superior as compared to SEQ ID No3.

In a more preferred embodiment, the polypeptide of the invention comprises the sequence SEQ ID No4.

In a more preferred embodiment, the polypeptide of the invention comprises the sequence SEQ ID No6.

As used herein, "percentage of identity" between two amino acids sequences, means the percentage of identical amino-acids, between the two sequences to be compared, obtained with the best alignment of said sequences, this percentage being purely statistical and the differences between these two sequences being randomly spread over the amino acids sequences. As used herein, "best alignment" or "optimal alignment", means the alignment for which the determined percentage of identity (see below) is the highest. Sequences comparison between two amino acids sequences are usually realized by comparing these sequences that have been previously aligned according to the best alignment; this comparison is realized on segments of comparison in order to identify and compare the local regions of similarity. The best sequences alignment to perform comparison can be realized, beside by a manual way, by using the global homology algorithm developed by SMITH and WATERMAN (*Ad. App. Math.*, vol. 2, p: 482, 1981), by using the local homology algorithm developed by NEDDLEMAN and WUNSCH (*J. Mol. Biol.*, vol. 48, p: 443, 1970), by using the method of similarities developed by PEARSON and LIPMAN (*Proc. Natl. Acd. Sci. USA*, vol. 85, p: 2444, 1988), by using computer softwares using such algorithms (GAP, BESTFIT, BLAST P, BLAST N, FASTA, TFASTA in the Wisconsin Genetics software Package, Genetics Computer Group, 575 Science Dr., Madison, Wis. USA), by using the MUSCLE multiple alignment algorithms (Edgar, Robert C., *Nucleic Acids Research*, vol. 32, p: 1792, 2004). To get the best local alignment, one can preferably use BLAST software, with the BLOSUM 62 matrix, or the PAM 30 matrix. The identity percentage between two sequences of amino acids is determined by comparing these two sequences optimally aligned, the amino acids sequences being able to comprise additions or deletions in respect to the reference sequence in order to get the optimal alignment between these two sequences. The percentage of identity is calculated by determining the number of identical position between these two sequences, by dividing this number by the total number of compared positions, and by multiplying the result obtained by 100 to get the percentage of identity between these two sequences.

According to a preferred embodiment, the polypeptide of the invention has an identity of at least 95%, preferably of at least 99%, and most preferably of 100% with the amino acids sequences SEQ ID No1 or SEQ ID No2.

As used herein, a fragment of SEQ ID No1 or SEQ ID No2 refers to a polypeptide having a length of at least 300 amino acids, preferably having a length of at least 400 amino acids, more preferably having a length of at least 500 amino acids.

As an example, a fragment of SEQ ID No1 or SEQ ID No2 with a DXS activity, one can cite SEQ ID No5 corresponding to truncated MODXS2 polypeptide, or SEQ ID No7 corresponding to truncated GWDXS2 polypeptide.

As an example, a consensus of plant DXS sequence is SEQ ID No23. It comprises the sequence of DXS of *V. vinifera* (Mo_DXS1), and the sequence of DXS of *A. thaliana, P. densiflora, C. reinhardtii* and *D. salina*.

A fifth object of the invention relates to an isolated polynucleotide encoding for a polypeptide according to the present invention.

The polynucleotide of the present invention may be in the form of RNA or in the form of DNA, preferably in the form of DNA.

The DNA may be double-stranded or single-stranded.

According to a preferred embodiment, the polynucleotide comprises a sequence selected in the group comprising SEQ ID No9 (MODXS2), SEQ ID No10 (GWDXS2), SEQ ID No15 (*E. coli* DXS-K213N) and SEQ ID No16 (*E. coli* DXS-K234C).

A sixth object of the invention relates to a vector comprising the polynucleotide according to the present invention.

Said vector can be a cloning or an expression vector, preferably an expression vector, and may be for example in the form of a plasmid, a cosmid, a phagemid, a viral particle, a phage, etc.

Such vectors may include bacterial plasmids, phage DNA, baculovirus, yeast plasmids, vectors derived from combinations of plasmids and phage DNA, viral DNA such as vaccinia, adenovirus, fowl pox virus, and pseudorabies. Large numbers of suitable vectors are known to those of skill in the art and are commercially available. The following vectors are provided by way of example. Bacterial: pQE70, pQE60, pQE-9 (QIAGEN), pbs, pD10, phagescript, psiX174, pbluescript 5K, pbsks, pNHBA, pNH16a, pNH18A, pNH46A (STRATAGENE), ptrc99a, pKK223-3, pKK233-3, pDR540, pRIT5 (PHARMACIA). Eukaryotic: pWLNEO, p5V2CAT, pOG44, pXT1, p5G (STRATAGENE), p5VK3, pBPV, pMSG, pSVL (PHARMACIA). However, any other vector may be used as long as it is replicable and viable in the host.

The polynucleotide sequence, preferably the DNA sequence in the expression vector is operatively linked to an appropriate expression control sequence(s) (promoter) to direct mRNA synthesis. As representative examples of such promoters, one can mention prokaryotic or eukaryotic promoters such as CMV immediate early, HSV thymidine kinase, early and late SV40, LTRs from retrovirus, and mouse metallothionein-I. The expression vector also contains a ribosome binding site for translation initiation and a transcription vector. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector of the invention containing the appropriate polynucleotide sequence as herein above described, as well as an appropriate promoter or control sequence, may be employed to transform an appropriate host to permit the host to express the polypeptide.

As an example, transcription of a DNA encoding for the polypeptide described previously by higher eukaryotes can be increased by inserting an enhancer sequence into the vector. Enhancers are cis-acting elements of DNA, usually about from 10 to 300 pb that act on a promoter to increase its transcription. Examples of enhancer include the SV40 enhancer, the CMV early promoter enhancer, and adenovirus enhancers.

A seventh object of the invention relates to a transformed host cell comprising the polynucleotide or the vector described previously.

The terms "transformed host cell," "transformed" and "transformation" refer to the introduction of DNA into a cell. The cell is termed a "host cell", and it may be a prokaryotic or a eukaryotic cell. Typical prokaryotic host cells include various strains of *E. coli*. Typical eukaryotic host cells are plant cells, such as maize cells, yeast cells, insect cells or animal cells. The selection of an appropriate host is deemed to be within the scope of those skilled in the art from the teachings herein.

The transformed host cell according to the present invention is a prokaryotic or an eukaryotic cell. The introduction of the polynucleotide or vector described previously into the host cell can be effected by method well known from one of skill in the art such as calcium phosphate transfection, DEAE-Dextran mediated transfection, or electroporation.

According to a preferred embodiment, the transformed host cell according to the present invention is a prokaryotic cell selected in the group comprising eubacterial, archaebacterial and cyano-bacterial cells.

More preferably, the transformed host cell according to the present invention is a prokaryotic cell and even more preferably is an *Escherichia coli* cell.

Prokaryotes may also be used as host cells for the initial cloning steps of this invention. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include *E. coli* K12 strain 94 (ATCC No. 31,446), *E. coli* strain W3110 (ATCC No. 27,325) *E. coli* X1776 (ATCC No. 31,537), and *E. coli* B; however many other strains of *E. coli*, such as HB101, JM101, NM522, NM538, NM539, and many other species and genera of prokaryotes including bacilli such as *Bacillus subtilis*, other enterobacteriaceae such as *Salmonella typhimurium* or *Serratia marcesans*, and various *Pseudomonas* species may all be used as hosts.

According to another preferred embodiment, the transformed host cell according to the present invention is a eukaryotic cell selected in the group comprising animal, fungal, yeast, and plant cells.

Preferably, the eukaryotic cell is a fungal microorganism, more particularly a yeast.

A non-exhaustive list of suitable microorganisms will include the following: a species belonging to the genera *Saccharomyces*—e.g. *S. cerevisiae, S. bayanus, S. pastorianus, S. paradoxus, S. exiguous, S. servazzi, S. uvarum, S. kluyveri,* and *S. castellii*—, a species belonging to the genera *Kluyveromyces*—e.g. *K. lactis, K marxianus* var. *marxianus, K. thermotolorens, K waltii, K. delphensis, K. nonfermentas,* and *K. wickerhamii*—a species belonging to the genera *Candida*—e.g. *C. utilis, C. tropicalis, C. castellii,* and *C. humilis*—, a species belonging to the genera *Zygosaccharomyces*—e.g. *Z. rouxii, Z bailii, Z. fermentati, Z. bisporus,* and *Z. florentinus*—, a species belonging to the genera *Pichia*—e.g. *P. stipidis, P. pastoris, P. sorbithophila,* and *P. anomala*—, or other species—e.g. *Hansenula polymorpha, Yarrowia lipolytica, Debaromyces hansenii, Schizosaccharomyces pombe, Torulaspora delbueckii, Ashbya gossipie, Aspergillus niger, Aspergillus awamori, Aspergillus oryzae, Aspergillus nidulans, Penecillium chrysogenum, Rhizopus oryzae,* and *Mucor circenelloides*—.

More preferably, the eukaryotic cell is yeast and even more preferably, the microorganism is *Saccharomyces cerevisiae*. For example, it is the *S. cerevisiae* strain deposited at DSMZ-Deutsche Sammlung von Mikroorganismen and Zellkulturen GmbH. Mascheroder Weg 1b, D-38124 Braunschweig, Germany, accession number: DSMZ 17900, on Jan. 27, 2006.

A heterologous pathway, for the purpose of the present invention, is a pathway which, in its activity to form a compound by defined intermediate steps and from defined starting materials, is not present in the wild-type of the microorganism. More preferably, the heterologous pathway is a pathway derived from DNA of a different species.

Alternatively, the eukaryotic cell is a plant cell, more preferably a plant cell selected in the group comprising *Vitis vinifera, Nicotiana tabacum,* and *Arabidopsis thaliana* cells, even more preferably said plant cell is a *Vitis vinifera* cell, preferably a *Vitis vinifera* Cv Muscat Ottonel or a *Vitis vinifera* Cv Gewurztraminer cell, more preferably a *Vitis vinifera* Cv Gewurztraminer cell.

An eighth object of the invention relates to a transgenic bacterium comprising the polynucleotide or the vector described previously.

A ninth object of the invention relates to a transgenic plant comprising the polynucleotide, the vector or the host cell described previously.

Transformation of cultured plant host cells is normally accomplished through *Agrobacterium tumifaciens*. Thus, transgenic plants can be obtained, for example, by transferring vector of the present invention (i.e. encoding 1-deoxyxylulose-5-phosphate synthase) and a selectable marker gene (e.g., the kan gene encoding resistance to kanamycin) into *Agrobacterium tumifaciens* containing a helper Ti plasmid as described in HOECKEMA et al. (*Nature*, 303:179-181, 1983) and culturing the Agrobacterium cells with leaf slices, or other tissues or cells, of the plant to be transformed as described by A N et at (Plant Physiology, 81:301-305, 1986). However, other methods for introducing DNA into cells can be used such as Polybrene (Kawai and Nishizawa, Mol. Cell. Biol., 4:1172 [1984]), protoplast fusion (Schaffner, Proc. Natal. Acad. Sci. USA, 77:2163 [1980]), electroporation (Neumann et al., EMBO J., 1:841 [1982]), and direct microinjection into nuclei (Capecchi, Cell, 22:479 [1980]).

Transformed plant calli may be selected through the selectable marker by growing the cells on a medium containing, e.g., kanamycin, and appropriate amounts of phytohormone such as naphthalene acetic acid and benzyladenine for callus and shoot induction. The plant cells may then be regenerated and the resulting plants transferred to soil using techniques well known to those skilled in the art.

According to a preferred embodiment, the transgenic plant of the invention has incorporated into its genome a polynucleotide or a vector as described previously.

Preferably said plant is selected in the group comprising trees, vegetables, succulents and ornamental plants.

Still preferably, said transgenic plant is resistant to clomazone also called dimethazone (FMC 57020; 2-(2-chlorophenyl)methyl-4,4-dimethyl-3-isoxalidinone).

As used herein a transgenic plant which is resistant to clomazone corresponds to a plant which grows in the presence of 10 μM clomazone (Carretero-Paulet L, Cairó A, Batella-Pavía P, Besumbes O, Campos N, Boronat A, Rodríguez-Concepción M. (2006) Enhanced flux through the methylerythritol 4-phosphate pathway in Arabidopsis plants overexpressing deoxyxylulose 5-phosphate reductoisomerase. Plant Mol Biol 62: 683-95).

Still preferably, said transgenic plant has enhanced aromas.

As an example, said transgenic plant is selected in the group comprising *Lamiaceae* (e.g. *Ocimum* (basil), *Lavandula* (Lavender), *Origanum* (oregano), *Mentha* (mint), *Salvia* (sage), *Rosmecinus* (rosemary), *Thymus* (thyme), *Satureja* and *Monarda); Umbelliferae* (e.g. *Carum* (caraway), *Anethum* (dill), *feniculum* (fennel) and *baucus* (carrot)); *Asteraceae* (Compositae) (e.g. *Artemisia* (tarragon, sage brush), and *Tanacetum* (tansy)); *Rutaceae* (e.g., citrus plants); *Rosaceae* (e.g., roses); *Myrtaceae* (e.g., eucalyptus, *Melaleuca*); the *Gramineae* (e.g., *Cymbopogon* (citronella)); *Geranaceae* (Geranium) and certain conifers including *Abies* (e.g., Canadian balsam), *Cedrus* (cedar) and *Thuja* and *Juniperus*.

A tenth object of the invention relates to a progeny of any generation of the transgenic plant of the present invention, said progeny comprising the polypeptide—, the polynucleotide—, the vector—, or the host cell described previously.

Said progeny can have the form of a plant or of a seed.

An eleventh object of the invention relates to a method of preparing a transgenic plant as described previously, comprising the steps of:
 a. transforming a plant cell with a vector as described previously;
 b. selecting a transformed plant cell which express a polypeptide as described previously; and
 c. generating a transgenic plant from said transformed plant cell.

The step (a) of transformation can be done by well known methods as described previously such as electroporation, transfection, naked DNA uptake, protoplast generation, direct transfer of DNA into pollen, embryo or pluripotent plant cell, Agro-bacterium-mediated transformation, particle bombardment, or microprojectile bombardment.

The step (b) of selection can be done by well known methods.

The step (c) of generating a clomazone-resistant transgenic plant from said transformed plant cell can be done by well known methods like the generation of pluripotent plant cells from said transformed plant cell.

According to a preferred embodiment, said method is for preparing a plant seed, said method further comprises the step of:
 d. obtaining a seed from said transgenic plant.

According to a particular embodiment, the method of the invention is for obtaining a transgenic plant which is resistant to clomazone.

Preferably, said transgenic plant is obtained by well known methods such as those described in Klee H, Horsch R, Rogers 5 (1987) *Agrobacterium*-Mediated Plant Transformation and its Further Applications to Plant Biology. Annual Review of Plant Physiology 38, 467-486 and Potrykus I (1991) Gene Transfer to Plants: Assessment of Published Approaches and Results. Annual Review of Plant Physiology and Plant Molecular Biology 42, 205-225.

According to another particular embodiment, the method of the invention is for obtaining a transgenic plant which has enhanced terpene biosynthetic capabilities. A plant with enhanced terpene biosynthetic capabilities will synthesis a least 50% more of terpenes as compared to the wild type of said transgenic plant, preferably at least 70%, more preferably at least 100%.

Preferably, terpene relates to geraniol, linalol, citronellol, nerol and alpha-terpineol.

Preferably, the polypeptide of the invention has an enzymatic activity, which is at least 50% superior as compared to the polypeptide SEQ ID No3, preferably at least 70%, and most preferably at least 100% superior as compared to SEQ ID No3.

Said plant having terpene biosynthetic capabilities may be aromatic plants as for example *Mentha piperita, Lavandula latifolia*, or *Rosmarinus officinalis* and medicinal plants, as for example *Artemisia annus, Taxus baccata, Catharanthus roseus*, or *Lithospermum erythrorhizon* as well as any plant species producing valuable terpene compounds, as for example plants producing carotenoids, as *Lycopersicon esculentum, Manihot esculenta*, or *Oryza sativa*.

Preferably, said transgenic plant is selected by well known methods such as those described in Klee et al. (1987) and Potrykus (1991).

A twelfth object of the invention relates to a method of production of enhanced DXS enzyme which increases terpenes production in plants, bacteria or yeast comprising the following steps:
  a. Culturing a transformed host cell as defined previously;
  b. Obtaining an enhanced DXS enzyme which permit to increase terpenes production in plants or bacteria.

Preferably, the polypeptide having an enhanced DXS activity is likely to be obtained by the method described previously.

A thirteenth object of the invention relates to a method of production of terpenes in a host cell comprising the steps of:
  a. Culturing a transformed host cell as defined previously under conditions effective to produce the terpene. (e.g., plant, bacteria or yeast cell) as described previously under conditions effective to produce more terpene substrate (monoterpene, diterpene, triterpene, and/or polyterpene) by the DXS2 enzyme, said production of more terpene substrate resulting in production of more terpene by enzymatic modification of the terpene substrate.
  b. Obtaining said terpene from said host cell A terpene is a saturated or unsaturated, optionally substituted hydrocarbon based on, or composed essentially of, isoprene units ($C_5$). Terpenes may be acyclic or cyclic. Terpenes, as used herein include terpenes, terpene derivatives, and compounds referred to as terpenoids, which may or may not fall in one of the two foregoing classes of compounds. Terpene derivatives include compounds that have undergone one or more steps of functionalization such as hydroxylations, isomerizations, oxido-reductions or acylations, for example. Preferably, for the purpose of the present invention, a terpene is a compound which fulfils the above condition and/or whose carbon skeleton originates, at least in part but preferably totally, from the MEP and/or MEV pathway. Accordingly, terpenes include terpene alcohols, for example $C_{15}H_{26}O$ and $C_{10}H_{18}O$ compounds such as patchoulol, epi-cedrol, cubebol, linalool, nerolidol, for example, and dialcohols, for example sclareol. Terpenes also include diphosphate compounds such as bornyl-diphosphate (monoterpene) and copalyl-diphosphate (diterpene), just to mention a few specimens of the vast category of terpenes.

As used herein, a "derivative" is any compound obtained from a known or putative compound and containing essential elements of the parent substance.

For example, terpenes are compounds having carbon skeletons of $C_{10}$, $C_{15}$, $C_{20}$, $C_{30}$, $C_{40}$, $C_{45}$ and so forth.

Accordingly, the term "terpene" encompasses mono, sesqui, di, tri, tetra and/or polyterpenes.

Preferably, said terpenes comprise geraniol, linalol, citronellol, nerol and alpha-terpineol.

According to a preferred embodiment, the microorganism of the invention provides a yield of at least 30 µg, more preferably at least 100 µg of terpene per g fresh-weight of the microorganism. The terpene yield of a microorganism is preferably established by the protocol in Example 2.

The terpenes may accumulate in the cells. For example, they may accumulate in the cytoplasm, in mitochondria, cellular membranes or other cell organelles. Many terpenes are lipophilic compounds, which accumulate in the plasma membrane of the cell.

For the purpose of the present invention, the term "accumulating in the medium" also encompasses accumulation in a solvent during a two-phase fermentation process.

The method comprises the step of cultivating the transformed host cell under conditions conducive to the production of said terpene. These conditions are known to the skilled person. Generally, they may be adjusted by selection of an adequate medium, fermentation vessel, temperature, and pH.

The method for producing a terpene may comprise the step of isolating the terpene from the medium, from the cells and/or from an organic solvent, in case a two-phase fermentation is performed. The terpene may be isolated by any method used in the art including but not limited to chromatography, extraction and distillation, for example.

It is well known to the man skilled in the art that, for example, monoterpenes are normally produced in the plastid, and that sesquiterpenes in the cytosol.

In contrast to plants, microbial systems are more amenable to large-sale engineering projects where many different modifications may be compared and combined. However, microbes do suffer some technical drawbacks compared with plants, particularly when it comes to expressing heterologous genes.

A fourteenth object of the invention relates to a method of selecting an aromatic plant comprising the steps of:
  a. Identifying at least one mutation of DXS that lead to an allelic variation of DXS with enhanced synthesis of terpene and/or analysis of the accumulation of terpene in the biological sample of said plant
  b. Selecting the plant comprising said mutation.

A fifteenth object of the invention relates to a method of producing a DXS enzyme which are more resistant to clomazone comprising the steps of:
  a. Culturing a transformed host cell as described previously;
  b. Obtaining a DXS enzyme which is more resistant to clomazone from cell extract, cell suspension, protein fraction, crystal fraction, cell culture, cell homogenate, cell lysate, cell supernatant, cell filtrate, or cell pellet of said transformed host cell.

The following examples are included to demonstrate preferred embodiments of the invention. It should be appreciated by those of skill in the art that the techniques disclosed in the following examples represent well-functioning techniques to the practice of the invention as discovered by the inventor, and thus can be considered to constitute preferred modes for its practice.

EXAMPLES

1) Cloning of DXS cDNAs from *Vitis vinifera* cv Muscat Ottonel and Gewurztraminer DXS cDNAs from *Vitis vinifera* cv Muscat Ottonel (MO) and Gewurztraminer (Gw) were amplified using RT-PCR and cloned. Sequencing of these clones revealed that both MO and Gw are heterozygous at the DXS locus. MO and Gw share the same allele designated MoDXS1 (FIG. 1). In addition, Mo and Gw possess the MoDXS2 and GwDXS2 alleles, respectively. MoDXS2 and GwDXS2 alleles differ from MoDXS1 in 2 and 1 SNP, respectively, which modify the amino-acid sequence of the corresponding proteins (FIG. 2). The K284→N and R306→C mutations (in reference to SEQ ID No2), characteristic of MoDXS2 and GwDXS2, respectively, affect amino-acids that are conserved in all plant DXS sequences available in databases (FIG. 3). Furthermore, the amino-acids K284 and R306 belong to the active site of the enzyme (Xiang et al., 2007), indicating that they may modify the activity of the MoDXS2 and GwDXS2 alleles, in comparison to MoDXS1.

2) Impact of the MoDXS2 and GwDXS2 Alleles on Terpenol Content in Grape Berries

Material and Methods:
Isolation of Free and Bound Monoterpenols by Solid Phase Extraction (SPE)

For each sampling point, three replicates of terpenol analysis were performed. For each replicate, at least 25 berries were used. Seeds were removed and skins separated from mesocarps. After weighing, skins were ground under liquid nitrogen and then suspended in 40 mL of water after addition of 40 mg of sodium sulphite. The supernatant obtained after a 15-min centrifugation (11400 g at 4° C.) was passed through a glass fibre pre-filter and a glass filter. Twenty microliters of a 1 g/L 4-nonanol solution was added as external standard to allow the quantification of the main terpenols. Extraction of terpenols was adapted from Mateo et al. (1997), ethanol being used instead of methanol. The filtrate was passed through a 1 g phase C18 silica-bonded non-polar SPE column (BOND ELUT JR.), previously washed with 5 mL of methanol and 15 mL of ultra-pure water, at a rate of approximately one drop/s. The sample was then divided in two equal subsamples, one for the analysis of free and glycosidically bound monoterpenols and one for the analysis of free terpenols. Total fractions of free and bound monoterpenols were eluted with 4 mL of absolute ethanol. This total terpenol extract was diluted in 40 mL of citrate/phosphate buffer (pH 4.5) and the resulting solution was incubated with 50 mg of AR2000 glycolytic enzyme (Gist-Brocades, Seclin, France) overnight at 37.5° C. to release the glycosidically bound terpenols (Tamborra et al. 2004). The released terpenols were separated by SPE on a C18 column and eluted with 4 mL of dichloromethane after rinsing with 3×5 mL water. For free terpenol analysis, the hydrolysis step was not performed and terpenols were directly eluted with dichloromethane after rinsing with water. Extracts were dried in Pasteur pipettes filled with 0.5 g of anhydrous sodium sulphite and concentrated to 500 µL under a gentle nitrogen flux. Twenty microliters of a 1 g/L solution of m-cresol was added to each sample as internal control. Samples were stored at −20° C. prior to gas chromatography (GC) analysis.

Results:
Example 2 shows that DXS alleles have a major impact on terpenol content in grape berries, as shown by the investigation of terpenol contents as a function of DXS alleles in a MO (FIG. 4) and in a GW (FIG. 5) progeny. MoDXS1 (=GwDXS1) homozygous genotypes exhibit extremely low levels of terpenols, whereas heterozygous or DXS2 homozygous genotypes accumulate large amounts of terpenols.

3) Functional Characterization of DXS Alleles in Plants

In order to characterize DXS alleles activity, the inventors used Agrobacterium-mediated transient transformation of tobacco (Nicotiana benthamiana), which allows a fast and efficient gene expression in tobacco leaves (Batoko et al., 2000). This approach was already used successfully to characterize genes involved in grapevine secondary metabolism (Schmidlin et al., 2008; Hugueney et al., 2009). MoDXS1, MoDXS2 and GwDXS2 alleles were expressed in tobacco leaves, together with a cDNA encoding the enzyme geraniol synthase (GES) from basilicum (Ocimum basalicum) (Iijima et al., 2004). In this system, GE5 was used as a reporter gene responsible for the biosynthesis of the monoterpenol geraniol, which normally does not accumulate in tobacco. As DXS activity has been shown to be limiting for terpenes biosynthesis in plants (Estevez et al., 2001; Enfissi et al., 2005), the amount of geraniol formed by GES activity depended directly on DXP substrate availability, and therefore, on DXS activity in tobacco leaves. Thus, GC-M5 analyses of tobacco leaves co-expressing GES and DXS alleles allowed an accurate comparison of DXS alleles activity in planta.

Material and Methods:
Grapevine DXS cDNAs were amplified by PCR using the upstream primer 5'-GGGGACAAGTTTGTA-CAAAAAAGCAGGCTTGGTTCCGCGTGGATCAATG-GCTCTCTG TACGCTCTCATTTCC-3' (SEQ ID No11) and the downstream primer 5'-GGGGACCACTTTGTA-CAAGAAAGCTGGGTTCACTATAACATGATCTCCA-GGGCCTCC-3' (SEQ ID No12), and cloned into the pDONR207 Gateway compatible vector (Invitrogen, Carlsbad, Calif.) using Gateway BP clonase (Invitrogen) according to the manufacturer's instructions. DXS cDNAs were sequenced to verify that no mutation had been introduced. For Agrobacterium-mediated transient expression, DXS cDNAs were subsequently transferred into the GATEWAY binary vector pMDC32 (Curtis and Grossniklaus., 2003). Geraniol synthase cDNA from basilicum (Ocimum basilicum) (Iijima et al., 2004) was cloned into the GATEWAY binary vector pMDC83 (Curtis and Grossniklaus., 2003) and expressed as a GFP fusion protein. All constructs were introduced into Agrobacterium tumefaciens strain C58 (pMP90) by electroporation. Nicotiana benthamiana leaves were infiltrated with A. tumefaciens cultures (OD600 0.5) according to Voinnet et al. (2003). Leaf sectors were and analysed for terpene content 96 h after Agrobacterium infiltration.

Then, an extraction of terpenols from tobacco leaves was realized:

For each sampling point, three replicates of terpenol analysis were performed. After weighing, tobacco leaf sectors (about 1 g) were ground under liquid nitrogen and then suspended in 2 mL of ultra-pure water. After a 5-min centrifugation (6000 g at 4° C.), the supernatant was colleted and 20 µL of a 1 g/L 4-nonanol solution was added as an external standard. The supernatant was passed through a 1 g phase C18 silica-bonded non-polar SPE column (Bond Elut Jr., Varian), previously washed with 5 mL of methanol and 15 mL of ultra-pure water. Total terpenols were eluted with 2 mL of absolute ethanol. This total terpenol extract was diluted in 20 mL of citrate/phosphate buffer (pH 4.5) and the resulting solution was incubated with 25 mg of AR2000 glycolytic enzyme (Gist-Brocades, Seclin, France) overnight at 37.5° C. The released terpenols were separated by SPE on a C18 column and eluted with 4 mL of dichloromethane after washing with 3×5 mL water. Extracts were dried in Pasteur pipettes filled with 0.5 g of anhydrous sodium sulphite and concentrated to 500 µL under a gentle nitrogen flux. Twenty microliters of a 1 g/L solution of m-cresol was added to each sample as internal control. Samples were stored at −20° C. prior to gas chromatography (GC) analysis.

Finally, the terpenes were analysed by gas chromatography and mass spectrometry (GC-MS) using an Agilent 6890N gas chromatograph equipped with a Gerstel MPS2 XL sampler and coupled to an Agilent 5975B inert mass spectrometer (Agilent Technologies). The gas chromatograph was fitted with a DB-Wax capillary column (60 m×0.32 mm i.d.×0.5 µm film thickness, J&W Scientific) and helium was used as carrier gas (1 ml min-1 constant flow). The GC oven temperature was programmed without initial hold time from 45° C. to 82° C. at a rate of 20° C. min-1 (hold 1 min) then from 82° C. to 235° C. (hold 15 min) at a rate of 2.7° C./min. The injector was set to 250° C. and used in pulsed splitless mode (25 psi for 0.50 min). The temperatures of the interface, MS ion source and quadrupole were 270° C., 230° C. and 150° C., respectively. The Mass spectrometer was operated in electron impact ionization mode (EI, 70 eV) and the masses were scanned over a m/z range of 29-300 amu. Agilent MSD ChemStation software (G1701DA, Rev D.03.00) was used for instrument control and data processing. The mass spectra were compared with the Wiley's library reference spectral bank.

Results:

*Agrobacterium*-mediated transient expression of GES alone led to the accumulation of significant amounts of geraniol, whose biosynthesis depended on the endogenous DXS activity in tobacco (FIG. 6, FIG. 7). Co-expression of GES and MoDXS1 led to substantial increases in geraniol biosynthesis, due to the enhanced DXP substrate availability. However, co-expression of GES and MoDXS2 or GwDXS2 led, in average, to a three time increase in geraniol accumulation in tobacco leaves (FIG. 7), indicating that these alleles possessed an enhanced DXS activity, compared to MoDXS1.

Therefore, the inventors conclude that the massive accumulation of terpenols in MO and GW is due to the presence of the MoDXS2 or GwDXS2. The K284→N and R306→C mutations, which affect amino-acids in the active site of the enzyme, confer an enhanced DXS activity compared to MoDXS1, which in turn is responsible for the increased accumulation of terpenes in planta.

The aim of the following experiments is to investigate whether the role of these mutations can be extended to DXS enzymes from other sources. As a model, the inventors have selected the DXS from *Escherichia coli*, whose enzymatic properties are well characterized (Querol et al., 2001; Xiang et al., 2007).

Comparison of the DXS proteins sequences from *E. coli* and *V. vinifera* indicated that the amino acid K284 and R306 in grapevine DXS correspond to K213 and K234 in the DXS from *E. coli*, respectively (FIG. 10). In order to assess the impact of MO- and GW-like mutations on the activity of a non-plant DXS, the mutations K213→N and the K234→C were introduced in the DXS protein of *E. coli*. The impacts of these mutations on the terpene biosynthetic capabilities of *E. coli* were subsequently investigated.

4) Cloning and Site-Directed Mutagenesis of the DXS Gene from *Escherichia coli*

Material and Methods:

The DXS gene from *Escherichia coli* (Lois et al., 1998) was amplified by PCR using the upstream primer GGGGA-CAAGTTTGTACAAAAAAGCAGGCTTGGTTC-CGCGTGGATCAATGAGTTTTG ATATTGC-CAAATACCC (SEQ ID No24) and the downstream primer GGGGACCACTTTGTACAAGAAAGCTGGGTTCAT-TATGCCAGCCAGGCCTTGATTTTG (SEQ ID No25) and cloned into the pDONR207 Gateway compatible vector (A technology that enables rapid cloning of one or more genes. The entry vector confers resistance to gentamycin) (Invitrogen, Carlsbad, Calif.) using BP clonase, a mixture of proteins that catalyse the in vitro recombination of PCR products or DNA segments from clones, (Invitrogen) according to the manufacturer's instructions. The DXS gene was subsequently transferred into the GATEWAY-compatible expression vector pHGWA (Busso et al., 2003) using LR clonase, a mixture of enzymes that catalyse the in vitro recombination between an entry clone and a destination vector to generate the expression clone, (Invitrogen), yielding the plasmid pHGWA-*Ecoli*DXS. This plasmid was used for site-directed mutagenesis, in order to introduce the K213→N and the K234→C mutations into the DXS protein form *E. coli*. Site-directed mutagenesis was performed using the QuikChange kit (Stratagene, La Jolla, Calif.) according to the manufacturer's instructions. QuikChange kit is based on mutagenic primers and DNA polymerase. It is designed to help introduce single or multiple point mutations into a gene of choice to produce enzymes mutants with amino acids changes, insertions or deletions.

The forward primer GCGC-GAAGGCGGGAACAAAGTTTTCTCTGGCGTGCC (SEQ ID No26) and the reverse primer GGCACGCCAGA-GAAAACTTTGTTCCCGCCTTCGCGC (SEQ ID No27) were used to introduce the K213→N mutation, yielding the plasmid pHGWA-*Ecoli*DXS-K213N.

The forward primer CGCACCGAAGAACATATTT-GCGGCATGGTAGTGCCTGG (SEQ ID No28) and the reverse primer CCAGGCACTACCATGCCGCAAATAT-GTTCTTCGGTGCG (SEQ ID No29) were used to introduce the K234→C mutation, yielding the plasmid pHGWA-*Ecoli*DXS-K234C.

Results:

During the site-directed mutagenesis, a mutant DXS gene harbouring a frameshift was isolated. This frameshift resulted in the synthesis of a truncated DXS protein, which was used as a control. The plasmid encoding this truncated DXS is termed pHGWA-truncated-*Ecoli*DXS.

5) Expression of Wild Type and Mutant *E. coli* DXS Proteins in *E. coli*

Material and Methods:

pHGWA-*Ecoli*DXS, pHGWA-truncated-*Ecoli*DXS, pHGWA-*Ecoli*DXS-K213N and pHGWA-*Ecoli*DXS-K234C plasmids were transformed into the BL21-Gold (DE3)pLysS *E. coli* strain (Stratagene, La Jolla, Calif.). BL21-Gold(DE3)pLysS *E. coli* strain are competent cells that provide increased transformation efficiency. They are resistant to tetracycline and chloramphenicol. Transformants were grown at 28° C. in 50 mL LB medium supplemented with glucose (10 g/L), in the presence of ampicillin (100 µg/mL), chloramphenicol (25 µg/mL), and tetracyclin (2 µg/mL). When the cultures reached an OD of 0.1, DXS expression was induced with 1 mM of isopropyl β-D-1-thiogalactopyranoside (IPTG) and the culture was grown for 24 h.

6) Impact of DXS Mutants on Terpene Biosynthesis in *E. coli*

The impact of MO- and GW-like mutations (K213→N and K234→C, respectively) on the activity the DXS enzyme from *E. coli* was assessed by quantifying the terpenes in culture media, after induction of DXS expression.

Material and Methods:

Analysis of terpenes in *E. coli* culture media

Terpenes in culture media were analysed using stir bar sorptive extraction (SBSE), using a method adapted from Coelho et al. (2009). A stir bar with PDMS coating (0.5 mm×10 mm; Twister; Gerstel, Mullheim, Germany) was introduced into each culture medium sample (10 mL). Extractions were performed at 20° C. for 150 min, at a rotation speed of 800 rpm. Terpenes were then analysed by gas chromatography and mass spectrometry (GC-MS) using an Agilent 6890N gas chromatograph equipped with a Gerstel MPS2 XL sampler and coupled to an Agilent 5975B mass spectrometer (Agilent Technologies), as described above.

Results:

Example shows that the mutations introduced in the DXS from *E. coli* impact the monoterpene content in culture media (FIG. 5). In particular, the mutation K234→C in the DXS from *E. coli* leads to a greatly enhanced accumulation of terpenes in culture media. Therefore, the inventors conclude that non-plant DXS enzymes can be modified at the positions corresponding to K284 and R306 in the DXS proteins of grapevine, in order to improve DXS activity. Such improved DXS mutants may be used for the metabolic engineering of microorganisms, in order to enhance the production of isoprenoids of interest.

We claim:

1. An isolated polypeptide of bacteria, the polypeptide having 1-deoxy-D-xylulose 5-phosphate synthase (DXS) activity,
   wherein the polypeptide has at least 90% sequence identity with SEQ ID NO: 21,
   wherein the polypeptide has an amino acid at position 213 of SEQ ID NO: 21 that is substituted with an asparagine, and/or an amino acid at position 234 of SEQ ID NO: 21 that is substituted with a cysteine,
   and wherein the polypeptide has enhanced DXS activity and increases the production of terpene greater than a corresponding polypeptide not having said substitutions.

2. The polypeptide of claim 1, wherein said polypeptide comprises the sequence SEQ ID NO: 19.

3. The polypeptide of claim 1, wherein said polypeptide comprises the sequence SEQ ID NO: 20.

4. An isolated polynucleotide comprising a sequence that encodes the polypeptide as defined in claim 1.

5. A vector comprising the polynucleotide as defined in claim 4.

6. A recombinant host cell comprising the polynucleotide as defined in claim 4, wherein the recombinant host cell is transformed to express the polypeptide in a higher quantity than a host cell not so transformed.

7. The host cell of claim 6, wherein said host cell is a prokaryotic cell selected from the group consisting of eubacterial, archaebacterial and cyano-bacterial cells.

8. The host cell of claim 7, wherein said host cell is an *Escherichia coli* cell.

9. The host cell of claim 6, wherein said host cell is a eukaryotic cell selected in the group comprising animal, fungal, yeast, and plant cells.

10. The host cell of claim 9, wherein said transformed host cell is a plant cell selected from the group consisting of *Vitisvinifera, Nicotianatabacum*, and *Arabidopsis thaliana* cells.

11. A transgenic plant comprising the polynucleotide as defined in claim 4, a vector comprising said polynucleotide, or a recombinant host cell comprising said polynucleotide or vector.

12. A method of preparing a transgenic plant comprising a polynucleotide comprising a sequence that encodes a polypeptide of bacteria, the polypeptide having 1-deoxy-D-xylulose 5-phosphate synthase (DXS) activity, the method comprising the steps of:
   a. transforming a plant cell with the vector as defined in claim 5;
   b. selecting a transformed plant cell which expresses said polypeptide; and
   c. generating a transgenic plant from said transformed plant cell.

13. A method of production of a 1-deoxy-D-xylulose 5-phosphate synthase (DXS) enzyme which increases terpenes production in plants, bacteria or yeast, comprising the following steps:
   a. cultivating the recombinant host cell as defined in claim 6 under conditions conducive to the production of said DXS enzyme; and
   b. Obtaining the DXS enzyme having enhanced enzyme activity, which permits increased terpenes production in plants, bacteria or yeast.

14. A method of production of terpene in a host cell, comprising the following steps:
   a. cultivating the recombinant host cell as defined in claim 6 under conditions conducive to production of the terpene, the recombinant host cell being transformed to express the polypeptide encoded by the polynucleotide;
   b. Obtaining said terpene from said host cell.

* * * * *

SEQUENCE LISTING

```
<160> NUMBER OF SEQ ID NOS: 29

<210> SEQ ID NO 1
<211> LENGTH: 720
<212> TYPE: PRT
<213> ORGANISM: Artificial sequence
<220> FEATURE:
<223> OTHER INFORMATION: plant DXS consens sequence
<220> FEATURE:
<221> NAME/KEY: MISC_FEATURE
<222> LOCATION: (3)..(3)
<223> OTHER INFORMATION: X=L or S
<220> FEATURE:
<221> NAME/KEY: MISC_FEATURE
<222> LOCATION: (4)..(4)
<223> OTHER INFORMATION: X=C or S
<220> FEATURE:
<221> NAME/KEY: MISC_FEATURE
<222> LOCATION: (5)..(5)
<223> OTHER INFORMATION: X= T, N or A
<220> FEATURE:
<221> NAME/KEY: MISC_FEATURE
<222> LOCATION: (6)..(6)
<223> OTHER INFORMATION: X= L, F or Y
<220> FEATURE:
<221> NAME/KEY: MISC_FEATURE
<222> LOCATION: (7)..(7)
<223> OTHER INFORMATION: X= S or A
<220> FEATURE:
<221> NAME/KEY: MISC_FEATURE
<222> LOCATION: (8)..(8)
<223> OTHER INFORMATION: X= F or V
<220> FEATURE:
<221> NAME/KEY: MISC_FEATURE
<222> LOCATION: (10)..(10)
<223> OTHER INFORMATION: X= A, S or G
<220> FEATURE:
<221> NAME/KEY: MISC_FEATURE
<222> LOCATION: (11)..(11)
<223> OTHER INFORMATION: X= H, Y or I
<220> FEATURE:
<221> NAME/KEY: MISC_FEATURE
<222> LOCATION: (12)..(12)
<223> OTHER INFORMATION: X=F, I or L
<220> FEATURE:
<221> NAME/KEY: MISC_FEATURE
<222> LOCATION: (13)..(13)
<223> OTHER INFORMATION: X=S, I or N
<220> FEATURE:
<221> NAME/KEY: MISC_FEATURE
<222> LOCATION: (14)..(14)
<223> OTHER INFORMATION: X= Q, T or R
<220> FEATURE:
<221> NAME/KEY: MISC_FEATURE
<222> LOCATION: (15)..(15)
<223> OTHER INFORMATION: X= A, K or T
<220> FEATURE:
<221> NAME/KEY: MISC_FEATURE
<222> LOCATION: (16)..(16)
```

```
<223> OTHER INFORMATION: X= G, V or no amino acids
<220> FEATURE:
<221> NAME/KEY: MISC_FEATURE
<222> LOCATION: (17)..(17)
<223> OTHER INFORMATION: X= G, A or no amino acid
<220> FEATURE:
<221> NAME/KEY: MISC_FEATURE
<222> LOCATION: (18)..(18)
<223> OTHER INFORMATION: X= A, L or V
<220> FEATURE:
<221> NAME/KEY: MISC_FEATURE
<222> LOCATION: (19)..(19)
<223> OTHER INFORMATION: X= A or S
<220> FEATURE:
<221> NAME/KEY: MISC_FEATURE
<222> LOCATION: (20)..(20)
<223> OTHER INFORMATION: X= S or T
<220> FEATURE:
<221> NAME/KEY: MISC_FEATURE
<222> LOCATION: (21)..(21)
<223> OTHER INFORMATION: X= N or D
<220> FEATURE:
<221> NAME/KEY: MISC_FEATURE
<222> LOCATION: (22)..(22)
<223> OTHER INFORMATION: X= P, S, A or Y
<220> FEATURE:
<221> NAME/KEY: MISC_FEATURE
<222> LOCATION: (23)..(23)
<223> OTHER INFORMATION: X= Q, C or S
<220> FEATURE:
<221> NAME/KEY: MISC_FEATURE
<222> LOCATION: (24)..(24)
<223> OTHER INFORMATION: X= R or K
<220> FEATURE:
<221> NAME/KEY: MISC_FEATURE
<222> LOCATION: (25)..(25)
<223> OTHER INFORMATION: X=L, S, P or Q
<220> FEATURE:
<221> NAME/KEY: MISC_FEATURE
<222> LOCATION: (26)..(26)
<223> OTHER INFORMATION: X= T, L or S
<220> FEATURE:
<221> NAME/KEY: MISC_FEATURE
<222> LOCATION: (27)..(27)
<223> OTHER INFORMATION: X= P or S
<220> FEATURE:
<221> NAME/KEY: MISC_FEATURE
<222> LOCATION: (28)..(28)
<223> OTHER INFORMATION: X= Q or L
<220> FEATURE:
<221> NAME/KEY: MISC_FEATURE
<222> LOCATION: (29)..(29)
<223> OTHER INFORMATION: X= C, F, S or P
<220> FEATURE:
<221> NAME/KEY: MISC_FEATURE
<222> LOCATION: (31)..(31)
<223> OTHER INFORMATION: X= H, S or E
<220> FEATURE:
<221> NAME/KEY: MISC_FEATURE
<222> LOCATION: (32)..(32)
<223> OTHER INFORMATION: X= L, R, S or W
<220> FEATURE:
<221> NAME/KEY: MISC_FEATURE
<222> LOCATION: (33)..(33)
<223> OTHER INFORMATION: X= F, S, I or Q
<220> FEATURE:
<221> NAME/KEY: MISC_FEATURE
<222> LOCATION: (34)..(34)
<223> OTHER INFORMATION: X= L, H or W
<220> FEATURE:
<221> NAME/KEY: MISC_FEATURE
<222> LOCATION: (35)..(35)
<223> OTHER INFORMATION: X= G or V
<220> FEATURE:
<221> NAME/KEY: MISC_FEATURE
<222> LOCATION: (36)..(36)
<223> OTHER INFORMATION: X= no amino acid, V or T
<220> FEATURE:
<221> NAME/KEY: MISC_FEATURE
```

```
<222> LOCATION: (37)..(37)
<223> OTHER INFORMATION: X= D or no amino acid
<220> FEATURE:
<221> NAME/KEY: MISC_FEATURE
<222> LOCATION: (39)..(39)
<223> OTHER INFORMATION: X= Q, P or H
<220> FEATURE:
<221> NAME/KEY: MISC_FEATURE
<222> LOCATION: (40)..(40)
<223> OTHER INFORMATION: X= C, S, F or Y
<220> FEATURE:
<221> NAME/KEY: MISC_FEATURE
<222> LOCATION: (41)..(41)
<223> OTHER INFORMATION: X= Q, P or L
<220> FEATURE:
<221> NAME/KEY: MISC_FEATURE
<222> LOCATION: (42)..(42)
<223> OTHER INFORMATION: X= C, F, A or no amino acid
<220> FEATURE:
<221> NAME/KEY: MISC_FEATURE
<222> LOCATION: (43)..(43)
<223> OTHER INFORMATION: X= S, L, H or Q
<220> FEATURE:
<221> NAME/KEY: MISC_FEATURE
<222> LOCATION: (44)..(44)
<223> OTHER INFORMATION: X= Q, K, A or H
<220> FEATURE:
<221> NAME/KEY: MISC_FEATURE
<222> LOCATION: (45)..(45)
<223> OTHER INFORMATION: X= Q, P, K or H
<220> FEATURE:
<221> NAME/KEY: MISC_FEATURE
<222> LOCATION: (46)..(46)
<223> OTHER INFORMATION: X= R, N or L
<220> FEATURE:
<221> NAME/KEY: MISC_FEATURE
<222> LOCATION: (47)..(47)
<223> OTHER INFORMATION: X= S, N, T or L
<220> FEATURE:
<221> NAME/KEY: MISC_FEATURE
<222> LOCATION: (48)..(48)
<223> OTHER INFORMATION: X= K, N, Q, H or R
<220> FEATURE:
<221> NAME/KEY: MISC_FEATURE
<222> LOCATION: (49)..(49)
<223> OTHER INFORMATION: X= A, S, V or Q
<220> FEATURE:
<221> NAME/KEY: MISC_FEATURE
<222> LOCATION: (50)..(50)
<223> OTHER INFORMATION: X= H, M or no amino acid
<220> FEATURE:
<221> NAME/KEY: MISC_FEATURE
<222> LOCATION: (51)..(51)
<223> OTHER INFORMATION: X= R, S or K
<220> FEATURE:
<221> NAME/KEY: MISC_FEATURE
<222> LOCATION: (52)..(52)
<223> OTHER INFORMATION: X= K or N
<220> FEATURE:
<221> NAME/KEY: MISC_FEATURE
<222> LOCATION: (54)..(54)
<223> OTHER INFORMATION: X=P, R or S
<220> FEATURE:
<221> NAME/KEY: MISC_FEATURE
<222> LOCATION: (55)..(55)
<223> OTHER INFORMATION: X= N, A, R or C
<220> FEATURE:
<221> NAME/KEY: MISC_FEATURE
<222> LOCATION: (56)..(56)
<223> OTHER INFORMATION: X= G, K or T
<220> FEATURE:
<221> NAME/KEY: MISC_FEATURE
<222> LOCATION: (58)..(58)
<223> OTHER INFORMATION: X= C, Q, Y or A
<220> FEATURE:
<221> NAME/KEY: MISC_FEATURE
<222> LOCATION: (61)..(61)
<223> OTHER INFORMATION: X= L or G
<220> FEATURE:
```

```
<221> NAME/KEY: MISC_FEATURE
<222> LOCATION: (62)..(62)
<223> OTHER INFORMATION: X= S or A
<220> FEATURE:
<221> NAME/KEY: MISC_FEATURE
<222> LOCATION: (63)..(63)
<223> OTHER INFORMATION: X= D, E or W
<220> FEATURE:
<221> NAME/KEY: MISC_FEATURE
<222> LOCATION: (64)..(64)
<223> OTHER INFORMATION: X=R, K or S
<220> FEATURE:
<221> NAME/KEY: MISC_FEATURE
<222> LOCATION: (65)..(65)
<223> OTHER INFORMATION: X=E, G or I
<220> FEATURE:
<221> NAME/KEY: MISC_FEATURE
<222> LOCATION: (66)..(66)
<223> OTHER INFORMATION: X=E or D
<220> FEATURE:
<221> NAME/KEY: MISC_FEATURE
<222> LOCATION: (67)..(67)
<223> OTHER INFORMATION: X= F or Y
<220> FEATURE:
<221> NAME/KEY: MISC_FEATURE
<222> LOCATION: (68)..(68)
<223> OTHER INFORMATION: X=H, Y or S
<220> FEATURE:
<221> NAME/KEY: MISC_FEATURE
<222> LOCATION: (69)..(69)
<223> OTHER INFORMATION: X=S, T, G or A
<220> FEATURE:
<221> NAME/KEY: MISC_FEATURE
<222> LOCATION: (70)..(70)
<223> OTHER INFORMATION: X= Q, N, E or H
<220> FEATURE:
<221> NAME/KEY: MISC_FEATURE
<222> LOCATION: (71)..(71)
<223> OTHER INFORMATION: X=R or K
<220> FEATURE:
<221> NAME/KEY: MISC_FEATURE
<222> LOCATION: (73)..(73)
<223> OTHER INFORMATION: X=P or A
<220> FEATURE:
<221> NAME/KEY: MISC_FEATURE
<222> LOCATION: (74)..(74)
<223> OTHER INFORMATION: X=T or V
<220> FEATURE:
<221> NAME/KEY: MISC_FEATURE
<222> LOCATION: (76)..(76)
<223> OTHER INFORMATION: X=L or I
<220> FEATURE:
<221> NAME/KEY: MISC_FEATURE
<222> LOCATION: (77)..(77)
<223> OTHER INFORMATION: X=L or V
<220> FEATURE:
<221> NAME/KEY: MISC_FEATURE
<222> LOCATION: (80)..(80)
<223> OTHER INFORMATION: X=I or V
<220> FEATURE:
<221> NAME/KEY: MISC_FEATURE
<222> LOCATION: (82)..(82)
<223> OTHER INFORMATION: X=Y or D
<220> FEATURE:
<221> NAME/KEY: MISC_FEATURE
<222> LOCATION: (84)..(84)
<223> OTHER INFORMATION: X=I, V or A
<220> FEATURE:
<221> NAME/KEY: MISC_FEATURE
<222> LOCATION: (91)..(91)
<223> OTHER INFORMATION: X=V, L, A or T
<220> FEATURE:
<221> NAME/KEY: MISC_FEATURE
<222> LOCATION: (92)..(92)
<223> OTHER INFORMATION: X=K, H, Q or P
<220> FEATURE:
<221> NAME/KEY: MISC_FEATURE
<222> LOCATION: (93)..(93)
<223> OTHER INFORMATION: X=E or D
```

```
<220> FEATURE:
<221> NAME/KEY: MISC_FEATURE
<222> LOCATION: (95)..(95)
<223> OTHER INFORMATION: X=K or E
<220> FEATURE:
<221> NAME/KEY: MISC_FEATURE
<222> LOCATION: (98)..(98)
<223> OTHER INFORMATION: X=A or S
<220> FEATURE:
<221> NAME/KEY: MISC_FEATURE
<222> LOCATION: (99)..(99)
<223> OTHER INFORMATION: X=D, A, S or E
<220> FEATURE:
<221> NAME/KEY: MISC_FEATURE
<222> LOCATION: (103)..(103)
<223> OTHER INFORMATION: X=S, A or L
<220> FEATURE:
<221> NAME/KEY: MISC_FEATURE
<222> LOCATION: (104)..(104)
<223> OTHER INFORMATION: X=D or E
<220> FEATURE:
<221> NAME/KEY: MISC_FEATURE
<222> LOCATION: (105)..(105)
<223> OTHER INFORMATION: X=V, T or I
<220> FEATURE:
<221> NAME/KEY: MISC_FEATURE
<222> LOCATION: (106)..(106)
<223> OTHER INFORMATION: X= V or I
<220> FEATURE:
<221> NAME/KEY: MISC_FEATURE
<222> LOCATION: (107)..(107)
<223> OTHER INFORMATION: X= F, Y or H
<220> FEATURE:
<221> NAME/KEY: MISC_FEATURE
<222> LOCATION: (108)..(108)
<223> OTHER INFORMATION: X= N, S or T
<220> FEATURE:
<221> NAME/KEY: MISC_FEATURE
<222> LOCATION: (110)..(110)
<223> OTHER INFORMATION: X=S or A
<220> FEATURE:
<221> NAME/KEY: MISC_FEATURE
<222> LOCATION: (111)..(111)
<223> OTHER INFORMATION: X=K or R
<220> FEATURE:
<221> NAME/KEY: MISC_FEATURE
<222> LOCATION: (117)..(117)
<223> OTHER INFORMATION: X=G or S
<220> FEATURE:
<221> NAME/KEY: MISC_FEATURE
<222> LOCATION: (118)..(118)
<223> OTHER INFORMATION: X=S or A
<220> FEATURE:
<221> NAME/KEY: MISC_FEATURE
<222> LOCATION: (124)..(124)
<223> OTHER INFORMATION: X=D or E
<220> FEATURE:
<221> NAME/KEY: MISC_FEATURE
<222> LOCATION: (126)..(126)
<223> OTHER INFORMATION: X=T or A
<220> FEATURE:
<221> NAME/KEY: MISC_FEATURE
<222> LOCATION: (128)..(128)
<223> OTHER INFORMATION: X=V or A
<220> FEATURE:
<221> NAME/KEY: MISC_FEATURE
<222> LOCATION: (131)..(131)
<223> OTHER INFORMATION: X=Y or H
<220> FEATURE:
<221> NAME/KEY: MISC_FEATURE
<222> LOCATION: (132)..(132)
<223> OTHER INFORMATION: X=V or I
<220> FEATURE:
<221> NAME/KEY: MISC_FEATURE
<222> LOCATION: (134)..(134)
<223> OTHER INFORMATION: X=N or D
<220> FEATURE:
<221> NAME/KEY: MISC_FEATURE
<222> LOCATION: (135)..(135)
```

```
<223> OTHER INFORMATION: X=A or T
<220> FEATURE:
<221> NAME/KEY: MISC_FEATURE
<222> LOCATION: (137)..(137)
<223> OTHER INFORMATION: X=Q, E or D
<220> FEATURE:
<221> NAME/KEY: MISC_FEATURE
<222> LOCATION: (139)..(139)
<223> OTHER INFORMATION: X= R or K
<220> FEATURE:
<221> NAME/KEY: MISC_FEATURE
<222> LOCATION: (141)..(141)
<223> OTHER INFORMATION: X= L or I
<220> FEATURE:
<221> NAME/KEY: MISC_FEATURE
<222> LOCATION: (148)..(148)
<223> OTHER INFORMATION: X= S or A
<220> FEATURE:
<221> NAME/KEY: MISC_FEATURE
<222> LOCATION: (150)..(150)
<223> OTHER INFORMATION: X= P or A
<220> FEATURE:
<221> NAME/KEY: MISC_FEATURE
<222> LOCATION: (159)..(159)
<223> OTHER INFORMATION: X= D, G, E or S
<220> FEATURE:
<221> NAME/KEY: MISC_FEATURE
<222> LOCATION: (160)..(160)
<223> OTHER INFORMATION: X= K, Q or R
<220> FEATURE:
<221> NAME/KEY: MISC_FEATURE
<222> LOCATION: (162)..(162)
<223> OTHER INFORMATION: X= H, P or S
<220> FEATURE:
<221> NAME/KEY: MISC_FEATURE
<222> LOCATION: (164)..(164)
<223> OTHER INFORMATION: X= M, L or I
<220> FEATURE:
<221> NAME/KEY: MISC_FEATURE
<222> LOCATION: (168)..(168)
<223> OTHER INFORMATION: X= D, N or S
<220> FEATURE:
<221> NAME/KEY: MISC_FEATURE
<222> LOCATION: (171)..(171)
<223> OTHER INFORMATION: X= A or S
<220> FEATURE:
<221> NAME/KEY: MISC_FEATURE
<222> LOCATION: (174)..(174)
<223> OTHER INFORMATION: X= T or P
<220> FEATURE:
<221> NAME/KEY: MISC_FEATURE
<222> LOCATION: (177)..(177)
<223> OTHER INFORMATION: X= G, S or D
<220> FEATURE:
<221> NAME/KEY: MISC_FEATURE
<222> LOCATION: (180)..(180)
<223> OTHER INFORMATION: X= E, I, V or A
<220> FEATURE:
<221> NAME/KEY: MISC_FEATURE
<222> LOCATION: (181)..(181)
<223> OTHER INFORMATION: X= Y, H, or F
<220> FEATURE:
<221> NAME/KEY: MISC_FEATURE
<222> LOCATION: (183)..(183)
<223> OTHER INFORMATION: X= C or A
<220> FEATURE:
<221> NAME/KEY: MISC_FEATURE
<222> LOCATION: (186)..(186)
<223> OTHER INFORMATION: X= T or A
<220> FEATURE:
<221> NAME/KEY: MISC_FEATURE
<222> LOCATION: (192)..(192)
<223> OTHER INFORMATION: X= T or S
<220> FEATURE:
<221> NAME/KEY: MISC_FEATURE
<222> LOCATION: (196)..(196)
<223> OTHER INFORMATION: X= G or A
<220> FEATURE:
<221> NAME/KEY: MISC_FEATURE
```

```
<222> LOCATION: (202)..(202)
<223> OTHER INFORMATION: X= G or A
<220> FEATURE:
<221> NAME/KEY: MISC_FEATURE
<222> LOCATION: (205)..(205)
<223> OTHER INFORMATION: X= L or I
<220> FEATURE:
<221> NAME/KEY: MISC_FEATURE
<222> LOCATION: (206)..(206)
<223> OTHER INFORMATION: X= L or K
<220> FEATURE:
<221> NAME/KEY: MISC_FEATURE
<222> LOCATION: (208)..(208)
<223> OTHER INFORMATION: X= R or K
<220> FEATURE:
<221> NAME/KEY: MISC_FEATURE
<222> LOCATION: (209)..(209)
<223> OTHER INFORMATION: X= N, S or K
<220> FEATURE:
<221> NAME/KEY: MISC_FEATURE
<222> LOCATION: (211)..(211)
<223> OTHER INFORMATION: X= N or H
<220> FEATURE:
<221> NAME/KEY: MISC_FEATURE
<222> LOCATION: (213)..(213)
<223> OTHER INFORMATION: X= I or V
<220> FEATURE:
<221> NAME/KEY: MISC_FEATURE
<222> LOCATION: (214)..(214)
<223> OTHER INFORMATION: X= A or S
<220> FEATURE:
<221> NAME/KEY: MISC_FEATURE
<222> LOCATION: (220)..(220)
<223> OTHER INFORMATION: X= A or V
<220> FEATURE:
<221> NAME/KEY: MISC_FEATURE
<222> LOCATION: (233)..(233)
<223> OTHER INFORMATION: X= A, S or V
<220> FEATURE:
<221> NAME/KEY: MISC_FEATURE
<222> LOCATION: (235)..(235)
<223> OTHER INFORMATION: X= Y or F
<220> FEATURE:
<221> NAME/KEY: MISC_FEATURE
<222> LOCATION: (238)..(238)
<223> OTHER INFORMATION: X=S or A
<220> FEATURE:
<221> NAME/KEY: MISC_FEATURE
<222> LOCATION: (239)..(239)
<223> OTHER INFORMATION: X= N or D
<220> FEATURE:
<221> NAME/KEY: MISC_FEATURE
<222> LOCATION: (240)..(240)
<223> OTHER INFORMATION: X=M or L
<220> FEATURE:
<221> NAME/KEY: MISC_FEATURE
<222> LOCATION: (243)..(243)
<223> OTHER INFORMATION: X=I or V
<220> FEATURE:
<221> NAME/KEY: MISC_FEATURE
<222> LOCATION: (248)..(248)
<223> OTHER INFORMATION: X= K or R
<220> FEATURE:
<221> NAME/KEY: MISC_FEATURE
<222> LOCATION: (258)..(258)
<223> OTHER INFORMATION: X= D or N
<220> FEATURE:
<221> NAME/KEY: MISC_FEATURE
<222> LOCATION: (261)..(261)
<223> OTHER INFORMATION: X= I, S, V or A
<220> FEATURE:
<221> NAME/KEY: MISC_FEATURE
<222> LOCATION: (262)..(262)
<223> OTHER INFORMATION: X= P or T
<220> FEATURE:
<221> NAME/KEY: MISC_FEATURE
<222> LOCATION: (269)..(269)
<223> OTHER INFORMATION: X= S, G, R or K
<220> FEATURE:
```

-continued

```
<221> NAME/KEY: MISC_FEATURE
<222> LOCATION: (272)..(272)
<223> OTHER INFORMATION: X= S, A or T
<220> FEATURE:
<221> NAME/KEY: MISC_FEATURE
<222> LOCATION: (273)..(273)
<223> OTHER INFORMATION: X= R or K
<220> FEATURE:
<221> NAME/KEY: MISC_FEATURE
<222> LOCATION: (276)..(276)
<223> OTHER INFORMATION: X= S or A
<220> FEATURE:
<221> NAME/KEY: MISC_FEATURE
<222> LOCATION: (277)..(277)
<223> OTHER INFORMATION: X= S or N
<220> FEATURE:
<221> NAME/KEY: MISC_FEATURE
<222> LOCATION: (278)..(278)
<223> OTHER INFORMATION: X= R, P, A or T
<220> FEATURE:
<221> NAME/KEY: MISC_FEATURE
<222> LOCATION: (279)..(279)
<223> OTHER INFORMATION: X= K, P or A
<220> FEATURE:
<221> NAME/KEY: MISC_FEATURE
<222> LOCATION: (280)..(280)
<223> OTHER INFORMATION: X= L or F
<220> FEATURE:
<221> NAME/KEY: MISC_FEATURE
<222> LOCATION: (282)..(282)
<223> OTHER INFORMATION: X= E or Q
<220> FEATURE:
<221> NAME/KEY: MISC_FEATURE
<222> LOCATION: (286)..(286)
<223> OTHER INFORMATION: X= V or A
<220> FEATURE:
<221> NAME/KEY: MISC_FEATURE
<222> LOCATION: (288)..(288)
<223> OTHER INFORMATION: X= K or N
<220> FEATURE:
<221> NAME/KEY: MISC_FEATURE
<222> LOCATION: (289)..(289)
<223> OTHER INFORMATION: X= G, S or T
<220> FEATURE:
<221> NAME/KEY: MISC_FEATURE
<222> LOCATION: (290)..(290)
<223> OTHER INFORMATION: X= V, M or I
<220> FEATURE:
<221> NAME/KEY: MISC_FEATURE
<222> LOCATION: (293)..(293)
<223> OTHER INFORMATION: X= Q or R
<220> FEATURE:
<221> NAME/KEY: MISC_FEATURE
<222> LOCATION: (296)..(296)
<223> OTHER INFORMATION: X= G or P
<220> FEATURE:
<221> NAME/KEY: MISC_FEATURE
<222> LOCATION: (297)..(297)
<223> OTHER INFORMATION: X= Q or P
<220> FEATURE:
<221> NAME/KEY: MISC_FEATURE
<222> LOCATION: (298)..(298)
<223> OTHER INFORMATION: X= M or A
<220> FEATURE:
<221> NAME/KEY: MISC_FEATURE
<222> LOCATION: (300)..(300)
<223> OTHER INFORMATION: X= E or Q
<220> FEATURE:
<221> NAME/KEY: MISC_FEATURE
<222> LOCATION: (301)..(301)
<223> OTHER INFORMATION: X= L or V
<220> FEATURE:
<221> NAME/KEY: MISC_FEATURE
<222> LOCATION: (307)..(307)
<223> OTHER INFORMATION: X= E or V
<220> FEATURE:
<221> NAME/KEY: MISC_FEATURE
<222> LOCATION: (310)..(310)
<223> OTHER INFORMATION: X= R or C
```

-continued

```
<220> FEATURE:
<221> NAME/KEY: MISC_FEATURE
<222> LOCATION: (313)..(313)
<223> OTHER INFORMATION: X= I, L or V
<220> FEATURE:
<221> NAME/KEY: MISC_FEATURE
<222> LOCATION: (315)..(315)
<223> OTHER INFORMATION: X= G or A
<220> FEATURE:
<221> NAME/KEY: MISC_FEATURE
<222> LOCATION: (316)..(316)
<223> OTHER INFORMATION: X= S or T
<220> FEATURE:
<221> NAME/KEY: MISC_FEATURE
<222> LOCATION: (318)..(318)
<223> OTHER INFORMATION: X= S or A
<220> FEATURE:
<221> NAME/KEY: MISC_FEATURE
<222> LOCATION: (319)..(319)
<223> OTHER INFORMATION: X= S or T
<220> FEATURE:
<221> NAME/KEY: MISC_FEATURE
<222> LOCATION: (336)..(336)
<223> OTHER INFORMATION: X= S or N
<220> FEATURE:
<221> NAME/KEY: MISC_FEATURE
<222> LOCATION: (337)..(337)
<223> OTHER INFORMATION: X= I or V
<220> FEATURE:
<221> NAME/KEY: MISC_FEATURE
<222> LOCATION: (338)..(338)
<223> OTHER INFORMATION: X= D or E
<220> FEATURE:
<221> NAME/KEY: MISC_FEATURE
<222> LOCATION: (341)..(341)
<223> OTHER INFORMATION: X= I or V
<220> FEATURE:
<221> NAME/KEY: MISC_FEATURE
<222> LOCATION: (342)..(342)
<223> OTHER INFORMATION: X= A, S, or T
<220> FEATURE:
<221> NAME/KEY: MISC_FEATURE
<222> LOCATION: (344)..(344)
<223> OTHER INFORMATION: X= L or F
<220> FEATURE:
<221> NAME/KEY: MISC_FEATURE
<222> LOCATION: (345)..(345)
<223> OTHER INFORMATION: X= K, Q or N
<220> FEATURE:
<221> NAME/KEY: MISC_FEATURE
<222> LOCATION: (346)..(346)
<223> OTHER INFORMATION: X= K or E
<220> FEATURE:
<221> NAME/KEY: MISC_FEATURE
<222> LOCATION: (348)..(348)
<223> OTHER INFORMATION: X= K or R
<220> FEATURE:
<221> NAME/KEY: MISC_FEATURE
<222> LOCATION: (349)..(349)
<223> OTHER INFORMATION: X= S or A
<220> FEATURE:
<221> NAME/KEY: MISC_FEATURE
<222> LOCATION: (350)..(350)
<223> OTHER INFORMATION: X= T or M
<220> FEATURE:
<221> NAME/KEY: MISC_FEATURE
<222> LOCATION: (351)..(351)
<223> OTHER INFORMATION: X= K, R or P
<220> FEATURE:
<221> NAME/KEY: MISC_FEATURE
<222> LOCATION: (352)..(352)
<223> OTHER INFORMATION: X= T, A or S
<220> FEATURE:
<221> NAME/KEY: MISC_FEATURE
<222> LOCATION: (353)..(353)
<223> OTHER INFORMATION: X= T or P
<220> FEATURE:
<221> NAME/KEY: MISC_FEATURE
<222> LOCATION: (358)..(358)
```

-continued

```
<223> OTHER INFORMATION: X= I or V
<220> FEATURE:
<221> NAME/KEY: MISC_FEATURE
<222> LOCATION: (360)..(360)
<223> OTHER INFORMATION: X= I or V
<220> FEATURE:
<221> NAME/KEY: MISC_FEATURE
<222> LOCATION: (361)..(361)
<223> OTHER INFORMATION: X= I or V
<220> FEATURE:
<221> NAME/KEY: MISC_FEATURE
<222> LOCATION: (366)..(366)
<223> OTHER INFORMATION: X= R or K
<220> FEATURE:
<221> NAME/KEY: MISC_FEATURE
<222> LOCATION: (370)..(370)
<223> OTHER INFORMATION: X= Y or P
<220> FEATURE:
<221> NAME/KEY: MISC_FEATURE
<222> LOCATION: (373)..(373)
<223> OTHER INFORMATION: X= K, R, V or A
<220> FEATURE:
<221> NAME/KEY: MISC_FEATURE
<222> LOCATION: (375)..(375)
<223> OTHER INFORMATION: X= D or A
<220> FEATURE:
<221> NAME/KEY: MISC_FEATURE
<222> LOCATION: (377)..(377)
<223> OTHER INFORMATION: X= K or R
<220> FEATURE:
<221> NAME/KEY: MISC_FEATURE
<222> LOCATION: (378)..(378)
<223> OTHER INFORMATION: X= Y or M
<220> FEATURE:
<221> NAME/KEY: MISC_FEATURE
<222> LOCATION: (382)..(382)
<223> OTHER INFORMATION: X= T, A or V
<220> FEATURE:
<221> NAME/KEY: MISC_FEATURE
<222> LOCATION: (387)..(387)
<223> OTHER INFORMATION: X= T, A, P or K
<220> FEATURE:
<221> NAME/KEY: MISC_FEATURE
<222> LOCATION: (390)..(390)
<223> OTHER INFORMATION: X= R or K
<220> FEATURE:
<221> NAME/KEY: MISC_FEATURE
<222> LOCATION: (394)..(394)
<223> OTHER INFORMATION: X= S, T, G or V
<220> FEATURE:
<221> NAME/KEY: MISC_FEATURE
<222> LOCATION: (395)..(395)
<223> OTHER INFORMATION: X= S, T or K
<220> FEATURE:
<221> NAME/KEY: MISC_FEATURE
<222> LOCATION: (396)..(396)
<223> OTHER INFORMATION: X= S, A, N, F or C
<220> FEATURE:
<221> NAME/KEY: MISC_FEATURE
<222> LOCATION: (397)..(397)
<223> OTHER INFORMATION: X= P, E, K, T or S
<220> FEATURE:
<221> NAME/KEY: MISC_FEATURE
<222> LOCATION: (399)..(399)
<223> OTHER INFORMATION: X= Q or L
<220> FEATURE:
<221> NAME/KEY: MISC_FEATURE
<222> LOCATION: (403)..(403)
<223> OTHER INFORMATION: X= Q or T
<220> FEATURE:
<221> NAME/KEY: MISC_FEATURE
<222> LOCATION: (408)..(408)
<223> OTHER INFORMATION: X= A or S
<220> FEATURE:
<221> NAME/KEY: MISC_FEATURE
<222> LOCATION: (410)..(410)
<223> OTHER INFORMATION: X= I or V
<220> FEATURE:
<221> NAME/KEY: MISC_FEATURE
```

```
<222> LOCATION: (411)..(411)
<223> OTHER INFORMATION: X= A, K or R
<220> FEATURE:
<221> NAME/KEY: MISC_FEATURE
<222> LOCATION: (415)..(415)
<223> OTHER INFORMATION: X= A, V or I
<220> FEATURE:
<221> NAME/KEY: MISC_FEATURE
<222> LOCATION: (417)..(417)
<223> OTHER INFORMATION: X= K, N, E or D
<220> FEATURE:
<221> NAME/KEY: MISC_FEATURE
<222> LOCATION: (418)..(418)
<223> OTHER INFORMATION: X= K or D
<220> FEATURE:
<221> NAME/KEY: MISC_FEATURE
<222> LOCATION: (419)..(419)
<223> OTHER INFORMATION: X= I or V
<220> FEATURE:
<221> NAME/KEY: MISC_FEATURE
<222> LOCATION: (420)..(420)
<223> OTHER INFORMATION: X= I or V
<220> FEATURE:
<221> NAME/KEY: MISC_FEATURE
<222> LOCATION: (421)..(421)
<223> OTHER INFORMATION: X= A or G
<220> FEATURE:
<221> NAME/KEY: MISC_FEATURE
<222> LOCATION: (432)..(432)
<223> OTHER INFORMATION: X= L or M
<220> FEATURE:
<221> NAME/KEY: MISC_FEATURE
<222> LOCATION: (434)..(434)
<223> OTHER INFORMATION: X= L, Y, F or I
<220> FEATURE:
<221> NAME/KEY: MISC_FEATURE
<222> LOCATION: (436)..(436)
<223> OTHER INFORMATION: X= L, H or Q
<220> FEATURE:
<221> NAME/KEY: MISC_FEATURE
<222> LOCATION: (437)..(437)
<223> OTHER INFORMATION: X= R or K
<220> FEATURE:
<221> NAME/KEY: MISC_FEATURE
<222> LOCATION: (438)..(438)
<223> OTHER INFORMATION: X= R or K
<220> FEATURE:
<221> NAME/KEY: MISC_FEATURE
<222> LOCATION: (441)..(441)
<223> OTHER INFORMATION: X= T, D, N or E
<220> FEATURE:
<221> NAME/KEY: MISC_FEATURE
<222> LOCATION: (462)..(462)
<223> OTHER INFORMATION: X= T, C or A
<220> FEATURE:
<221> NAME/KEY: MISC_FEATURE
<222> LOCATION: (465)..(465)
<223> OTHER INFORMATION: X= L or I
<220> FEATURE:
<221> NAME/KEY: MISC_FEATURE
<222> LOCATION: (476)..(476)
<223> OTHER INFORMATION: X= L or M
<220> FEATURE:
<221> NAME/KEY: MISC_FEATURE
<222> LOCATION: (479)..(479)
<223> OTHER INFORMATION: X= A or G
<220> FEATURE:
<221> NAME/KEY: MISC_FEATURE
<222> LOCATION: (491)..(491)
<223> OTHER INFORMATION: X= K or R
<220> FEATURE:
<221> NAME/KEY: MISC_FEATURE
<222> LOCATION: (495)..(495)
<223> OTHER INFORMATION: X= K or R
<220> FEATURE:
<221> NAME/KEY: MISC_FEATURE
<222> LOCATION: (498)..(498)
<223> OTHER INFORMATION: X= M or L
<220> FEATURE:
```

-continued

```
<221> NAME/KEY: MISC_FEATURE
<222> LOCATION: (514)..(514)
<223> OTHER INFORMATION: X= A or S
<220> FEATURE:
<221> NAME/KEY: MISC_FEATURE
<222> LOCATION: (518)..(518)
<223> OTHER INFORMATION: X= A or T
<220> FEATURE:
<221> NAME/KEY: MISC_FEATURE
<222> LOCATION: (519)..(519)
<223> OTHER INFORMATION: X= F or Y
<220> FEATURE:
<221> NAME/KEY: MISC_FEATURE
<222> LOCATION: (527)..(527)
<223> OTHER INFORMATION: X= V or I
<220> FEATURE:
<221> NAME/KEY: MISC_FEATURE
<222> LOCATION: (532)..(532)
<223> OTHER INFORMATION: X= A or S
<220> FEATURE:
<221> NAME/KEY: MISC_FEATURE
<222> LOCATION: (535)..(535)
<223> OTHER INFORMATION: X= A or T
<220> FEATURE:
<221> NAME/KEY: MISC_FEATURE
<222> LOCATION: (536)..(536)
<223> OTHER INFORMATION: X= E or D
<220> FEATURE:
<221> NAME/KEY: MISC_FEATURE
<222> LOCATION: (538)..(538)
<223> OTHER INFORMATION: X= F or M
<220> FEATURE:
<221> NAME/KEY: MISC_FEATURE
<222> LOCATION: (539)..(539)
<223> OTHER INFORMATION: X= H or N
<220> FEATURE:
<221> NAME/KEY: MISC_FEATURE
<222> LOCATION: (540)..(540)
<223> OTHER INFORMATION: X= I or M
<220> FEATURE:
<221> NAME/KEY: MISC_FEATURE
<222> LOCATION: (545)..(545)
<223> OTHER INFORMATION: X= A or V
<220> FEATURE:
<221> NAME/KEY: MISC_FEATURE
<222> LOCATION: (546)..(546)
<223> OTHER INFORMATION: X= A or K
<220> FEATURE:
<221> NAME/KEY: MISC_FEATURE
<222> LOCATION: (548)..(548)
<223> OTHER INFORMATION: X= D or N
<220> FEATURE:
<221> NAME/KEY: MISC_FEATURE
<222> LOCATION: (552)..(552)
<223> OTHER INFORMATION: X= S or C
<220> FEATURE:
<221> NAME/KEY: MISC_FEATURE
<222> LOCATION: (556)..(556)
<223> OTHER INFORMATION: X= Y or F
<220> FEATURE:
<221> NAME/KEY: MISC_FEATURE
<222> LOCATION: (562)..(562)
<223> OTHER INFORMATION: X= V or I
<220> FEATURE:
<221> NAME/KEY: MISC_FEATURE
<222> LOCATION: (564)..(564)
<223> OTHER INFORMATION: X= V, A or I
<220> FEATURE:
<221> NAME/KEY: MISC_FEATURE
<222> LOCATION: (565)..(565)
<223> OTHER INFORMATION: X= E, A, Q or V
<220> FEATURE:
<221> NAME/KEY: MISC_FEATURE
<222> LOCATION: (568)..(568)
<223> OTHER INFORMATION: X= P, A, T, S or V
<220> FEATURE:
<221> NAME/KEY: MISC_FEATURE
<222> LOCATION: (569)..(569)
<223> OTHER INFORMATION: X= G, N  or D
```

```
-continued

<220> FEATURE:
<221> NAME/KEY: MISC_FEATURE
<222> LOCATION: (570)..(570)
<223> OTHER INFORMATION: X= Y, N  or H
<220> FEATURE:
<221> NAME/KEY: MISC_FEATURE
<222> LOCATION: (573)..(573)
<223> OTHER INFORMATION: X= I, V  or T
<220> FEATURE:
<221> NAME/KEY: MISC_FEATURE
<222> LOCATION: (575)..(575)
<223> OTHER INFORMATION: X= I  or  L
<220> FEATURE:
<221> NAME/KEY: MISC_FEATURE
<222> LOCATION: (577)..(577)
<223> OTHER INFORMATION: X= I  or V
<220> FEATURE:
<221> NAME/KEY: MISC_FEATURE
<222> LOCATION: (579)..(579)
<223> OTHER INFORMATION: X= K  or R
<220> FEATURE:
<221> NAME/KEY: MISC_FEATURE
<222> LOCATION: (582)..(582)
<223> OTHER INFORMATION: X= I,  or V
<220> FEATURE:
<221> NAME/KEY: MISC_FEATURE
<222> LOCATION: (584)..(584)
<223> OTHER INFORMATION: X= I, K, M  or V
<220> FEATURE:
<221> NAME/KEY: MISC_FEATURE
<222> LOCATION: (585)..(585)
<223> OTHER INFORMATION: X= E  or G
<220> FEATURE:
<221> NAME/KEY: MISC_FEATURE
<222> LOCATION: (587)..(587)
<223> OTHER INFORMATION: X= E, S, D  or N
<220> FEATURE:
<221> NAME/KEY: MISC_FEATURE
<222> LOCATION: (588)..(588)
<223> OTHER INFORMATION: X= R or K
<220> FEATURE:
<221> NAME/KEY: MISC_FEATURE
<222> LOCATION: (591)..(591)
<223> OTHER INFORMATION: X= L or I
<220> FEATURE:
<221> NAME/KEY: MISC_FEATURE
<222> LOCATION: (596)..(596)
<223> OTHER INFORMATION: X= T or S
<220> FEATURE:
<221> NAME/KEY: MISC_FEATURE
<222> LOCATION: (597)..(597)
<223> OTHER INFORMATION: X= A, I or M
<220> FEATURE:
<221> NAME/KEY: MISC_FEATURE
<222> LOCATION: (600)..(600)
<223> OTHER INFORMATION: X= A, S, N or Q
<220> FEATURE:
<221> NAME/KEY: MISC_FEATURE
<222> LOCATION: (602)..(602)
<223> OTHER INFORMATION: X= L or M
<220> FEATURE:
<221> NAME/KEY: MISC_FEATURE
<222> LOCATION: (603)..(603)
<223> OTHER INFORMATION: X= V, G, A or K
<220> FEATURE:
<221> NAME/KEY: MISC_FEATURE
<222> LOCATION: (605)..(605)
<223> OTHER INFORMATION: X= A or S
<220> FEATURE:
<221> NAME/KEY: MISC_FEATURE
<222> LOCATION: (606)..(606)
<223> OTHER INFORMATION: X= A, V, E, G or S
<220> FEATURE:
<221> NAME/KEY: MISC_FEATURE
<222> LOCATION: (607)..(607)
<223> OTHER INFORMATION: X= A, V, L, M or S
<220> FEATURE:
<221> NAME/KEY: MISC_FEATURE
<222> LOCATION: (608)..(608)
```

```
<223> OTHER INFORMATION: X= L or V
<220> FEATURE:
<221> NAME/KEY: MISC_FEATURE
<222> LOCATION: (609)..(609)
<223> OTHER INFORMATION: X= E, K, R or V
<220> FEATURE:
<221> NAME/KEY: MISC_FEATURE
<222> LOCATION: (610)..(610)
<223> OTHER INFORMATION: X= E, Q, S, C or T
<220> FEATURE:
<221> NAME/KEY: MISC_FEATURE
<222> LOCATION: (611)..(611)
<223> OTHER INFORMATION: X= H or R
<220> FEATURE:
<221> NAME/KEY: MISC_FEATURE
<222> LOCATION: (612)..(612)
<223> OTHER INFORMATION: X= G or N
<220> FEATURE:
<221> NAME/KEY: MISC_FEATURE
<222> LOCATION: (613)..(613)
<223> OTHER INFORMATION: X= L, V or I
<220> FEATURE:
<221> NAME/KEY: MISC_FEATURE
<222> LOCATION: (614)..(614)
<223> OTHER INFORMATION: X= R, N, Q, S or Y
<220> FEATURE:
<221> NAME/KEY: MISC_FEATURE
<222> LOCATION: (615)..(615)
<223> OTHER INFORMATION: X= I, V, P, L or A
<220> FEATURE:
<221> NAME/KEY: MISC_FEATURE
<222> LOCATION: (620)..(620)
<223> OTHER INFORMATION: X= A or G
<220> FEATURE:
<221> NAME/KEY: MISC_FEATURE
<222> LOCATION: (621)..(621)
<223> OTHER INFORMATION: X= R or K
<220> FEATURE:
<221> NAME/KEY: MISC_FEATURE
<222> LOCATION: (628)..(628)
<223> OTHER INFORMATION: X= R, H, G, S or T
<220> FEATURE:
<221> NAME/KEY: MISC_FEATURE
<222> LOCATION: (629)..(629)
<223> OTHER INFORMATION: X= A, D, G, S or E
<220> FEATURE:
<221> NAME/KEY: MISC_FEATURE
<222> LOCATION: (632)..(632)
<223> OTHER INFORMATION: X= R or K
<220> FEATURE:
<221> NAME/KEY: MISC_FEATURE
<222> LOCATION: (633)..(633)
<223> OTHER INFORMATION: X= T, R, S or E
<220> FEATURE:
<221> NAME/KEY: MISC_FEATURE
<222> LOCATION: (635)..(635)
<223> OTHER INFORMATION: X= A or V
<220> FEATURE:
<221> NAME/KEY: MISC_FEATURE
<222> LOCATION: (636)..(636)
<223> OTHER INFORMATION: X= A, K or N
<220> FEATURE:
<221> NAME/KEY: MISC_FEATURE
<222> LOCATION: (637)..(637)
<223> OTHER INFORMATION: X= S or E
<220> FEATURE:
<221> NAME/KEY: MISC_FEATURE
<222> LOCATION: (640)..(640)
<223> OTHER INFORMATION: X= V or I
<220> FEATURE:
<221> NAME/KEY: MISC_FEATURE
<222> LOCATION: (642)..(642)
<223> OTHER INFORMATION: X= V or I
<220> FEATURE:
<221> NAME/KEY: MISC_FEATURE
<222> LOCATION: (646)..(646)
<223> OTHER INFORMATION: X= E or K
<220> FEATURE:
<221> NAME/KEY: MISC_FEATURE
```

-continued

```
<222> LOCATION: (653)..(653)
<223> OTHER INFORMATION: X= G or A
<220> FEATURE:
<221> NAME/KEY: MISC_FEATURE
<222> LOCATION: (657)..(657)
<223> OTHER INFORMATION: X= V, T, S or A
<220> FEATURE:
<221> NAME/KEY: MISC_FEATURE
<222> LOCATION: (658)..(658)
<223> OTHER INFORMATION: X= Q or H
<220> FEATURE:
<221> NAME/KEY: MISC_FEATURE
<222> LOCATION: (659)..(659)
<223> OTHER INFORMATION: X= F or Y
<220> FEATURE:
<221> NAME/KEY: MISC_FEATURE
<222> LOCATION: (660)..(660)
<223> OTHER INFORMATION: X= L or M
<220> FEATURE:
<221> NAME/KEY: MISC_FEATURE
<222> LOCATION: (661)..(661)
<223> OTHER INFORMATION: X= A or S
<220> FEATURE:
<221> NAME/KEY: MISC_FEATURE
<222> LOCATION: (663)..(663)
<223> OTHER INFORMATION: X= N, D, T or S
<220> FEATURE:
<221> NAME/KEY: MISC_FEATURE
<222> LOCATION: (665)..(665)
<223> OTHER INFORMATION: X= L or I
<220> FEATURE:
<221> NAME/KEY: MISC_FEATURE
<222> LOCATION: (669)..(669)
<223> OTHER INFORMATION: X= T, K, P or H
<220> FEATURE:
<221> NAME/KEY: MISC_FEATURE
<222> LOCATION: (670)..(670)
<223> OTHER INFORMATION: X= T, L or I
<220> FEATURE:
<221> NAME/KEY: MISC_FEATURE
<222> LOCATION: (672)..(672)
<223> OTHER INFORMATION: X= W, V or L
<220> FEATURE:
<221> NAME/KEY: MISC_FEATURE
<222> LOCATION: (673)..(673)
<223> OTHER INFORMATION: X= S or R
<220> FEATURE:
<221> NAME/KEY: MISC_FEATURE
<222> LOCATION: (674)..(674)
<223> OTHER INFORMATION: X= S or P
<220> FEATURE:
<221> NAME/KEY: MISC_FEATURE
<222> LOCATION: (675)..(675)
<223> OTHER INFORMATION: X= I, L or M
<220> FEATURE:
<221> NAME/KEY: MISC_FEATURE
<222> LOCATION: (676)..(676)
<223> OTHER INFORMATION: X= V or F
<220> FEATURE:
<221> NAME/KEY: MISC_FEATURE
<222> LOCATION: (686)..(686)
<223> OTHER INFORMATION: X= A or S
<220> FEATURE:
<221> NAME/KEY: MISC_FEATURE
<222> LOCATION: (688)..(688)
<223> OTHER INFORMATION: X= A, V or K
<220> FEATURE:
<221> NAME/KEY: MISC_FEATURE
<222> LOCATION: (691)..(691)
<223> OTHER INFORMATION: X= L or I
<220> FEATURE:
<221> NAME/KEY: MISC_FEATURE
<222> LOCATION: (692)..(692)
<223> OTHER INFORMATION: X= A, E, or S
<220> FEATURE:
<221> NAME/KEY: MISC_FEATURE
<222> LOCATION: (693)..(693)
<223> OTHER INFORMATION: X= M, E, or L
<220> FEATURE:
```

-continued

```
<221> NAME/KEY: MISC_FEATURE
<222> LOCATION: (697)..(697)
<223> OTHER INFORMATION: X= M, T, or S
<220> FEATURE:
<221> NAME/KEY: MISC_FEATURE
<222> LOCATION: (698)..(698)
<223> OTHER INFORMATION: X= P or S
<220> FEATURE:
<221> NAME/KEY: MISC_FEATURE
<222> LOCATION: (699)..(699)
<223> OTHER INFORMATION: X= R, K or S
<220> FEATURE:
<221> NAME/KEY: MISC_FEATURE
<222> LOCATION: (702)..(702)
<223> OTHER INFORMATION: X= A or C
<220> FEATURE:
<221> NAME/KEY: MISC_FEATURE
<222> LOCATION: (703)..(703)
<223> OTHER INFORMATION: X= A or G
<220> FEATURE:
<221> NAME/KEY: MISC_FEATURE
<222> LOCATION: (705)..(705)
<223> OTHER INFORMATION: X= A, V or I
<220> FEATURE:
<221> NAME/KEY: MISC_FEATURE
<222> LOCATION: (706)..(706)
<223> OTHER INFORMATION: X= F or L
<220> FEATURE:
<221> NAME/KEY: MISC_FEATURE
<222> LOCATION: (707)..(707)
<223> OTHER INFORMATION: X= N or S
<220> FEATURE:
<221> NAME/KEY: MISC_FEATURE
<222> LOCATION: (708)..(708)
<223> OTHER INFORMATION: X= I, L or V
<220> FEATURE:
<221> NAME/KEY: MISC_FEATURE
<222> LOCATION: (709)..(709)
<223> OTHER INFORMATION: X= I or L
<220> FEATURE:
<221> NAME/KEY: MISC_FEATURE
<222> LOCATION: (710)..(710)
<223> OTHER INFORMATION: X=G or R
<220> FEATURE:
<221> NAME/KEY: MISC_FEATURE
<222> LOCATION: (711)..(711)
<223> OTHER INFORMATION: X= Q, A, K or R
<220> FEATURE:
<221> NAME/KEY: MISC_FEATURE
<222> LOCATION: (712)..(712)
<223> OTHER INFORMATION: X= T or P
<220> FEATURE:
<221> NAME/KEY: MISC_FEATURE
<222> LOCATION: (713)..(713)
<223> OTHER INFORMATION: X= L, M, K or R
<220> FEATURE:
<221> NAME/KEY: MISC_FEATURE
<222> LOCATION: (716)..(716)
<223> OTHER INFORMATION: X= L or F
<220> FEATURE:
<221> NAME/KEY: MISC_FEATURE
<222> LOCATION: (717)..(717)
<223> OTHER INFORMATION: X= Q, E or F
<220> FEATURE:
<221> NAME/KEY: MISC_FEATURE
<222> LOCATION: (718)..(718)
<223> OTHER INFORMATION: X= I, V, L or no amino acid

<400> SEQUENCE: 1

Met Ala Xaa Xaa Xaa Xaa Xaa Xaa Pro Xaa Xaa Xaa Xaa Xaa Xaa
 1               5                  10                  15

Xaa Xaa Xaa Xaa Xaa Xaa Xaa Xaa Xaa Xaa Xaa Xaa Ser Xaa Xaa
             20                  25                  30

Xaa Xaa Xaa Xaa Xaa Leu Xaa Xaa Xaa Xaa Xaa Xaa Xaa Xaa Xaa
         35                  40                  45
```

-continued

```
Xaa Xaa Xaa Xaa Arg Xaa Xaa Xaa Val Xaa Ala Ser Xaa Xaa Xaa Xaa
    50                  55                  60

Xaa Xaa Xaa Xaa Xaa Xaa Xaa Pro Xaa Xaa Pro Xaa Xaa Asp Thr Xaa
65                  70                  75                  80

Asn Xaa Pro Xaa His Met Lys Asn Leu Ser Xaa Xaa Xaa Leu Xaa Gln
                85                  90                  95

Leu Xaa Xaa Glu Leu Arg Xaa Xaa Xaa Xaa Xaa Xaa Val Xaa Xaa Thr
            100                 105                 110

Gly Gly His Leu Xaa Xaa Ser Leu Gly Val Val Xaa Leu Xaa Val Xaa
        115                 120                 125

Leu His Xaa Xaa Phe Xaa Xaa Pro Xaa Asp Xaa Ile Xaa Trp Asp Val
    130                 135                 140

Gly His Lys Xaa Tyr Xaa His Lys Ile Leu Thr Gly Arg Arg Xaa Xaa
145                 150                 155                 160

Met Xaa Thr Xaa Arg Gln Thr Xaa Gly Leu Xaa Gly Phe Xaa Lys Arg
                165                 170                 175

Xaa Glu Ser Xaa Xaa Asp Xaa Phe Gly Xaa Gly His Ser Ser Thr Xaa
            180                 185                 190

Ile Ser Ala Xaa Leu Gly Met Ala Val Xaa Arg Asp Xaa Xaa Gly Xaa
        195                 200                 205

Xaa Asn Xaa Val Xaa Xaa Val Ile Gly Asp Gly Xaa Met Thr Ala Gly
    210                 215                 220

Gln Ala Tyr Glu Ala Met Asn Asn Xaa Gly Xaa Leu Asp Xaa Xaa Xaa
225                 230                 235                 240

Ile Val Xaa Leu Asn Asp Asn Xaa Gln Val Ser Leu Pro Thr Ala Thr
                245                 250                 255

Leu Xaa Gly Pro Xaa Xaa Pro Val Gly Ala Leu Ser Xaa Ala Leu Xaa
            260                 265                 270

Xaa Leu Gln Xaa Xaa Xaa Xaa Xaa Arg Xaa Leu Arg Glu Xaa Ala Xaa
        275                 280                 285

Xaa Xaa Thr Lys Xaa Ile Gly Xaa Xaa Xaa His Xaa Xaa Ala Ala Lys
    290                 295                 300

Val Asp Xaa Tyr Ala Xaa Gly Met Xaa Ser Xaa Xaa Gly Xaa Xaa Leu
305                 310                 315                 320

Phe Glu Glu Leu Gly Leu Tyr Tyr Ile Gly Pro Val Asp Gly His Xaa
                325                 330                 335

Xaa Xaa Asp Leu Xaa Xaa Ile Xaa Xaa Xaa Val Xaa Xaa Xaa Xaa Xaa
            340                 345                 350

Xaa Gly Pro Val Leu Xaa His Xaa Xaa Thr Glu Lys Gly Xaa Gly Tyr
        355                 360                 365

Pro Xaa Ala Glu Xaa Ala Xaa Asp Xaa Xaa His Gly Val Xaa Lys Phe
    370                 375                 380

Asp Pro Xaa Thr Gly Xaa Gln Phe Lys Xaa Xaa Xaa Xaa Thr Xaa Ser
385                 390                 395                 400

Tyr Thr Xaa Tyr Phe Ala Glu Xaa Leu Xaa Xaa Glu Ala Glu Xaa Asp
                405                 410                 415

Xaa Xaa Xaa Xaa Xaa Ile His Ala Ala Met Gly Gly Gly Thr Gly Xaa
            420                 425                 430

Asn Xaa Phe Xaa Xaa Xaa Phe Pro Xaa Arg Cys Phe Asp Val Gly Ile
        435                 440                 445

Ala Glu Gln His Ala Val Thr Phe Ala Ala Gly Leu Ala Xaa Glu Gly
    450                 455                 460

Xaa Lys Pro Phe Cys Ala Ile Tyr Ser Ser Phe Xaa Gln Arg Xaa Tyr
```

```
                465                 470                 475                 480
Asp Gln Val Val His Asp Val Asp Leu Gln Xaa Leu Pro Val Xaa Phe
                    485                 490                 495
Ala Xaa Asp Arg Ala Gly Leu Val Gly Ala Asp Gly Pro Thr His Cys
            500                 505                 510
Gly Xaa Phe Asp Val Xaa Xaa Met Ala Cys Leu Pro Asn Met Xaa Val
        515                 520                 525
Met Ala Pro Xaa Asp Glu Xaa Xaa Leu Xaa Xaa Xaa Val Ala Thr Ala
    530                 535                 540
Xaa Xaa Ile Xaa Asp Arg Pro Xaa Cys Phe Arg Xaa Pro Arg Gly Asn
545                 550                 555                 560
Gly Xaa Gly Xaa Xaa Leu Pro Xaa Xaa Xaa Lys Gly Xaa Pro Xaa Glu
                565                 570                 575
Xaa Gly Xaa Gly Arg Xaa Leu Xaa Xaa Gly Xaa Xaa Val Ala Xaa Leu
            580                 585                 590
Gly Tyr Gly Xaa Xaa Val Gln Xaa Cys Xaa Xaa Ala Xaa Xaa Xaa Xaa
        595                 600                 605
Xaa Xaa Xaa Xaa Xaa Xaa Thr Val Ala Asp Xaa Xaa Phe Cys Lys
    610                 615                 620
Pro Leu Asp Xaa Xaa Leu Ile Xaa Xaa Leu Xaa Xaa Xaa His Glu Xaa
625                 630                 635                 640
Leu Xaa Thr Val Glu Xaa Gly Ser Ile Gly Gly Phe Xaa Ser His Val
                645                 650                 655
Xaa Xaa Xaa Xaa Xaa Leu Xaa Gly Xaa Leu Asp Gly Xaa Xaa Lys Xaa
            660                 665                 670
Xaa Xaa Xaa Xaa Leu Pro Asp Arg Tyr Ile Asp His Gly Xaa Pro Xaa
        675                 680                 685
Asp Gln Xaa Xaa Xaa Ala Gly Leu Xaa Xaa Xaa His Ile Xaa Xaa Thr
    690                 695                 700
Xaa Xaa Xaa Xaa Xaa Xaa Xaa Xaa Glu Ala Xaa Xaa Xaa Met Leu
705                 710                 715                 720

<210> SEQ ID NO 2
<211> LENGTH: 716
<212> TYPE: PRT
<213> ORGANISM: Vitis Vinifera
<220> FEATURE:
<221> NAME/KEY: misc_feature
<222> LOCATION: (284)..(284)
<223> OTHER INFORMATION: Xaa can be any naturally occurring amino acid
<220> FEATURE:
<221> NAME/KEY: misc_feature
<222> LOCATION: (306)..(306)
<223> OTHER INFORMATION: Xaa can be any naturally occurring amino acid

<400> SEQUENCE: 2

Met Ala Leu Cys Thr Leu Ser Phe Pro Ala His Phe Ser Gln Ala Ala
1               5                   10                  15
Ala Ser Asn Pro Gln Arg Leu Thr Pro Gln Cys Ser His Leu Phe Leu
            20                  25                  30
Gly Val Asp Leu Gln Cys Gln Ser Gln Gln Arg Ser Lys Ala Arg Lys
        35                  40                  45
Arg Pro Asn Gly Val Cys Ala Ser Leu Ser Asp Arg Glu Glu Tyr His
    50                  55                  60
Ser Gln Arg Pro Pro Thr Pro Leu Leu Asp Thr Ile Asn Tyr Pro Ile
65                  70                  75                  80
His Met Lys Asn Leu Ser Val Lys Glu Leu Lys Gln Leu Ala Asp Glu
```

```
                    85                  90                  95
Leu Arg Ser Asp Val Val Phe Asn Val Ser Lys Thr Gly Gly His Leu
            100                 105                 110
Gly Ser Ser Leu Gly Val Val Glu Leu Thr Val Ala Leu His Tyr Val
            115                 120                 125
Phe Asn Ala Pro Gln Asp Arg Ile Leu Trp Asp Val Gly His Gln Ser
            130                 135                 140
Tyr Pro His Lys Ile Leu Thr Gly Arg Arg Asp Gln Met His Thr Met
145                 150                 155                 160
Arg Gln Thr Asp Gly Leu Ala Gly Phe Thr Lys Arg Ser Glu Ser Glu
                165                 170                 175
Tyr Asp Cys Phe Gly Thr Gly His Ser Ser Thr Ile Ser Ala Gly
            180                 185                 190
Leu Gly Met Ala Val Gly Arg Asp Leu Lys Gly Lys Asn Asn Val
            195                 200                 205
Ile Ala Val Ile Gly Asp Gly Ala Met Thr Ala Gly Gln Ala Tyr Glu
210                 215                 220
Ala Met Asn Asn Ala Gly Tyr Leu Asp Ser Asp Met Ile Val Ile Leu
225                 230                 235                 240
Asn Asp Asn Lys Gln Val Ser Leu Pro Thr Ala Thr Leu Asp Gly Pro
                245                 250                 255
Ile Pro Pro Val Gly Ala Leu Ser Ser Ala Leu Ser Arg Leu Gln Ser
            260                 265                 270
Asn Arg Pro Leu Arg Glu Leu Arg Glu Val Ala Xaa Gly Val Thr Lys
            275                 280                 285
Gln Ile Gly Gly Pro Met His Glu Leu Ala Ala Lys Val Asp Glu Tyr
290                 295                 300
Ala Xaa Gly Met Ile Ser Gly Ser Gly Ser Thr Leu Phe Glu Glu Leu
305                 310                 315                 320
Gly Leu Tyr Tyr Ile Gly Pro Val Asp Gly His Asn Ile Asp Asp Leu
            325                 330                 335
Val Ala Ile Leu Lys Glu Val Lys Ser Thr Lys Thr Thr Gly Pro Val
            340                 345                 350
Leu Ile His Val Val Thr Glu Lys Gly Arg Gly Tyr Pro Tyr Ala Glu
            355                 360                 365
Lys Ala Ala Asp Lys Tyr His Gly Val Thr Lys Phe Asp Pro Ala Thr
            370                 375                 380
Gly Lys Gln Phe Lys Ser Ser Ala Pro Thr Gln Ser Tyr Thr Thr Tyr
385                 390                 395                 400
Phe Ala Glu Ala Leu Ile Ala Glu Ala Glu Val Asp Lys Asp Ile Val
                405                 410                 415
Ala Ile His Ala Ala Met Gly Gly Gly Thr Gly Leu Asn Leu Phe His
            420                 425                 430
Arg Arg Phe Pro Thr Arg Cys Phe Asp Val Gly Ile Ala Glu Gln His
            435                 440                 445
Ala Val Thr Phe Ala Ala Gly Leu Ala Cys Glu Gly Ile Lys Pro Phe
            450                 455                 460
Cys Ala Ile Tyr Ser Ser Phe Met Gln Arg Ala Tyr Asp Gln Val Val
465                 470                 475                 480
His Asp Val Asp Leu Gln Lys Leu Pro Val Lys Phe Ala Met Asp Arg
                485                 490                 495
Ala Gly Leu Val Gly Ala Asp Gly Pro Thr His Cys Gly Ala Phe Asp
            500                 505                 510
```

```
Val Ala Phe Met Ala Cys Leu Pro Asn Met Val Met Ala Pro Ala
            515                 520                 525

Asp Glu Ala Glu Leu Phe His Met Val Ala Thr Ala Ala Ile Asp
        530                 535                 540

Asp Arg Pro Ser Cys Phe Arg Tyr Pro Arg Gly Asn Gly Val Gly Val
545                 550                 555                 560

Glu Leu Pro Pro Gly Asn Lys Gly Ile Pro Ile Glu Val Gly Arg Gly
                565                 570                 575

Arg Ile Leu Ile Glu Gly Glu Arg Val Ala Leu Leu Gly Tyr Gly Thr
                580                 585                 590

Ala Val Gln Ser Cys Leu Val Ala Ser Ser Leu Leu Glu Gln His Gly
            595                 600                 605

Leu Arg Ile Thr Val Ala Asp Ala Arg Phe Cys Lys Pro Leu Asp His
        610                 615                 620

Ala Leu Ile Arg Ser Leu Ala Lys Ser His Glu Val Leu Ile Thr Val
625                 630                 635                 640

Glu Glu Gly Ser Ile Gly Gly Phe Gly Ser His Val Ala Gln Phe Leu
                645                 650                 655

Ala Leu Asn Gly Leu Leu Asp Gly Thr Thr Lys Trp Ser Pro Met Val
            660                 665                 670

Leu Pro Asp Arg Tyr Ile Asp His Gly Ala Pro Ala Asp Gln Leu Ala
        675                 680                 685

Met Ala Gly Leu Thr Pro Ser His Ile Ala Ala Thr Val Phe Asn Ile
        690                 695                 700

Leu Gly Gln Thr Arg Glu Ala Leu Glu Ile Met Leu
705                 710                 715

<210> SEQ ID NO 3
<211> LENGTH: 716
<212> TYPE: PRT
<213> ORGANISM: Vitis Vinifera

<400> SEQUENCE: 3

Met Ala Leu Cys Thr Leu Ser Phe Pro Ala His Phe Ser Gln Ala Ala
1               5                   10                  15

Ala Ser Asn Pro Gln Arg Leu Thr Pro Gln Cys Ser His Leu Phe Leu
            20                  25                  30

Gly Val Asp Leu Gln Cys Gln Ser Gln Gln Arg Ser Lys Ala Arg Lys
        35                  40                  45

Arg Pro Asn Gly Val Cys Ala Ser Leu Ser Asp Arg Glu Glu Tyr His
50                  55                  60

Ser Gln Arg Pro Pro Thr Pro Leu Leu Asp Thr Ile Asn Tyr Pro Ile
65                  70                  75                  80

His Met Lys Asn Leu Ser Val Lys Glu Leu Lys Gln Leu Ala Asp Glu
                85                  90                  95

Leu Arg Ser Asp Val Val Phe Asn Val Ser Lys Thr Gly Gly His Leu
            100                 105                 110

Gly Ser Ser Leu Gly Val Val Glu Leu Thr Val Ala Leu His Tyr Val
        115                 120                 125

Phe Asn Ala Pro Gln Asp Arg Ile Leu Trp Asp Val Gly His Gln Ser
    130                 135                 140

Tyr Pro His Lys Ile Leu Thr Gly Arg Arg Asp Gln Met His Thr Met
145                 150                 155                 160

Arg Gln Thr Asp Gly Leu Ala Gly Phe Thr Lys Arg Ser Glu Ser Glu
```

```
                  165                 170                 175
Tyr Asp Cys Phe Gly Thr Gly His Ser Ser Thr Thr Ile Ser Ala Gly
            180                 185                 190

Leu Gly Met Ala Val Gly Arg Asp Leu Lys Gly Lys Asn Asn Asn Val
            195                 200                 205

Ile Ala Val Ile Gly Asp Gly Ala Met Thr Ala Gly Gln Ala Tyr Glu
            210                 215                 220

Ala Met Asn Asn Ala Gly Tyr Leu Asp Ser Asp Met Ile Val Ile Leu
225                 230                 235                 240

Asn Asp Asn Lys Gln Val Ser Leu Pro Thr Ala Thr Leu Asp Gly Pro
            245                 250                 255

Ile Pro Pro Val Gly Ala Leu Ser Ser Ala Leu Ser Arg Leu Gln Ser
            260                 265                 270

Asn Arg Pro Leu Arg Glu Leu Arg Glu Val Ala Lys Gly Val Thr Lys
            275                 280                 285

Gln Ile Gly Gly Pro Met His Glu Leu Ala Ala Lys Val Asp Glu Tyr
            290                 295                 300

Ala Arg Gly Met Ile Ser Gly Ser Gly Ser Thr Leu Phe Glu Glu Leu
305                 310                 315                 320

Gly Leu Tyr Tyr Ile Gly Pro Val Asp Gly His Asn Ile Asp Asp Leu
            325                 330                 335

Val Ala Ile Leu Lys Glu Val Lys Ser Thr Lys Thr Thr Gly Pro Val
            340                 345                 350

Leu Ile His Val Val Thr Glu Lys Gly Arg Gly Tyr Pro Tyr Ala Glu
            355                 360                 365

Lys Ala Ala Asp Lys Tyr His Gly Val Thr Lys Phe Asp Pro Ala Thr
            370                 375                 380

Gly Lys Gln Phe Lys Ser Ser Ala Pro Thr Gln Ser Tyr Thr Thr Tyr
385                 390                 395                 400

Phe Ala Glu Ala Leu Ile Ala Glu Ala Glu Val Asp Lys Asp Ile Val
            405                 410                 415

Ala Ile His Ala Ala Met Gly Gly Gly Thr Gly Leu Asn Leu Phe His
            420                 425                 430

Arg Arg Phe Pro Thr Arg Cys Phe Asp Val Gly Ile Ala Glu Gln His
            435                 440                 445

Ala Val Thr Phe Ala Ala Gly Leu Ala Cys Glu Gly Ile Lys Pro Phe
            450                 455                 460

Cys Ala Ile Tyr Ser Ser Phe Met Gln Arg Ala Tyr Asp Gln Val Val
465                 470                 475                 480

His Asp Val Asp Leu Gln Lys Leu Pro Val Lys Phe Ala Met Asp Arg
            485                 490                 495

Ala Gly Leu Val Gly Ala Asp Gly Pro Thr His Cys Gly Ala Phe Asp
            500                 505                 510

Val Ala Phe Met Ala Cys Leu Pro Asn Met Val Val Met Ala Pro Ala
            515                 520                 525

Asp Glu Ala Glu Leu Phe His Met Val Ala Thr Ala Ala Ile Asp
            530                 535                 540

Asp Arg Pro Ser Cys Phe Arg Tyr Pro Arg Gly Asn Gly Val Gly Val
545                 550                 555                 560

Glu Leu Pro Pro Gly Asn Lys Gly Ile Pro Ile Glu Val Gly Arg Gly
            565                 570                 575

Arg Ile Leu Ile Glu Gly Glu Arg Val Ala Leu Leu Gly Tyr Gly Thr
            580                 585                 590
```

```
Ala Val Gln Ser Cys Leu Val Ala Ser Ser Leu Leu Glu Gln His Gly
            595                 600                 605

Leu Arg Ile Thr Val Ala Asp Ala Arg Phe Cys Lys Pro Leu Asp His
        610                 615                 620

Ala Leu Ile Arg Ser Leu Ala Lys Ser His Glu Val Leu Ile Thr Val
625                 630                 635                 640

Glu Glu Gly Ser Ile Gly Gly Phe Gly Ser His Val Ala Gln Phe Leu
                645                 650                 655

Ala Leu Asn Gly Leu Leu Asp Gly Thr Thr Lys Trp Ser Pro Met Val
            660                 665                 670

Leu Pro Asp Arg Tyr Ile Asp His Gly Ala Pro Ala Asp Gln Leu Ala
        675                 680                 685

Met Ala Gly Leu Thr Pro Ser His Ile Ala Ala Thr Val Phe Asn Ile
690                 695                 700

Leu Gly Gln Thr Arg Glu Ala Leu Glu Ile Met Leu
705                 710                 715

<210> SEQ ID NO 4
<211> LENGTH: 716
<212> TYPE: PRT
<213> ORGANISM: Vitis Vinifera

<400> SEQUENCE: 4

Met Ala Leu Cys Thr Leu Ser Phe Pro Ala His Phe Ser Gln Ala Ala
1               5                   10                  15

Ala Ser Asn Pro Gln Arg Leu Thr Pro Gln Cys Ser His Leu Phe Leu
            20                  25                  30

Gly Val Asp Leu Gln Cys Gln Ser Gln Gln Arg Ser Lys Ala Arg Lys
        35                  40                  45

Arg Pro Asn Gly Val Cys Ala Ser Leu Ser Asp Arg Glu Glu Tyr His
    50                  55                  60

Ser Gln Arg Pro Pro Thr Pro Leu Leu Asp Thr Ile Asn Tyr Pro Ile
65                  70                  75                  80

His Met Lys Asn Leu Ser Val Lys Glu Leu Lys Gln Leu Ala Asp Glu
                85                  90                  95

Leu Arg Ser Asp Val Val Phe Asn Val Ser Lys Thr Gly Gly His Leu
            100                 105                 110

Gly Ser Ser Leu Gly Val Val Glu Leu Thr Val Ala Leu His Tyr Val
        115                 120                 125

Phe Asn Ala Pro Gln Asp Arg Ile Leu Trp Asp Val Gly His Gln Ser
    130                 135                 140

Tyr Pro His Lys Ile Leu Thr Gly Arg Arg Asp Gln Met His Thr Met
145                 150                 155                 160

Arg Gln Thr Asp Gly Leu Ala Gly Phe Thr Lys Arg Ser Glu Ser Glu
                165                 170                 175

Tyr Asp Cys Phe Gly Thr Gly His Ser Ser Thr Thr Ile Ser Ala Gly
            180                 185                 190

Leu Gly Met Ala Val Gly Arg Asp Leu Lys Gly Lys Asn Asn Asn Val
        195                 200                 205

Ile Ala Val Ile Gly Asp Gly Ala Met Thr Ala Gly Gln Ala Tyr Glu
    210                 215                 220

Ala Met Asn Asn Ala Gly Tyr Leu Asp Ser Asp Met Ile Val Ile Leu
225                 230                 235                 240

Asn Asp Asn Lys Gln Val Ser Leu Pro Thr Ala Thr Leu Asp Gly Pro
```

```
                245                 250                 255
Ile Pro Pro Val Gly Ala Leu Ser Ser Ala Leu Ser Arg Leu Gln Ser
            260                 265                 270

Asn Arg Pro Leu Arg Glu Leu Arg Glu Val Ala Asn Gly Val Thr Lys
            275                 280                 285

Gln Ile Gly Gly Pro Met His Glu Leu Ala Ala Lys Val Asp Glu Tyr
            290                 295                 300

Ala Arg Gly Met Ile Ser Gly Ser Gly Ser Thr Leu Phe Glu Glu Leu
305                 310                 315                 320

Gly Leu Tyr Tyr Ile Gly Pro Val Asp Gly His Asn Ile Asp Asp Leu
                325                 330                 335

Val Ala Ile Leu Lys Glu Val Lys Ser Thr Lys Thr Thr Gly Pro Val
                340                 345                 350

Leu Ile His Val Val Thr Glu Lys Gly Arg Gly Tyr Pro Tyr Ala Glu
                355                 360                 365

Lys Ala Ala Asp Lys Tyr His Gly Val Thr Lys Phe Asp Pro Ala Thr
            370                 375                 380

Gly Lys Gln Phe Lys Ser Ser Ala Pro Thr Gln Ser Tyr Thr Thr Tyr
385                 390                 395                 400

Phe Ala Glu Ala Leu Ile Ala Glu Ala Glu Val Asp Lys Asp Ile Val
                405                 410                 415

Ala Ile His Ala Ala Met Gly Gly Gly Thr Gly Leu Asn Leu Phe His
                420                 425                 430

Arg Arg Phe Pro Thr Arg Cys Phe Asp Val Gly Ile Ala Glu Gln His
                435                 440                 445

Ala Val Thr Phe Ala Ala Gly Leu Ala Cys Glu Gly Ile Lys Pro Phe
                450                 455                 460

Cys Ala Ile Tyr Ser Ser Phe Met Gln Arg Ala Tyr Asp Gln Val Val
465                 470                 475                 480

His Asp Val Asp Leu Gln Lys Leu Pro Val Lys Phe Ala Met Asp Arg
                485                 490                 495

Ala Gly Leu Val Gly Ala Asp Gly Pro Thr His Cys Gly Ala Phe Asp
                500                 505                 510

Val Ala Phe Met Ala Cys Leu Pro Asn Met Val Val Met Ala Pro Ala
                515                 520                 525

Asp Glu Ala Glu Leu Phe His Met Val Ala Thr Ala Ala Ala Ile Asp
                530                 535                 540

Asp Arg Pro Ser Cys Phe Arg Tyr Pro Arg Gly Asn Gly Val Gly Ile
545                 550                 555                 560

Glu Leu Pro Pro Gly Asn Lys Gly Ile Pro Ile Glu Val Gly Arg Gly
                565                 570                 575

Arg Ile Leu Ile Glu Gly Glu Arg Val Ala Leu Leu Gly Tyr Gly Thr
                580                 585                 590

Ala Val Gln Ser Cys Leu Val Ala Ser Ser Leu Leu Glu Gln His Gly
                595                 600                 605

Leu Arg Ile Thr Val Ala Asp Ala Arg Phe Cys Lys Pro Leu Asp His
                610                 615                 620

Ala Leu Ile Arg Ser Leu Ala Lys Ser His Glu Val Leu Ile Thr Val
625                 630                 635                 640

Glu Glu Gly Ser Ile Gly Gly Phe Gly Ser His Val Ala Gln Phe Leu
                645                 650                 655

Ala Leu Asn Gly Leu Leu Asp Gly Thr Thr Lys Trp Ser Pro Met Val
                660                 665                 670
```

-continued

```
Leu Pro Asp Arg Tyr Ile Asp His Gly Ala Pro Ala Asp Gln Leu Ala
        675                 680                 685

Met Ala Gly Leu Thr Pro Ser His Ile Ala Ala Thr Val Phe Asn Ile
        690                 695                 700

Leu Gly Gln Thr Arg Glu Ala Leu Glu Ile Met Leu
705                 710                 715

<210> SEQ ID NO 5
<211> LENGTH: 664
<212> TYPE: PRT
<213> ORGANISM: Artificial sequence
<220> FEATURE:
<223> OTHER INFORMATION: Truncated DXS polypeptide

<400> SEQUENCE: 5

Val Cys Ala Ser Leu Ser Asp Arg Glu Glu Tyr His Ser Gln Arg Pro
1               5                   10                  15

Pro Thr Pro Leu Leu Asp Thr Ile Asn Tyr Pro Ile His Met Lys Asn
            20                  25                  30

Leu Ser Val Lys Glu Leu Lys Gln Leu Ala Asp Glu Leu Arg Ser Asp
        35                  40                  45

Val Val Phe Asn Val Ser Lys Thr Gly Gly His Leu Gly Ser Ser Leu
    50                  55                  60

Gly Val Val Glu Leu Thr Val Ala Leu His Tyr Val Phe Asn Ala Pro
65                  70                  75                  80

Gln Asp Arg Ile Leu Trp Asp Val Gly His Gln Ser Tyr Pro His Lys
                85                  90                  95

Ile Leu Thr Gly Arg Arg Asp Gln Met His Thr Met Arg Gln Thr Asp
            100                 105                 110

Gly Leu Ala Gly Phe Thr Lys Arg Ser Glu Ser Glu Tyr Asp Cys Phe
        115                 120                 125

Gly Thr Gly His Ser Ser Thr Thr Ile Ser Ala Gly Leu Gly Met Ala
    130                 135                 140

Val Gly Arg Asp Leu Lys Gly Lys Asn Asn Asn Val Ile Ala Val Ile
145                 150                 155                 160

Gly Asp Gly Ala Met Thr Ala Gly Gln Ala Tyr Glu Ala Met Asn Asn
                165                 170                 175

Ala Gly Tyr Leu Asp Ser Asp Met Ile Val Ile Leu Asn Asp Asn Lys
            180                 185                 190

Gln Val Ser Leu Pro Thr Ala Thr Leu Asp Gly Pro Ile Pro Pro Val
        195                 200                 205

Gly Ala Leu Ser Ser Ala Leu Ser Arg Leu Gln Ser Asn Arg Pro Leu
    210                 215                 220

Arg Glu Leu Arg Glu Val Ala Asn Gly Val Thr Lys Gln Ile Gly Gly
225                 230                 235                 240

Pro Met His Glu Leu Ala Ala Lys Val Asp Glu Tyr Ala Arg Gly Met
                245                 250                 255

Ile Ser Gly Ser Gly Ser Thr Leu Phe Glu Glu Leu Gly Leu Tyr Tyr
            260                 265                 270

Ile Gly Pro Val Asp Gly His Asn Ile Asp Asp Leu Val Ala Ile Leu
        275                 280                 285

Lys Glu Val Lys Ser Thr Lys Thr Thr Gly Pro Val Leu Ile His Val
    290                 295                 300

Val Thr Glu Lys Gly Arg Gly Tyr Pro Tyr Ala Glu Lys Ala Ala Asp
305                 310                 315                 320
```

Lys Tyr His Gly Val Thr Lys Phe Asp Pro Ala Thr Gly Lys Gln Phe
                325                 330                 335

Lys Ser Ser Ala Pro Thr Gln Ser Tyr Thr Thr Tyr Phe Ala Glu Ala
            340                 345                 350

Leu Ile Ala Glu Ala Glu Val Asp Lys Asp Ile Val Ala Ile His Ala
        355                 360                 365

Ala Met Gly Gly Gly Thr Gly Leu Asn Leu Phe His Arg Arg Phe Pro
    370                 375                 380

Thr Arg Cys Phe Asp Val Gly Ile Ala Glu Gln His Ala Val Thr Phe
385                 390                 395                 400

Ala Ala Gly Leu Ala Cys Glu Gly Ile Lys Pro Phe Cys Ala Ile Tyr
                405                 410                 415

Ser Ser Phe Met Gln Arg Ala Tyr Asp Gln Val Val His Asp Val Asp
            420                 425                 430

Leu Gln Lys Leu Pro Val Lys Phe Ala Met Asp Arg Ala Gly Leu Val
        435                 440                 445

Gly Ala Asp Gly Pro Thr His Cys Gly Ala Phe Asp Val Ala Phe Met
    450                 455                 460

Ala Cys Leu Pro Asn Met Val Val Met Ala Pro Ala Asp Glu Ala Glu
465                 470                 475                 480

Leu Phe His Met Val Ala Thr Ala Ala Ile Asp Asp Arg Pro Ser
                485                 490                 495

Cys Phe Arg Tyr Pro Arg Gly Asn Gly Val Gly Ile Glu Leu Pro Pro
            500                 505                 510

Gly Asn Lys Gly Ile Pro Ile Glu Val Gly Arg Gly Ile Leu Ile
        515                 520                 525

Glu Gly Glu Arg Val Ala Leu Leu Gly Tyr Gly Thr Ala Val Gln Ser
    530                 535                 540

Cys Leu Val Ala Ser Ser Leu Leu Glu Gln His Gly Leu Arg Ile Thr
545                 550                 555                 560

Val Ala Asp Ala Arg Phe Cys Lys Pro Leu Asp His Ala Leu Ile Arg
                565                 570                 575

Ser Leu Ala Lys Ser His Glu Val Leu Ile Thr Val Glu Glu Gly Ser
            580                 585                 590

Ile Gly Gly Phe Gly Ser His Val Ala Gln Phe Leu Ala Leu Asn Gly
        595                 600                 605

Leu Leu Asp Gly Thr Thr Lys Trp Ser Pro Met Val Leu Pro Asp Arg
    610                 615                 620

Tyr Ile Asp His Gly Ala Pro Ala Asp Gln Leu Ala Met Ala Gly Leu
625                 630                 635                 640

Thr Pro Ser His Ile Ala Ala Thr Val Phe Asn Ile Leu Gly Gln Thr
                645                 650                 655

Arg Glu Ala Leu Glu Ile Met Leu
            660

<210> SEQ ID NO 6
<211> LENGTH: 716
<212> TYPE: PRT
<213> ORGANISM: Vitis Vinifera

<400> SEQUENCE: 6

Met Ala Leu Cys Thr Leu Ser Phe Pro Ala His Phe Ser Gln Ala Ala
1               5                   10                  15

Ala Ser Asn Pro Gln Arg Leu Thr Pro Gln Cys Ser His Leu Phe Leu

```
                    20                  25                  30
Gly Val Asp Leu Gln Cys Gln Ser Gln Gln Arg Ser Lys Ala Arg Lys
                35                  40                  45
Arg Pro Asn Gly Val Cys Ala Ser Leu Ser Asp Arg Glu Glu Tyr His
 50                  55                  60
Ser Gln Arg Pro Pro Thr Pro Leu Leu Asp Thr Ile Asn Tyr Pro Ile
 65                  70                  75                  80
His Met Lys Asn Leu Ser Val Lys Glu Leu Lys Gln Leu Ala Asp Glu
                85                  90                  95
Leu Arg Ser Asp Val Val Phe Asn Val Ser Lys Thr Gly Gly His Leu
                100                 105                 110
Gly Ser Ser Leu Gly Val Val Glu Leu Thr Val Ala Leu His Tyr Val
                115                 120                 125
Phe Asn Ala Pro Gln Asp Arg Ile Leu Trp Asp Val Gly His Gln Ser
                130                 135                 140
Tyr Pro His Lys Ile Leu Thr Gly Arg Arg Asp Gln Met His Thr Met
145                 150                 155                 160
Arg Gln Thr Asp Gly Leu Ala Gly Phe Thr Lys Arg Ser Glu Ser Glu
                165                 170                 175
Tyr Asp Cys Phe Gly Thr Gly His Ser Ser Thr Thr Ile Ser Ala Gly
                180                 185                 190
Leu Gly Met Ala Val Gly Arg Asp Leu Lys Gly Lys Asn Asn Asn Val
                195                 200                 205
Ile Ala Val Ile Gly Asp Gly Ala Met Thr Ala Gly Gln Ala Tyr Glu
                210                 215                 220
Ala Met Asn Asn Ala Gly Tyr Leu Asp Ser Asp Met Ile Val Ile Leu
225                 230                 235                 240
Asn Asp Asn Lys Gln Val Ser Leu Pro Thr Ala Thr Leu Asp Gly Pro
                245                 250                 255
Ile Pro Pro Val Gly Ala Leu Ser Ser Ala Leu Ser Arg Leu Gln Ser
                260                 265                 270
Asn Arg Pro Leu Arg Glu Leu Arg Glu Val Ala Lys Gly Val Thr Lys
                275                 280                 285
Gln Ile Gly Gly Pro Met His Glu Leu Ala Ala Lys Val Asp Glu Tyr
                290                 295                 300
Ala Cys Gly Met Ile Ser Gly Ser Gly Ser Thr Leu Phe Glu Glu Leu
305                 310                 315                 320
Gly Leu Tyr Tyr Ile Gly Pro Val Asp Gly His Asn Ile Asp Asp Leu
                325                 330                 335
Val Ala Ile Leu Lys Glu Val Lys Ser Thr Lys Thr Thr Gly Pro Val
                340                 345                 350
Leu Ile His Val Val Thr Glu Lys Gly Arg Gly Tyr Pro Tyr Ala Glu
                355                 360                 365
Lys Ala Ala Asp Lys Tyr His Gly Val Thr Lys Phe Asp Pro Ala Thr
                370                 375                 380
Gly Lys Gln Phe Lys Ser Ser Ala Pro Thr Gln Ser Tyr Thr Thr Tyr
385                 390                 395                 400
Phe Ala Glu Ala Leu Ile Ala Glu Ala Glu Val Asp Lys Asp Ile Val
                405                 410                 415
Ala Ile His Ala Ala Met Gly Gly Gly Thr Gly Leu Asn Leu Phe His
                420                 425                 430
Arg Arg Phe Pro Thr Arg Cys Phe Asp Val Gly Ile Ala Glu Gln His
                435                 440                 445
```

```
Ala Val Thr Phe Ala Ala Gly Leu Ala Cys Glu Gly Ile Lys Pro Phe
    450                 455                 460
Cys Ala Ile Tyr Ser Ser Phe Met Gln Arg Ala Tyr Asp Gln Val Val
465                 470                 475                 480
His Asp Val Asp Leu Gln Lys Leu Pro Val Lys Phe Ala Met Asp Arg
                485                 490                 495
Ala Gly Leu Val Gly Ala Asp Gly Pro Thr His Cys Gly Ala Phe Asp
                500                 505                 510
Val Ala Phe Met Ala Cys Leu Pro Asn Met Val Val Met Ala Pro Ala
                515                 520                 525
Asp Glu Ala Glu Leu Phe His Met Val Ala Thr Ala Ala Ala Ile Asp
    530                 535                 540
Asp Arg Pro Ser Cys Phe Arg Tyr Pro Arg Gly Asn Gly Val Gly Val
545                 550                 555                 560
Glu Leu Pro Pro Gly Asn Lys Gly Ile Pro Ile Glu Val Gly Arg Gly
                565                 570                 575
Arg Ile Leu Ile Glu Gly Glu Arg Val Ala Leu Leu Gly Tyr Gly Thr
                580                 585                 590
Ala Val Gln Ser Cys Leu Val Ala Ser Ser Leu Leu Glu Gln His Gly
    595                 600                 605
Leu Arg Ile Thr Val Ala Asp Ala Arg Phe Cys Lys Pro Leu Asp His
    610                 615                 620
Ala Leu Ile Arg Ser Leu Ala Lys Ser His Glu Val Leu Ile Thr Val
625                 630                 635                 640
Glu Glu Gly Ser Ile Gly Gly Phe Gly Ser His Val Ala Gln Phe Leu
                645                 650                 655
Ala Leu Asn Gly Leu Leu Asp Gly Thr Thr Lys Trp Ser Pro Met Val
                660                 665                 670
Leu Pro Asp Arg Tyr Ile Asp His Gly Ala Pro Ala Asp Gln Leu Ala
                675                 680                 685
Met Ala Gly Leu Thr Pro Ser His Ile Ala Ala Thr Val Phe Asn Ile
    690                 695                 700
Leu Gly Gln Thr Arg Glu Ala Leu Glu Ile Met Leu
705                 710                 715

<210> SEQ ID NO 7
<211> LENGTH: 664
<212> TYPE: PRT
<213> ORGANISM: Artificial sequence
<220> FEATURE:
<223> OTHER INFORMATION: Truncated DXS polypeptide

<400> SEQUENCE: 7

Val Cys Ala Ser Leu Ser Asp Arg Glu Glu Tyr His Ser Gln Arg Pro
1               5                   10                  15
Pro Thr Pro Leu Leu Asp Thr Ile Asn Tyr Pro Ile His Met Lys Asn
                20                  25                  30
Leu Ser Val Lys Glu Leu Lys Gln Leu Ala Asp Glu Leu Arg Ser Asp
            35                  40                  45
Val Val Phe Asn Val Ser Lys Thr Gly Gly His Leu Gly Ser Ser Leu
        50                  55                  60
Gly Val Val Glu Leu Thr Val Ala Leu His Tyr Val Phe Asn Ala Pro
65              70                  75                  80
Gln Asp Arg Ile Leu Trp Asp Val Gly His Gln Ser Tyr Pro His Lys
                85                  90                  95
```

```
Ile Leu Thr Gly Arg Arg Asp Gln Met His Thr Met Arg Gln Thr Asp
                100                 105                 110

Gly Leu Ala Gly Phe Thr Lys Arg Ser Glu Ser Glu Tyr Asp Cys Phe
            115                 120                 125

Gly Thr Gly His Ser Ser Thr Thr Ile Ser Ala Gly Leu Gly Met Ala
        130                 135                 140

Val Gly Arg Asp Leu Lys Gly Lys Asn Asn Asn Val Ile Ala Val Ile
145                 150                 155                 160

Gly Asp Gly Ala Met Thr Ala Gly Gln Ala Tyr Glu Ala Met Asn Asn
                165                 170                 175

Ala Gly Tyr Leu Asp Ser Asp Met Ile Val Ile Leu Asn Asp Asn Lys
            180                 185                 190

Gln Val Ser Leu Pro Thr Ala Thr Leu Asp Gly Pro Ile Pro Pro Val
        195                 200                 205

Gly Ala Leu Ser Ser Ala Leu Ser Arg Leu Gln Ser Asn Arg Pro Leu
        210                 215                 220

Arg Glu Leu Arg Glu Val Ala Lys Gly Val Thr Lys Gln Ile Gly Gly
225                 230                 235                 240

Pro Met His Glu Leu Ala Ala Lys Val Asp Glu Tyr Ala Cys Gly Met
                245                 250                 255

Ile Ser Gly Ser Gly Ser Thr Leu Phe Glu Glu Leu Gly Leu Tyr Tyr
            260                 265                 270

Ile Gly Pro Val Asp Gly His Asn Ile Asp Asp Leu Val Ala Ile Leu
        275                 280                 285

Lys Glu Val Lys Ser Thr Lys Thr Thr Gly Pro Val Leu Ile His Val
        290                 295                 300

Val Thr Glu Lys Gly Arg Gly Tyr Pro Tyr Ala Glu Lys Ala Ala Asp
305                 310                 315                 320

Lys Tyr His Gly Val Thr Lys Phe Asp Pro Ala Thr Gly Lys Gln Phe
                325                 330                 335

Lys Ser Ser Ala Pro Thr Gln Ser Tyr Thr Thr Tyr Phe Ala Glu Ala
            340                 345                 350

Leu Ile Ala Glu Ala Glu Val Asp Lys Asp Ile Val Ala Ile His Ala
        355                 360                 365

Ala Met Gly Gly Gly Thr Gly Leu Asn Leu Phe His Arg Arg Phe Pro
        370                 375                 380

Thr Arg Cys Phe Asp Val Gly Ile Ala Glu Gln His Ala Val Thr Phe
385                 390                 395                 400

Ala Ala Gly Leu Ala Cys Glu Gly Ile Lys Pro Phe Cys Ala Ile Tyr
                405                 410                 415

Ser Ser Phe Met Gln Arg Ala Tyr Asp Gln Val Val His Asp Val Asp
            420                 425                 430

Leu Gln Lys Leu Pro Val Lys Phe Ala Met Asp Arg Ala Gly Leu Val
        435                 440                 445

Gly Ala Asp Gly Pro Thr His Cys Gly Ala Phe Asp Val Ala Phe Met
        450                 455                 460

Ala Cys Leu Pro Asn Met Val Val Met Ala Pro Ala Asp Glu Ala Glu
465                 470                 475                 480

Leu Phe His Met Val Ala Thr Ala Ala Ala Ile Asp Asp Arg Pro Ser
                485                 490                 495

Cys Phe Arg Tyr Pro Arg Gly Asn Gly Val Gly Val Glu Leu Pro Pro
            500                 505                 510
```

```
Gly Asn Lys Gly Ile Pro Ile Glu Val Gly Arg Gly Ile Leu Ile
            515                 520                 525

Glu Gly Glu Arg Val Ala Leu Leu Gly Tyr Gly Thr Ala Val Gln Ser
        530                 535                 540

Cys Leu Val Ala Ser Ser Leu Leu Glu Gln His Gly Leu Arg Ile Thr
545                 550                 555                 560

Val Ala Asp Ala Arg Phe Cys Lys Pro Leu Asp His Ala Leu Ile Arg
                565                 570                 575

Ser Leu Ala Lys Ser His Glu Val Leu Ile Thr Val Glu Glu Gly Ser
                580                 585                 590

Ile Gly Gly Phe Gly Ser His Val Ala Gln Phe Leu Ala Leu Asn Gly
            595                 600                 605

Leu Leu Asp Gly Thr Thr Lys Trp Ser Pro Met Val Leu Pro Asp Arg
        610                 615                 620

Tyr Ile Asp His Gly Ala Pro Ala Asp Gln Leu Ala Met Ala Gly Leu
625                 630                 635                 640

Thr Pro Ser His Ile Ala Ala Thr Val Phe Asn Ile Leu Gly Gln Thr
                645                 650                 655

Arg Glu Ala Leu Glu Ile Met Leu
            660
```

<210> SEQ ID NO 8
<211> LENGTH: 1846
<212> TYPE: DNA
<213> ORGANISM: Vitis Vinifera

<400> SEQUENCE: 8

```
cttcaatgtt tccaaaactg ggggtcactt gggctccagc ctcggggttg tggagctcac     60
tgtggctctt cattatgtct tcaatgcccc tcaagacagg atactatggg atgttggtca    120
tcagtcttac ccacacaaaa ttctaactgg agaagagat caaatgcata ccatgaggca    180
aacagatggg ttagcgggat tcaccaagcg ctcggagagt gaatatgact gctttggaac    240
cggccacagt tctactacca tctcagcagg cttgggaatg gcggtcggcc gggatctaaa    300
aggaaaaaac aacaacgtca ttgctgtcat aggtgatgga gccatgactg cagggcaagc    360
ttatgaagca atgaacaatg ctggttacct ggattctgac atgattgtta tccttaatga    420
caacaagcag gtttctttac ccactgctac tctagatggg cccataccac tgtaggagc    480
tttgagcagt gctcttagta ggttacaatc aaacagacct cttagagaat acgagaggt    540
tgccaagggc gttaccaaac agattggcgg accgatgcat gaattggctg caaaagttga    600
tgaatatgct cgtgggatga tcagtggttc tggatcaaca cttttttgaag agcttggact    660
ctattatata ggtcctgttg atggccacaa catagatgac cttgttgcca ttctcaagga    720
ggttaagagt accaagacaa caggtccagt tctgatccat gttgtcacag agaaaggccg    780
cggatatcca tatgctgaga aagctgcaga taagtaccat ggagtgacca agttcgatcc    840
tgctactgga aaacaattca atccagtgc tcctactcag tcctacacaa catattttgc    900
agaggctttg attgcagaag cagaggtgga caaggatatt gttgcaattc atgcagcaat    960
gggggggtgga acgggcttga atctcttcca tcgccggttc cccacacgat gctttgatgt   1020
tgggatagca gaacagcatg ctgttacctt tgctgctggt ctagcctgtg aaggcattaa   1080
accttttttgt gcaatctact catctttcat gcagagagct tatgaccagg tggtgcatga   1140
tgtagatttg cagaagctgc cagtgaaatt tgcaatggac agagctgggc tggttggagc   1200
agatggccca acacattgtg gagcttttga tgtcgctttc atggcttgcc ttccaaacat   1260
```

```
ggtggtgatg gctcctgctg atgaggctga gcttttttcac atggtggcca cagctgctgc    1320
catagatgac aggcccagtt gtttccggta cccaagagga atggggtgg gtgttgaact      1380 gccaccaggg aacaaaggca ttcctattga ggttggaagg ggccgaatat tgattgaggg     1440
ggagagagtt gcactcttgg gctatggaac agcagtacag agctgtttgg ttgcgtcttc    1500
tttgctggaa caacatggct tacgaataac agtcgcagat gcccgcttct gcaaaccatt    1560
ggaccatgct cttattcgta gcctagcaaa atcacatgaa gttttgatta cagtagaaga    1620
agggtcaatt ggtggttttg ggtctcatgt tgctcagttt ttggccctta atggtcttct    1680
tgatggcaca acaaagtgga gtcccatggt tcttcctgat cggtacatag accatggagc    1740
gccagcggac cagttggcca tgcgggtct ga caccatct catattgcag caacagtatt    1800
caatatactt ggacaaacaa gggaggccct ggagatcatg ttatag                   1846

<210> SEQ ID NO 9
<211> LENGTH: 2151
<212> TYPE: DNA
<213> ORGANISM: Vitis Vinifera

<400> SEQUENCE: 9
atggctctct gtacgctctc atttcctgcc cattttagcc aggctgctgc ttcaaatcct      60
cagagactta ctcctcagtg tttcccatttg ttcttggggg tggatttgca gtgccaatcc   120
cagcaaagga gtaaggccag gaaaaggcca aatggggttt gtgcatcact ttcggatagg    180
gaggagtatc attcccagag accaccaact cctctcctgg acactatcaa ttatccaatt    240
cacatgaaaa atctgtctgt caaggagctg aaacaactcg cagatgaact aaggtctgat    300
gttgtcttca atgtttccaa aactgggggt cacttgggct ccagcctcgg ggttgtggag    360
ctcactgtgg ctcttcatta tgtcttcaat gcccctcaag acaggatact atgggatgtt    420
ggtcatcagt cttacccaca caaaattcta actgggagaa gagatcaaat gcataccatg    480
aggcaaacag atgggttagc gggattcacc aagcgctcgg agagtgaata tgactgcttt    540
ggaaccggcc acagttctac taccatctca gcaggcttgg gaatggcggt cggccgggat    600
ctaaaaggaa aaacaacaa cgtcattgct gtcataggtg atggagccat gactgcaggg    660
caagcttatg aagcaatgaa caatgctggt tacctggatt ctgacatgat tgttatcctt    720
aatgacaaca agcaggtttc tttacccact gctactctag atgggcccat accacctgta    780
ggagctttga gcagtgctct tagtaggtta caatcaaaca gacctcttag agaattacga    840
gaggttgcca atggcgttac caaacagatt ggcggaccga tgcatgaatt ggctgcaaaa    900
gttgatgaat atgctcgtgg gatgatcagt ggttctggat caacacttt tgaagagctt    960 ggactctatt atataggtcc tgttgatggc acaacatag atgaccttgt tgccattctc    1020
aaggaggtta agagtaccaa gacaacaggt ccagttctga tccatgttgt cacagagaaa    1080
ggccgcggat atccatatgc tgagaaagct gcagataagt accatggagt gaccaagttc    1140
gatcctgcta ctggaaaaaca attcaaatcc agtgctccta ctcagtccta cacaacatat    1200
tttgcagagg ctttgattgc agaagcagag gtggacaagg atattgttgc aattcatgca    1260
gcaatggggg gtgaacggg cttgaatctc ttccatcgcc ggttccccac acgatgcttt    1320
gatgttggga tagcagaaca gcatgctgtt accttttgctg ctggtctagc ctgtgaaggc    1380
attaaacctt tttgtgcaat ctactcatct ttcatgcaga gagcttatga ccaggtggtg    1440
catgatgtag atttgcagaa gctgccagtg aaatttgcaa tggacagagc tgggctggtt    1500
```

-continued

| | |
|---|---|
| ggagcagatg gcccaacaca ttgtggagct tttgatgtcg ctttcatggc ttgccttcca | 1560 |
| aacatggtgg tgatggctcc tgctgatgag gctgagcttt tcacatggt ggccacagct | 1620 |
| gctgccatag atgacaggcc cagttgtttc cggtacccaa aggaaatgg ggtgggtatt | 1680 |
| gaactgccac cagggaacaa aggcattcct attgaggttg aaggggccg aatattgatt | 1740 |
| gaggggagaa gagttgcact cttgggctat ggaacagcag tacagagctg tttggttgcg | 1800 |
| tcttctttgc tggaacaaca tggcttacga ataacagtcg cagatgcccg cttctgcaaa | 1860 |
| ccattggacc atgctcttat tcgtagccta gcaaaatcac atgaagtttt gattacagta | 1920 |
| gaagaagggt caattggtgg ttttgggtct catgttgctc agtttttggc ccttaatggt | 1980 |
| cttcttgatg gcacaacaaa gtggagtccc atggttcttc ctgatcggta catagaccat | 2040 |
| ggagcgccag cggaccagtt ggccatggcg ggtctgacac catctcatat tgcagcaaca | 2100 |
| gtattcaata tacttggaca aacaagggag gccctggaga tcatgttata g | 2151 |

<210> SEQ ID NO 10
<211> LENGTH: 2151
<212> TYPE: DNA
<213> ORGANISM: Vitis Vinifera

<400> SEQUENCE: 10

| | |
|---|---|
| atggctctct gtacgctctc atttcctgcc cattttagcc aggctgctgc ttcaaatcct | 60 |
| cagagactta ctcctcagtg ttcccatttg ttcttggggg tggatttgca gtgccaatcc | 120 |
| cagcaaagga gtaaggccag gaaaaggcca atgggggttt gtgcatcact ttcggatagg | 180 |
| gaggagtatc attcccagag accaccaact cctctcctgg acactatcaa ttatccaatt | 240 |
| cacatgaaaa atctgtctgt caaggagctg aaacaactcg cagatgaact aaggtctgat | 300 |
| gttgtcttca atgtttccaa aactgggggt cacttgggct ccagcctcgg ggttgtggag | 360 |
| ctcactgtgg ctcttcatta tgtcttcaat gcccctcaag acaggatact atgggatgtt | 420 |
| ggtcatcagt cttacccaca caaaattcta actgggagaa gagatcaaat gcataccatg | 480 |
| aggcaaacag atgggttagc gggattcacc aagcgctcgg agagtgaata tgactgcttt | 540 |
| ggaaccggcc acagttctac taccatctca gcaggcttgg gaatggcggt cggccgggat | 600 |
| ctaaaaggaa aaacaacaa cgtcattgct gtcataggtg atggagccat gactgcaggg | 660 |
| caagcttatg aagcaatgaa caatgctggt tacctggatt ctgacatgat tgttatcctt | 720 |
| aatgacaaca agcaggtttc tttacccact gctactctag atgggcccat accacctgta | 780 |
| ggagctttga gcagtgctct tagtaggtta caatcaaaca gacctcttag agaattacga | 840 |
| gaggttgcca agggcgttac caaacagatt ggcggaccga tgcatgaatt ggctgcaaaa | 900 |
| gttgatgaat atgcttgtgg gatgatcagt ggttctggat caacactttt tgaagagctt | 960 |
| ggactctatt atataggtcc tgttgatggc acaacatag atgaccttgt tgccattctc | 1020 |
| aaggaggtta agagtaccaa gacaacaggt ccagttctga tccatgttgt cacagagaaa | 1080 |
| ggccgcggat atccatatgc tgagaaagct gcagataagt accatggagt gaccaagttc | 1140 |
| gatcctgcta ctggaaaaca attcaaatcc agtgctccta ctcagtccta cacaacatat | 1200 |
| tttgcagagg ctttgattgc agaagcagag gtggacaagg atattgttgc aattcatgca | 1260 |
| gcaatggggg gtggaacggg cttgaatctc ttccatcgcc ggttccccac acgatgcttt | 1320 |
| gatgttggga tagcagaaca gcatgctgtt acctttgctg ctggtctagc ctgtgaaggc | 1380 |
| attaaacctt tttgtgcaat ctactcatct ttcatgcaga gagcttatga ccaggtggtg | 1440 |
| catgatgtag atttgcagaa gctgccagtg aaatttgcaa tggacagagc tgggctggtt | 1500 |

| | |
|---|---|
| ggagcagatg cccaacacac ttgtggagct tttgatgtcg ctttcatggc ttgccttcca | 1560 |
| aacatggtgg tgatggctcc tgctgatgag gctgagcttt tcacatggt ggccacagct | 1620 |
| gctgccatag atgacaggcc cagttgtttc cggtacccaa gaggaaatgg ggtgggtgtt | 1680 |
| gaactgccac cagggaacaa aggcattcct attgaggttg aaggggccg aatattgatt | 1740 |
| gaggggggaga gagttgcact cttgggctat ggaacagcag tacagagctg tttggttgcg | 1800 |
| tcttctttgc tggaacaaca tggcttacga ataacagtcg cagatgcccg cttctgcaaa | 1860 |
| ccattggacc atgctcttat tcgtagccta gcaaaatcac atgaagtttt gattacagta | 1920 |
| gaagaagggt caattggtgg ttttgggtct catgttgctc agttttttggc ccttaatggt | 1980 |
| cttcttgatg gcacaacaaa gtggagtccc atggttcttc ctgatcggta catagaccat | 2040 |
| ggagcgccag cggaccagtt ggccatggcg ggtctgacac catctcatat tgcagcaaca | 2100 |
| gtattcaata tacttggaca aacaagggag ccctggaga tcatgttata g | 2151 |

<210> SEQ ID NO 11
<211> LENGTH: 72
<212> TYPE: DNA
<213> ORGANISM: Artificial sequence
<220> FEATURE:
<223> OTHER INFORMATION: PCR primer

<400> SEQUENCE: 11

| | |
|---|---|
| ggggacaagt ttgtacaaaa aagcaggctt ggttccgcgt ggatcaatgg ctctctgtac | 60 |
| gctctcattt cc | 72 |

<210> SEQ ID NO 12
<211> LENGTH: 57
<212> TYPE: DNA
<213> ORGANISM: Artificial sequence
<220> FEATURE:
<223> OTHER INFORMATION: PCR primer

<400> SEQUENCE: 12

| | |
|---|---|
| ggggaccact ttgtacaaga aagctgggtt cactataaca tgatctccag ggcctcc | 57 |

<210> SEQ ID NO 13
<211> LENGTH: 1863
<212> TYPE: DNA
<213> ORGANISM: Escherichia coli

<400> SEQUENCE: 13

| | |
|---|---|
| atgagttttg atattgccaa atacccgacc ctggcactgg tcgactccac ccaggagtta | 60 |
| cgactgttgc cgaaagagag tttaccgaaa ctctgcgacg aactgcgccg ctatttactc | 120 |
| gacagcgtga gccgttccag cgggcacttc gcctccgggc tggcacggt cgaactgacc | 180 |
| gtggcgctgc actatgtcta caacaccccg tttgaccaat tgatttggga tgtggggcat | 240 |
| caggcttatc cgcataaaat tttgaccgga cgccgcgaca aaatcggcac catccgtcag | 300 |
| aaaggcggtc tgcacccgtt cccgtggcgc ggcgaaagcg aatatgacgt attaagcgtc | 360 |
| ggcattcat caacctccat cagtgccgga attggtattg cggttgctgc cgaaaaagaa | 420 |
| ggcaaaaatc gccgcaccgt ctgtgtcatt ggcgatggcg cgattaccgc aggcatggcg | 480 |
| tttgaagcga tgaatcacgc gggcgatatc cgtcctgata tgctggtgat tctcaacgac | 540 |
| aatgaaatgt cgatttccga aaatgtcggc gcgctcaaca accatctggc acagctgctt | 600 |
| tccggtaagc tttactcttc actgcgcgaa ggcgggaaaa aagttttctc tggcgtgccg | 660 |

```
ccaattaaag agctgctcaa acgcaccgaa gaacatatta aaggcatggt agtgcctggc      720
acgttgtttg aagagctggg ctttaactac atcggcccgg tggacggtca cgatgtgctg      780
gggcttatca ccacgctaaa gaacatgcgc gacctgaaag cccgcagtt cctgcatatc       840 atgaccaaaa aaggtcgtgg ttatgaaccg gcagaaaaag acccgatcac tttccacgcc      900
gtgcctaaat tgatccctc cagcggttgt ttgccgaaaa gtagcggcgg tttgccgagc       960
tattcaaaaa tctttggcga ctggttgtgc gaaacggcag cgaaagacaa caagctgatg     1020
gcgattactc cggcgatgcg tgaaggttcc ggcatggtcg agttttcacg taaattcccg     1080
gatcgctact tcgacgtggc aattgccgag caacacgcgg tgaccttgc tgcgggtctg      1140 gcgattggtg ggtacaaacc cattgtcgcg atttactcca ctttcctgca acgcgcctat     1200
gatcaggtgc tgcatgacgt ggcgattcaa aagcttccgg tcctgttcgc catcgaccgc     1260
gcgggcattg ttggtgctga cggtcaaacc catcaggtg cttttgatct ctcttacctg      1320
cgctgcatac cggaaatggt cattatgacc ccgagcgatg aaaacgaatg tcgccagatg     1380
ctctataccg gctatcacta taacgatggc ccgtcagcgg tgcgctaccc gcgtggcaac     1440
gcggtcggcg tggaactgac gccgctggaa aaactaccaa ttggcaaagg cattgtgaag     1500
cgtcgtggcg agaaactggc gatccttaac tttggtacgc tgatgccaga agcggcgaaa     1560
gtcgccgaat cgctgaacgc cacgctggtc gatatgcgtt ttgtgaaacc gcttgatgaa     1620
gcgttaattc tggaaatggc cgccagccat gaagcgctgg tcaccgtaga agaaaacgcc     1680
attatgggcg gcgcaggcag cggcgtgaac gaagtgctga tggcccatcg taaaccagta     1740
cccgtgctga acattggcct gccggacttc tttattccgc aaggaactca ggaagaaatg     1800
cgcgccgaac tcggcctcga tgccgctggt atggaagcca aaatcaaggc ctggctggca     1860
taa                                                                   1863

<210> SEQ ID NO 14
<211> LENGTH: 2505
<212> TYPE: DNA
<213> ORGANISM: Artificial sequence
<220> FEATURE:
<223> OTHER INFORMATION: Truncated DXS nucleotide
<220> FEATURE:
<221> NAME/KEY: misc_feature
<222> LOCATION: (653)..(653)
<223> OTHER INFORMATION: n=no nucleotide

<400> SEQUENCE: 14
atgagttttg atattgccaa atacccgacc ctggcactgg tcgactccac ccaggagtta       60
cgactgttgc cgaaagagag tttaccgaaa ctctgcgacg aactgcgccg ctatttactc      120
gacagcgtga gccgttccag cgggcacttc gcctccgggc tgggcacggt cgaactgacc      180
gtggcgctgc actatgtcta caacaccccg tttgaccaat tgatttggga tgtggggcat      240
caggcttatc cgcataaaat tttgaccgga cgccgcgaca aaatcggcac catccgtcag      300
aaaggcggtc tgcacccgtt cccgtggcgc ggcgaaagcg aatatgacgt attaagcgtc      360
gggcattcat caacctccat cagtgccgga attggtattg cggttgctgc gaaaaagaa       420 ggcaaaaatc gccgcaccgt ctgtgtcatt ggcgatggcg cgattaccgc aggcatggcg      480
tttgaagcga tgaatcacgc gggcgatatc cgtcctgata tgctggtgat tctcaacgac      540
aatgaaatgt cgatttccga aaatgtcggc gcgctcaaca accatctggc acagctgctt      600
tccggtaagc tttactcttc actgcgcgaa ggcgggaaca aagttttctc tgnattttaa      660
ttcaataccc gaccctggca ctggtcgact ccccaggag ttacgactgt tgccgaaaga      720
```

```
gagtttaccg aaactctgcg acgaactgcg ccgctattta ctcgacagcg tgagccgttc    780
cagcgggcac ttcgcctccg ggctgggcac ggtcgaactg accgtggcgc tgcactatgt    840
ctacaacacc ccgtttgacc aattgatttg ggatgtgggg catcaggctt atccgcataa    900
aattttgacc ggacgccgcg acaaaatcgg caccatccgt cagaaaggcg gtctgcaccc    960
gttcccgtgg cgcggcgaaa gcgaatatga cgtattaagc gtcgggcatt catcaacctc   1020
catcagtgcc ggaattggta ttgcggttgc tgccgaaaaa gaaggcaaaa atcgccgcac   1080
cgtctgtgtc attggcgatg gcgcgattac cgcaggcatg gcgtttgaag cgatgaatca   1140
cgcgggcgat atccgtcctg atatgctggt gattctcaac gacaatgaaa tgtcgatttc   1200
cgaaaatgtc ggcgcgctca caaccatct ggcacagctg ctttccggta agctttactc   1260
ttcactgcgc gaaggcggga acaaagtttt ctctgcgtgc cgccaattaa agagctgctc   1320
aaacgcaccg aagaacatat taaaggcatg gtagtgcctg gcacgttgtt tgaagagctg   1380
ggctttaact acatcggccc ggtggacggt cacgatgtgc tggggcttat caccacgcta   1440
aagaacatgc gcgacctgaa aggcccgcag ttcctgcata tcatgaccaa aaaaggtcgt   1500
ggttatgaac cggcagaaaa agacccgatc actttccacg ccgtgcctaa atttgatccc   1560
tccagcggtt gtttgccgaa aagtagcggc ggtttgccga gctattcaaa aatctttggc   1620
gactggttgt gcgaaacggc agcgaaagac aacaagctga tggcgattac tccggcgatg   1680
cgtgaaggtt ccggcatggt cgagttttca cgtaaattcc cggatcgcta cttcgacgtg   1740
gcaattgccg agcaacacgc ggtgaccttt gctgcgggtc tggcgattgg tgggtacaaa   1800
cccattgtcg cgatttactc cactttcctg caacgcgcct atgatcaggt gctgcatgac   1860
gtggcgattc aaaagcttcc ggtcctgttc gccatcgacc gcgcgggcat tgttggtgct   1920
gacggtcaaa cccatcaggg tgcttttgat ctctcttacc tgcgctgcat accggaaatg   1980
gtcattatga ccccgagcga tgaaaacgaa tgtcgccaga tgctctatac cggctatcac   2040
tataacgatg gcccgtcagc ggtgcgctac ccgcgtggca acgcggtcgg cgtggaactg   2100
acgccgctgg aaaaactacc aattggcaaa gcattgtga gcgtcgtgg cgagaaactg   2160 gcgatcctta actttggtac gctgatgcca gaagcggcga agtcgccga atcgctgaac   2220 gccacgctgg tcgatatgcg ttttgtgaaa ccgcttgatg aagcgttaat tctggaaatg   2280
gccgccagcc atgaagcgct ggtcaccgta aagaaaacg ccattatggg cggcgcaggc   2340
agcggcgtga acgaagtgct gatggcccat cgtaaaccag tacccgtgct gaacattggc   2400
ctgccggact tctttattcc gcaaggaact caggaagaaa tgcgcgccga actcggcctc   2460
gatgccgctg gtatggaagc caaaatcaag gcctggctgg cataa                  2505

<210> SEQ ID NO 15
<211> LENGTH: 1863
<212> TYPE: DNA
<213> ORGANISM: Escherichia coli

<400> SEQUENCE: 15
atgagttttg atattgccaa atacccgacc ctggcactgg tcgactccac ccaggagtta     60
cgactgttgc cgaaagagag tttaccgaaa ctctgcgacg aactgcgccg ctatttactc    120
gacagcgtga gccgttccag cgggcacttc gcctccgggc tgggcacggt cgaactgacc    180
gtggcgctgc actatgtcta caacaccccg tttgaccaat tgatttggga tgtgggcat    240 caggcttatc cgcataaaat tttgaccgga cgccgcgaca aaatcggcac catccgtcag    300
```

```
aaaggcggtc tgcacccgtt cccgtggcgc ggcgaaagcg aatatgacgt attaagcgtc    360
gggcattcat caacctccat cagtgccgga attggtattg cggttgctgc cgaaaaagaa    420
ggcaaaaatc gccgcaccgt ctgtgtcatt ggcgatggcg cgattaccgc aggcatggcg    480
tttgaagcga tgaatcacgc gggcgatatc cgtcctgata tgctggtgat tctcaacgac    540
aatgaaatgt cgatttccga aaatgtcggc gcgctcaaca accatctggc acagctgctt    600
tccggtaagc tttactcttc actgcgcgaa ggcgggaaca agttttctc tggcgtgccg    660 ccaattaaag agctgctcaa acgcaccgaa gaacatatta aaggcatggt agtgcctggc    720
acgttgtttg aagagctggg cttaactac atcggcccgg tggacggtca cgatgtgctg    780
gggcttatca ccacgctaaa gaacatgcgc gacctgaaag gcccgcagtt cctgcatatc    840
atgaccaaaa aaggtcgtgg ttatgaaccg gcagaaaaag acccgatcac tttccacgcc    900
gtgcctaaat ttgatccctc cagcggttgt ttgccgaaaa gtagcggcgg tttgccgagc    960
tattcaaaaa tctttggcga ctggttgtgc gaaacggcag cgaaagacaa caagctgatg   1020
gcgattactc cggcgatgcg tgaaggttcc ggcatggtcg agttttcacg taaattcccg   1080
gatcgctact tcgacgtggc aattgccgag caacacgcgg tgacctttgc tgcgggtctg   1140
gcgattggtg ggtacaaacc cattgtcgcg atttactcca ctttcctgca acgcgcctat   1200
gatcaggtgc tgcatgacgt ggcgattcaa aagcttccgg tcctgttcgc catcgaccgc   1260
gcgggcattg ttggtgctga cggtcaaacc catcagggtg cttttgatct ctcttacctg   1320
cgctgcatac cggaaatggt cattatgacc ccgagcgatg aaaacgaatg tcgccagatg   1380
ctctataccg gctatcacta taacgatggc ccgtcagcgg tgcgctaccc gcgtggcaac   1440
gcggtcggcg tggaactgac gccgctggaa aaactaccaa ttggcaaagg cattgtgaag   1500
cgtcgtggcg agaaactggc gatccttaac tttggtacgc tgatgccaga agcggcgaaa   1560
gtcgccgaat cgctgaacgc cacgctggtc gatatgcgtt ttgtgaaacc gcttgatgaa   1620
gcgttaattc tggaaatggc cgccagccat gaagcgctgg tcaccgtaga agaaaacgcc   1680
attatgggcg gcgcaggcag cggcgtgaac gaagtgctga tggcccatcg taaaccagta   1740
cccgtgctga acattggcct gccggacttc tttattccgc aaggaactca ggaagaaatg   1800
cgcgccgaac tcggcctcga tgccgctggt atggaagcca aaatcaaggc ctggctggca   1860
taa                                                                 1863
```

<210> SEQ ID NO 16
<211> LENGTH: 1863
<212> TYPE: DNA
<213> ORGANISM: Escherichia coli

<400> SEQUENCE: 16

```
atgagttttg atattgccaa atacccgacc ctggcactgg tcgactccac ccaggagtta     60
cgactgttgc cgaaagagag tttaccgaaa ctctgcgacg aactgcgccg ctatttactc    120
gacagcgtga gccgttccag cgggcacttc gcctccgggc tgggcacggt cgaactgacc    180
gtggcgctgc actatgtcta caacaccccg tttgaccaat tgatttggga tgtggggcat    240
caggcttatc cgcataaaat tttgaccgga gcccgcgaca aaatcggcac catccgtcag    300
aaaggcggtc tgcacccgtt cccgtggcgc ggcgaaagcg aatatgacgt attaagcgtc    360
gggcattcat caacctccat cagtgccgga attggtattg cggttgctgc cgaaaaagaa    420
ggcaaaaatc gccgcaccgt ctgtgtcatt ggcgatggcg cgattaccgc aggcatggcg    480
tttgaagcga tgaatcacgc gggcgatatc cgtcctgata tgctggtgat tctcaacgac    540
```

```
aatgaaatgt cgatttccga aaatgtcggc gcgctcaaca accatctggc acagctgctt    600
tccggtaagc tttactcttc actgcgcgaa ggcgggaaaa agttttctc tggcgtgccg      660
ccaattaaag agctgctcaa acgcaccgaa gaacatattt gcggcatggt agtgcctggc    720
acgttgtttg aagagctggg ctttaactac atcggcccgg tggacggtca cgatgtgctg    780
gggcttatca ccacgctaaa gaacatgcgc gacctgaaag cccgcagtt cctgcatatc     840
atgaccaaaa aaggtcgtgg ttatgaaccg gcagaaaaag acccgatcac tttccacgcc   900
gtgcctaaat tgatccctc cagcggttgt ttgccgaaaa gtagcggcgg tttgccgagc     960
tattcaaaaa tctttggcga ctggttgtgc gaaacggcag cgaaagacaa caagctgatg   1020
gcgattactc cggcgatgcg tgaaggttcc ggcatggtcg agttttcacg taaattcccg    1080
gatcgctact cgacgtggc aattgccgag caacacgcgg tgacctttgc tgcgggtctg     1140
gcgattggtg ggtacaaacc cattgtcgcg atttactcca ctttcctgca acgcgcctat   1200
gatcaggtgc tgcatgacgt ggcgattcaa aagcttccgg tcctgttcgc catcgaccgc   1260
gcgggcattg ttggtgctga cggtcaaacc catcagggtg cttttgatct ctcttacctg   1320
cgctgcatac cggaaatggt cattatgacc ccgagcgatg aaaacgaatg tcgccagatg   1380
ctctataccg gctatcacta taacgatggc ccgtcagcgg tgcgctaccc gcgtggcaac   1440
gcggtcggcg tggaactgac gccgctgaaa aaactaccaa ttggcaaagg cattgtgaag   1500
cgtcgtggcg agaaactggc gatccttaac tttggtacgc tgatgccaga gcggcgaaa    1560
gtcgccgaat cgctgaacgc cacgctggtc gatatgcgtt ttgtgaaacc gcttgatgaa   1620
gcgttaattc tggaaatggc cgccagccat gaagcgctgg tcaccgtaga agaaaacgcc   1680
attatgggcg cgcaggcag cggcgtgaac gaagtgctga tggcccatcg taaaccagta    1740
cccgtgctga acattggcct gccggacttc tttattccgc aaggaactca ggaagaaatg   1800
cgcgccgaac tcggcctcga tgccgctggt atggaagcca aaatcaaggc ctggctggca   1860
taa                                                                   1863
```

<210> SEQ ID NO 17
<211> LENGTH: 620
<212> TYPE: PRT
<213> ORGANISM: Escherichia coli

<400> SEQUENCE: 17

Met Ser Phe Asp Ile Ala Lys Tyr Pro Thr Leu Ala Leu Val Asp Ser
1               5                   10                  15

Thr Gln Glu Leu Arg Leu Leu Pro Lys Glu Ser Leu Pro Lys Leu Cys
            20                  25                  30

Asp Glu Leu Arg Arg Tyr Leu Leu Asp Ser Val Ser Arg Ser Ser Gly
        35                  40                  45

His Phe Ala Ser Gly Leu Gly Thr Val Glu Leu Thr Val Ala Leu His
    50                  55                  60

Tyr Val Tyr Asn Thr Pro Phe Asp Gln Leu Ile Trp Asp Val Gly His
65                  70                  75                  80

Gln Ala Tyr Pro His Lys Ile Leu Thr Gly Arg Arg Asp Lys Ile Gly
                85                  90                  95

Thr Ile Arg Gln Lys Gly Gly Leu His Pro Phe Pro Trp Arg Gly Glu
            100                 105                 110

Ser Glu Tyr Asp Val Leu Ser Val Gly His Ser Ser Thr Ser Ile Ser
        115                 120                 125

-continued

```
Ala Gly Ile Gly Ile Ala Val Ala Ala Glu Lys Glu Gly Lys Asn Arg
    130                 135                 140
Arg Thr Val Cys Val Ile Gly Asp Gly Ala Ile Thr Ala Gly Met Ala
145                 150                 155                 160
Phe Glu Ala Met Asn His Ala Gly Asp Ile Arg Pro Asp Met Leu Val
                165                 170                 175
Ile Leu Asn Asp Asn Glu Met Ser Ile Ser Glu Asn Val Gly Ala Leu
            180                 185                 190
Asn Asn His Leu Ala Gln Leu Leu Ser Gly Lys Leu Tyr Ser Ser Leu
        195                 200                 205
Arg Glu Gly Gly Lys Lys Val Phe Ser Gly Val Pro Pro Ile Lys Glu
210                 215                 220
Leu Leu Lys Arg Thr Glu Glu His Ile Lys Gly Met Val Val Pro Gly
225                 230                 235                 240
Thr Leu Phe Glu Glu Leu Gly Phe Asn Tyr Ile Gly Pro Val Asp Gly
                245                 250                 255
His Asp Val Leu Gly Leu Ile Thr Thr Leu Lys Asn Met Arg Asp Leu
            260                 265                 270
Lys Gly Pro Gln Phe Leu His Ile Met Thr Lys Lys Gly Arg Gly Tyr
        275                 280                 285
Glu Pro Ala Glu Lys Asp Pro Ile Thr Phe His Ala Val Pro Lys Phe
290                 295                 300
Asp Pro Ser Ser Gly Cys Leu Pro Lys Ser Ser Gly Gly Leu Pro Ser
305                 310                 315                 320
Tyr Ser Lys Ile Phe Gly Asp Trp Leu Cys Glu Thr Ala Ala Lys Asp
                325                 330                 335
Asn Lys Leu Met Ala Ile Thr Pro Ala Met Arg Glu Gly Ser Gly Met
            340                 345                 350
Val Glu Phe Ser Arg Lys Phe Pro Asp Arg Tyr Phe Asp Val Ala Ile
        355                 360                 365
Ala Glu Gln His Ala Val Thr Phe Ala Ala Gly Leu Ala Ile Gly Gly
370                 375                 380
Tyr Lys Pro Ile Val Ala Ile Tyr Ser Thr Phe Leu Gln Arg Ala Tyr
385                 390                 395                 400
Asp Gln Val Leu His Asp Val Ala Ile Gln Lys Leu Pro Val Leu Phe
                405                 410                 415
Ala Ile Asp Arg Ala Gly Ile Val Gly Ala Asp Gly Gln Thr His Gln
            420                 425                 430
Gly Ala Phe Asp Leu Ser Tyr Leu Arg Cys Ile Pro Glu Met Val Ile
        435                 440                 445
Met Thr Pro Ser Asp Glu Asn Glu Cys Arg Gln Met Leu Tyr Thr Gly
450                 455                 460
Tyr His Tyr Asn Asp Gly Pro Ser Ala Val Arg Tyr Pro Arg Gly Asn
465                 470                 475                 480
Ala Val Gly Val Glu Leu Thr Pro Leu Glu Lys Leu Pro Ile Gly Lys
                485                 490                 495
Gly Ile Val Lys Arg Arg Gly Glu Lys Leu Ala Ile Leu Asn Phe Gly
            500                 505                 510
Thr Leu Met Pro Glu Ala Ala Lys Val Ala Glu Ser Leu Asn Ala Thr
        515                 520                 525
Leu Val Asp Met Arg Phe Val Lys Pro Leu Asp Glu Ala Leu Ile Leu
530                 535                 540
Glu Met Ala Ala Ser His Glu Ala Leu Val Thr Val Glu Glu Asn Ala
```

```
                545                 550                 555                 560
Ile Met Gly Gly Ala Gly Ser Gly Val Asn Glu Val Leu Met Ala His
                    565                 570                 575

Arg Lys Pro Val Pro Val Leu Asn Ile Gly Leu Pro Asp Phe Phe Ile
                580                 585                 590

Pro Gln Gly Thr Gln Glu Met Arg Ala Glu Leu Gly Leu Asp Ala
                595                 600                 605

Ala Gly Met Glu Ala Lys Ile Lys Ala Trp Leu Ala
            610                 615                 620

<210> SEQ ID NO 18
<211> LENGTH: 219
<212> TYPE: PRT
<213> ORGANISM: Artificial sequence
<220> FEATURE:
<223> OTHER INFORMATION: Truncated DXS polypeptide

<400> SEQUENCE: 18

Met Ser Phe Asp Ile Ala Lys Tyr Pro Thr Leu Ala Leu Val Asp Ser
1               5                   10                  15

Thr Gln Glu Leu Arg Leu Leu Pro Lys Glu Ser Leu Pro Lys Leu Cys
            20                  25                  30

Asp Glu Leu Arg Arg Tyr Leu Leu Asp Ser Val Ser Arg Ser Ser Gly
        35                  40                  45

His Phe Ala Ser Gly Leu Gly Thr Val Glu Leu Thr Val Ala Leu His
    50                  55                  60

Tyr Val Tyr Asn Thr Pro Phe Asp Gln Leu Ile Trp Asp Val Gly His
65                  70                  75                  80

Gln Ala Tyr Pro His Lys Ile Leu Thr Gly Arg Arg Asp Lys Ile Gly
                85                  90                  95

Thr Ile Arg Gln Lys Gly Gly Leu His Pro Phe Pro Trp Arg Gly Glu
            100                 105                 110

Ser Glu Tyr Asp Val Leu Ser Val Gly His Ser Ser Thr Ser Ile Ser
        115                 120                 125

Ala Gly Ile Gly Ile Ala Val Ala Ala Glu Lys Glu Gly Lys Asn Arg
    130                 135                 140

Arg Thr Val Cys Val Ile Gly Asp Gly Ala Ile Thr Ala Gly Met Ala
145                 150                 155                 160

Phe Glu Ala Met Asn His Ala Gly Asp Ile Arg Pro Asp Met Leu Val
                165                 170                 175

Ile Leu Asn Asp Asn Glu Met Ser Ile Ser Glu Asn Val Gly Ala Leu
            180                 185                 190

Asn Asn His Leu Ala Gln Leu Leu Ser Gly Lys Leu Tyr Ser Ser Leu
        195                 200                 205

Arg Glu Gly Gly Asn Lys Val Phe Ser Gly Phe
    210                 215

<210> SEQ ID NO 19
<211> LENGTH: 620
<212> TYPE: PRT
<213> ORGANISM: Escherichia coli

<400> SEQUENCE: 19

Met Ser Phe Asp Ile Ala Lys Tyr Pro Thr Leu Ala Leu Val Asp Ser
1               5                   10                  15

Thr Gln Glu Leu Arg Leu Leu Pro Lys Glu Ser Leu Pro Lys Leu Cys
            20                  25                  30
```

Asp Glu Leu Arg Arg Tyr Leu Leu Asp Ser Val Ser Arg Ser Ser Gly
         35                  40                  45

His Phe Ala Ser Gly Leu Gly Thr Val Glu Leu Thr Val Ala Leu His
 50                  55                  60

Tyr Val Tyr Asn Thr Pro Phe Asp Gln Leu Ile Trp Asp Val Gly His
 65                  70                  75                  80

Gln Ala Tyr Pro His Lys Ile Leu Thr Gly Arg Arg Asp Lys Ile Gly
                 85                  90                  95

Thr Ile Arg Gln Lys Gly Gly Leu His Pro Phe Pro Trp Arg Gly Glu
                100                 105                 110

Ser Glu Tyr Asp Val Leu Ser Val Gly His Ser Ser Thr Ser Ile Ser
            115                 120                 125

Ala Gly Ile Gly Ile Ala Val Ala Ala Glu Lys Glu Gly Lys Asn Arg
        130                 135                 140

Arg Thr Val Cys Val Ile Gly Asp Gly Ala Ile Thr Ala Gly Met Ala
145                 150                 155                 160

Phe Glu Ala Met Asn His Ala Gly Asp Ile Arg Pro Asp Met Leu Val
                165                 170                 175

Ile Leu Asn Asp Asn Glu Met Ser Ile Ser Glu Asn Val Gly Ala Leu
            180                 185                 190

Asn Asn His Leu Ala Gln Leu Leu Ser Gly Lys Leu Tyr Ser Ser Leu
        195                 200                 205

Arg Glu Gly Gly Asn Lys Val Phe Ser Gly Val Pro Pro Ile Lys Glu
210                 215                 220

Leu Leu Lys Arg Thr Glu Glu His Ile Lys Gly Met Val Val Pro Gly
225                 230                 235                 240

Thr Leu Phe Glu Glu Leu Gly Phe Asn Tyr Ile Gly Pro Val Asp Gly
                245                 250                 255

His Asp Val Leu Gly Leu Ile Thr Thr Leu Lys Asn Met Arg Asp Leu
            260                 265                 270

Lys Gly Pro Gln Phe Leu His Ile Met Thr Lys Lys Gly Arg Gly Tyr
        275                 280                 285

Glu Pro Ala Glu Lys Asp Pro Ile Thr Phe His Ala Val Pro Lys Phe
290                 295                 300

Asp Pro Ser Ser Gly Cys Leu Pro Lys Ser Ser Gly Gly Leu Pro Ser
305                 310                 315                 320

Tyr Ser Lys Ile Phe Gly Asp Trp Leu Cys Glu Thr Ala Ala Lys Asp
                325                 330                 335

Asn Lys Leu Met Ala Ile Thr Pro Ala Met Arg Glu Gly Ser Gly Met
            340                 345                 350

Val Glu Phe Ser Arg Lys Phe Pro Asp Arg Tyr Phe Asp Val Ala Ile
        355                 360                 365

Ala Glu Gln His Ala Val Thr Phe Ala Ala Gly Leu Ala Ile Gly Gly
370                 375                 380

Tyr Lys Pro Ile Val Ala Ile Tyr Ser Thr Phe Leu Gln Arg Ala Tyr
385                 390                 395                 400

Asp Gln Val Leu His Asp Val Ala Ile Gln Lys Leu Pro Val Leu Phe
                405                 410                 415

Ala Ile Asp Arg Ala Gly Ile Val Gly Ala Asp Gly Gln Thr His Gln
            420                 425                 430

Gly Ala Phe Asp Leu Ser Tyr Leu Arg Cys Ile Pro Glu Met Val Ile
        435                 440                 445

Met Thr Pro Ser Asp Glu Asn Glu Cys Arg Gln Met Leu Tyr Thr Gly
450                 455                 460

Tyr His Tyr Asn Asp Gly Pro Ser Ala Val Arg Tyr Pro Arg Gly Asn
465                 470                 475                 480

Ala Val Gly Val Glu Leu Thr Pro Leu Glu Lys Leu Pro Ile Gly Lys
            485                 490                 495

Gly Ile Val Lys Arg Gly Glu Lys Leu Ala Ile Leu Asn Phe Gly
            500                 505                 510

Thr Leu Met Pro Glu Ala Ala Lys Val Ala Glu Ser Leu Asn Ala Thr
            515                 520                 525

Leu Val Asp Met Arg Phe Val Lys Pro Leu Asp Glu Ala Leu Ile Leu
530                 535                 540

Glu Met Ala Ala Ser His Glu Ala Leu Val Thr Val Glu Glu Asn Ala
545                 550                 555                 560

Ile Met Gly Gly Ala Gly Ser Gly Val Asn Glu Val Leu Met Ala His
            565                 570                 575

Arg Lys Pro Val Pro Val Leu Asn Ile Gly Leu Pro Asp Phe Phe Ile
            580                 585                 590

Pro Gln Gly Thr Gln Glu Glu Met Arg Ala Glu Leu Gly Leu Asp Ala
            595                 600                 605

Ala Gly Met Glu Ala Lys Ile Lys Ala Trp Leu Ala
610                 615                 620

<210> SEQ ID NO 20
<211> LENGTH: 620
<212> TYPE: PRT
<213> ORGANISM: Escherichia coli

<400> SEQUENCE: 20

Met Ser Phe Asp Ile Ala Lys Tyr Pro Thr Leu Ala Leu Val Asp Ser
1               5                   10                  15

Thr Gln Glu Leu Arg Leu Leu Pro Lys Glu Ser Leu Pro Lys Leu Cys
            20                  25                  30

Asp Glu Leu Arg Arg Tyr Leu Leu Asp Ser Val Ser Arg Ser Ser Gly
        35                  40                  45

His Phe Ala Ser Gly Leu Gly Thr Val Glu Leu Thr Val Ala Leu His
    50                  55                  60

Tyr Val Tyr Asn Thr Pro Phe Asp Gln Leu Ile Trp Asp Val Gly His
65                  70                  75                  80

Gln Ala Tyr Pro His Lys Ile Leu Thr Gly Arg Arg Asp Lys Ile Gly
            85                  90                  95

Thr Ile Arg Gln Lys Gly Gly Leu His Pro Phe Pro Trp Arg Gly Glu
            100                 105                 110

Ser Glu Tyr Asp Val Leu Ser Val Gly His Ser Ser Thr Ser Ile Ser
        115                 120                 125

Ala Gly Ile Gly Ile Ala Val Ala Ala Glu Lys Glu Gly Lys Asn Arg
    130                 135                 140

Arg Thr Val Cys Val Ile Gly Asp Gly Ala Ile Thr Ala Gly Met Ala
145                 150                 155                 160

Phe Glu Ala Met Asn His Ala Gly Asp Ile Arg Pro Asp Met Leu Val
            165                 170                 175

Ile Leu Asn Asp Asn Glu Met Ser Ile Ser Glu Asn Val Gly Ala Leu
            180                 185                 190

Asn Asn His Leu Ala Gln Leu Leu Ser Gly Lys Leu Tyr Ser Ser Leu
        195                 200                 205

```
Arg Glu Gly Gly Lys Lys Val Phe Ser Gly Val Pro Pro Ile Lys Glu
            210                 215                 220
Leu Leu Lys Arg Thr Glu Glu His Ile Cys Gly Met Val Val Pro Gly
225                 230                 235                 240
Thr Leu Phe Glu Glu Leu Gly Phe Asn Tyr Ile Gly Pro Val Asp Gly
                245                 250                 255
His Asp Val Leu Gly Leu Ile Thr Thr Leu Lys Asn Met Arg Asp Leu
            260                 265                 270
Lys Gly Pro Gln Phe Leu His Ile Met Thr Lys Lys Gly Arg Gly Tyr
        275                 280                 285
Glu Pro Ala Glu Lys Asp Pro Ile Thr Phe His Ala Val Pro Lys Phe
290                 295                 300
Asp Pro Ser Ser Gly Cys Leu Pro Lys Ser Ser Gly Gly Leu Pro Ser
305                 310                 315                 320
Tyr Ser Lys Ile Phe Gly Asp Trp Leu Cys Glu Thr Ala Ala Lys Asp
                325                 330                 335
Asn Lys Leu Met Ala Ile Thr Pro Ala Met Arg Glu Gly Ser Gly Met
            340                 345                 350
Val Glu Phe Ser Arg Lys Phe Pro Asp Arg Tyr Phe Asp Val Ala Ile
        355                 360                 365
Ala Glu Gln His Ala Val Thr Phe Ala Ala Gly Leu Ala Ile Gly Gly
370                 375                 380
Tyr Lys Pro Ile Val Ala Ile Tyr Ser Thr Phe Leu Gln Arg Ala Tyr
385                 390                 395                 400
Asp Gln Val Leu His Asp Val Ala Ile Gln Lys Leu Pro Val Leu Phe
                405                 410                 415
Ala Ile Asp Arg Ala Gly Ile Val Gly Ala Asp Gly Gln Thr His Gln
            420                 425                 430
Gly Ala Phe Asp Leu Ser Tyr Leu Arg Cys Ile Pro Glu Met Val Ile
        435                 440                 445
Met Thr Pro Ser Asp Glu Asn Glu Cys Arg Gln Met Leu Tyr Thr Gly
450                 455                 460
Tyr His Tyr Asn Asp Gly Pro Ser Ala Val Arg Tyr Pro Arg Gly Asn
465                 470                 475                 480
Ala Val Gly Val Glu Leu Thr Pro Leu Glu Lys Leu Pro Ile Gly Lys
                485                 490                 495
Gly Ile Val Lys Arg Arg Gly Glu Lys Leu Ala Ile Leu Asn Phe Gly
            500                 505                 510
Thr Leu Met Pro Glu Ala Ala Lys Val Ala Glu Ser Leu Asn Ala Thr
        515                 520                 525
Leu Val Asp Met Arg Phe Val Lys Pro Leu Asp Glu Ala Leu Ile Leu
530                 535                 540
Glu Met Ala Ala Ser His Glu Ala Leu Val Thr Val Glu Glu Asn Ala
545                 550                 555                 560
Ile Met Gly Gly Ala Gly Ser Gly Val Asn Glu Val Leu Met Ala His
                565                 570                 575
Arg Lys Pro Val Pro Val Leu Asn Ile Gly Leu Pro Asp Phe Phe Ile
            580                 585                 590
Pro Gln Gly Thr Gln Glu Glu Met Arg Ala Glu Leu Gly Leu Asp Ala
        595                 600                 605
Ala Gly Met Glu Ala Lys Ile Lys Ala Trp Leu Ala
610                 615                 620
```

```
<210> SEQ ID NO 21
<211> LENGTH: 626
<212> TYPE: PRT
<213> ORGANISM: Artificial sequence
<220> FEATURE:
<223> OTHER INFORMATION: Bacterial consensus DXS sequence including
      Deinococcus radiodurans
<220> FEATURE:
<221> NAME/KEY: MISC_FEATURE
<222> LOCATION: (2)..(2)
<223> OTHER INFORMATION: X=S, T or L
<220> FEATURE:
<221> NAME/KEY: MISC_FEATURE
<222> LOCATION: (3)..(3)
<223> OTHER INFORMATION: X=L, F, I or P
<220> FEATURE:
<221> NAME/KEY: MISC_FEATURE
<222> LOCATION: (4)..(4)
<223> OTHER INFORMATION: X=D, E or G
<220> FEATURE:
<221> NAME/KEY: MISC_FEATURE
<222> LOCATION: (5)..(5)
<223> OTHER INFORMATION: X= I, T, S or L
<220> FEATURE:
<221> NAME/KEY: MISC_FEATURE
<222> LOCATION: (6)..(6)
<223> OTHER INFORMATION: X= A, T or S
<220> FEATURE:
<221> NAME/KEY: MISC_FEATURE
<222> LOCATION: (7)..(7)
<223> OTHER INFORMATION: X= K or D
<220> FEATURE:
<221> NAME/KEY: MISC_FEATURE
<222> LOCATION: (8)..(8)
<223> OTHER INFORMATION: X= Y or T
<220> FEATURE:
<221> NAME/KEY: MISC_FEATURE
<222> LOCATION: (10)..(10)
<223> OTHER INFORMATION: X= T or L
<220> FEATURE:
<221> NAME/KEY: MISC_FEATURE
<222> LOCATION: (12)..(12)
<223> OTHER INFORMATION: X= A or D
<220> FEATURE:
<221> NAME/KEY: MISC_FEATURE
<222> LOCATION: (13)..(13)
<223> OTHER INFORMATION: X= L or Q
<220> FEATURE:
<221> NAME/KEY: MISC_FEATURE
<222> LOCATION: (14)..(14)
<223> OTHER INFORMATION: X= V, A or I
<220> FEATURE:
<221> NAME/KEY: MISC_FEATURE
<222> LOCATION: (15)..(15)
<223> OTHER INFORMATION: X= D, E, S or H
<220> FEATURE:
<221> NAME/KEY: MISC_FEATURE
<222> LOCATION: (16)..(16)
<223> OTHER INFORMATION: X=S, N, T or G
<220> FEATURE:
<221> NAME/KEY: MISC_FEATURE
<222> LOCATION: (17)..(17)
<223> OTHER INFORMATION: X=T, P or V
<220> FEATURE:
<221> NAME/KEY: MISC_FEATURE
<222> LOCATION: (18)..(18)
<223> OTHER INFORMATION: X=Q, A, E, D or K
<220> FEATURE:
<221> NAME/KEY: MISC_FEATURE
<222> LOCATION: (19)..(19)
<223> OTHER INFORMATION: X=A, E or D
<220> FEATURE:
<221> NAME/KEY: MISC_FEATURE
<222> LOCATION: (21)..(21)
<223> OTHER INFORMATION: X=R or K
<220> FEATURE:
<221> NAME/KEY: MISC_FEATURE
<222> LOCATION: (22)..(22)
```

-continued

```
<223> OTHER INFORMATION: X=L, M, A, S or R
<220> FEATURE:
<221> NAME/KEY: MISC_FEATURE
<222> LOCATION: (24)..(24)
<223> OTHER INFORMATION: X=P or S
<220> FEATURE:
<221> NAME/KEY: MISC_FEATURE
<222> LOCATION: (25)..(25)
<223> OTHER INFORMATION: X=K or R
<220> FEATURE:
<221> NAME/KEY: MISC_FEATURE
<222> LOCATION: (26)..(26)
<223> OTHER INFORMATION: X=E or D
<220> FEATURE:
<221> NAME/KEY: MISC_FEATURE
<222> LOCATION: (27)..(27)
<223> OTHER INFORMATION: X=S, K, T or Q
<220> FEATURE:
<221> NAME/KEY: MISC_FEATURE
<222> LOCATION: (30)..(30)
<223> OTHER INFORMATION: X=K, T or A
<220> FEATURE:
<221> NAME/KEY: MISC_FEATURE
<222> LOCATION: (32)..(32)
<223> OTHER INFORMATION: X=C, S or P
<220> FEATURE:
<221> NAME/KEY: MISC_FEATURE
<222> LOCATION: (33)..(33)
<223> OTHER INFORMATION: X=D, N or E
<220> FEATURE:
<221> NAME/KEY: MISC_FEATURE
<222> LOCATION: (37)..(37)
<223> OTHER INFORMATION: X=R, Q or G
<220> FEATURE:
<221> NAME/KEY: MISC_FEATURE
<222> LOCATION: (38)..(38)
<223> OTHER INFORMATION: X=Y, F or E
<220> FEATURE:
<221> NAME/KEY: MISC_FEATURE
<222> LOCATION: (39)..(39)
<223> OTHER INFORMATION: X=L or I
<220> FEATURE:
<221> NAME/KEY: MISC_FEATURE
<222> LOCATION: (40)..(40)
<223> OTHER INFORMATION: X=L or V
<220> FEATURE:
<221> NAME/KEY: MISC_FEATURE
<222> LOCATION: (41)..(41)
<223> OTHER INFORMATION: X=D, T, N, A or R
<220> FEATURE:
<221> NAME/KEY: MISC_FEATURE
<222> LOCATION: (42)..(42)
<223> OTHER INFORMATION: X=S, C or V
<220> FEATURE:
<221> NAME/KEY: MISC_FEATURE
<222> LOCATION: (43)..(43)
<223> OTHER INFORMATION: X=V or C
<220> FEATURE:
<221> NAME/KEY: MISC_FEATURE
<222> LOCATION: (45)..(45)
<223> OTHER INFORMATION: X=R or Q
<220> FEATURE:
<221> NAME/KEY: MISC_FEATURE
<222> LOCATION: (46)..(46)
<223> OTHER INFORMATION: X=S or G
<220> FEATURE:
<221> NAME/KEY: MISC_FEATURE
<222> LOCATION: (47)..(47)
<223> OTHER INFORMATION: X=S or G
<220> FEATURE:
<221> NAME/KEY: MISC_FEATURE
<222> LOCATION: (48)..(48)
<223> OTHER INFORMATION: X=G or L
<220> FEATURE:
<221> NAME/KEY: MISC_FEATURE
<222> LOCATION: (50)..(50)
<223> OTHER INFORMATION: X=F or L
<220> FEATURE:
<221> NAME/KEY: MISC_FEATURE
```

```
<222> LOCATION: (53)..(53)
<223> OTHER INFORMATION: X=G or S
<220> FEATURE:
<221> NAME/KEY: MISC_FEATURE
<222> LOCATION: (56)..(56)
<223> OTHER INFORMATION: X=T, V or A
<220> FEATURE:
<221> NAME/KEY: MISC_FEATURE
<222> LOCATION: (58)..(58)
<223> OTHER INFORMATION: X=E or D
<220> FEATURE:
<221> NAME/KEY: MISC_FEATURE
<222> LOCATION: (59)..(59)
<223> OTHER INFORMATION: X=L or I
<220> FEATURE:
<221> NAME/KEY: MISC_FEATURE
<222> LOCATION: (60)..(60)
<223> OTHER INFORMATION: X=T or I
<220> FEATURE:
<221> NAME/KEY: MISC_FEATURE
<222> LOCATION: (61)..(61)
<223> OTHER INFORMATION: X=V or T
<220> FEATURE:
<221> NAME/KEY: MISC_FEATURE
<222> LOCATION: (63)..(63)
<223> OTHER INFORMATION: X=L or M
<220> FEATURE:
<221> NAME/KEY: MISC_FEATURE
<222> LOCATION: (67)..(67)
<223> OTHER INFORMATION: X=Y or L
<220> FEATURE:
<221> NAME/KEY: MISC_FEATURE
<222> LOCATION: (68)..(68)
<223> OTHER INFORMATION: X=N, K or D
<220> FEATURE:
<221> NAME/KEY: MISC_FEATURE
<222> LOCATION: (69)..(69)
<223> OTHER INFORMATION: X=T or S
<220> FEATURE:
<221> NAME/KEY: MISC_FEATURE
<222> LOCATION: (71)..(71)
<223> OTHER INFORMATION: X=F or R
<220> FEATURE:
<221> NAME/KEY: MISC_FEATURE
<222> LOCATION: (73)..(73)
<223> OTHER INFORMATION: X=Q, R, H or N
<220> FEATURE:
<221> NAME/KEY: MISC_FEATURE
<222> LOCATION: (74)..(74)
<223> OTHER INFORMATION: X=L, V or I
<220> FEATURE:
<221> NAME/KEY: MISC_FEATURE
<222> LOCATION: (75)..(75)
<223> OTHER INFORMATION: X=I, V or L
<220> FEATURE:
<221> NAME/KEY: MISC_FEATURE
<222> LOCATION: (76)..(76)
<223> OTHER INFORMATION: X=W or F
<220> FEATURE:
<221> NAME/KEY: MISC_FEATURE
<222> LOCATION: (84)..(84)
<223> OTHER INFORMATION: X=P or A
<220> FEATURE:
<221> NAME/KEY: MISC_FEATURE
<222> LOCATION: (94)..(94)
<223> OTHER INFORMATION: X=K, R or Q
<220> FEATURE:
<221> NAME/KEY: MISC_FEATURE
<222> LOCATION: (95)..(95)
<223> OTHER INFORMATION: X=I or M
<220> FEATURE:
<221> NAME/KEY: MISC_FEATURE
<222> LOCATION: (96)..(96)
<223> OTHER INFORMATION: X=G, S, A or D
<220> FEATURE:
<221> NAME/KEY: MISC_FEATURE
<222> LOCATION: (97)..(97)
<223> OTHER INFORMATION: X=T, S or D
<220> FEATURE:
```

```
<221> NAME/KEY: MISC_FEATURE
<222> LOCATION: (99)..(99)
<223> OTHER INFORMATION: X=R or K
<220> FEATURE:
<221> NAME/KEY: MISC_FEATURE
<222> LOCATION: (100)..(100)
<223> OTHER INFORMATION: X=Q or K
<220> FEATURE:
<221> NAME/KEY: MISC_FEATURE
<222> LOCATION: (101)..(101)
<223> OTHER INFORMATION: X=K or E
<220> FEATURE:
<221> NAME/KEY: MISC_FEATURE
<222> LOCATION: (102)..(102)
<223> OTHER INFORMATION: X=G, D or N
<220> FEATURE:
<221> NAME/KEY: MISC_FEATURE
<222> LOCATION: (104)..(104)
<223> OTHER INFORMATION: X=L, V or I
<220> FEATURE:
<221> NAME/KEY: MISC_FEATURE
<222> LOCATION: (105)..(105)
<223> OTHER INFORMATION: X=H or S
<220> FEATURE:
<221> NAME/KEY: MISC_FEATURE
<222> LOCATION: (106)..(106)
<223> OTHER INFORMATION: X=P or G
<220> FEATURE:
<221> NAME/KEY: MISC_FEATURE
<222> LOCATION: (108)..(108)
<223> OTHER INFORMATION: X=P or T
<220> FEATURE:
<221> NAME/KEY: MISC_FEATURE
<222> LOCATION: (109)..(109)
<223> OTHER INFORMATION: X= W or K
<220> FEATURE:
<221> NAME/KEY: MISC_FEATURE
<222> LOCATION: (110)..(110)
<223> OTHER INFORMATION: X= R or V
<220> FEATURE:
<221> NAME/KEY: MISC_FEATURE
<222> LOCATION: (111)..(111)
<223> OTHER INFORMATION: X= G, E, D, A or S
<220> FEATURE:
<221> NAME/KEY: MISC_FEATURE
<222> LOCATION: (114)..(114)
<223> OTHER INFORMATION: X=E or D
<220> FEATURE:
<221> NAME/KEY: MISC_FEATURE
<222> LOCATION: (115)..(115)
<223> OTHER INFORMATION: X=Y, F or H
<220> FEATURE:
<221> NAME/KEY: MISC_FEATURE
<222> LOCATION: (117)..(117)
<223> OTHER INFORMATION: X=V, T or A
<220> FEATURE:
<221> NAME/KEY: MISC_FEATURE
<222> LOCATION: (118)..(118)
<223> OTHER INFORMATION: X=L or I
<220> FEATURE:
<221> NAME/KEY: MISC_FEATURE
<222> LOCATION: (119)..(119)
<223> OTHER INFORMATION: X=S, N, C or T
<220> FEATURE:
<221> NAME/KEY: MISC_FEATURE
<222> LOCATION: (123)..(123)
<223> OTHER INFORMATION: X=S or A
<220> FEATURE:
<221> NAME/KEY: MISC_FEATURE
<222> LOCATION: (127)..(127)
<223> OTHER INFORMATION: X=I or L
<220> FEATURE:
<221> NAME/KEY: MISC_FEATURE
<222> LOCATION: (128)..(128)
<223> OTHER INFORMATION: X=S or A
<220> FEATURE:
<221> NAME/KEY: MISC_FEATURE
<222> LOCATION: (129)..(129)
<223> OTHER INFORMATION: X=A or N
```

```
<220> FEATURE:
<221> NAME/KEY: MISC_FEATURE
<222> LOCATION: (130)..(130)
<223> OTHER INFORMATION: X=G or A
<220> FEATURE:
<221> NAME/KEY: MISC_FEATURE
<222> LOCATION: (131)..(131)
<223> OTHER INFORMATION: X=I or L
<220> FEATURE:
<221> NAME/KEY: MISC_FEATURE
<222> LOCATION: (133)..(133)
<223> OTHER INFORMATION: X=I, V or M
<220> FEATURE:
<221> NAME/KEY: MISC_FEATURE
<222> LOCATION: (135)..(135)
<223> OTHER INFORMATION: X=V, I, A or L
<220> FEATURE:
<221> NAME/KEY: MISC_FEATURE
<222> LOCATION: (137)..(137)
<223> OTHER INFORMATION: X=A or R
<220> FEATURE:
<221> NAME/KEY: MISC_FEATURE
<222> LOCATION: (138)..(138)
<223> OTHER INFORMATION: X=E, A or D
<220> FEATURE:
<221> NAME/KEY: MISC_FEATURE
<222> LOCATION: (139)..(139)
<223> OTHER INFORMATION: X=K, R or A
<220> FEATURE:
<221> NAME/KEY: MISC_FEATURE
<222> LOCATION: (140)..(140)
<223> OTHER INFORMATION: X=E or Q
<220> FEATURE:
<221> NAME/KEY: MISC_FEATURE
<222> LOCATION: (141)..(141)
<223> OTHER INFORMATION: X=G, N, D or A
<220> FEATURE:
<221> NAME/KEY: MISC_FEATURE
<222> LOCATION: (142)..(142)
<223> OTHER INFORMATION: X=K, Q or L
<220> FEATURE:
<221> NAME/KEY: MISC_FEATURE
<222> LOCATION: (143)..(143)
<223> OTHER INFORMATION: X=N, D, Q or G
<220> FEATURE:
<221> NAME/KEY: MISC_FEATURE
<222> LOCATION: (144)..(144)
<223> OTHER INFORMATION: X=R or F
<220> FEATURE:
<221> NAME/KEY: MISC_FEATURE
<222> LOCATION: (145)..(145)
<223> OTHER INFORMATION: X=R, K or H
<220> FEATURE:
<221> NAME/KEY: MISC_FEATURE
<222> LOCATION: (146)..(146)
<223> OTHER INFORMATION: X=T, A or V
<220> FEATURE:
<221> NAME/KEY: MISC_FEATURE
<222> LOCATION: (147)..(147)
<223> OTHER INFORMATION: X=V or A
<220> FEATURE:
<221> NAME/KEY: MISC_FEATURE
<222> LOCATION: (148)..(148)
<223> OTHER INFORMATION: X=C or A
<220> FEATURE:
<221> NAME/KEY: MISC_FEATURE
<222> LOCATION: (154)..(154)
<223> OTHER INFORMATION: X=A or S
<220> FEATURE:
<221> NAME/KEY: MISC_FEATURE
<222> LOCATION: (155)..(155)
<223> OTHER INFORMATION: X=I or L
<220> FEATURE:
<221> NAME/KEY: MISC_FEATURE
<222> LOCATION: (157)..(157)
<223> OTHER INFORMATION: X=A or G
<220> FEATURE:
<221> NAME/KEY: MISC_FEATURE
<222> LOCATION: (161)..(161)
```

```
<223> OTHER INFORMATION: X=F or L
<220> FEATURE:
<221> NAME/KEY: MISC_FEATURE
<222> LOCATION: (162)..(162)
<223> OTHER INFORMATION: X=E or A
<220> FEATURE:
<221> NAME/KEY: MISC_FEATURE
<222> LOCATION: (164)..(164)
<223> OTHER INFORMATION: X=M or L
<220> FEATURE:
<221> NAME/KEY: MISC_FEATURE
<222> LOCATION: (165)..(165)
<223> OTHER INFORMATION: X=N or S
<220> FEATURE:
<221> NAME/KEY: MISC_FEATURE
<222> LOCATION: (166)..(166)
<223> OTHER INFORMATION: X=H or T
<220> FEATURE:
<221> NAME/KEY: MISC_FEATURE
<222> LOCATION: (167)..(167)
<223> OTHER INFORMATION: X=A or I
<220> FEATURE:
<221> NAME/KEY: MISC_FEATURE
<222> LOCATION: (170)..(170)
<223> OTHER INFORMATION: X=I or M
<220> FEATURE:
<221> NAME/KEY: MISC_FEATURE
<222> LOCATION: (171)..(171)
<223> OTHER INFORMATION: X=R, K, H, D or N
<220> FEATURE:
<221> NAME/KEY: MISC_FEATURE
<222> LOCATION: (172)..(172)
<223> OTHER INFORMATION: X=P, S, A or R
<220> FEATURE:
<221> NAME/KEY: MISC_FEATURE
<222> LOCATION: (173)..(173)
<223> OTHER INFORMATION: X=D or K
<220> FEATURE:
<221> NAME/KEY: MISC_FEATURE
<222> LOCATION: (174)..(174)
<223> OTHER INFORMATION: X=M or L
<220> FEATURE:
<221> NAME/KEY: MISC_FEATURE
<222> LOCATION: (176)..(176)
<223> OTHER INFORMATION: X=V or I
<220> FEATURE:
<221> NAME/KEY: MISC_FEATURE
<222> LOCATION: (177)..(177)
<223> OTHER INFORMATION: X=I or V
<220> FEATURE:
<221> NAME/KEY: MISC_FEATURE
<222> LOCATION: (182)..(182)
<223> OTHER INFORMATION: X=E or G
<220> FEATURE:
<221> NAME/KEY: MISC_FEATURE
<222> LOCATION: (191)..(191)
<223> OTHER INFORMATION: X=A or G
<220> FEATURE:
<221> NAME/KEY: MISC_FEATURE
<222> LOCATION: (192)..(192)
<223> OTHER INFORMATION: X=L or M
<220> FEATURE:
<221> NAME/KEY: MISC_FEATURE
<222> LOCATION: (194)..(194)
<223> OTHER INFORMATION: X=N or K
<220> FEATURE:
<221> NAME/KEY: MISC_FEATURE
<222> LOCATION: (195)..(195)
<223> OTHER INFORMATION: X=H or F
<220> FEATURE:
<221> NAME/KEY: MISC_FEATURE
<222> LOCATION: (196)..(196)
<223> OTHER INFORMATION: X=L or M
<220> FEATURE:
<221> NAME/KEY: MISC_FEATURE
<222> LOCATION: (197)..(197)
<223> OTHER INFORMATION: X=A or R
<220> FEATURE:
<221> NAME/KEY: MISC_FEATURE
```

```
<222> LOCATION: (198)..(198)
<223> OTHER INFORMATION: X=Q or G
<220> FEATURE:
<221> NAME/KEY: MISC_FEATURE
<222> LOCATION: (199)..(199)
<223> OTHER INFORMATION: X=L or I
<220> FEATURE:
<221> NAME/KEY: MISC_FEATURE
<222> LOCATION: (200)..(200)
<223> OTHER INFORMATION: X=L or Q
<220> FEATURE:
<221> NAME/KEY: MISC_FEATURE
<222> LOCATION: (201)..(201)
<223> OTHER INFORMATION: X=S or V
<220> FEATURE:
<221> NAME/KEY: MISC_FEATURE
<222> LOCATION: (202)..(202)
<223> OTHER INFORMATION: X=G or Q
<220> FEATURE:
<221> NAME/KEY: MISC_FEATURE
<222> LOCATION: (204)..(204)
<223> OTHER INFORMATION: X=L, T or W
<220> FEATURE:
<221> NAME/KEY: MISC_FEATURE
<222> LOCATION: (205)..(205)
<223> OTHER INFORMATION: X=Y or F
<220> FEATURE:
<221> NAME/KEY: MISC_FEATURE
<222> LOCATION: (206)..(206)
<223> OTHER INFORMATION: X=S, A, T or Q
<220> FEATURE:
<221> NAME/KEY: MISC_FEATURE
<222> LOCATION: (207)..(207)
<223> OTHER INFORMATION: X=S, T, R or E
<220> FEATURE:
<221> NAME/KEY: MISC_FEATURE
<222> LOCATION: (208)..(208)
<223> OTHER INFORMATION: X=L or G
<220> FEATURE:
<221> NAME/KEY: MISC_FEATURE
<222> LOCATION: (209)..(209)
<223> OTHER INFORMATION: X=R or E
<220> FEATURE:
<221> NAME/KEY: MISC_FEATURE
<222> LOCATION: (210)..(210)
<223> OTHER INFORMATION: X=E or G
<220> FEATURE:
<221> NAME/KEY: MISC_FEATURE
<222> LOCATION: (211)..(211)
<223> OTHER INFORMATION: X=G, S or A
<220> FEATURE:
<221> NAME/KEY: MISC_FEATURE
<222> LOCATION: (214)..(214)
<223> OTHER INFORMATION: X=K or R
<220> FEATURE:
<221> NAME/KEY: MISC_FEATURE
<222> LOCATION: (215)..(215)
<223> OTHER INFORMATION: X=V or A
<220> FEATURE:
<221> NAME/KEY: MISC_FEATURE
<222> LOCATION: (216)..(216)
<223> OTHER INFORMATION: X=F, L or V
<220> FEATURE:
<221> NAME/KEY: MISC_FEATURE
<222> LOCATION: (217)..(217)
<223> OTHER INFORMATION: X=S, D, T or E
<220> FEATURE:
<221> NAME/KEY: MISC_FEATURE
<222> LOCATION: (218)..(218)
<223> OTHER INFORMATION: X=G, N or A
<220> FEATURE:
<221> NAME/KEY: MISC_FEATURE
<222> LOCATION: (219)..(219)
<223> OTHER INFORMATION: X=V or L
<220> FEATURE:
<221> NAME/KEY: MISC_FEATURE
<222> LOCATION: (220)..(220)
<223> OTHER INFORMATION: X=P or S
<220> FEATURE:
```

```
<221> NAME/KEY: MISC_FEATURE
<222> LOCATION: (221)..(221)
<223> OTHER INFORMATION: X=K or no amino acid
<220> FEATURE:
<221> NAME/KEY: MISC_FEATURE
<222> LOCATION: (223)..(223)
<223> OTHER INFORMATION: X=I or L
<220> FEATURE:
<221> NAME/KEY: MISC_FEATURE
<222> LOCATION: (224)..(224)
<223> OTHER INFORMATION: X=K or A
<220> FEATURE:
<221> NAME/KEY: MISC_FEATURE
<222> LOCATION: (225)..(225)
<223> OTHER INFORMATION: X=E or D
<220> FEATURE:
<221> NAME/KEY: MISC_FEATURE
<222> LOCATION: (226)..(226)
<223> OTHER INFORMATION: X=L or F
<220> FEATURE:
<221> NAME/KEY: MISC_FEATURE
<222> LOCATION: (227)..(227)
<223> OTHER INFORMATION: X=L, V or M
<220> FEATURE:
<221> NAME/KEY: MISC_FEATURE
<222> LOCATION: (228)..(228)
<223> OTHER INFORMATION: X=K, R or S
<220> FEATURE:
<221> NAME/KEY: MISC_FEATURE
<222> LOCATION: (229)..(229)
<223> OTHER INFORMATION: X=R or K
<220> FEATURE:
<221> NAME/KEY: MISC_FEATURE
<222> LOCATION: (230)..(230)
<223> OTHER INFORMATION: X=T or A
<220> FEATURE:
<221> NAME/KEY: MISC_FEATURE
<222> LOCATION: (231)..(231)
<223> OTHER INFORMATION: X=E or K
<220> FEATURE:
<221> NAME/KEY: MISC_FEATURE
<222> LOCATION: (232)..(232)
<223> OTHER INFORMATION: X=E or N
<220> FEATURE:
<221> NAME/KEY: MISC_FEATURE
<222> LOCATION: (233)..(233)
<223> OTHER INFORMATION: X=H or S
<220> FEATURE:
<221> NAME/KEY: MISC_FEATURE
<222> LOCATION: (234)..(234)
<223> OTHER INFORMATION: X=I, L or T
<220> FEATURE:
<221> NAME/KEY: MISC_FEATURE
<222> LOCATION: (235)..(235)
<223> OTHER INFORMATION: X=K or R
<220> FEATURE:
<221> NAME/KEY: MISC_FEATURE
<222> LOCATION: (236)..(236)
<223> OTHER INFORMATION: X=G or H
<220> FEATURE:
<221> NAME/KEY: MISC_FEATURE
<222> LOCATION: (237)..(237)
<223> OTHER INFORMATION: X=M or F
<220> FEATURE:
<221> NAME/KEY: MISC_FEATURE
<222> LOCATION: (238)..(238)
<223> OTHER INFORMATION: X=V, M or F
<220> FEATURE:
<221> NAME/KEY: MISC_FEATURE
<222> LOCATION: (239)..(239)
<223> OTHER INFORMATION: X=V or D
<220> FEATURE:
<221> NAME/KEY: MISC_FEATURE
<222> LOCATION: (241)..(241)
<223> OTHER INFORMATION: X=G, S or A
<220> FEATURE:
<221> NAME/KEY: MISC_FEATURE
<222> LOCATION: (242)..(242)
<223> OTHER INFORMATION: X=T or S
```

-continued

```
<220> FEATURE:
<221> NAME/KEY: MISC_FEATURE
<222> LOCATION: (243)..(243)
<223> OTHER INFORMATION: X=L or V
<220> FEATURE:
<221> NAME/KEY: MISC_FEATURE
<222> LOCATION: (244)..(244)
<223> OTHER INFORMATION: X=N or no amino acid
<220> FEATURE:
<221> NAME/KEY: MISC_FEATURE
<222> LOCATION: (245)..(245)
<223> OTHER INFORMATION: X=P or no amino acid
<220> FEATURE:
<221> NAME/KEY: MISC_FEATURE
<222> LOCATION: (247)..(247)
<223> OTHER INFORMATION: X=E or A
<220> FEATURE:
<221> NAME/KEY: MISC_FEATURE
<222> LOCATION: (248)..(248)
<223> OTHER INFORMATION: X=E or A
<220> FEATURE:
<221> NAME/KEY: MISC_FEATURE
<222> LOCATION: (249)..(249)
<223> OTHER INFORMATION: X=L or M
<220> FEATURE:
<221> NAME/KEY: MISC_FEATURE
<222> LOCATION: (251)..(251)
<223> OTHER INFORMATION: X=F or V
<220> FEATURE:
<221> NAME/KEY: MISC_FEATURE
<222> LOCATION: (252)..(252)
<223> OTHER INFORMATION: X=N or R
<220> FEATURE:
<221> NAME/KEY: MISC_FEATURE
<222> LOCATION: (254)..(254)
<223> OTHER INFORMATION: X=I or V
<220> FEATURE:
<221> NAME/KEY: MISC_FEATURE
<222> LOCATION: (261)..(261)
<223> OTHER INFORMATION: X=D or N
<220> FEATURE:
<221> NAME/KEY: MISC_FEATURE
<222> LOCATION: (263)..(263)
<223> OTHER INFORMATION: X=L, M, H, Q or V
<220> FEATURE:
<221> NAME/KEY: MISC_FEATURE
<222> LOCATION: (264)..(264)
<223> OTHER INFORMATION: X=G, T, A, S or E
<220> FEATURE:
<221> NAME/KEY: MISC_FEATURE
<222> LOCATION: (266)..(266)
<223> OTHER INFORMATION: X=I, V, T, S or A
<220> FEATURE:
<221> NAME/KEY: MISC_FEATURE
<222> LOCATION: (267)..(267)
<223> OTHER INFORMATION: X=T, S, N, Q, H, A or W
<220> FEATURE:
<221> NAME/KEY: MISC_FEATURE
<222> LOCATION: (268)..(268)
<223> OTHER INFORMATION: X=T or L
<220> FEATURE:
<221> NAME/KEY: MISC_FEATURE
<222> LOCATION: (270)..(270)
<223> OTHER INFORMATION: X=K, R, S or E
<220> FEATURE:
<221> NAME/KEY: MISC_FEATURE
<222> LOCATION: (271)..(271)
<223> OTHER INFORMATION: X=N or R
<220> FEATURE:
<221> NAME/KEY: MISC_FEATURE
<222> LOCATION: (272)..(272)
<223> OTHER INFORMATION: X=M or L
<220> FEATURE:
<221> NAME/KEY: MISC_FEATURE
<222> LOCATION: (273)..(273)
<223> OTHER INFORMATION: X=R or V
<220> FEATURE:
<221> NAME/KEY: MISC_FEATURE
<222> LOCATION: (274)..(274)
```

```
<223> OTHER INFORMATION: X=D, A, S or E
<220> FEATURE:
<221> NAME/KEY: MISC_FEATURE
<222> LOCATION: (276)..(276)
<223> OTHER INFORMATION: X=K or D
<220> FEATURE:
<221> NAME/KEY: MISC_FEATURE
<222> LOCATION: (277)..(277)
<223> OTHER INFORMATION: X=G or S
<220> FEATURE:
<221> NAME/KEY: MISC_FEATURE
<222> LOCATION: (279)..(279)
<223> OTHER INFORMATION: X=Q or T
<220> FEATURE:
<221> NAME/KEY: MISC_FEATURE
<222> LOCATION: (280)..(280)
<223> OTHER INFORMATION: X=F, L or I
<220> FEATURE:
<221> NAME/KEY: MISC_FEATURE
<222> LOCATION: (283)..(283)
<223> OTHER INFORMATION: X=I or V
<220> FEATURE:
<221> NAME/KEY: MISC_FEATURE
<222> LOCATION: (284)..(284)
<223> OTHER INFORMATION: X=M or V
<220> FEATURE:
<221> NAME/KEY: MISC_FEATURE
<222> LOCATION: (286)..(286)
<223> OTHER INFORMATION: X=T or K
<220> FEATURE:
<221> NAME/KEY: MISC_FEATURE
<222> LOCATION: (289)..(289)
<223> OTHER INFORMATION: X=R or K
<220> FEATURE:
<221> NAME/KEY: MISC_FEATURE
<222> LOCATION: (291)..(291)
<223> OTHER INFORMATION: X=Y or L
<220> FEATURE:
<221> NAME/KEY: MISC_FEATURE
<222> LOCATION: (292)..(292)
<223> OTHER INFORMATION: X=E, A or S
<220> FEATURE:
<221> NAME/KEY: MISC_FEATURE
<222> LOCATION: (293)..(293)
<223> OTHER INFORMATION: X=P or Y
<220> FEATURE:
<221> NAME/KEY: MISC_FEATURE
<222> LOCATION: (296)..(296)
<223> OTHER INFORMATION: X=K, Q or A
<220> FEATURE:
<221> NAME/KEY: MISC_FEATURE
<222> LOCATION: (300)..(300)
<223> OTHER INFORMATION: X=T, G, S or Y
<220> FEATURE:
<221> NAME/KEY: MISC_FEATURE
<222> LOCATION: (301)..(301)
<223> OTHER INFORMATION: X=F or W
<220> FEATURE:
<221> NAME/KEY: MISC_FEATURE
<222> LOCATION: (303)..(303)
<223> OTHER INFORMATION: X=A or G
<220> FEATURE:
<221> NAME/KEY: MISC_FEATURE
<222> LOCATION: (304)..(304)
<223> OTHER INFORMATION: X=V or P
<220> FEATURE:
<221> NAME/KEY: MISC_FEATURE
<222> LOCATION: (305)..(305)
<223> OTHER INFORMATION: X=P or A
<220> FEATURE:
<221> NAME/KEY: MISC_FEATURE
<222> LOCATION: (309)..(309)
<223> OTHER INFORMATION: X=P, H or V
<220> FEATURE:
<221> NAME/KEY: MISC_FEATURE
<222> LOCATION: (310)..(310)
<223> OTHER INFORMATION: X=S, T, E or A
<220> FEATURE:
<221> NAME/KEY: misc_feature
```

```
<222> LOCATION: (311)..(311)
<223> OTHER INFORMATION: Xaa can be any naturally occurring amino acid
<220> FEATURE:
<221> NAME/KEY: MISC_FEATURE
<222> LOCATION: (313)..(313)
<223> OTHER INFORMATION: X=C, T, L or E
<220> FEATURE:
<221> NAME/KEY: MISC_FEATURE
<222> LOCATION: (314)..(314)
<223> OTHER INFORMATION: X=L or Y
<220> FEATURE:
<221> NAME/KEY: MISC_FEATURE
<222> LOCATION: (315)..(315)
<223> OTHER INFORMATION: X=P or V
<220> FEATURE:
<221> NAME/KEY: MISC_FEATURE
<222> LOCATION: (316)..(316)
<223> OTHER INFORMATION: X=K or P
<220> FEATURE:
<221> NAME/KEY: MISC_FEATURE
<222> LOCATION: (317)..(317)
<223> OTHER INFORMATION: X=S or N
<220> FEATURE:
<221> NAME/KEY: MISC_FEATURE
<222> LOCATION: (318)..(318)
<223> OTHER INFORMATION: X=S, Q, A or K
<220> FEATURE:
<221> NAME/KEY: MISC_FEATURE
<222> LOCATION: (319)..(319)
<223> OTHER INFORMATION: X=G, S, E, D or A
<220> FEATURE:
<221> NAME/KEY: MISC_FEATURE
<222> LOCATION: (320)..(320)
<223> OTHER INFORMATION: X=G, S, A, T or Y
<220> FEATURE:
<221> NAME/KEY: MISC_FEATURE
<222> LOCATION: (321)..(321)
<223> OTHER INFORMATION: X=A or no amino acid
<220> FEATURE:
<221> NAME/KEY: MISC_FEATURE
<222> LOCATION: (322)..(322)
<223> OTHER INFORMATION: X=L, M, Q, R or no amino acid
<220> FEATURE:
<221> NAME/KEY: MISC_FEATURE
<222> LOCATION: (323)..(323)
<223> OTHER INFORMATION: X=P or no amino acid
<220> FEATURE:
<221> NAME/KEY: MISC_FEATURE
<222> LOCATION: (324)..(324)
<223> OTHER INFORMATION: X=S, G or T
<220> FEATURE:
<221> NAME/KEY: MISC_FEATURE
<222> LOCATION: (325)..(325)
<223> OTHER INFORMATION: X=Y, F or W
<220> FEATURE:
<221> NAME/KEY: MISC_FEATURE
<222> LOCATION: (327)..(327)
<223> OTHER INFORMATION: X=K or A
<220> FEATURE:
<221> NAME/KEY: MISC_FEATURE
<222> LOCATION: (328)..(328)
<223> OTHER INFORMATION: X=I, V or A
<220> FEATURE:
<221> NAME/KEY: MISC_FEATURE
<222> LOCATION: (331)..(331)
<223> OTHER INFORMATION: X=D, E, Q or N
<220> FEATURE:
<221> NAME/KEY: MISC_FEATURE
<222> LOCATION: (332)..(332)
<223> OTHER INFORMATION: X=W or A
<220> FEATURE:
<221> NAME/KEY: MISC_FEATURE
<222> LOCATION: (333)..(333)
<223> OTHER INFORMATION: X=L or V
<220> FEATURE:
<221> NAME/KEY: MISC_FEATURE
<222> LOCATION: (334)..(334)
<223> OTHER INFORMATION: X=C, S, K, Q or T
<220> FEATURE:
```

```
<221> NAME/KEY: MISC_FEATURE
<222> LOCATION: (336)..(336)
<223> OTHER INFORMATION: X=T, M, E or W
<220> FEATURE:
<221> NAME/KEY: MISC_FEATURE
<222> LOCATION: (338)..(338)
<223> OTHER INFORMATION: X=A or K
<220> FEATURE:
<221> NAME/KEY: MISC_FEATURE
<222> LOCATION: (339)..(339)
<223> OTHER INFORMATION: X=K, V, H, A, Q or T
<220> FEATURE:
<221> NAME/KEY: MISC_FEATURE
<222> LOCATION: (341)..(341)
<223> OTHER INFORMATION: X=N, D, S, T, K or P
<220> FEATURE:
<221> NAME/KEY: MISC_FEATURE
<222> LOCATION: (342)..(342)
<223> OTHER INFORMATION: X=K, S or R
<220> FEATURE:
<221> NAME/KEY: MISC_FEATURE
<222> LOCATION: (343)..(343)
<223> OTHER INFORMATION: X=L or T
<220> FEATURE:
<221> NAME/KEY: MISC_FEATURE
<222> LOCATION: (344)..(344)
<223> OTHER INFORMATION: X=M or F
<220> FEATURE:
<221> NAME/KEY: MISC_FEATURE
<222> LOCATION: (345)..(345)
<223> OTHER INFORMATION: X=A or V
<220> FEATURE:
<221> NAME/KEY: MISC_FEATURE
<222> LOCATION: (346)..(346)
<223> OTHER INFORMATION: X=I or V
<220> FEATURE:
<221> NAME/KEY: MISC_FEATURE
<222> LOCATION: (356)..(356)
<223> OTHER INFORMATION: X=M or L
<220> FEATURE:
<221> NAME/KEY: MISC_FEATURE
<222> LOCATION: (357)..(357)
<223> OTHER INFORMATION: X=V or L
<220> FEATURE:
<221> NAME/KEY: MISC_FEATURE
<222> LOCATION: (358)..(358)
<223> OTHER INFORMATION: X=E, R, S, G, Q
<220> FEATURE:
<221> NAME/KEY: MISC_FEATURE
<222> LOCATION: (361)..(361)
<223> OTHER INFORMATION: X=R or K
<220> FEATURE:
<221> NAME/KEY: MISC_FEATURE
<222> LOCATION: (362)..(362)
<223> OTHER INFORMATION: X=K, E, D, T or V
<220> FEATURE:
<221> NAME/KEY: MISC_FEATURE
<222> LOCATION: (363)..(363)
<223> OTHER INFORMATION: X=F, Y or H
<220> FEATURE:
<221> NAME/KEY: MISC_FEATURE
<222> LOCATION: (365)..(365)
<223> OTHER INFORMATION: X=D, A, Q, N, E or H
<220> FEATURE:
<221> NAME/KEY: MISC_FEATURE
<222> LOCATION: (366)..(366)
<223> OTHER INFORMATION: X=R or Q
<220> FEATURE:
<221> NAME/KEY: MISC_FEATURE
<222> LOCATION: (368)..(368)
<223> OTHER INFORMATION: X=F or L
<220> FEATURE:
<221> NAME/KEY: MISC_FEATURE
<222> LOCATION: (371)..(371)
<223> OTHER INFORMATION: X=A or G
<220> FEATURE:
<221> NAME/KEY: MISC_FEATURE
<222> LOCATION: (375)..(375)
<223> OTHER INFORMATION: X=Q or E
```

-continued

```
<220> FEATURE:
<221> NAME/KEY: MISC_FEATURE
<222> LOCATION: (376)..(376)
<223> OTHER INFORMATION: X=H or V
<220> FEATURE:
<221> NAME/KEY: MISC_FEATURE
<222> LOCATION: (377)..(377)
<223> OTHER INFORMATION: X=A or S
<220> FEATURE:
<221> NAME/KEY: MISC_FEATURE
<222> LOCATION: (378)..(378)
<223> OTHER INFORMATION: X=V or A
<220> FEATURE:
<221> NAME/KEY: MISC_FEATURE
<222> LOCATION: (380)..(380)
<223> OTHER INFORMATION: X=F or T
<220> FEATURE:
<221> NAME/KEY: MISC_FEATURE
<222> LOCATION: (384)..(384)
<223> OTHER INFORMATION: X=L or M
<220> FEATURE:
<221> NAME/KEY: MISC_FEATURE
<222> LOCATION: (386)..(386)
<223> OTHER INFORMATION: X=I, V or L
<220> FEATURE:
<221> NAME/KEY: MISC_FEATURE
<222> LOCATION: (387)..(387)
<223> OTHER INFORMATION: X=V or Q
<220> FEATURE:
<221> NAME/KEY: MISC_FEATURE
<222> LOCATION: (388)..(388)
<223> OTHER INFORMATION: X=G or D
<220> FEATURE:
<221> NAME/KEY: MISC_FEATURE
<222> LOCATION: (389)..(389)
<223> OTHER INFORMATION: X=Y or M
<220> FEATURE:
<221> NAME/KEY: MISC_FEATURE
<222> LOCATION: (390)..(390)
<223> OTHER INFORMATION: X=K, H or R
<220> FEATURE:
<221> NAME/KEY: MISC_FEATURE
<222> LOCATION: (392)..(392)
<223> OTHER INFORMATION: X=I or V
<220> FEATURE:
<221> NAME/KEY: MISC_FEATURE
<222> LOCATION: (407)..(407)
<223> OTHER INFORMATION: X=V or L
<220> FEATURE:
<221> NAME/KEY: MISC_FEATURE
<222> LOCATION: (408)..(408)
<223> OTHER INFORMATION: X=L or I
<220> FEATURE:
<221> NAME/KEY: MISC_FEATURE
<222> LOCATION: (411)..(411)
<223> OTHER INFORMATION: X=V or I
<220> FEATURE:
<221> NAME/KEY: MISC_FEATURE
<222> LOCATION: (414)..(414)
<223> OTHER INFORMATION: X=Q or E
<220> FEATURE:
<221> NAME/KEY: MISC_FEATURE
<222> LOCATION: (415)..(415)
<223> OTHER INFORMATION: X=K, N, S or H
<220> FEATURE:
<221> NAME/KEY: MISC_FEATURE
<222> LOCATION: (417)..(417)
<223> OTHER INFORMATION: X=P or N
<220> FEATURE:
<221> NAME/KEY: MISC_FEATURE
<222> LOCATION: (419)..(419)
<223> OTHER INFORMATION: X=L, M or T
<220> FEATURE:
<221> NAME/KEY: MISC_FEATURE
<222> LOCATION: (421)..(421)
<223> OTHER INFORMATION: X=A, T or C
<220> FEATURE:
<221> NAME/KEY: MISC_FEATURE
<222> LOCATION: (422)..(422)
```

```
<223> OTHER INFORMATION: X=I or V
<220> FEATURE:
<221> NAME/KEY: MISC_FEATURE
<222> LOCATION: (425)..(425)
<223> OTHER INFORMATION: X=A or G
<220> FEATURE:
<221> NAME/KEY: MISC_FEATURE
<222> LOCATION: (427)..(427)
<223> OTHER INFORMATION: X=I or L
<220> FEATURE:
<221> NAME/KEY: MISC_FEATURE
<222> LOCATION: (433)..(433)
<223> OTHER INFORMATION: X=Q or A
<220> FEATURE:
<221> NAME/KEY: MISC_FEATURE
<222> LOCATION: (436)..(436)
<223> OTHER INFORMATION: X=Q or N
<220> FEATURE:
<221> NAME/KEY: MISC_FEATURE
<222> LOCATION: (438)..(438)
<223> OTHER INFORMATION: X=A, S or V
<220> FEATURE:
<221> NAME/KEY: MISC_FEATURE
<222> LOCATION: (442)..(442)
<223> OTHER INFORMATION: X=S or A
<220> FEATURE:
<221> NAME/KEY: MISC_FEATURE
<222> LOCATION: (443)..(443)
<223> OTHER INFORMATION: X=Y or F
<220> FEATURE:
<221> NAME/KEY: MISC_FEATURE
<222> LOCATION: (444)..(444)
<223> OTHER INFORMATION: X=L or M
<220> FEATURE:
<221> NAME/KEY: MISC_FEATURE
<222> LOCATION: (446)..(446)
<223> OTHER INFORMATION: X=C or S
<220> FEATURE:
<221> NAME/KEY: MISC_FEATURE
<222> LOCATION: (447)..(447)
<223> OTHER INFORMATION: X=I or V
<220> FEATURE:
<221> NAME/KEY: MISC_FEATURE
<222> LOCATION: (449)..(449)
<223> OTHER INFORMATION: X=E, D, N, Q, T or G
<220> FEATURE:
<221> NAME/KEY: MISC_FEATURE
<222> LOCATION: (450)..(450)
<223> OTHER INFORMATION: X=M or V
<220> FEATURE:
<221> NAME/KEY: MISC_FEATURE
<222> LOCATION: (451)..(451)
<223> OTHER INFORMATION: X=V, I, T, R
<220> FEATURE:
<221> NAME/KEY: MISC_FEATURE
<222> LOCATION: (452)..(452)
<223> OTHER INFORMATION: X=I or V
<220> FEATURE:
<221> NAME/KEY: MISC_FEATURE
<222> LOCATION: (453)..(453)
<223> OTHER INFORMATION: X=M or G
<220> FEATURE:
<221> NAME/KEY: MISC_FEATURE
<222> LOCATION: (454)..(454)
<223> OTHER INFORMATION: X=T, A or L
<220> FEATURE:
<221> NAME/KEY: MISC_FEATURE
<222> LOCATION: (456)..(456)
<223> OTHER INFORMATION: X=S or K
<220> FEATURE:
<221> NAME/KEY: MISC_FEATURE
<222> LOCATION: (458)..(458)
<223> OTHER INFORMATION: X=E or A
<220> FEATURE:
<221> NAME/KEY: MISC_FEATURE
<222> LOCATION: (459)..(459)
<223> OTHER INFORMATION: X=N or A
<220> FEATURE:
<221> NAME/KEY: MISC_FEATURE
```

```
<222> LOCATION: (461)..(461)
<223> OTHER INFORMATION: X=C or L
<220> FEATURE:
<221> NAME/KEY: MISC_FEATURE
<222> LOCATION: (463)..(463)
<223> OTHER INFORMATION: X=Q, L or G
<220> FEATURE:
<221> NAME/KEY: MISC_FEATURE
<222> LOCATION: (466)..(466)
<223> OTHER INFORMATION: X=Y, F, H or K
<220> FEATURE:
<221> NAME/KEY: MISC_FEATURE
<222> LOCATION: (467)..(467)
<223> OTHER INFORMATION: X=T or Y
<220> FEATURE:
<221> NAME/KEY: MISC_FEATURE
<222> LOCATION: (468)..(468)
<223> OTHER INFORMATION: X=G or A
<220> FEATURE:
<221> NAME/KEY: MISC_FEATURE
<222> LOCATION: (469)..(469)
<223> OTHER INFORMATION: X=Y, H or Q
<220> FEATURE:
<221> NAME/KEY: MISC_FEATURE
<222> LOCATION: (470)..(470)
<223> OTHER INFORMATION: X=H or T
<220> FEATURE:
<221> NAME/KEY: MISC_FEATURE
<222> LOCATION: (471)..(471)
<223> OTHER INFORMATION: X=Y or H
<220> FEATURE:
<221> NAME/KEY: MISC_FEATURE
<222> LOCATION: (472)..(472)
<223> OTHER INFORMATION: X=N, Q, S, E or no amino acid
<220> FEATURE:
<221> NAME/KEY: MISC_FEATURE
<222> LOCATION: (473)..(473)
<223> OTHER INFORMATION: X=D, G, Q, K, S, E or no amino acid
<220> FEATURE:
<221> NAME/KEY: MISC_FEATURE
<222> LOCATION: (476)..(476)
<223> OTHER INFORMATION: X=S, T, C, A, V or F
<220> FEATURE:
<221> NAME/KEY: MISC_FEATURE
<222> LOCATION: (477)..(477)
<223> OTHER INFORMATION: X=A, V or T
<220> FEATURE:
<221> NAME/KEY: MISC_FEATURE
<222> LOCATION: (478)..(478)
<223> OTHER INFORMATION: X=V or I
<220> FEATURE:
<221> NAME/KEY: MISC_FEATURE
<222> LOCATION: (484)..(484)
<223> OTHER INFORMATION: X=N, S, T or A
<220> FEATURE:
<221> NAME/KEY: MISC_FEATURE
<222> LOCATION: (485)..(485)
<223> OTHER INFORMATION: X=A, G, V or T
<220> FEATURE:
<221> NAME/KEY: MISC_FEATURE
<222> LOCATION: (486)..(486)
<223> OTHER INFORMATION: X=V, Q, L, T or A
<220> FEATURE:
<221> NAME/KEY: MISC_FEATURE
<222> LOCATION: (487)..(487)
<223> OTHER INFORMATION: X=G, S or Q
<220> FEATURE:
<221> NAME/KEY: MISC_FEATURE
<222> LOCATION: (488)..(488)
<223> OTHER INFORMATION: X=V, A or T
<220> FEATURE:
<221> NAME/KEY: MISC_FEATURE
<222> LOCATION: (489)..(489)
<223> OTHER INFORMATION: X=E, A, T, V, P or Q
<220> FEATURE:
<221> NAME/KEY: MISC_FEATURE
<222> LOCATION: (490)..(490)
<223> OTHER INFORMATION: X=L, F, S or A
<220> FEATURE:
```

```
<221> NAME/KEY: MISC_FEATURE
<222> LOCATION: (491)..(491)
<223> OTHER INFORMATION: X=T, E, Q or G
<220> FEATURE:
<221> NAME/KEY: MISC_FEATURE
<222> LOCATION: (492)..(492)
<223> OTHER INFORMATION: X=P or T
<220> FEATURE:
<221> NAME/KEY: MISC_FEATURE
<222> LOCATION: (493)..(493)
<223> OTHER INFORMATION: X=L or W
<220> FEATURE:
<221> NAME/KEY: MISC_FEATURE
<222> LOCATION: (494)..(494)
<223> OTHER INFORMATION: X=E, T, Q, A, S, G or P
<220> FEATURE:
<221> NAME/KEY: MISC_FEATURE
<222> LOCATION: (495)..(495)
<223> OTHER INFORMATION: X=K, Q, S, M, A, T, E and D
<220> FEATURE:
<221> NAME/KEY: MISC_FEATURE
<222> LOCATION: (496)..(496)
<223> OTHER INFORMATION: X=L or M
<220> FEATURE:
<221> NAME/KEY: MISC_FEATURE
<222> LOCATION: (497)..(497)
<223> OTHER INFORMATION: X=P or K
<220> FEATURE:
<221> NAME/KEY: MISC_FEATURE
<222> LOCATION: (498)..(498)
<223> OTHER INFORMATION: X=I, L or W
<220> FEATURE:
<221> NAME/KEY: MISC_FEATURE
<222> LOCATION: (500)..(500)
<223> OTHER INFORMATION: X=K or E
<220> FEATURE:
<221> NAME/KEY: MISC_FEATURE
<222> LOCATION: (501)..(501)
<223> OTHER INFORMATION: X=G or W
<220> FEATURE:
<221> NAME/KEY: MISC_FEATURE
<222> LOCATION: (502)..(502)
<223> OTHER INFORMATION: X=I, L, V or E
<220> FEATURE:
<221> NAME/KEY: MISC_FEATURE
<222> LOCATION: (503)..(503)
<223> OTHER INFORMATION: X=V, L, I or R
<220> FEATURE:
<221> NAME/KEY: MISC_FEATURE
<222> LOCATION: (504)..(504)
<223> OTHER INFORMATION: X=K, R or L
<220> FEATURE:
<221> NAME/KEY: MISC_FEATURE
<222> LOCATION: (505)..(505)
<223> OTHER INFORMATION: X=R or K
<220> FEATURE:
<221> NAME/KEY: MISC_FEATURE
<222> LOCATION: (506)..(506)
<223> OTHER INFORMATION: X=R, H, Q or G
<220> FEATURE:
<221> NAME/KEY: MISC_FEATURE
<222> LOCATION: (508)..(508)
<223> OTHER INFORMATION: X=E, K or D
<220> FEATURE:
<221> NAME/KEY: MISC_FEATURE
<222> LOCATION: (509)..(509)
<223> OTHER INFORMATION: X=K, T or D
<220> FEATURE:
<221> NAME/KEY: MISC_FEATURE
<222> LOCATION: (510)..(510)
<223> OTHER INFORMATION: X=L, V or I
<220> FEATURE:
<221> NAME/KEY: MISC_FEATURE
<222> LOCATION: (511)..(511)
<223> OTHER INFORMATION: X=A or V
<220> FEATURE:
<221> NAME/KEY: MISC_FEATURE
<222> LOCATION: (512)..(512)
<223> OTHER INFORMATION: X=I or L
```

-continued

```
<220> FEATURE:
<221> NAME/KEY: MISC_FEATURE
<222> LOCATION: (514)..(514)
<223> OTHER INFORMATION: X=N, C or A
<220> FEATURE:
<221> NAME/KEY: MISC_FEATURE
<222> LOCATION: (515)..(515)
<223> OTHER INFORMATION: X=F or G
<220> FEATURE:
<221> NAME/KEY: MISC_FEATURE
<222> LOCATION: (517)..(517)
<223> OTHER INFORMATION: X=T or K
<220> FEATURE:
<221> NAME/KEY: MISC_FEATURE
<222> LOCATION: (518)..(518)
<223> OTHER INFORMATION: X=L or A
<220> FEATURE:
<221> NAME/KEY: MISC_FEATURE
<222> LOCATION: (519)..(519)
<223> OTHER INFORMATION: X=M or L
<220> FEATURE:
<221> NAME/KEY: MISC_FEATURE
<222> LOCATION: (520)..(520)
<223> OTHER INFORMATION: X=P, A or D
<220> FEATURE:
<221> NAME/KEY: MISC_FEATURE
<222> LOCATION: (521)..(521)
<223> OTHER INFORMATION: X=E, Q or Y
<220> FEATURE:
<221> NAME/KEY: MISC_FEATURE
<222> LOCATION: (523)..(523)
<223> OTHER INFORMATION: X=A, T, Q, S or L
<220> FEATURE:
<221> NAME/KEY: MISC_FEATURE
<222> LOCATION: (524)..(524)
<223> OTHER INFORMATION: X=K, Q, A, L or V
<220> FEATURE:
<221> NAME/KEY: MISC_FEATURE
<222> LOCATION: (525)..(525)
<223> OTHER INFORMATION: X=V, A or T
<220> FEATURE:
<221> NAME/KEY: MISC_FEATURE
<222> LOCATION: (527)..(527)
<223> OTHER INFORMATION: X=E or D
<220> FEATURE:
<221> NAME/KEY: MISC_FEATURE
<222> LOCATION: (528)..(528)
<223> OTHER INFORMATION: X=S, A, K, N, T or D
<220> FEATURE:
<221> NAME/KEY: MISC_FEATURE
<222> LOCATION: (529)..(529)
<223> OTHER INFORMATION: X=L, M or R
<220> FEATURE:
<221> NAME/KEY: MISC_FEATURE
<222> LOCATION: (530)..(530)
<223> OTHER INFORMATION: X=P or no amino acid
<220> FEATURE:
<221> NAME/KEY: MISC_FEATURE
<222> LOCATION: (531)..(531)
<223> OTHER INFORMATION: X=N or G
<220> FEATURE:
<221> NAME/KEY: MISC_FEATURE
<222> LOCATION: (532)..(532)
<223> OTHER INFORMATION: X=A or V
<220> FEATURE:
<221> NAME/KEY: MISC_FEATURE
<222> LOCATION: (533)..(533)
<223> OTHER INFORMATION: X=T or G
<220> FEATURE:
<221> NAME/KEY: MISC_FEATURE
<222> LOCATION: (534)..(534)
<223> OTHER INFORMATION: X=L or V
<220> FEATURE:
<221> NAME/KEY: MISC_FEATURE
<222> LOCATION: (536)..(536)
<223> OTHER INFORMATION: X=D or N
<220> FEATURE:
<221> NAME/KEY: MISC_FEATURE
<222> LOCATION: (537)..(537)
```

```
<223> OTHER INFORMATION: X=M or A
<220> FEATURE:
<221> NAME/KEY: MISC_FEATURE
<222> LOCATION: (545)..(545)
<223> OTHER INFORMATION: X=E, D, T or K
<220> FEATURE:
<221> NAME/KEY: MISC_FEATURE
<222> LOCATION: (546)..(546)
<223> OTHER INFORMATION: X=A, T, E, S or Q
<220> FEATURE:
<221> NAME/KEY: MISC_FEATURE
<222> LOCATION: (547)..(547)
<223> OTHER INFORMATION: X=L or M
<220> FEATURE:
<221> NAME/KEY: MISC_FEATURE
<222> LOCATION: (548)..(548)
<223> OTHER INFORMATION: X=I, V, L or T
<220> FEATURE:
<221> NAME/KEY: MISC_FEATURE
<222> LOCATION: (549)..(549)
<223> OTHER INFORMATION: X=L, M, A, E, Q or R
<220> FEATURE:
<221> NAME/KEY: MISC_FEATURE
<222> LOCATION: (550)..(550)
<223> OTHER INFORMATION: X=E, Q or S
<220> FEATURE:
<221> NAME/KEY: MISC_FEATURE
<222> LOCATION: (551)..(551)
<223> OTHER INFORMATION: X=M, L or V
<220> FEATURE:
<221> NAME/KEY: MISC_FEATURE
<222> LOCATION: (552)..(552)
<223> OTHER INFORMATION: X=A or G
<220> FEATURE:
<221> NAME/KEY: MISC_FEATURE
<222> LOCATION: (553)..(553)
<223> OTHER INFORMATION: X=A, S, G or Q
<220> FEATURE:
<221> NAME/KEY: MISC_FEATURE
<222> LOCATION: (554)..(554)
<223> OTHER INFORMATION: X=S, Q, R, E or K
<220> FEATURE:
<221> NAME/KEY: MISC_FEATURE
<222> LOCATION: (555)..(555)
<223> OTHER INFORMATION: X=H or A
<220> FEATURE:
<221> NAME/KEY: MISC_FEATURE
<222> LOCATION: (556)..(556)
<223> OTHER INFORMATION: X=E, D, Q, S or R
<220> FEATURE:
<221> NAME/KEY: MISC_FEATURE
<222> LOCATION: (557)..(557)
<223> OTHER INFORMATION: X=A, V, S, T or L
<220> FEATURE:
<221> NAME/KEY: MISC_FEATURE
<222> LOCATION: (558)..(558)
<223> OTHER INFORMATION: X=L or F
<220> FEATURE:
<221> NAME/KEY: MISC_FEATURE
<222> LOCATION: (559)..(559)
<223> OTHER INFORMATION: X=V or I
<220> FEATURE:
<221> NAME/KEY: MISC_FEATURE
<222> LOCATION: (561)..(561)
<223> OTHER INFORMATION: X=V, I or L
<220> FEATURE:
<221> NAME/KEY: MISC_FEATURE
<222> LOCATION: (563)..(563)
<223> OTHER INFORMATION: X=E or D
<220> FEATURE:
<221> NAME/KEY: MISC_FEATURE
<222> LOCATION: (564)..(564)
<223> OTHER INFORMATION: X=N or G
<220> FEATURE:
<221> NAME/KEY: MISC_FEATURE
<222> LOCATION: (565)..(565)
<223> OTHER INFORMATION: X=A or T
<220> FEATURE:
<221> NAME/KEY: MISC_FEATURE
```

```
<222> LOCATION: (566)..(566)
<223> OTHER INFORMATION: X=V or I
<220> FEATURE:
<221> NAME/KEY: MISC_FEATURE
<222> LOCATION: (567)..(567)
<223> OTHER INFORMATION: X=M, K or V
<220> FEATURE:
<221> NAME/KEY: MISC_FEATURE
<222> LOCATION: (570)..(570)
<223> OTHER INFORMATION: X=A or F
<220> FEATURE:
<221> NAME/KEY: MISC_FEATURE
<222> LOCATION: (572)..(572)
<223> OTHER INFORMATION: X=S or G
<220> FEATURE:
<221> NAME/KEY: MISC_FEATURE
<222> LOCATION: (573)..(573)
<223> OTHER INFORMATION: X=G or A
<220> FEATURE:
<221> NAME/KEY: MISC_FEATURE
<222> LOCATION: (575)..(575)
<223> OTHER INFORMATION: X=N or L
<220> FEATURE:
<221> NAME/KEY: MISC_FEATURE
<222> LOCATION: (577)..(577)
<223> OTHER INFORMATION: X=V, L, F, Y or A
<220> FEATURE:
<221> NAME/KEY: MISC_FEATURE
<222> LOCATION: (578)..(578)
<223> OTHER INFORMATION: X=L or V
<220> FEATURE:
<221> NAME/KEY: MISC_FEATURE
<222> LOCATION: (579)..(579)
<223> OTHER INFORMATION: X=M or N
<220> FEATURE:
<221> NAME/KEY: MISC_FEATURE
<222> LOCATION: (580)..(580)
<223> OTHER INFORMATION: X=A, Q or S
<220> FEATURE:
<221> NAME/KEY: MISC_FEATURE
<222> LOCATION: (581)..(581)
<223> OTHER INFORMATION: X=H, N, K, E, R or M
<220> FEATURE:
<221> NAME/KEY: MISC_FEATURE
<222> LOCATION: (582)..(582)
<223> OTHER INFORMATION: X=R, K or N
<220> FEATURE:
<221> NAME/KEY: MISC_FEATURE
<222> LOCATION: (583)..(583)
<223> OTHER INFORMATION: X=K, R, L or I
<220> FEATURE:
<221> NAME/KEY: MISC_FEATURE
<222> LOCATION: (584)..(584)
<223> OTHER INFORMATION: X=P, A, W, G, L or H
<220> FEATURE:
<221> NAME/KEY: MISC_FEATURE
<222> LOCATION: (585)..(585)
<223> OTHER INFORMATION: X=V, I or P
<220> FEATURE:
<221> NAME/KEY: MISC_FEATURE
<222> LOCATION: (586)..(586)
<223> OTHER INFORMATION: X=P, S or T
<220> FEATURE:
<221> NAME/KEY: MISC_FEATURE
<222> LOCATION: (588)..(588)
<223> OTHER INFORMATION: X=L or R
<220> FEATURE:
<221> NAME/KEY: MISC_FEATURE
<222> LOCATION: (589)..(589)
<223> OTHER INFORMATION: X=N or V
<220> FEATURE:
<221> NAME/KEY: MISC_FEATURE
<222> LOCATION: (590)..(590)
<223> OTHER INFORMATION: X=I or L
<220> FEATURE:
<221> NAME/KEY: MISC_FEATURE
<222> LOCATION: (592)..(592)
<223> OTHER INFORMATION: X=L or I
<220> FEATURE:
```

-continued

```
<221> NAME/KEY: MISC_FEATURE
<222> LOCATION: (593)..(593)
<223> OTHER INFORMATION: X=P or A
<220> FEATURE:
<221> NAME/KEY: MISC_FEATURE
<222> LOCATION: (595)..(595)
<223> OTHER INFORMATION: X=F, R, H, Y, L, E, I, V or S
<220> FEATURE:
<221> NAME/KEY: MISC_FEATURE
<222> LOCATION: (597)..(597)
<223> OTHER INFORMATION: X=I, V or Q
<220> FEATURE:
<221> NAME/KEY: MISC_FEATURE
<222> LOCATION: (598)..(598)
<223> OTHER INFORMATION: X=P, S or E
<220> FEATURE:
<221> NAME/KEY: MISC_FEATURE
<222> LOCATION: (599)..(599)
<223> OTHER INFORMATION: X=Q, P or H
<220> FEATURE:
<221> NAME/KEY: MISC_FEATURE
<222> LOCATION: (600)..(600)
<223> OTHER INFORMATION: X=G or A
<220> FEATURE:
<221> NAME/KEY: MISC_FEATURE
<222> LOCATION: (601)..(601)
<223> OTHER INFORMATION: X=T, E or S
<220> FEATURE:
<221> NAME/KEY: MISC_FEATURE
<222> LOCATION: (602)..(602)
<223> OTHER INFORMATION: X=Q or A
<220> FEATURE:
<221> NAME/KEY: MISC_FEATURE
<222> LOCATION: (603)..(603)
<223> OTHER INFORMATION: X=E, D or A
<220> FEATURE:
<221> NAME/KEY: MISC_FEATURE
<222> LOCATION: (604)..(604)
<223> OTHER INFORMATION: X=E or S
<220> FEATURE:
<221> NAME/KEY: MISC_FEATURE
<222> LOCATION: (605)..(605)
<223> OTHER INFORMATION: X=M, A, I, L or V
<220> FEATURE:
<221> NAME/KEY: MISC_FEATURE
<222> LOCATION: (606)..(606)
<223> OTHER INFORMATION: X=R or H
<220> FEATURE:
<221> NAME/KEY: MISC_FEATURE
<222> LOCATION: (607)..(607)
<223> OTHER INFORMATION: X=A, S, H, T or V
<220> FEATURE:
<221> NAME/KEY: MISC_FEATURE
<222> LOCATION: (608)..(608)
<223> OTHER INFORMATION: X=E, D or R
<220> FEATURE:
<221> NAME/KEY: MISC_FEATURE
<222> LOCATION: (609)..(609)
<223> OTHER INFORMATION: X=L, I, Y or A
<220> FEATURE:
<221> NAME/KEY: MISC_FEATURE
<222> LOCATION: (610)..(610)
<223> OTHER INFORMATION: X=G, Q or S
<220> FEATURE:
<221> NAME/KEY: MISC_FEATURE
<222> LOCATION: (611)..(611)
<223> OTHER INFORMATION: X=L or I
<220> FEATURE:
<221> NAME/KEY: MISC_FEATURE
<222> LOCATION: (612)..(612)
<223> OTHER INFORMATION: X=D, N or T
<220> FEATURE:
<221> NAME/KEY: MISC_FEATURE
<222> LOCATION: (613)..(613)
<223> OTHER INFORMATION: X=A or I
<220> FEATURE:
<221> NAME/KEY: MISC_FEATURE
<222> LOCATION: (614)..(614)
<223> OTHER INFORMATION: X=A, S, N, D, E or P
```

```
-continued

<220> FEATURE:
<221> NAME/KEY: MISC_FEATURE
<222> LOCATION: (615)..(615)
<223> OTHER INFORMATION: X=G or A
<220> FEATURE:
<221> NAME/KEY: MISC_FEATURE
<222> LOCATION: (616)..(616)
<223> OTHER INFORMATION: X=M or I
<220> FEATURE:
<221> NAME/KEY: MISC_FEATURE
<222> LOCATION: (617)..(617)
<223> OTHER INFORMATION: X=E, Q, R, K or D
<220> FEATURE:
<221> NAME/KEY: MISC_FEATURE
<222> LOCATION: (618)..(618)
<223> OTHER INFORMATION: X=A, T, Q, R or N
<220> FEATURE:
<221> NAME/KEY: MISC_FEATURE
<222> LOCATION: (619)..(619)
<223> OTHER INFORMATION: X=K, R, Q or V
<220> FEATURE:
<221> NAME/KEY: MISC_FEATURE
<222> LOCATION: (620)..(620)
<223> OTHER INFORMATION: X=I, V or L
<220> FEATURE:
<221> NAME/KEY: MISC_FEATURE
<222> LOCATION: (621)..(621)
<223> OTHER INFORMATION: X=K, R, E, T, S or A
<220> FEATURE:
<221> NAME/KEY: MISC_FEATURE
<222> LOCATION: (622)..(622)
<223> OTHER INFORMATION: X=A, T, D, R, N, K, Q or E
<220> FEATURE:
<221> NAME/KEY: MISC_FEATURE
<222> LOCATION: (623)..(623)
<223> OTHER INFORMATION: X=W, Y or L
<220> FEATURE:
<221> NAME/KEY: MISC_FEATURE
<222> LOCATION: (624)..(624)
<223> OTHER INFORMATION: X=L, Q, M or G
<220> FEATURE:
<221> NAME/KEY: MISC_FEATURE
<222> LOCATION: (625)..(625)
<223> OTHER INFORMATION: X=A, V or no amino acid
<220> FEATURE:
<221> NAME/KEY: MISC_FEATURE
<222> LOCATION: (626)..(626)
<223> OTHER INFORMATION: X=D or no amino acid

<400> SEQUENCE: 21

Met Xaa Xaa Xaa Xaa Xaa Xaa Pro Xaa Leu Xaa Xaa Xaa Xaa
1               5                   10                  15

Xaa Xaa Xaa Leu Xaa Xaa Leu Xaa Xaa Xaa Xaa Leu Pro Xaa Leu Xaa
                20                  25                  30

Xaa Glu Leu Arg Xaa Xaa Xaa Xaa Xaa Xaa Ser Xaa Xaa Xaa Xaa
        35                  40                  45

His Xaa Ala Ser Xaa Leu Gly Xaa Val Xaa Xaa Xaa Xaa Ala Xaa His
    50                  55                  60

Tyr Val Xaa Xaa Xaa Pro Xaa Asp Xaa Xaa Xaa Xaa Asp Val Gly His
65                  70                  75                  80

Gln Ala Tyr Xaa His Lys Ile Leu Thr Gly Arg Arg Asp Xaa Xaa Xaa
            85                  90                  95

Xaa Ile Xaa Xaa Xaa Xaa Gly Xaa Xaa Xaa Phe Xaa Xaa Xaa Xaa Glu
            100                 105                 110

Ser Xaa Xaa Asp Xaa Xaa Xaa Val Gly His Xaa Ser Thr Ser Xaa Xaa
            115                 120                 125

Xaa Xaa Xaa Gly Xaa Ala Xaa Ala Xaa Xaa Xaa Glx Xaa Xaa Xaa Xaa
            130                 135                 140

Xaa Xaa Xaa Xaa Val Ile Gly Asp Gly Xaa Xaa Thr Xaa Gly Met Ala
```

```
                145                 150                 155                 160
Xaa Xaa Ala Xaa Xaa Xaa Xaa Gly Asp Xaa Xaa Xaa Xaa Leu Xaa
                    165                 170                 175
Xaa Leu Asn Asp Asn Xaa Met Ser Ile Ser Glu Asn Val Gly Xaa Xaa
                180                 185                 190
Asn Xaa Xaa Xaa Xaa Xaa Xaa Xaa Xaa Lys Xaa Xaa Xaa Xaa Xaa
                    195                 200                 205
Xaa Xaa Xaa Gly Lys Xaa Xaa Xaa Xaa Xaa Xaa Xaa Pro Xaa Xaa
                210                 215                 220
Xaa Xaa Xaa Xaa Xaa Xaa Xaa Xaa Xaa Xaa Xaa Xaa Xaa Xaa Pro
225                 230                 235                 240
Xaa Xaa Xaa Xaa Xaa Phe Xaa Xaa Gly Xaa Xaa Tyr Xaa Gly Pro
                    245                 250                 255
Val Asp Gly His Xaa Val Xaa Xaa Leu Xaa Xaa Xaa Leu Xaa Xaa Xaa
                260                 265                 270
Xaa Xaa Leu Xaa Xaa Pro Xaa Xaa Leu His Xaa Xaa Thr Xaa Lys Gly
            275                 280                 285
Xaa Gly Xaa Xaa Xaa Ala Glu Xaa Asp Pro Ile Xaa Xaa His Xaa Xaa
    290                 295                 300
Xaa Lys Phe Asp Xaa Xaa Xaa Gly Xaa Xaa Xaa Xaa Xaa Xaa Xaa Xaa
305                 310                 315                 320
Xaa Xaa Xaa Xaa Xaa Ser Xaa Xaa Phe Gly Xaa Xaa Xaa Xaa Glu Xaa
                    325                 330                 335
Ala Xaa Xaa Asp Xaa Xaa Xaa Xaa Xaa Thr Pro Ala Met Arg Glu
                340                 345                 350
Gly Ser Gly Xaa Xaa Xaa Phe Ser Xaa Xaa Pro Xaa Xaa Tyr Xaa
        355                 360                 365
Asp Val Xaa Ile Ala Glu Xaa Xaa Xaa Thr Xaa Ala Ala Gly Xaa
        370                 375                 380
Ala Xaa Xaa Xaa Xaa Xaa Pro Xaa Val Ala Ile Tyr Ser Thr Phe Leu
385                 390                 395                 400
Gln Arg Ala Tyr Asp Gln Xaa Xaa His Asp Xaa Ala Ile Xaa Xaa Leu
                405                 410                 415
Xaa Val Xaa Phe Xaa Xaa Asp Arg Xaa Gly Xaa Val Gly Ala Asp Gly
            420                 425                 430
Xaa Thr His Xaa Gly Xaa Phe Asp Leu Xaa Xaa Xaa Arg Xaa Xaa Pro
        435                 440                 445
Xaa Xaa Xaa Xaa Xaa Xaa Pro Xaa Asp Xaa Xaa Glu Xaa Arg Xaa Met
450                 455                 460
Leu Xaa Xaa Xaa Xaa Xaa Xaa Xaa Gly Pro Xaa Xaa Xaa Arg Tyr
465                 470                 475                 480
Pro Arg Gly Xaa Xaa Xaa Xaa Xaa Xaa Xaa Xaa Xaa Xaa Xaa Xaa
                    485                 490                 495
Xaa Xaa Gly Xaa Xaa Xaa Xaa Xaa Xaa Gly Xaa Xaa Xaa Xaa Xaa
                500                 505                 510
Leu Xaa Xaa Gly Xaa Xaa Xaa Xaa Xaa Ala Xaa Xaa Xaa Ala Xaa Xaa
        515                 520                 525
Xaa Xaa Xaa Xaa Xaa Xaa Val Xaa Xaa Arg Phe Val Lys Pro Leu Asp
            530                 535                 540
Xaa Xaa Xaa Xaa Xaa Xaa Xaa Xaa Xaa Xaa Xaa Xaa Xaa Xaa Thr
545                 550                 555                 560
Xaa Glu Xaa Xaa Xaa Xaa Xaa Gly Gly Xaa Gly Xaa Xaa Val Xaa Glu
                565                 570                 575
```

```
Xaa Xaa Xaa Xaa Xaa Xaa Xaa Xaa Xaa Val Xaa Xaa Xaa Gly Xaa
            580                 585                 590

Xaa Asp Xaa Phe Xaa Xaa Xaa Xaa Xaa Xaa Xaa Xaa Xaa Xaa Xaa
        595                 600                 605

Xaa Xaa Xaa Xaa Xaa Xaa Xaa Xaa Xaa Xaa Xaa Xaa Xaa Xaa Xaa
    610                 615                 620

Xaa Xaa
625

<210> SEQ ID NO 22
<211> LENGTH: 621
<212> TYPE: PRT
<213> ORGANISM: Artificial sequence
<220> FEATURE:
<223> OTHER INFORMATION: Bacterial DXS consensus sequence
<220> FEATURE:
<221> NAME/KEY: MISC_FEATURE
<222> LOCATION: (2)..(2)
<223> OTHER INFORMATION: X= S or T
<220> FEATURE:
<221> NAME/KEY: MISC_FEATURE
<222> LOCATION: (3)..(3)
<223> OTHER INFORMATION: X= F, L or I
<220> FEATURE:
<221> NAME/KEY: MISC_FEATURE
<222> LOCATION: (4)..(4)
<223> OTHER INFORMATION: X= D or E
<220> FEATURE:
<221> NAME/KEY: MISC_FEATURE
<222> LOCATION: (5)..(5)
<223> OTHER INFORMATION: X= I, T, S or L
<220> FEATURE:
<221> NAME/KEY: MISC_FEATURE
<222> LOCATION: (6)..(6)
<223> OTHER INFORMATION: X= A or T
<220> FEATURE:
<221> NAME/KEY: MISC_FEATURE
<222> LOCATION: (13)..(13)
<223> OTHER INFORMATION: X= L or Q
<220> FEATURE:
<221> NAME/KEY: MISC_FEATURE
<222> LOCATION: (14)..(14)
<223> OTHER INFORMATION: X= V or A
<220> FEATURE:
<221> NAME/KEY: MISC_FEATURE
<222> LOCATION: (15)..(15)
<223> OTHER INFORMATION: X= D, E or S
<220> FEATURE:
<221> NAME/KEY: MISC_FEATURE
<222> LOCATION: (16)..(16)
<223> OTHER INFORMATION: X= S, N or T
<220> FEATURE:
<221> NAME/KEY: MISC_FEATURE
<222> LOCATION: (17)..(17)
<223> OTHER INFORMATION: X= T, P or V
<220> FEATURE:
<221> NAME/KEY: MISC_FEATURE
<222> LOCATION: (18)..(18)
<223> OTHER INFORMATION: X= Q, A, E or D
<220> FEATURE:
<221> NAME/KEY: MISC_FEATURE
<222> LOCATION: (19)..(19)
<223> OTHER INFORMATION: X= A, E or D
<220> FEATURE:
<221> NAME/KEY: MISC_FEATURE
<222> LOCATION: (22)..(22)
<223> OTHER INFORMATION: X= L, M, A or S
<220> FEATURE:
<221> NAME/KEY: MISC_FEATURE
<222> LOCATION: (25)..(25)
<223> OTHER INFORMATION: X= K or R
<220> FEATURE:
<221> NAME/KEY: MISC_FEATURE
<222> LOCATION: (26)..(26)
```

```
<223> OTHER INFORMATION: X= E or D
<220> FEATURE:
<221> NAME/KEY: MISC_FEATURE
<222> LOCATION: (27)..(27)
<223> OTHER INFORMATION: X= S, K or T
<220> FEATURE:
<221> NAME/KEY: MISC_FEATURE
<222> LOCATION: (30)..(30)
<223> OTHER INFORMATION: X= K, T or A
<220> FEATURE:
<221> NAME/KEY: MISC_FEATURE
<222> LOCATION: (32)..(32)
<223> OTHER INFORMATION: X= C or S
<220> FEATURE:
<221> NAME/KEY: MISC_FEATURE
<222> LOCATION: (33)..(33)
<223> OTHER INFORMATION: X= D or N
<220> FEATURE:
<221> NAME/KEY: MISC_FEATURE
<222> LOCATION: (37)..(37)
<223> OTHER INFORMATION: X= R or Q
<220> FEATURE:
<221> NAME/KEY: MISC_FEATURE
<222> LOCATION: (38)..(38)
<223> OTHER INFORMATION: X= Y or F
<220> FEATURE:
<221> NAME/KEY: MISC_FEATURE
<222> LOCATION: (41)..(41)
<223> OTHER INFORMATION: X= D, T, N or A
<220> FEATURE:
<221> NAME/KEY: MISC_FEATURE
<222> LOCATION: (42)..(42)
<223> OTHER INFORMATION: X= S or C
<220> FEATURE:
<221> NAME/KEY: MISC_FEATURE
<222> LOCATION: (45)..(45)
<223> OTHER INFORMATION: X= R or Q
<220> FEATURE:
<221> NAME/KEY: MISC_FEATURE
<222> LOCATION: (56)..(56)
<223> OTHER INFORMATION: X= T, V or A
<220> FEATURE:
<221> NAME/KEY: MISC_FEATURE
<222> LOCATION: (63)..(63)
<223> OTHER INFORMATION: X=L or M
<220> FEATURE:
<221> NAME/KEY: MISC_FEATURE
<222> LOCATION: (68)..(68)
<223> OTHER INFORMATION: X=N or K
<220> FEATURE:
<221> NAME/KEY: MISC_FEATURE
<222> LOCATION: (73)..(73)
<223> OTHER INFORMATION: X= Q, R, H or N
<220> FEATURE:
<221> NAME/KEY: MISC_FEATURE
<222> LOCATION: (74)..(74)
<223> OTHER INFORMATION: X= L or V
<220> FEATURE:
<221> NAME/KEY: MISC_FEATURE
<222> LOCATION: (75)..(75)
<223> OTHER INFORMATION: X= I or V
<220> FEATURE:
<221> NAME/KEY: MISC_FEATURE
<222> LOCATION: (94)..(94)
<223> OTHER INFORMATION: X= K or R
<220> FEATURE:
<221> NAME/KEY: MISC_FEATURE
<222> LOCATION: (96)..(96)
<223> OTHER INFORMATION: X= G, S, A or D
<220> FEATURE:
<221> NAME/KEY: MISC_FEATURE
<222> LOCATION: (97)..(97)
<223> OTHER INFORMATION: X= T or S
<220> FEATURE:
<221> NAME/KEY: MISC_FEATURE
<222> LOCATION: (102)..(102)
<223> OTHER INFORMATION: X= G, D or N
<220> FEATURE:
<221> NAME/KEY: MISC_FEATURE
```

```
<222> LOCATION: (104)..(104)
<223> OTHER INFORMATION: X= L or V
<220> FEATURE:
<221> NAME/KEY: MISC_FEATURE
<222> LOCATION: (111)..(111)
<223> OTHER INFORMATION: X= G, D, E or A
<220> FEATURE:
<221> NAME/KEY: MISC_FEATURE
<222> LOCATION: (114)..(114)
<223> OTHER INFORMATION: X= E or D
<220> FEATURE:
<221> NAME/KEY: MISC_FEATURE
<222> LOCATION: (115)..(115)
<223> OTHER INFORMATION: X= Y or F
<220> FEATURE:
<221> NAME/KEY: MISC_FEATURE
<222> LOCATION: (117)..(117)
<223> OTHER INFORMATION: X= V or T
<220> FEATURE:
<221> NAME/KEY: MISC_FEATURE
<222> LOCATION: (119)..(119)
<223> OTHER INFORMATION: X= S, N or C
<220> FEATURE:
<221> NAME/KEY: MISC_FEATURE
<222> LOCATION: (131)..(131)
<223> OTHER INFORMATION: X= I or L
<220> FEATURE:
<221> NAME/KEY: MISC_FEATURE
<222> LOCATION: (133)..(133)
<223> OTHER INFORMATION: X= I, V or M
<220> FEATURE:
<221> NAME/KEY: MISC_FEATURE
<222> LOCATION: (135)..(135)
<223> OTHER INFORMATION: X= V, I or A
<220> FEATURE:
<221> NAME/KEY: MISC_FEATURE
<222> LOCATION: (138)..(138)
<223> OTHER INFORMATION: X= E, A or D
<220> FEATURE:
<221> NAME/KEY: MISC_FEATURE
<222> LOCATION: (139)..(139)
<223> OTHER INFORMATION: X= K or R
<220> FEATURE:
<221> NAME/KEY: MISC_FEATURE
<222> LOCATION: (141)..(141)
<223> OTHER INFORMATION: X= G, N, D or A
<220> FEATURE:
<221> NAME/KEY: MISC_FEATURE
<222> LOCATION: (142)..(142)
<223> OTHER INFORMATION: X= K, Q or L
<220> FEATURE:
<221> NAME/KEY: MISC_FEATURE
<222> LOCATION: (143)..(143)
<223> OTHER INFORMATION: X= N, E, D, Q or G
<220> FEATURE:
<221> NAME/KEY: MISC_FEATURE
<222> LOCATION: (145)..(145)
<223> OTHER INFORMATION: X= R or K
<220> FEATURE:
<221> NAME/KEY: MISC_FEATURE
<222> LOCATION: (146)..(146)
<223> OTHER INFORMATION: X= T or A
<220> FEATURE:
<221> NAME/KEY: MISC_FEATURE
<222> LOCATION: (147)..(147)
<223> OTHER INFORMATION: X= V or A
<220> FEATURE:
<221> NAME/KEY: MISC_FEATURE
<222> LOCATION: (165)..(165)
<223> OTHER INFORMATION: X= N or S
<220> FEATURE:
<221> NAME/KEY: MISC_FEATURE
<222> LOCATION: (171)..(171)
<223> OTHER INFORMATION: X= R, K, H, D or N
<220> FEATURE:
<221> NAME/KEY: MISC_FEATURE
<222> LOCATION: (172)..(172)
<223> OTHER INFORMATION: X= P, S or A
<220> FEATURE:
```

```
<221> NAME/KEY: MISC_FEATURE
<222> LOCATION: (174)..(174)
<223> OTHER INFORMATION: X= M or L
<220> FEATURE:
<221> NAME/KEY: MISC_FEATURE
<222> LOCATION: (177)..(177)
<223> OTHER INFORMATION: X= I or V
<220> FEATURE:
<221> NAME/KEY: MISC_FEATURE
<222> LOCATION: (182)..(182)
<223> OTHER INFORMATION: X= E or G
<220> FEATURE:
<221> NAME/KEY: MISC_FEATURE
<222> LOCATION: (191)..(191)
<223> OTHER INFORMATION: X= A or G
<220> FEATURE:
<221> NAME/KEY: MISC_FEATURE
<222> LOCATION: (195)..(195)
<223> OTHER INFORMATION: X= H or R
<220> FEATURE:
<221> NAME/KEY: MISC_FEATURE
<222> LOCATION: (199)..(199)
<223> OTHER INFORMATION: X= L or I
<220> FEATURE:
<221> NAME/KEY: MISC_FEATURE
<222> LOCATION: (204)..(204)
<223> OTHER INFORMATION: X= L or T
<220> FEATURE:
<221> NAME/KEY: MISC_FEATURE
<222> LOCATION: (206)..(206)
<223> OTHER INFORMATION: X= S, A or T
<220> FEATURE:
<221> NAME/KEY: MISC_FEATURE
<222> LOCATION: (207)..(207)
<223> OTHER INFORMATION: X= S, T or R
<220> FEATURE:
<221> NAME/KEY: MISC_FEATURE
<222> LOCATION: (211)..(211)
<223> OTHER INFORMATION: X= G or S
<220> FEATURE:
<221> NAME/KEY: MISC_FEATURE
<222> LOCATION: (214)..(214)
<223> OTHER INFORMATION: X= K or R
<220> FEATURE:
<221> NAME/KEY: MISC_FEATURE
<222> LOCATION: (215)..(215)
<223> OTHER INFORMATION: X= V or A
<220> FEATURE:
<221> NAME/KEY: MISC_FEATURE
<222> LOCATION: (216)..(216)
<223> OTHER INFORMATION: X= F or L
<220> FEATURE:
<221> NAME/KEY: MISC_FEATURE
<222> LOCATION: (217)..(217)
<223> OTHER INFORMATION: X= S, D or T
<220> FEATURE:
<221> NAME/KEY: MISC_FEATURE
<222> LOCATION: (218)..(218)
<223> OTHER INFORMATION: X= G, N or A
<220> FEATURE:
<221> NAME/KEY: MISC_FEATURE
<222> LOCATION: (219)..(219)
<223> OTHER INFORMATION: X= V or L
<220> FEATURE:
<221> NAME/KEY: MISC_FEATURE
<222> LOCATION: (224)..(224)
<223> OTHER INFORMATION: X= E or D
<220> FEATURE:
<221> NAME/KEY: MISC_FEATURE
<222> LOCATION: (226)..(226)
<223> OTHER INFORMATION: X= L or V
<220> FEATURE:
<221> NAME/KEY: MISC_FEATURE
<222> LOCATION: (227)..(227)
<223> OTHER INFORMATION: X= K or R
<220> FEATURE:
<221> NAME/KEY: MISC_FEATURE
<222> LOCATION: (228)..(228)
<223> OTHER INFORMATION: X= R or K
```

```
-continued

<220> FEATURE:
<221> NAME/KEY: MISC_FEATURE
<222> LOCATION: (233)..(233)
<223> OTHER INFORMATION: X= I or L
<220> FEATURE:
<221> NAME/KEY: MISC_FEATURE
<222> LOCATION: (237)..(237)
<223> OTHER INFORMATION: X= V or M
<220> FEATURE:
<221> NAME/KEY: MISC_FEATURE
<222> LOCATION: (240)..(240)
<223> OTHER INFORMATION: X= G or S
<220> FEATURE:
<221> NAME/KEY: MISC_FEATURE
<222> LOCATION: (260)..(260)
<223> OTHER INFORMATION: X= L, M, H, Q or V
<220> FEATURE:
<221> NAME/KEY: MISC_FEATURE
<222> LOCATION: (261)..(261)
<223> OTHER INFORMATION: X= G, T, A, S
<220> FEATURE:
<221> NAME/KEY: MISC_FEATURE
<222> LOCATION: (263)..(263)
<223> OTHER INFORMATION: X= I, V, T, S or A
<220> FEATURE:
<221> NAME/KEY: MISC_FEATURE
<222> LOCATION: (264)..(264)
<223> OTHER INFORMATION: X= T, S, N, Q, H or A
<220> FEATURE:
<221> NAME/KEY: MISC_FEATURE
<222> LOCATION: (267)..(267)
<223> OTHER INFORMATION: X= K, R or S
<220> FEATURE:
<221> NAME/KEY: MISC_FEATURE
<222> LOCATION: (271)..(271)
<223> OTHER INFORMATION: X= D, A, S or E
<220> FEATURE:
<221> NAME/KEY: MISC_FEATURE
<222> LOCATION: (274)..(274)
<223> OTHER INFORMATION: X= G or S
<220> FEATURE:
<221> NAME/KEY: MISC_FEATURE
<222> LOCATION: (277)..(277)
<223> OTHER INFORMATION: X= F or L
<220> FEATURE:
<221> NAME/KEY: MISC_FEATURE
<222> LOCATION: (280)..(280)
<223> OTHER INFORMATION: X= I or V
<220> FEATURE:
<221> NAME/KEY: MISC_FEATURE
<222> LOCATION: (286)..(286)
<223> OTHER INFORMATION: X= R or K
<220> FEATURE:
<221> NAME/KEY: MISC_FEATURE
<222> LOCATION: (289)..(289)
<223> OTHER INFORMATION: X= E or A
<220> FEATURE:
<221> NAME/KEY: MISC_FEATURE
<222> LOCATION: (293)..(293)
<223> OTHER INFORMATION: X= K or Q
<220> FEATURE:
<221> NAME/KEY: MISC_FEATURE
<222> LOCATION: (297)..(297)
<223> OTHER INFORMATION: X= T, G or S
<220> FEATURE:
<221> NAME/KEY: MISC_FEATURE
<222> LOCATION: (298)..(298)
<223> OTHER INFORMATION: X= F or W
<220> FEATURE:
<221> NAME/KEY: MISC_FEATURE
<222> LOCATION: (306)..(306)
<223> OTHER INFORMATION: X= P, H or V
<220> FEATURE:
<221> NAME/KEY: MISC_FEATURE
<222> LOCATION: (307)..(307)
<223> OTHER INFORMATION: X= S, T, E or A
<220> FEATURE:
<221> NAME/KEY: MISC_FEATURE
<222> LOCATION: (308)..(308)
```

-continued

```
<223> OTHER INFORMATION: X= S or T
<220> FEATURE:
<221> NAME/KEY: MISC_FEATURE
<222> LOCATION: (310)..(310)
<223> OTHER INFORMATION: X= C, T, V, L, E or S
<220> FEATURE:
<221> NAME/KEY: MISC_FEATURE
<222> LOCATION: (314)..(314)
<223> OTHER INFORMATION: X= S or N
<220> FEATURE:
<221> NAME/KEY: MISC_FEATURE
<222> LOCATION: (315)..(315)
<223> OTHER INFORMATION: X= S, Q, A or K
<220> FEATURE:
<221> NAME/KEY: MISC_FEATURE
<222> LOCATION: (316)..(316)
<223> OTHER INFORMATION: X= G, S, E or D
<220> FEATURE:
<221> NAME/KEY: MISC_FEATURE
<222> LOCATION: (317)..(317)
<223> OTHER INFORMATION: X= G, S, A or T
<220> FEATURE:
<221> NAME/KEY: MISC_FEATURE
<222> LOCATION: (318)..(318)
<223> OTHER INFORMATION: X= A or no amino acid
<220> FEATURE:
<221> NAME/KEY: MISC_FEATURE
<222> LOCATION: (319)..(319)
<223> OTHER INFORMATION: X= L, M, Q or R
<220> FEATURE:
<221> NAME/KEY: MISC_FEATURE
<222> LOCATION: (321)..(321)
<223> OTHER INFORMATION: X= S, G or T
<220> FEATURE:
<221> NAME/KEY: MISC_FEATURE
<222> LOCATION: (322)..(322)
<223> OTHER INFORMATION: X= Y or F
<220> FEATURE:
<221> NAME/KEY: MISC_FEATURE
<222> LOCATION: (324)..(324)
<223> OTHER INFORMATION: X= K or A
<220> FEATURE:
<221> NAME/KEY: MISC_FEATURE
<222> LOCATION: (325)..(325)
<223> OTHER INFORMATION: X= I or V
<220> FEATURE:
<221> NAME/KEY: MISC_FEATURE
<222> LOCATION: (328)..(328)
<223> OTHER INFORMATION: X= D, E, Q or N
<220> FEATURE:
<221> NAME/KEY: MISC_FEATURE
<222> LOCATION: (331)..(331)
<223> OTHER INFORMATION: X= C, K or Q
<220> FEATURE:
<221> NAME/KEY: MISC_FEATURE
<222> LOCATION: (333)..(333)
<223> OTHER INFORMATION: X= T, M or E
<220> FEATURE:
<221> NAME/KEY: MISC_FEATURE
<222> LOCATION: (336)..(336)
<223> OTHER INFORMATION: X= K, V, H, A or Q
<220> FEATURE:
<221> NAME/KEY: MISC_FEATURE
<222> LOCATION: (338)..(338)
<223> OTHER INFORMATION: X= N, S, D, T or K
<220> FEATURE:
<221> NAME/KEY: MISC_FEATURE
<222> LOCATION: (339)..(339)
<223> OTHER INFORMATION: X= K, R or S
<220> FEATURE:
<221> NAME/KEY: MISC_FEATURE
<222> LOCATION: (343)..(343)
<223> OTHER INFORMATION: X= I or V
<220> FEATURE:
<221> NAME/KEY: MISC_FEATURE
<222> LOCATION: (354)..(354)
<223> OTHER INFORMATION: X= V or L
<220> FEATURE:
<221> NAME/KEY: MISC_FEATURE
```

```
<222> LOCATION: (355)..(355)
<223> OTHER INFORMATION: X= E, R, S, G or Q
<220> FEATURE:
<221> NAME/KEY: MISC_FEATURE
<222> LOCATION: (358)..(358)
<223> OTHER INFORMATION: X= R or K
<220> FEATURE:
<221> NAME/KEY: MISC_FEATURE
<222> LOCATION: (359)..(359)
<223> OTHER INFORMATION: X= K, E, D or T
<220> FEATURE:
<221> NAME/KEY: MISC_FEATURE
<222> LOCATION: (360)..(360)
<223> OTHER INFORMATION: X= F or Y
<220> FEATURE:
<221> NAME/KEY: MISC_FEATURE
<222> LOCATION: (362)..(362)
<223> OTHER INFORMATION: X= D, A, Q, N or E
<220> FEATURE:
<221> NAME/KEY: MISC_FEATURE
<222> LOCATION: (363)..(363)
<223> OTHER INFORMATION: X= R or Q
<220> FEATURE:
<221> NAME/KEY: MISC_FEATURE
<222> LOCATION: (374)..(374)
<223> OTHER INFORMATION: X= A or S
<220> FEATURE:
<221> NAME/KEY: MISC_FEATURE
<222> LOCATION: (375)..(375)
<223> OTHER INFORMATION: X= V or A
<220> FEATURE:
<221> NAME/KEY: MISC_FEATURE
<222> LOCATION: (383)..(383)
<223> OTHER INFORMATION: X= I or V
<220> FEATURE:
<221> NAME/KEY: MISC_FEATURE
<222> LOCATION: (385)..(385)
<223> OTHER INFORMATION: X= G or D
<220> FEATURE:
<221> NAME/KEY: MISC_FEATURE
<222> LOCATION: (387)..(387)
<223> OTHER INFORMATION: X= K, R or H
<220> FEATURE:
<221> NAME/KEY: MISC_FEATURE
<222> LOCATION: (389)..(389)
<223> OTHER INFORMATION: X= I or V
<220> FEATURE:
<221> NAME/KEY: MISC_FEATURE
<222> LOCATION: (404)..(404)
<223> OTHER INFORMATION: X= V or L
<220> FEATURE:
<221> NAME/KEY: MISC_FEATURE
<222> LOCATION: (405)..(405)
<223> OTHER INFORMATION: X= I or L
<220> FEATURE:
<221> NAME/KEY: MISC_FEATURE
<222> LOCATION: (408)..(408)
<223> OTHER INFORMATION: X= I or V
<220> FEATURE:
<221> NAME/KEY: MISC_FEATURE
<222> LOCATION: (412)..(412)
<223> OTHER INFORMATION: X= K, N or S
<220> FEATURE:
<221> NAME/KEY: MISC_FEATURE
<222> LOCATION: (416)..(416)
<223> OTHER INFORMATION: X= L or M
<220> FEATURE:
<221> NAME/KEY: MISC_FEATURE
<222> LOCATION: (418)..(418)
<223> OTHER INFORMATION: X= A or T
<220> FEATURE:
<221> NAME/KEY: MISC_FEATURE
<222> LOCATION: (419)..(419)
<223> OTHER INFORMATION: X=I or V
<220> FEATURE:
<221> NAME/KEY: MISC_FEATURE
<222> LOCATION: (422)..(422)
<223> OTHER INFORMATION: X=A or G
<220> FEATURE:
```

```
<221> NAME/KEY: MISC_FEATURE
<222> LOCATION: (424)..(424)
<223> OTHER INFORMATION: X= I or L
<220> FEATURE:
<221> NAME/KEY: MISC_FEATURE
<222> LOCATION: (435)..(435)
<223> OTHER INFORMATION: X= A or S
<220> FEATURE:
<221> NAME/KEY: MISC_FEATURE
<222> LOCATION: (439)..(439)
<223> OTHER INFORMATION: X= A or S
<220> FEATURE:
<221> NAME/KEY: MISC_FEATURE
<222> LOCATION: (440)..(440)
<223> OTHER INFORMATION: X= Y or F
<220> FEATURE:
<221> NAME/KEY: MISC_FEATURE
<222> LOCATION: (441)..(441)
<223> OTHER INFORMATION: X= L or M
<220> FEATURE:
<221> NAME/KEY: MISC_FEATURE
<222> LOCATION: (444)..(444)
<223> OTHER INFORMATION: X= I or V
<220> FEATURE:
<221> NAME/KEY: MISC_FEATURE
<222> LOCATION: (446)..(446)
<223> OTHER INFORMATION: X= E, D, N, Q or T
<220> FEATURE:
<221> NAME/KEY: MISC_FEATURE
<222> LOCATION: (448)..(448)
<223> OTHER INFORMATION: X= V, I or T
<220> FEATURE:
<221> NAME/KEY: MISC_FEATURE
<222> LOCATION: (449)..(449)
<223> OTHER INFORMATION: X= I or V
<220> FEATURE:
<221> NAME/KEY: MISC_FEATURE
<222> LOCATION: (451)..(451)
<223> OTHER INFORMATION: X= T or A
<220> FEATURE:
<221> NAME/KEY: MISC_FEATURE
<222> LOCATION: (460)..(460)
<223> OTHER INFORMATION: X= Q or L
<220> FEATURE:
<221> NAME/KEY: MISC_FEATURE
<222> LOCATION: (463)..(463)
<223> OTHER INFORMATION: X= Y, F or H
<220> FEATURE:
<221> NAME/KEY: MISC_FEATURE
<222> LOCATION: (466)..(466)
<223> OTHER INFORMATION: X= Y or H
<220> FEATURE:
<221> NAME/KEY: MISC_FEATURE
<222> LOCATION: (468)..(468)
<223> OTHER INFORMATION: X= Y or H
<220> FEATURE:
<221> NAME/KEY: MISC_FEATURE
<222> LOCATION: (469)..(469)
<223> OTHER INFORMATION: X= N, Q, S or E
<220> FEATURE:
<221> NAME/KEY: MISC_FEATURE
<222> LOCATION: (470)..(470)
<223> OTHER INFORMATION: X= D, G, Q, K, S, E or no amino acid
<220> FEATURE:
<221> NAME/KEY: MISC_FEATURE
<222> LOCATION: (473)..(473)
<223> OTHER INFORMATION: X= S, T, C, A or V
<220> FEATURE:
<221> NAME/KEY: MISC_FEATURE
<222> LOCATION: (474)..(474)
<223> OTHER INFORMATION: X= A, V or T
<220> FEATURE:
<221> NAME/KEY: MISC_FEATURE
<222> LOCATION: (481)..(481)
<223> OTHER INFORMATION: X= N, S, T or A
<220> FEATURE:
<221> NAME/KEY: MISC_FEATURE
<222> LOCATION: (482)..(482)
<223> OTHER INFORMATION: X= A, G or V
```

```
<220> FEATURE:
<221> NAME/KEY: MISC_FEATURE
<222> LOCATION: (483)..(483)
<223> OTHER INFORMATION: X= V, Q, L or T
<220> FEATURE:
<221> NAME/KEY: MISC_FEATURE
<222> LOCATION: (484)..(484)
<223> OTHER INFORMATION: X= G or S
<220> FEATURE:
<221> NAME/KEY: MISC_FEATURE
<222> LOCATION: (485)..(485)
<223> OTHER INFORMATION: X= V, A or T
<220> FEATURE:
<221> NAME/KEY: MISC_FEATURE
<222> LOCATION: (486)..(486)
<223> OTHER INFORMATION: X= E, A, T, V, P or Q
<220> FEATURE:
<221> NAME/KEY: MISC_FEATURE
<222> LOCATION: (487)..(487)
<223> OTHER INFORMATION: X= L, F or S
<220> FEATURE:
<221> NAME/KEY: MISC_FEATURE
<222> LOCATION: (488)..(488)
<223> OTHER INFORMATION: X= T, E or Q
<220> FEATURE:
<221> NAME/KEY: MISC_FEATURE
<222> LOCATION: (491)..(491)
<223> OTHER INFORMATION: X= E, T, Q, A, S or G
<220> FEATURE:
<221> NAME/KEY: MISC_FEATURE
<222> LOCATION: (492)..(492)
<223> OTHER INFORMATION: X= K, Q, S, M, A, T or E
<220> FEATURE:
<221> NAME/KEY: MISC_FEATURE
<222> LOCATION: (493)..(493)
<223> OTHER INFORMATION: X= L or M
<220> FEATURE:
<221> NAME/KEY: MISC_FEATURE
<222> LOCATION: (495)..(495)
<223> OTHER INFORMATION: X= I or L
<220> FEATURE:
<221> NAME/KEY: MISC_FEATURE
<222> LOCATION: (499)..(499)
<223> OTHER INFORMATION: X= I, L or V
<220> FEATURE:
<221> NAME/KEY: MISC_FEATURE
<222> LOCATION: (500)..(500)
<223> OTHER INFORMATION: X= V, L or I
<220> FEATURE:
<221> NAME/KEY: MISC_FEATURE
<222> LOCATION: (501)..(501)
<223> OTHER INFORMATION: X= K or R
<220> FEATURE:
<221> NAME/KEY: MISC_FEATURE
<222> LOCATION: (503)..(503)
<223> OTHER INFORMATION: X= R, H, Q or E
<220> FEATURE:
<221> NAME/KEY: MISC_FEATURE
<222> LOCATION: (505)..(505)
<223> OTHER INFORMATION: X= E or K
<220> FEATURE:
<221> NAME/KEY: MISC_FEATURE
<222> LOCATION: (506)..(506)
<223> OTHER INFORMATION: X= K or T
<220> FEATURE:
<221> NAME/KEY: MISC_FEATURE
<222> LOCATION: (507)..(507)
<223> OTHER INFORMATION: X= L, V or I
<220> FEATURE:
<221> NAME/KEY: MISC_FEATURE
<222> LOCATION: (509)..(509)
<223> OTHER INFORMATION: X= I or L
<220> FEATURE:
<221> NAME/KEY: MISC_FEATURE
<222> LOCATION: (511)..(511)
<223> OTHER INFORMATION: X= N or C
<220> FEATURE:
<221> NAME/KEY: MISC_FEATURE
<222> LOCATION: (516)..(516)
```

-continued

```
<223> OTHER INFORMATION: X= M or L
<220> FEATURE:
<221> NAME/KEY: MISC_FEATURE
<222> LOCATION: (517)..(517)
<223> OTHER INFORMATION: X= P or A
<220> FEATURE:
<221> NAME/KEY: MISC_FEATURE
<222> LOCATION: (518)..(518)
<223> OTHER INFORMATION: X= E, Q or Y
<220> FEATURE:
<221> NAME/KEY: MISC_FEATURE
<222> LOCATION: (520)..(520)
<223> OTHER INFORMATION: X= A, T, Q, S or L
<220> FEATURE:
<221> NAME/KEY: MISC_FEATURE
<222> LOCATION: (521)..(521)
<223> OTHER INFORMATION: X= K, Q, A, L or V
<220> FEATURE:
<221> NAME/KEY: MISC_FEATURE
<222> LOCATION: (522)..(522)
<223> OTHER INFORMATION: X= V, A or T
<220> FEATURE:
<221> NAME/KEY: MISC_FEATURE
<222> LOCATION: (524)..(524)
<223> OTHER INFORMATION: X= E or D
<220> FEATURE:
<221> NAME/KEY: MISC_FEATURE
<222> LOCATION: (525)..(525)
<223> OTHER INFORMATION: X= S, A, K, N or T
<220> FEATURE:
<221> NAME/KEY: MISC_FEATURE
<222> LOCATION: (526)..(526)
<223> OTHER INFORMATION: X= L, M or R
<220> FEATURE:
<221> NAME/KEY: MISC_FEATURE
<222> LOCATION: (530)..(530)
<223> OTHER INFORMATION: X= L or V
<220> FEATURE:
<221> NAME/KEY: MISC_FEATURE
<222> LOCATION: (541)..(541)
<223> OTHER INFORMATION: X= E, D, T or K
<220> FEATURE:
<221> NAME/KEY: MISC_FEATURE
<222> LOCATION: (542)..(542)
<223> OTHER INFORMATION: X= A, T, E, S or Q
<220> FEATURE:
<221> NAME/KEY: MISC_FEATURE
<222> LOCATION: (544)..(544)
<223> OTHER INFORMATION: X= I, V, L or T
<220> FEATURE:
<221> NAME/KEY: MISC_FEATURE
<222> LOCATION: (545)..(545)
<223> OTHER INFORMATION: X= L, M, A or Q
<220> FEATURE:
<221> NAME/KEY: MISC_FEATURE
<222> LOCATION: (546)..(546)
<223> OTHER INFORMATION: X= E, Q or S
<220> FEATURE:
<221> NAME/KEY: MISC_FEATURE
<222> LOCATION: (547)..(547)
<223> OTHER INFORMATION: X= M or L
<220> FEATURE:
<221> NAME/KEY: MISC_FEATURE
<222> LOCATION: (549)..(549)
<223> OTHER INFORMATION: X= A, S, G or Q
<220> FEATURE:
<221> NAME/KEY: MISC_FEATURE
<222> LOCATION: (550)..(550)
<223> OTHER INFORMATION: X= S, Q, R, E or K
<220> FEATURE:
<221> NAME/KEY: MISC_FEATURE
<222> LOCATION: (552)..(552)
<223> OTHER INFORMATION: X= E, D, Q or S
<220> FEATURE:
<221> NAME/KEY: MISC_FEATURE
<222> LOCATION: (553)..(553)
<223> OTHER INFORMATION: X= A, V, S, T or L
<220> FEATURE:
<221> NAME/KEY: MISC_FEATURE
```

```
<222> LOCATION: (554)..(554)
<223> OTHER INFORMATION: X= L or F
<220> FEATURE:
<221> NAME/KEY: MISC_FEATURE
<222> LOCATION: (555)..(555)
<223> OTHER INFORMATION: X= I or V
<220> FEATURE:
<221> NAME/KEY: MISC_FEATURE
<222> LOCATION: (557)..(557)
<223> OTHER INFORMATION: X= V, I or L
<220> FEATURE:
<221> NAME/KEY: MISC_FEATURE
<222> LOCATION: (560)..(560)
<223> OTHER INFORMATION: X= N or G
<220> FEATURE:
<221> NAME/KEY: MISC_FEATURE
<222> LOCATION: (562)..(562)
<223> OTHER INFORMATION: X= I or V
<220> FEATURE:
<221> NAME/KEY: MISC_FEATURE
<222> LOCATION: (563)..(563)
<223> OTHER INFORMATION: X= M or K
<220> FEATURE:
<221> NAME/KEY: MISC_FEATURE
<222> LOCATION: (573)..(573)
<223> OTHER INFORMATION: X= V, L, F or Y
<220> FEATURE:
<221> NAME/KEY: MISC_FEATURE
<222> LOCATION: (574)..(574)
<223> OTHER INFORMATION: X= L or V
<220> FEATURE:
<221> NAME/KEY: MISC_FEATURE
<222> LOCATION: (576)..(576)
<223> OTHER INFORMATION: X= A, Q or S
<220> FEATURE:
<221> NAME/KEY: MISC_FEATURE
<222> LOCATION: (577)..(577)
<223> OTHER INFORMATION: X= H, N, K, R or E
<220> FEATURE:
<221> NAME/KEY: MISC_FEATURE
<222> LOCATION: (578)..(578)
<223> OTHER INFORMATION: X= R or K
<220> FEATURE:
<221> NAME/KEY: MISC_FEATURE
<222> LOCATION: (579)..(579)
<223> OTHER INFORMATION: X= K, R, L or I
<220> FEATURE:
<221> NAME/KEY: MISC_FEATURE
<222> LOCATION: (580)..(580)
<223> OTHER INFORMATION: X= P, A, W, G or L
<220> FEATURE:
<221> NAME/KEY: MISC_FEATURE
<222> LOCATION: (581)..(581)
<223> OTHER INFORMATION: X= V or I
<220> FEATURE:
<221> NAME/KEY: MISC_FEATURE
<222> LOCATION: (582)..(582)
<223> OTHER INFORMATION: X= P or S
<220> FEATURE:
<221> NAME/KEY: MISC_FEATURE
<222> LOCATION: (586)..(586)
<223> OTHER INFORMATION: X= I or L
<220> FEATURE:
<221> NAME/KEY: MISC_FEATURE
<222> LOCATION: (589)..(589)
<223> OTHER INFORMATION: X= P or A
<220> FEATURE:
<221> NAME/KEY: MISC_FEATURE
<222> LOCATION: (591)..(591)
<223> OTHER INFORMATION: X= F, R, H, Y, L, E, I, V or S
<220> FEATURE:
<221> NAME/KEY: MISC_FEATURE
<222> LOCATION: (593)..(593)
<223> OTHER INFORMATION: X= I or V
<220> FEATURE:
<221> NAME/KEY: MISC_FEATURE
<222> LOCATION: (594)..(594)
<223> OTHER INFORMATION: X= P or S
<220> FEATURE:
```

-continued

```
<221> NAME/KEY: MISC_FEATURE
<222> LOCATION: (595)..(595)
<223> OTHER INFORMATION: X= Q or P
<220> FEATURE:
<221> NAME/KEY: MISC_FEATURE
<222> LOCATION: (597)..(597)
<223> OTHER INFORMATION: X= T, E or S
<220> FEATURE:
<221> NAME/KEY: MISC_FEATURE
<222> LOCATION: (599)..(599)
<223> OTHER INFORMATION: X= E, D, A or Q
<220> FEATURE:
<221> NAME/KEY: MISC_FEATURE
<222> LOCATION: (601)..(601)
<223> OTHER INFORMATION: X= M, A, I, L or V
<220> FEATURE:
<221> NAME/KEY: MISC_FEATURE
<222> LOCATION: (602)..(602)
<223> OTHER INFORMATION: X= R or H
<220> FEATURE:
<221> NAME/KEY: MISC_FEATURE
<222> LOCATION: (603)..(603)
<223> OTHER INFORMATION: X= A, S, H, T or V
<220> FEATURE:
<221> NAME/KEY: MISC_FEATURE
<222> LOCATION: (604)..(604)
<223> OTHER INFORMATION: X= E or D
<220> FEATURE:
<221> NAME/KEY: MISC_FEATURE
<222> LOCATION: (605)..(605)
<223> OTHER INFORMATION: X= L, I or Y
<220> FEATURE:
<221> NAME/KEY: MISC_FEATURE
<222> LOCATION: (606)..(606)
<223> OTHER INFORMATION: X= G, Q or S
<220> FEATURE:
<221> NAME/KEY: MISC_FEATURE
<222> LOCATION: (608)..(608)
<223> OTHER INFORMATION: X= D, N or T
<220> FEATURE:
<221> NAME/KEY: MISC_FEATURE
<222> LOCATION: (609)..(609)
<223> OTHER INFORMATION: X= A or I
<220> FEATURE:
<221> NAME/KEY: MISC_FEATURE
<222> LOCATION: (610)..(610)
<223> OTHER INFORMATION: X= A, S, N, D or E
<220> FEATURE:
<221> NAME/KEY: MISC_FEATURE
<222> LOCATION: (612)..(612)
<223> OTHER INFORMATION: X= M or I
<220> FEATURE:
<221> NAME/KEY: MISC_FEATURE
<222> LOCATION: (613)..(613)
<223> OTHER INFORMATION: X= E, Q, R, K or D
<220> FEATURE:
<221> NAME/KEY: MISC_FEATURE
<222> LOCATION: (614)..(614)
<223> OTHER INFORMATION: X= A, T, Q, R or N
<220> FEATURE:
<221> NAME/KEY: MISC_FEATURE
<222> LOCATION: (615)..(615)
<223> OTHER INFORMATION: X= K, R or Q
<220> FEATURE:
<221> NAME/KEY: MISC_FEATURE
<222> LOCATION: (616)..(616)
<223> OTHER INFORMATION: X= I or V
<220> FEATURE:
<221> NAME/KEY: MISC_FEATURE
<222> LOCATION: (617)..(617)
<223> OTHER INFORMATION: X= K, R, E, T or S
<220> FEATURE:
<221> NAME/KEY: MISC_FEATURE
<222> LOCATION: (618)..(618)
<223> OTHER INFORMATION: X= A, T, D, R, N, Q or K
<220> FEATURE:
<221> NAME/KEY: MISC_FEATURE
<222> LOCATION: (619)..(619)
<223> OTHER INFORMATION: X= W or Y
```

```
<220> FEATURE:
<221> NAME/KEY: MISC_FEATURE
<222> LOCATION: (620)..(620)
<223> OTHER INFORMATION: X= L, Q or M

<400> SEQUENCE: 22

Met Xaa Xaa Xaa Xaa Lys Tyr Pro Thr Leu Ala Xaa Xaa Xaa Xaa
1               5                   10                  15

Xaa Xaa Xaa Leu Arg Xaa Leu Pro Xaa Xaa Leu Pro Xaa Leu Xaa
            20                  25                  30

Xaa Glu Leu Arg Xaa Xaa Leu Leu Xaa Xaa Val Ser Xaa Ser Ser Gly
        35                  40                  45

His Phe Ala Ser Gly Leu Gly Xaa Val Glu Leu Thr Val Ala Xaa His
50                  55                  60

Tyr Val Tyr Xaa Thr Pro Phe Asp Xaa Xaa Xaa Trp Asp Val Gly His
65              70                  75                  80

Gln Ala Tyr Pro His Lys Ile Leu Thr Gly Arg Arg Asp Xaa Ile Xaa
                85                  90                  95

Xaa Ile Arg Gln Lys Xaa Gly Xaa His Pro Phe Pro Trp Arg Xaa Glu
            100                 105                 110

Ser Xaa Xaa Asp Xaa Leu Xaa Val Gly His Ser Ser Thr Ser Ile Ser
    115                 120                 125

Ala Gly Xaa Gly Xaa Ala Xaa Ala Xaa Xaa Glu Xaa Xaa Xaa Arg
130                 135                 140

Xaa Xaa Xaa Cys Val Ile Gly Asp Gly Ala Ile Thr Ala Gly Met Ala
145                 150                 155                 160

Phe Glu Ala Met Xaa His Ala Gly Asp Ile Xaa Xaa Asp Xaa Leu Val
                165                 170                 175

Xaa Leu Asn Asp Asn Xaa Met Ser Ile Ser Glu Asn Val Gly Xaa Leu
            180                 185                 190

Asn Asn Xaa Leu Ala Gln Xaa Leu Ser Gly Lys Xaa Tyr Xaa Xaa Leu
        195                 200                 205

Arg Glu Xaa Gly Lys Xaa Xaa Xaa Xaa Xaa Pro Pro Ile Lys Xaa
210                 215                 220

Leu Xaa Xaa Xaa Thr Glu Glu His Xaa Lys Gly Met Xaa Val Pro Xaa
225                 230                 235                 240

Thr Leu Phe Glu Glu Leu Gly Phe Asn Tyr Ile Gly Pro Val Asp Gly
                245                 250                 255

His Asp Val Xaa Xaa Leu Xaa Xaa Thr Leu Xaa Asn Met Arg Xaa Leu
            260                 265                 270

Lys Xaa Pro Gln Xaa Leu His Xaa Met Thr Lys Lys Gly Xaa Gly Tyr
        275                 280                 285

Xaa Pro Ala Glu Xaa Asp Pro Ile Xaa Xaa His Ala Val Pro Lys Phe
290                 295                 300

Asp Xaa Xaa Xaa Gly Xaa Leu Pro Lys Xaa Xaa Xaa Xaa Xaa Pro
305                 310                 315                 320

Xaa Xaa Ser Xaa Xaa Phe Gly Xaa Trp Leu Xaa Glu Xaa Ala Ala Xaa
            325                 330                 335

Asp Xaa Xaa Leu Met Ala Xaa Thr Pro Ala Met Arg Glu Gly Ser Gly
        340                 345                 350

Met Xaa Xaa Phe Ser Xaa Xaa Xaa Pro Xaa Xaa Tyr Phe Asp Val Ala
    355                 360                 365

Ile Ala Glu Gln His Xaa Xaa Thr Phe Ala Ala Gly Leu Ala Xaa Gly
370                 375                 380
```

```
Xaa Tyr Xaa Pro Xaa Val Ala Ile Tyr Ser Thr Phe Leu Gln Arg Ala
385                 390                 395                 400

Tyr Asp Gln Xaa Xaa His Asp Xaa Ala Ile Gln Xaa Leu Pro Val Xaa
            405                 410                 415

Phe Xaa Xaa Asp Arg Xaa Gly Xaa Val Gly Ala Asp Gly Gln Thr His
        420                 425                 430

Gln Gly Xaa Phe Asp Leu Xaa Xaa Xaa Arg Cys Xaa Pro Xaa Met Xaa
        435                 440                 445

Xaa Met Xaa Pro Ser Asp Glu Asn Glu Cys Arg Xaa Met Leu Xaa Thr
    450                 455                 460

Gly Xaa His Xaa Xaa Xaa Gly Pro Xaa Xaa Val Arg Tyr Pro Arg Gly
465             470                 475                 480

Xaa Xaa Xaa Xaa Xaa Xaa Xaa Pro Leu Xaa Xaa Xaa Pro Xaa Gly
            485                 490                 495

Lys Gly Xaa Xaa Xaa Arg Xaa Gly Xaa Xaa Xaa Ala Xaa Leu Xaa Phe
        500                 505                 510

Gly Thr Leu Xaa Xaa Xaa Ala Xaa Xaa Xaa Ala Xaa Xaa Xaa Asn Ala
            515                 520                 525

Thr Xaa Val Asp Met Arg Phe Val Lys Pro Leu Asp Xaa Xaa Leu Xaa
    530                 535                 540

Xaa Xaa Xaa Ala Xaa Xaa His Xaa Xaa Xaa Xaa Thr Xaa Glu Glu Xaa
545             550                 555                 560

Ala Xaa Xaa Gly Gly Ala Gly Ser Gly Val Asn Glu Xaa Xaa Met Xaa
            565                 570                 575

Xaa Xaa Xaa Xaa Xaa Xaa Val Leu Asn Xaa Gly Leu Xaa Asp Xaa Phe
        580                 585                 590

Xaa Xaa Xaa Gly Xaa Gln Xaa Glu Xaa Xaa Xaa Xaa Xaa Xaa Leu Xaa
        595                 600                 605

Xaa Xaa Gly Xaa Xaa Xaa Xaa Xaa Xaa Xaa Xaa Ala
        610                 615                 620

<210> SEQ ID NO 23
<211> LENGTH: 657
<212> TYPE: PRT
<213> ORGANISM: Artificial sequence
<220> FEATURE:
<223> OTHER INFORMATION: Plant DXS consensus sequence
<220> FEATURE:
<221> NAME/KEY: MISC_FEATURE
<222> LOCATION: (7)..(7)
<223> OTHER INFORMATION: X= I or V
<220> FEATURE:
<221> NAME/KEY: MISC_FEATURE
<222> LOCATION: (11)..(11)
<223> OTHER INFORMATION: X= I or V
<220> FEATURE:
<221> NAME/KEY: MISC_FEATURE
<222> LOCATION: (13)..(13)
<223> OTHER INFORMATION: X= M, L or I
<220> FEATURE:
<221> NAME/KEY: MISC_FEATURE
<222> LOCATION: (16)..(16)
<223> OTHER INFORMATION: X= L or F
<220> FEATURE:
<221> NAME/KEY: MISC_FEATURE
<222> LOCATION: (17)..(17)
<223> OTHER INFORMATION: X= S or N
<220> FEATURE:
<221> NAME/KEY: MISC_FEATURE
<222> LOCATION: (18)..(18)
<223> OTHER INFORMATION: X= V, I, N or M
<220> FEATURE:
<221> NAME/KEY: MISC_FEATURE
<222> LOCATION: (19)..(19)
```

```
<223> OTHER INFORMATION: X= K, R, E or P
<220> FEATURE:
<221> NAME/KEY: MISC_FEATURE
<222> LOCATION: (20)..(20)
<223> OTHER INFORMATION: X= E or Q
<220> FEATURE:
<221> NAME/KEY: MISC_FEATURE
<222> LOCATION: (22)..(22)
<223> OTHER INFORMATION: X= K or R
<220> FEATURE:
<221> NAME/KEY: MISC_FEATURE
<222> LOCATION: (25)..(25)
<223> OTHER INFORMATION: X= A, S or C
<220> FEATURE:
<221> NAME/KEY: MISC_FEATURE
<222> LOCATION: (26)..(26)
<223> OTHER INFORMATION: X= D, N or K
<220> FEATURE:
<221> NAME/KEY: MISC_FEATURE
<222> LOCATION: (30)..(30)
<223> OTHER INFORMATION: X= S or A
<220> FEATURE:
<221> NAME/KEY: MISC_FEATURE
<222> LOCATION: (31)..(31)
<223> OTHER INFORMATION: X= D or E
<220> FEATURE:
<221> NAME/KEY: MISC_FEATURE
<222> LOCATION: (32)..(32)
<223> OTHER INFORMATION: X= V or I
<220> FEATURE:
<221> NAME/KEY: MISC_FEATURE
<222> LOCATION: (33)..(33)
<223> OTHER INFORMATION: X= V or I
<220> FEATURE:
<221> NAME/KEY: MISC_FEATURE
<222> LOCATION: (34)..(34)
<223> OTHER INFORMATION: X= F or H
<220> FEATURE:
<221> NAME/KEY: MISC_FEATURE
<222> LOCATION: (35)..(35)
<223> OTHER INFORMATION: X= N, E, T or G
<220> FEATURE:
<221> NAME/KEY: MISC_FEATURE
<222> LOCATION: (38)..(38)
<223> OTHER INFORMATION: X= K or R
<220> FEATURE:
<221> NAME/KEY: MISC_FEATURE
<222> LOCATION: (44)..(44)
<223> OTHER INFORMATION: X= G or S
<220> FEATURE:
<221> NAME/KEY: MISC_FEATURE
<222> LOCATION: (45)..(45)
<223> OTHER INFORMATION: X= S or A
<220> FEATURE:
<221> NAME/KEY: MISC_FEATURE
<222> LOCATION: (56)..(56)
<223> OTHER INFORMATION: X= L or M
<220> FEATURE:
<221> NAME/KEY: MISC_FEATURE
<222> LOCATION: (59)..(59)
<223> OTHER INFORMATION: X= V or I
<220> FEATURE:
<221> NAME/KEY: MISC_FEATURE
<222> LOCATION: (61)..(61)
<223> OTHER INFORMATION: X= N, D or S
<220> FEATURE:
<221> NAME/KEY: MISC_FEATURE
<222> LOCATION: (62)..(62)
<223> OTHER INFORMATION: X= A or T
<220> FEATURE:
<221> NAME/KEY: MISC_FEATURE
<222> LOCATION: (64)..(64)
<223> OTHER INFORMATION: X= Q, E or D
<220> FEATURE:
<221> NAME/KEY: MISC_FEATURE
<222> LOCATION: (66)..(66)
<223> OTHER INFORMATION: X= R or K
<220> FEATURE:
<221> NAME/KEY: MISC_FEATURE
```

```
<222> LOCATION: (67)..(67)
<223> OTHER INFORMATION: X= I or F
<220> FEATURE:
<221> NAME/KEY: MISC_FEATURE
<222> LOCATION: (68)..(68)
<223> OTHER INFORMATION: X= L or I
<220> FEATURE:
<221> NAME/KEY: MISC_FEATURE
<222> LOCATION: (75)..(75)
<223> OTHER INFORMATION: X= S or A
<220> FEATURE:
<221> NAME/KEY: MISC_FEATURE
<222> LOCATION: (77)..(77)
<223> OTHER INFORMATION: X= P, G or V
<220> FEATURE:
<221> NAME/KEY: MISC_FEATURE
<222> LOCATION: (81)..(81)
<223> OTHER INFORMATION: X= L or M
<220> FEATURE:
<221> NAME/KEY: MISC_FEATURE
<222> LOCATION: (86)..(86)
<223> OTHER INFORMATION: X= D, G or K
<220> FEATURE:
<221> NAME/KEY: MISC_FEATURE
<222> LOCATION: (87)..(87)
<223> OTHER INFORMATION: X= Q, K or G
<220> FEATURE:
<221> NAME/KEY: MISC_FEATURE
<222> LOCATION: (89)..(89)
<223> OTHER INFORMATION: X= H, P, A or Q
<220> FEATURE:
<221> NAME/KEY: MISC_FEATURE
<222> LOCATION: (91)..(91)
<223> OTHER INFORMATION: X= M, L or I
<220> FEATURE:
<221> NAME/KEY: MISC_FEATURE
<222> LOCATION: (93)..(93)
<223> OTHER INFORMATION: X= Q or K
<220> FEATURE:
<221> NAME/KEY: MISC_FEATURE
<222> LOCATION: (95)..(95)
<223> OTHER INFORMATION: X= D, N or G
<220> FEATURE:
<221> NAME/KEY: MISC_FEATURE
<222> LOCATION: (98)..(98)
<223> OTHER INFORMATION: X= A or S
<220> FEATURE:
<221> NAME/KEY: MISC_FEATURE
<222> LOCATION: (104)..(104)
<223> OTHER INFORMATION: X= S, G, D or A
<220> FEATURE:
<221> NAME/KEY: MISC_FEATURE
<222> LOCATION: (108)..(108)
<223> OTHER INFORMATION: X= Y or H
<220> FEATURE:
<221> NAME/KEY: MISC_FEATURE
<222> LOCATION: (110)..(110)
<223> OTHER INFORMATION: X= C or P
<220> FEATURE:
<221> NAME/KEY: MISC_FEATURE
<222> LOCATION: (113)..(113)
<223> OTHER INFORMATION: X= T or A
<220> FEATURE:
<221> NAME/KEY: MISC_FEATURE
<222> LOCATION: (119)..(119)
<223> OTHER INFORMATION: X= T or S
<220> FEATURE:
<221> NAME/KEY: MISC_FEATURE
<222> LOCATION: (123)..(123)
<223> OTHER INFORMATION: X= G or A
<220> FEATURE:
<221> NAME/KEY: MISC_FEATURE
<222> LOCATION: (128)..(128)
<223> OTHER INFORMATION: X= V or A
<220> FEATURE:
<221> NAME/KEY: MISC_FEATURE
<222> LOCATION: (132)..(132)
<223> OTHER INFORMATION: X= L, V or T
<220> FEATURE:
```

```
<221> NAME/KEY: MISC_FEATURE
<222> LOCATION: (134)..(134)
<223> OTHER INFORMATION: X= G or N
<220> FEATURE:
<221> NAME/KEY: MISC_FEATURE
<222> LOCATION: (135)..(135)
<223> OTHER INFORMATION: X= K or R
<220> FEATURE:
<221> NAME/KEY: MISC_FEATURE
<222> LOCATION: (136)..(136)
<223> OTHER INFORMATION: X= N or K
<220> FEATURE:
<221> NAME/KEY: MISC_FEATURE
<222> LOCATION: (138)..(138)
<223> OTHER INFORMATION: X= N, H, S or Q
<220> FEATURE:
<221> NAME/KEY: MISC_FEATURE
<222> LOCATION: (140)..(140)
<223> OTHER INFORMATION: X= I or V
<220> FEATURE:
<221> NAME/KEY: MISC_FEATURE
<222> LOCATION: (141)..(141)
<223> OTHER INFORMATION: X= A or S
<220> FEATURE:
<221> NAME/KEY: MISC_FEATURE
<222> LOCATION: (148)..(148)
<223> OTHER INFORMATION: X= M or I
<220> FEATURE:
<221> NAME/KEY: MISC_FEATURE
<222> LOCATION: (150)..(150)
<223> OTHER INFORMATION: X= A or G
<220> FEATURE:
<221> NAME/KEY: MISC_FEATURE
<222> LOCATION: (152)..(152)
<223> OTHER INFORMATION: X= Q or M
<220> FEATURE:
<221> NAME/KEY: MISC_FEATURE
<222> LOCATION: (154)..(154)
<223> OTHER INFORMATION: X= Y or F
<220> FEATURE:
<221> NAME/KEY: MISC_FEATURE
<222> LOCATION: (159)..(159)
<223> OTHER INFORMATION: X= N or H
<220> FEATURE:
<221> NAME/KEY: MISC_FEATURE
<222> LOCATION: (161)..(161)
<223> OTHER INFORMATION: X= G or R
<220> FEATURE:
<221> NAME/KEY: MISC_FEATURE
<222> LOCATION: (162)..(162)
<223> OTHER INFORMATION: X= Y or F
<220> FEATURE:
<221> NAME/KEY: MISC_FEATURE
<222> LOCATION: (165)..(165)
<223> OTHER INFORMATION: X= S or K
<220> FEATURE:
<221> NAME/KEY: MISC_FEATURE
<222> LOCATION: (166)..(166)
<223> OTHER INFORMATION: X= D or N
<220> FEATURE:
<221> NAME/KEY: MISC_FEATURE
<222> LOCATION: (175)..(175)
<223> OTHER INFORMATION: X= K or Q
<220> FEATURE:
<221> NAME/KEY: MISC_FEATURE
<222> LOCATION: (182)..(182)
<223> OTHER INFORMATION: X= A or Q
<220> FEATURE:
<221> NAME/KEY: MISC_FEATURE
<222> LOCATION: (183)..(183)
<223> OTHER INFORMATION: X= T, N or Y
<220> FEATURE:
<221> NAME/KEY: MISC_FEATURE
<222> LOCATION: (184)..(184)
<223> OTHER INFORMATION: X= L or N
<220> FEATURE:
<221> NAME/KEY: MISC_FEATURE
<222> LOCATION: (185)..(185)
<223> OTHER INFORMATION: X= D, N or S
```

```
<220> FEATURE:
<221> NAME/KEY: MISC_FEATURE
<222> LOCATION: (186)..(186)
<223> OTHER INFORMATION: X= G or K
<220> FEATURE:
<221> NAME/KEY: MISC_FEATURE
<222> LOCATION: (187)..(187)
<223> OTHER INFORMATION: X= P or N
<220> FEATURE:
<221> NAME/KEY: MISC_FEATURE
<222> LOCATION: (188)..(188)
<223> OTHER INFORMATION: X= I, S or Q
<220> FEATURE:
<221> NAME/KEY: MISC_FEATURE
<222> LOCATION: (189)..(189)
<223> OTHER INFORMATION: X= P, D or A
<220> FEATURE:
<221> NAME/KEY: MISC_FEATURE
<222> LOCATION: (194)..(194)
<223> OTHER INFORMATION: X= L or M
<220> FEATURE:
<221> NAME/KEY: MISC_FEATURE
<222> LOCATION: (195)..(195)
<223> OTHER INFORMATION: X= S or A
<220> FEATURE:
<221> NAME/KEY: MISC_FEATURE
<222> LOCATION: (196)..(196)
<223> OTHER INFORMATION: X= S, G or no amino acid
<220> FEATURE:
<221> NAME/KEY: MISC_FEATURE
<222> LOCATION: (197)..(197)
<223> OTHER INFORMATION: X= A, T or no amino acid
<220> FEATURE:
<221> NAME/KEY: MISC_FEATURE
<222> LOCATION: (198)..(198)
<223> OTHER INFORMATION: X= L or no amino acid
<220> FEATURE:
<221> NAME/KEY: MISC_FEATURE
<222> LOCATION: (199)..(199)
<223> OTHER INFORMATION: X= S, A or no amino acid
<220> FEATURE:
<221> NAME/KEY: MISC_FEATURE
<222> LOCATION: (200)..(200)
<223> OTHER INFORMATION: X= R or K
<220> FEATURE:
<221> NAME/KEY: MISC_FEATURE
<222> LOCATION: (201)..(201)
<223> OTHER INFORMATION: X= L or I
<220> FEATURE:
<221> NAME/KEY: MISC_FEATURE
<222> LOCATION: (203)..(203)
<223> OTHER INFORMATION: X= S or A
<220> FEATURE:
<221> NAME/KEY: MISC_FEATURE
<222> LOCATION: (204)..(204)
<223> OTHER INFORMATION: X= N or S
<220> FEATURE:
<221> NAME/KEY: MISC_FEATURE
<222> LOCATION: (205)..(205)
<223> OTHER INFORMATION: X= R, P or K
<220> FEATURE:
<221> NAME/KEY: MISC_FEATURE
<222> LOCATION: (206)..(206)
<223> OTHER INFORMATION: X= P or A
<220> FEATURE:
<221> NAME/KEY: MISC_FEATURE
<222> LOCATION: (213)..(213)
<223> OTHER INFORMATION: X= V or I
<220> FEATURE:
<221> NAME/KEY: MISC_FEATURE
<222> LOCATION: (217)..(217)
<223> OTHER INFORMATION: X= V or M
<220> FEATURE:
<221> NAME/KEY: MISC_FEATURE
<222> LOCATION: (221)..(221)
<223> OTHER INFORMATION: X= I or L
<220> FEATURE:
<221> NAME/KEY: MISC_FEATURE
<222> LOCATION: (222)..(222)
```

```
<223> OTHER INFORMATION: X= G or P
<220> FEATURE:
<221> NAME/KEY: MISC_FEATURE
<222> LOCATION: (223)..(223)
<223> OTHER INFORMATION: X= G, A, D or T
<220> FEATURE:
<221> NAME/KEY: MISC_FEATURE
<222> LOCATION: (224)..(224)
<223> OTHER INFORMATION: X= P, V or A
<220> FEATURE:
<221> NAME/KEY: MISC_FEATURE
<222> LOCATION: (225)..(225)
<223> OTHER INFORMATION: X= M or V
<220> FEATURE:
<221> NAME/KEY: MISC_FEATURE
<222> LOCATION: (226)..(226)
<223> OTHER INFORMATION: X= H or Q
<220> FEATURE:
<221> NAME/KEY: MISC_FEATURE
<222> LOCATION: (227)..(227)
<223> OTHER INFORMATION: X= E, Q, K or N
<220> FEATURE:
<221> NAME/KEY: MISC_FEATURE
<222> LOCATION: (228)..(228)
<223> OTHER INFORMATION: X= L or A
<220> FEATURE:
<221> NAME/KEY: MISC_FEATURE
<222> LOCATION: (229)..(229)
<223> OTHER INFORMATION: X= A or T
<220> FEATURE:
<221> NAME/KEY: MISC_FEATURE
<222> LOCATION: (232)..(232)
<223> OTHER INFORMATION: X= V or I
<220> FEATURE:
<221> NAME/KEY: MISC_FEATURE
<222> LOCATION: (234)..(234)
<223> OTHER INFORMATION: X= E or V
<220> FEATURE:
<221> NAME/KEY: MISC_FEATURE
<222> LOCATION: (243)..(243)
<223> OTHER INFORMATION: X= S or T
<220> FEATURE:
<221> NAME/KEY: MISC_FEATURE
<222> LOCATION: (244)..(244)
<223> OTHER INFORMATION: X= G or R
<220> FEATURE:
<221> NAME/KEY: MISC_FEATURE
<222> LOCATION: (246)..(246)
<223> OTHER INFORMATION: X= T or S
<220> FEATURE:
<221> NAME/KEY: MISC_FEATURE
<222> LOCATION: (259)..(259)
<223> OTHER INFORMATION: X= V or L
<220> FEATURE:
<221> NAME/KEY: MISC_FEATURE
<222> LOCATION: (264)..(264)
<223> OTHER INFORMATION: X= I or L
<220> FEATURE:
<221> NAME/KEY: MISC_FEATURE
<222> LOCATION: (268)..(268)
<223> OTHER INFORMATION: X= V, L or I
<220> FEATURE:
<221> NAME/KEY: MISC_FEATURE
<222> LOCATION: (269)..(269)
<223> OTHER INFORMATION: X= A, T or S
<220> FEATURE:
<221> NAME/KEY: MISC_FEATURE
<222> LOCATION: (270)..(270)
<223> OTHER INFORMATION: X= I or V
<220> FEATURE:
<221> NAME/KEY: MISC_FEATURE
<222> LOCATION: (272)..(272)
<223> OTHER INFORMATION: X= K, R or S
<220> FEATURE:
<221> NAME/KEY: MISC_FEATURE
<222> LOCATION: (273)..(273)
<223> OTHER INFORMATION: X= E or D
<220> FEATURE:
<221> NAME/KEY: MISC_FEATURE
```

```
<222> LOCATION: (275)..(275)
<223> OTHER INFORMATION: X= K or R
<220> FEATURE:
<221> NAME/KEY: MISC_FEATURE
<222> LOCATION: (276)..(276)
<223> OTHER INFORMATION: X= S or A
<220> FEATURE:
<221> NAME/KEY: MISC_FEATURE
<222> LOCATION: (277)..(277)
<223> OTHER INFORMATION: X= T or A
<220> FEATURE:
<221> NAME/KEY: MISC_FEATURE
<222> LOCATION: (278)..(278)
<223> OTHER INFORMATION: X= K, R, H or E
<220> FEATURE:
<221> NAME/KEY: MISC_FEATURE
<222> LOCATION: (280)..(280)
<223> OTHER INFORMATION: X= T, V or I
<220> FEATURE:
<221> NAME/KEY: MISC_FEATURE
<222> LOCATION: (285)..(285)
<223> OTHER INFORMATION: X= I or V
<220> FEATURE:
<221> NAME/KEY: MISC_FEATURE
<222> LOCATION: (288)..(288)
<223> OTHER INFORMATION: X= V or I
<220> FEATURE:
<221> NAME/KEY: MISC_FEATURE
<222> LOCATION: (293)..(293)
<223> OTHER INFORMATION: X= R or H
<220> FEATURE:
<221> NAME/KEY: MISC_FEATURE
<222> LOCATION: (296)..(296)
<223> OTHER INFORMATION: X= P, L or E
<220> FEATURE:
<221> NAME/KEY: MISC_FEATURE
<222> LOCATION: (297)..(297)
<223> OTHER INFORMATION: X= Y or P
<220> FEATURE:
<221> NAME/KEY: MISC_FEATURE
<222> LOCATION: (300)..(300)
<223> OTHER INFORMATION: X= K, R, T or A
<220> FEATURE:
<221> NAME/KEY: MISC_FEATURE
<222> LOCATION: (301)..(301)
<223> OTHER INFORMATION: X= A or S
<220> FEATURE:
<221> NAME/KEY: MISC_FEATURE
<222> LOCATION: (302)..(302)
<223> OTHER INFORMATION: X= A, D or Q
<220> FEATURE:
<221> NAME/KEY: MISC_FEATURE
<222> LOCATION: (305)..(305)
<223> OTHER INFORMATION: X= Y or M
<220> FEATURE:
<221> NAME/KEY: MISC_FEATURE
<222> LOCATION: (309)..(309)
<223> OTHER INFORMATION: X= T or V
<220> FEATURE:
<221> NAME/KEY: MISC_FEATURE
<222> LOCATION: (314)..(314)
<223> OTHER INFORMATION: X= A or R
<220> FEATURE:
<221> NAME/KEY: MISC_FEATURE
<222> LOCATION: (317)..(317)
<223> OTHER INFORMATION: X= K or R
<220> FEATURE:
<221> NAME/KEY: MISC_FEATURE
<222> LOCATION: (319)..(319)
<223> OTHER INFORMATION: X= F or V
<220> FEATURE:
<221> NAME/KEY: MISC_FEATURE
<222> LOCATION: (320)..(320)
<223> OTHER INFORMATION: X= K, Q or A
<220> FEATURE:
<221> NAME/KEY: MISC_FEATURE
<222> LOCATION: (321)..(321)
<223> OTHER INFORMATION: X= S, T, G or A
<220> FEATURE:
```

```
<221> NAME/KEY: MISC_FEATURE
<222> LOCATION: (322)..(322)
<223> OTHER INFORMATION: X= S, T or K
<220> FEATURE:
<221> NAME/KEY: MISC_FEATURE
<222> LOCATION: (323)..(323)
<223> OTHER INFORMATION: X= A, N, T or P
<220> FEATURE:
<221> NAME/KEY: MISC_FEATURE
<222> LOCATION: (324)..(324)
<223> OTHER INFORMATION: X= P, E or K
<220> FEATURE:
<221> NAME/KEY: MISC_FEATURE
<222> LOCATION: (325)..(325)
<223> OTHER INFORMATION: X= T or A
<220> FEATURE:
<221> NAME/KEY: MISC_FEATURE
<222> LOCATION: (326)..(326)
<223> OTHER INFORMATION: X= Q or M
<220> FEATURE:
<221> NAME/KEY: MISC_FEATURE
<222> LOCATION: (327)..(327)
<223> OTHER INFORMATION: X= S or T
<220> FEATURE:
<221> NAME/KEY: MISC_FEATURE
<222> LOCATION: (330)..(330)
<223> OTHER INFORMATION: X= T or N
<220> FEATURE:
<221> NAME/KEY: MISC_FEATURE
<222> LOCATION: (334)..(334)
<223> OTHER INFORMATION: X= E or D
<220> FEATURE:
<221> NAME/KEY: MISC_FEATURE
<222> LOCATION: (335)..(335)
<223> OTHER INFORMATION: X= A or S
<220> FEATURE:
<221> NAME/KEY: MISC_FEATURE
<222> LOCATION: (337)..(337)
<223> OTHER INFORMATION: X= I, V or T
<220> FEATURE:
<221> NAME/KEY: MISC_FEATURE
<222> LOCATION: (338)..(338)
<223> OTHER INFORMATION: X= A or S
<220> FEATURE:
<221> NAME/KEY: MISC_FEATURE
<222> LOCATION: (341)..(341)
<223> OTHER INFORMATION: X= E or K
<220> FEATURE:
<221> NAME/KEY: MISC_FEATURE
<222> LOCATION: (342)..(342)
<223> OTHER INFORMATION: X= V, A or R
<220> FEATURE:
<221> NAME/KEY: MISC_FEATURE
<222> LOCATION: (344)..(344)
<223> OTHER INFORMATION: X= K or S
<220> FEATURE:
<221> NAME/KEY: MISC_FEATURE
<222> LOCATION: (345)..(345)
<223> OTHER INFORMATION: X= D, N  or R
<220> FEATURE:
<221> NAME/KEY: MISC_FEATURE
<222> LOCATION: (346)..(346)
<223> OTHER INFORMATION: X= I or V
<220> FEATURE:
<221> NAME/KEY: MISC_FEATURE
<222> LOCATION: (347)..(347)
<223> OTHER INFORMATION: X= V or M
<220> FEATURE:
<221> NAME/KEY: MISC_FEATURE
<222> LOCATION: (349)..(349)
<223> OTHER INFORMATION: X= I or V
<220> FEATURE:
<221> NAME/KEY: MISC_FEATURE
<222> LOCATION: (354)..(354)
<223> OTHER INFORMATION: X= G or A
<220> FEATURE:
<221> NAME/KEY: MISC_FEATURE
<222> LOCATION: (360)..(360)
<223> OTHER INFORMATION: X= N, Y or T
```

-continued

```
<220> FEATURE:
<221> NAME/KEY: MISC_FEATURE
<222> LOCATION: (361)..(361)
<223> OTHER INFORMATION: X= L, M or R
<220> FEATURE:
<221> NAME/KEY: MISC_FEATURE
<222> LOCATION: (363)..(363)
<223> OTHER INFORMATION: X= H, Q, S or E
<220> FEATURE:
<221> NAME/KEY: MISC_FEATURE
<222> LOCATION: (364)..(364)
<223> OTHER INFORMATION: X= R, K or N
<220> FEATURE:
<221> NAME/KEY: MISC_FEATURE
<222> LOCATION: (365)..(365)
<223> OTHER INFORMATION: X= R, K or A
<220> FEATURE:
<221> NAME/KEY: MISC_FEATURE
<222> LOCATION: (366)..(366)
<223> OTHER INFORMATION: X= F or L
<220> FEATURE:
<221> NAME/KEY: MISC_FEATURE
<222> LOCATION: (368)..(368)
<223> OTHER INFORMATION: X= T or D
<220> FEATURE:
<221> NAME/KEY: MISC_FEATURE
<222> LOCATION: (370)..(370)
<223> OTHER INFORMATION: X= C, T or V
<220> FEATURE:
<221> NAME/KEY: MISC_FEATURE
<222> LOCATION: (384)..(384)
<223> OTHER INFORMATION: X= A or S
<220> FEATURE:
<221> NAME/KEY: MISC_FEATURE
<222> LOCATION: (392)..(392)
<223> OTHER INFORMATION: X= I or L
<220> FEATURE:
<221> NAME/KEY: MISC_FEATURE
<222> LOCATION: (393)..(393)
<223> OTHER INFORMATION: X= K or V
<220> FEATURE:
<221> NAME/KEY: MISC_FEATURE
<222> LOCATION: (397)..(397)
<223> OTHER INFORMATION: X= A or T
<220> FEATURE:
<221> NAME/KEY: MISC_FEATURE
<222> LOCATION: (401)..(401)
<223> OTHER INFORMATION: X= S or T
<220> FEATURE:
<221> NAME/KEY: MISC_FEATURE
<222> LOCATION: (403)..(403)
<223> OTHER INFORMATION: X= M or L
<220> FEATURE:
<221> NAME/KEY: MISC_FEATURE
<222> LOCATION: (406)..(406)
<223> OTHER INFORMATION: X= A or G
<220> FEATURE:
<221> NAME/KEY: MISC_FEATURE
<222> LOCATION: (410)..(410)
<223> OTHER INFORMATION: X= V or I
<220> FEATURE:
<221> NAME/KEY: MISC_FEATURE
<222> LOCATION: (411)..(411)
<223> OTHER INFORMATION: X= V or I
<220> FEATURE:
<221> NAME/KEY: MISC_FEATURE
<222> LOCATION: (415)..(415)
<223> OTHER INFORMATION: X= D, S or A
<220> FEATURE:
<221> NAME/KEY: MISC_FEATURE
<222> LOCATION: (418)..(418)
<223> OTHER INFORMATION: X= K or N
<220> FEATURE:
<221> NAME/KEY: MISC_FEATURE
<222> LOCATION: (422)..(422)
<223> OTHER INFORMATION: X= K or R
<220> FEATURE:
<221> NAME/KEY: MISC_FEATURE
<222> LOCATION: (430)..(430)
```

```
<223> OTHER INFORMATION: X= L or M
<220> FEATURE:
<221> NAME/KEY: MISC_FEATURE
<222> LOCATION: (436)..(436)
<223> OTHER INFORMATION: X= P, S or A
<220> FEATURE:
<221> NAME/KEY: MISC_FEATURE
<222> LOCATION: (444)..(444)
<223> OTHER INFORMATION: X= V or I
<220> FEATURE:
<221> NAME/KEY: MISC_FEATURE
<222> LOCATION: (445)..(445)
<223> OTHER INFORMATION: X= A or T
<220> FEATURE:
<221> NAME/KEY: MISC_FEATURE
<222> LOCATION: (446)..(446)
<223> OTHER INFORMATION: X= F or Y
<220> FEATURE:
<221> NAME/KEY: MISC_FEATURE
<222> LOCATION: (447)..(447)
<223> OTHER INFORMATION: X= M or L
<220> FEATURE:
<221> NAME/KEY: MISC_FEATURE
<222> LOCATION: (449)..(449)
<223> OTHER INFORMATION: X= C or S
<220> FEATURE:
<221> NAME/KEY: MISC_FEATURE
<222> LOCATION: (452)..(452)
<223> OTHER INFORMATION: X= N or H
<220> FEATURE:
<221> NAME/KEY: MISC_FEATURE
<222> LOCATION: (454)..(454)
<223> OTHER INFORMATION: X= V or I
<220> FEATURE:
<221> NAME/KEY: MISC_FEATURE
<222> LOCATION: (455)..(455)
<223> OTHER INFORMATION: X= V, T or C
<220> FEATURE:
<221> NAME/KEY: MISC_FEATURE
<222> LOCATION: (459)..(459)
<223> OTHER INFORMATION: X= A or S
<220> FEATURE:
<221> NAME/KEY: MISC_FEATURE
<222> LOCATION: (460)..(460)
<223> OTHER INFORMATION: X= D or N
<220> FEATURE:
<221> NAME/KEY: MISC_FEATURE
<222> LOCATION: (463)..(463)
<223> OTHER INFORMATION: X= E or D
<220> FEATURE:
<221> NAME/KEY: MISC_FEATURE
<222> LOCATION: (465)..(465)
<223> OTHER INFORMATION: X= F or I
<220> FEATURE:
<221> NAME/KEY: MISC_FEATURE
<222> LOCATION: (466)..(466)
<223> OTHER INFORMATION: X= H or N
<220> FEATURE:
<221> NAME/KEY: MISC_FEATURE
<222> LOCATION: (471)..(471)
<223> OTHER INFORMATION: X= A or C
<220> FEATURE:
<221> NAME/KEY: MISC_FEATURE
<222> LOCATION: (472)..(472)
<223> OTHER INFORMATION: X= A or V
<220> FEATURE:
<221> NAME/KEY: MISC_FEATURE
<222> LOCATION: (477)..(477)
<223> OTHER INFORMATION: X= R or A
<220> FEATURE:
<221> NAME/KEY: MISC_FEATURE
<222> LOCATION: (482)..(482)
<223> OTHER INFORMATION: X= R or G
<220> FEATURE:
<221> NAME/KEY: MISC_FEATURE
<222> LOCATION: (483)..(483)
<223> OTHER INFORMATION: X= Y or F
<220> FEATURE:
<221> NAME/KEY: MISC_FEATURE
```

```
<222> LOCATION: (489)..(489)
<223> OTHER INFORMATION: X= V, I or L
<220> FEATURE:
<221> NAME/KEY: MISC_FEATURE
<222> LOCATION: (491)..(491)
<223> OTHER INFORMATION: X= V, A or L
<220> FEATURE:
<221> NAME/KEY: MISC_FEATURE
<222> LOCATION: (492)..(492)
<223> OTHER INFORMATION: X= E, A, Q or D
<220> FEATURE:
<221> NAME/KEY: MISC_FEATURE
<222> LOCATION: (494)..(494)
<223> OTHER INFORMATION: X= P, A or E
<220> FEATURE:
<221> NAME/KEY: MISC_FEATURE
<222> LOCATION: (495)..(495)
<223> OTHER INFORMATION: X= P or A
<220> FEATURE:
<221> NAME/KEY: MISC_FEATURE
<222> LOCATION: (496)..(496)
<223> OTHER INFORMATION: X= G, Y, A or no amino acid
<220> FEATURE:
<221> NAME/KEY: MISC_FEATURE
<222> LOCATION: (497)..(497)
<223> OTHER INFORMATION: X= N or G
<220> FEATURE:
<221> NAME/KEY: MISC_FEATURE
<222> LOCATION: (498)..(498)
<223> OTHER INFORMATION: X= I or no amino acid
<220> FEATURE:
<221> NAME/KEY: MISC_FEATURE
<222> LOCATION: (499)..(499)
<223> OTHER INFORMATION: X= N, S, K or no amino acid
<220> FEATURE:
<221> NAME/KEY: MISC_FEATURE
<222> LOCATION: (500)..(500)
<223> OTHER INFORMATION: X= K or no amino acid
<220> FEATURE:
<221> NAME/KEY: MISC_FEATURE
<222> LOCATION: (501)..(501)
<223> OTHER INFORMATION: X= D or no amino acid
<220> FEATURE:
<221> NAME/KEY: MISC_FEATURE
<222> LOCATION: (502)..(502)
<223> OTHER INFORMATION: X= L, M or no amino acid
<220> FEATURE:
<221> NAME/KEY: MISC_FEATURE
<222> LOCATION: (505)..(505)
<223> OTHER INFORMATION: X= I, V or T
<220> FEATURE:
<221> NAME/KEY: MISC_FEATURE
<222> LOCATION: (507)..(507)
<223> OTHER INFORMATION: X= I or L
<220> FEATURE:
<221> NAME/KEY: MISC_FEATURE
<222> LOCATION: (509)..(509)
<223> OTHER INFORMATION: X= V or I
<220> FEATURE:
<221> NAME/KEY: MISC_FEATURE
<222> LOCATION: (511)..(511)
<223> OTHER INFORMATION: X= R or K
<220> FEATURE:
<221> NAME/KEY: MISC_FEATURE
<222> LOCATION: (513)..(513)
<223> OTHER INFORMATION: X= R or V
<220> FEATURE:
<221> NAME/KEY: MISC_FEATURE
<222> LOCATION: (514)..(514)
<223> OTHER INFORMATION: X= I or V
<220> FEATURE:
<221> NAME/KEY: MISC_FEATURE
<222> LOCATION: (515)..(515)
<223> OTHER INFORMATION: X= L or R
<220> FEATURE:
<221> NAME/KEY: MISC_FEATURE
<222> LOCATION: (516)..(516)
<223> OTHER INFORMATION: X= I, K, V or R
<220> FEATURE:
```

-continued

```
<221> NAME/KEY: MISC_FEATURE
<222> LOCATION: (517)..(517)
<223> OTHER INFORMATION: X= E or Q
<220> FEATURE:
<221> NAME/KEY: MISC_FEATURE
<222> LOCATION: (519)..(519)
<223> OTHER INFORMATION: X= E, D, K or T
<220> FEATURE:
<221> NAME/KEY: MISC_FEATURE
<222> LOCATION: (520)..(520)
<223> OTHER INFORMATION: X= R or D
<220> FEATURE:
<221> NAME/KEY: MISC_FEATURE
<222> LOCATION: (522)..(522)
<223> OTHER INFORMATION: X= A or C
<220> FEATURE:
<221> NAME/KEY: MISC_FEATURE
<222> LOCATION: (524)..(524)
<223> OTHER INFORMATION: X= L or V
<220> FEATURE:
<221> NAME/KEY: MISC_FEATURE
<222> LOCATION: (525)..(525)
<223> OTHER INFORMATION: X= G or A
<220> FEATURE:
<221> NAME/KEY: MISC_FEATURE
<222> LOCATION: (528)..(528)
<223> OTHER INFORMATION: X= T or S
<220> FEATURE:
<221> NAME/KEY: MISC_FEATURE
<222> LOCATION: (529)..(529)
<223> OTHER INFORMATION: X= A, V or S
<220> FEATURE:
<221> NAME/KEY: MISC_FEATURE
<222> LOCATION: (531)..(531)
<223> OTHER INFORMATION: X= Q or N
<220> FEATURE:
<221> NAME/KEY: MISC_FEATURE
<222> LOCATION: (532)..(532)
<223> OTHER INFORMATION: X= S, N or E
<220> FEATURE:
<221> NAME/KEY: MISC_FEATURE
<222> LOCATION: (533)..(533)
<223> OTHER INFORMATION: X= C or A
<220> FEATURE:
<221> NAME/KEY: MISC_FEATURE
<222> LOCATION: (534)..(534)
<223> OTHER INFORMATION: X= L or M
<220> FEATURE:
<221> NAME/KEY: MISC_FEATURE
<222> LOCATION: (535)..(535)
<223> OTHER INFORMATION: X= V, G or A
<220> FEATURE:
<221> NAME/KEY: MISC_FEATURE
<222> LOCATION: (537)..(537)
<223> OTHER INFORMATION: X= S or A
<220> FEATURE:
<221> NAME/KEY: MISC_FEATURE
<222> LOCATION: (538)..(538)
<223> OTHER INFORMATION: X= S, V, A, D or E
<220> FEATURE:
<221> NAME/KEY: MISC_FEATURE
<222> LOCATION: (539)..(539)
<223> OTHER INFORMATION: X= I, M, L or A
<220> FEATURE:
<221> NAME/KEY: MISC_FEATURE
<222> LOCATION: (541)..(541)
<223> OTHER INFORMATION: X= E or Q
<220> FEATURE:
<221> NAME/KEY: MISC_FEATURE
<222> LOCATION: (542)..(542)
<223> OTHER INFORMATION: X= Q, E, R or L
<220> FEATURE:
<221> NAME/KEY: MISC_FEATURE
<222> LOCATION: (543)..(543)
<223> OTHER INFORMATION: X= H, R, Q or D
<220> FEATURE:
<221> NAME/KEY: MISC_FEATURE
<222> LOCATION: (544)..(544)
<223> OTHER INFORMATION: X= G or D
```

-continued

```
<220> FEATURE:
<221> NAME/KEY: MISC_FEATURE
<222> LOCATION: (545)..(545)
<223> OTHER INFORMATION: X= L or V
<220> FEATURE:
<221> NAME/KEY: MISC_FEATURE
<222> LOCATION: (546)..(546)
<223> OTHER INFORMATION: X= R, N or S
<220> FEATURE:
<221> NAME/KEY: MISC_FEATURE
<222> LOCATION: (547)..(547)
<223> OTHER INFORMATION: X= I, V, T or A
<220> FEATURE:
<221> NAME/KEY: MISC_FEATURE
<222> LOCATION: (550)..(550)
<223> OTHER INFORMATION: X= A or I
<220> FEATURE:
<221> NAME/KEY: MISC_FEATURE
<222> LOCATION: (560)..(560)
<223> OTHER INFORMATION: X= H, R or T
<220> FEATURE:
<221> NAME/KEY: MISC_FEATURE
<222> LOCATION: (561)..(561)
<223> OTHER INFORMATION: X= A, D or K
<220> FEATURE:
<221> NAME/KEY: MISC_FEATURE
<222> LOCATION: (563)..(563)
<223> OTHER INFORMATION: X= I or V
<220> FEATURE:
<221> NAME/KEY: MISC_FEATURE
<222> LOCATION: (565)..(565)
<223> OTHER INFORMATION: X= S or K
<220> FEATURE:
<221> NAME/KEY: MISC_FEATURE
<222> LOCATION: (566)..(566)
<223> OTHER INFORMATION: X= L or A
<220> FEATURE:
<221> NAME/KEY: MISC_FEATURE
<222> LOCATION: (568)..(568)
<223> OTHER INFORMATION: X= K, R  or Q
<220> FEATURE:
<221> NAME/KEY: MISC_FEATURE
<222> LOCATION: (569)..(569)
<223> OTHER INFORMATION: X= S or E
<220> FEATURE:
<221> NAME/KEY: MISC_FEATURE
<222> LOCATION: (571)..(571)
<223> OTHER INFORMATION: X= E or P
<220> FEATURE:
<221> NAME/KEY: MISC_FEATURE
<222> LOCATION: (573)..(573)
<223> OTHER INFORMATION: X= L or M
<220> FEATURE:
<221> NAME/KEY: MISC_FEATURE
<222> LOCATION: (574)..(574)
<223> OTHER INFORMATION: X= I or V
<220> FEATURE:
<221> NAME/KEY: MISC_FEATURE
<222> LOCATION: (575)..(575)
<223> OTHER INFORMATION: X= T or S
<220> FEATURE:
<221> NAME/KEY: MISC_FEATURE
<222> LOCATION: (576)..(576)
<223> OTHER INFORMATION: X= V or I
<220> FEATURE:
<221> NAME/KEY: MISC_FEATURE
<222> LOCATION: (580)..(580)
<223> OTHER INFORMATION: X= S, T or A
<220> FEATURE:
<221> NAME/KEY: MISC_FEATURE
<222> LOCATION: (581)..(581)
<223> OTHER INFORMATION: X= I or V
<220> FEATURE:
<221> NAME/KEY: MISC_FEATURE
<222> LOCATION: (585)..(585)
<223> OTHER INFORMATION: X= G or A
<220> FEATURE:
<221> NAME/KEY: MISC_FEATURE
<222> LOCATION: (586)..(586)
```

-continued

```
<223> OTHER INFORMATION: X= S or A
<220> FEATURE:
<221> NAME/KEY: MISC_FEATURE
<222> LOCATION: (589)..(589)
<223> OTHER INFORMATION: X= A, V or M
<220> FEATURE:
<221> NAME/KEY: MISC_FEATURE
<222> LOCATION: (590)..(590)
<223> OTHER INFORMATION: X= Q or H
<220> FEATURE:
<221> NAME/KEY: MISC_FEATURE
<222> LOCATION: (593)..(593)
<223> OTHER INFORMATION: X= A or T
<220> FEATURE:
<221> NAME/KEY: MISC_FEATURE
<222> LOCATION: (595)..(595)
<223> OTHER INFORMATION: X= N, D or E
<220> FEATURE:
<221> NAME/KEY: MISC_FEATURE
<222> LOCATION: (597)..(597)
<223> OTHER INFORMATION: X= L or F
<220> FEATURE:
<221> NAME/KEY: MISC_FEATURE
<222> LOCATION: (601)..(601)
<223> OTHER INFORMATION: X= T, K or G
<220> FEATURE:
<221> NAME/KEY: MISC_FEATURE
<222> LOCATION: (602)..(602)
<223> OTHER INFORMATION: X= T or L
<220> FEATURE:
<221> NAME/KEY: MISC_FEATURE
<222> LOCATION: (604)..(604)
<223> OTHER INFORMATION: X= W or F
<220> FEATURE:
<221> NAME/KEY: MISC_FEATURE
<222> LOCATION: (605)..(605)
<223> OTHER INFORMATION: X= S or R
<220> FEATURE:
<221> NAME/KEY: MISC_FEATURE
<222> LOCATION: (608)..(608)
<223> OTHER INFORMATION: X= V, T or C
<220> FEATURE:
<221> NAME/KEY: MISC_FEATURE
<222> LOCATION: (609)..(609)
<223> OTHER INFORMATION: X= L or M
<220> FEATURE:
<221> NAME/KEY: MISC_FEATURE
<222> LOCATION: (612)..(612)
<223> OTHER INFORMATION: X= R or H
<220> FEATURE:
<221> NAME/KEY: MISC_FEATURE
<222> LOCATION: (613)..(613)
<223> OTHER INFORMATION: X= Y or F
<220> FEATURE:
<221> NAME/KEY: MISC_FEATURE
<222> LOCATION: (615)..(615)
<223> OTHER INFORMATION: X= D or E
<220> FEATURE:
<221> NAME/KEY: MISC_FEATURE
<222> LOCATION: (618)..(618)
<223> OTHER INFORMATION: X= A or D
<220> FEATURE:
<221> NAME/KEY: MISC_FEATURE
<222> LOCATION: (619)..(619)
<223> OTHER INFORMATION: X= P or Y
<220> FEATURE:
<221> NAME/KEY: MISC_FEATURE
<222> LOCATION: (620)..(620)
<223> OTHER INFORMATION: X= A, S or R
<220> FEATURE:
<221> NAME/KEY: MISC_FEATURE
<222> LOCATION: (623)..(623)
<223> OTHER INFORMATION: X= L or M
<220> FEATURE:
<221> NAME/KEY: MISC_FEATURE
<222> LOCATION: (624)..(624)
<223> OTHER INFORMATION: X= A, I or N
<220> FEATURE:
<221> NAME/KEY: MISC_FEATURE
```

-continued

```
<222> LOCATION: (625)..(625)
<223> OTHER INFORMATION: X= M, E or L
<220> FEATURE:
<221> NAME/KEY: MISC_FEATURE
<222> LOCATION: (629)..(629)
<223> OTHER INFORMATION: X= T or M
<220> FEATURE:
<221> NAME/KEY: MISC_FEATURE
<222> LOCATION: (630)..(630)
<223> OTHER INFORMATION: X= P, A or S
<220> FEATURE:
<221> NAME/KEY: MISC_FEATURE
<222> LOCATION: (631)..(631)
<223> OTHER INFORMATION: X= S, Q or G
<220> FEATURE:
<221> NAME/KEY: MISC_FEATURE
<222> LOCATION: (635)..(635)
<223> OTHER INFORMATION: X= A, S or G
<220> FEATURE:
<221> NAME/KEY: MISC_FEATURE
<222> LOCATION: (636)..(636)
<223> OTHER INFORMATION: X= T or S
<220> FEATURE:
<221> NAME/KEY: MISC_FEATURE
<222> LOCATION: (637)..(637)
<223> OTHER INFORMATION: X= V or A
<220> FEATURE:
<221> NAME/KEY: MISC_FEATURE
<222> LOCATION: (638)..(638)
<223> OTHER INFORMATION: X= F or L
<220> FEATURE:
<221> NAME/KEY: MISC_FEATURE
<222> LOCATION: (639)..(639)
<223> OTHER INFORMATION: X= N, T or Q
<220> FEATURE:
<221> NAME/KEY: MISC_FEATURE
<222> LOCATION: (640)..(640)
<223> OTHER INFORMATION: X= I, L, M or T
<220> FEATURE:
<221> NAME/KEY: MISC_FEATURE
<222> LOCATION: (641)..(641)
<223> OTHER INFORMATION: X= I or L
<220> FEATURE:
<221> NAME/KEY: MISC_FEATURE
<222> LOCATION: (643)..(643)
<223> OTHER INFORMATION: X= Q, A or R
<220> FEATURE:
<221> NAME/KEY: MISC_FEATURE
<222> LOCATION: (644)..(644)
<223> OTHER INFORMATION: X= T, P, A or K
<220> FEATURE:
<221> NAME/KEY: MISC_FEATURE
<222> LOCATION: (645)..(645)
<223> OTHER INFORMATION: X= R, K or A
<220> FEATURE:
<221> NAME/KEY: MISC_FEATURE
<222> LOCATION: (646)..(646)
<223> OTHER INFORMATION: X= E, D or G
<220> FEATURE:
<221> NAME/KEY: MISC_FEATURE
<222> LOCATION: (648)..(648)
<223> OTHER INFORMATION: X= L or A
<220> FEATURE:
<221> NAME/KEY: MISC_FEATURE
<222> LOCATION: (649)..(649)
<223> OTHER INFORMATION: X= E, F, Q or K
<220> FEATURE:
<221> NAME/KEY: MISC_FEATURE
<222> LOCATION: (650)..(650)
<223> OTHER INFORMATION: X= I, V, F, Y or no amino acid
<220> FEATURE:
<221> NAME/KEY: MISC_FEATURE
<222> LOCATION: (651)..(651)
<223> OTHER INFORMATION: X= M, S, A or no amino acid
<220> FEATURE:
<221> NAME/KEY: MISC_FEATURE
<222> LOCATION: (652)..(652)
<223> OTHER INFORMATION: X= L, S, I or no amino acid
<220> FEATURE:
```

```
<221> NAME/KEY: MISC_FEATURE
<222> LOCATION: (653)..(653)
<223> OTHER INFORMATION: X= S or no amino acid
<220> FEATURE:
<221> NAME/KEY: MISC_FEATURE
<222> LOCATION: (654)..(654)
<223> OTHER INFORMATION: X= A, N or no amino acid
<220> FEATURE:
<221> NAME/KEY: MISC_FEATURE
<222> LOCATION: (655)..(655)
<223> OTHER INFORMATION: X= L, T or no amino acid
<220> FEATURE:
<221> NAME/KEY: MISC_FEATURE
<222> LOCATION: (656)..(656)
<223> OTHER INFORMATION: X= Q, G or no amino acid
<220> FEATURE:
<221> NAME/KEY: MISC_FEATURE
<222> LOCATION: (657)..(657)
<223> OTHER INFORMATION: X= A, L or no amino acid

<400> SEQUENCE: 23
```

Thr Pro Leu Leu Asp Thr Xaa Asn Tyr Pro Xaa His Xaa Lys Asn Xaa
1               5                   10                  15

Xaa Xaa Xaa Glx Leu Xaa Gln Leu Xaa Xaa Glu Leu Arg Xaa Xaa Xaa
            20                  25                  30

Xaa Xaa Xaa Val Ser Xaa Thr Gly Gly His Leu Xaa Xaa Ser Leu Gly
        35                  40                  45

Val Val Glu Leu Thr Val Ala Xaa His Tyr Xaa Phe Xaa Xaa Pro Xaa
50                  55                  60

Asp Xaa Xaa Xaa Trp Asp Val Gly His Gln Xaa Tyr Xaa His Lys Ile
65                  70                  75                  80

Xaa Thr Gly Arg Arg Xaa Xaa Met Xaa Thr Xaa Arg Xaa Thr Xaa Gly
                85                  90                  95

Leu Xaa Gly Phe Thr Lys Arg Xaa Glu Ser Glu Xaa Asp Xaa Phe Gly
        100                 105                 110

Xaa Gly His Ser Ser Thr Xaa Ile Ser Ala Xaa Leu Gly Met Ala Xaa
            115                 120                 125

Gly Arg Asp Xaa Lys Xaa Xaa Xaa Asn Xaa Val Xaa Xaa Val Ile Gly
        130                 135                 140

Asp Gly Ala Xaa Thr Xaa Gly Xaa Ala Xaa Glu Ala Met Asn Xaa Ala
145                 150                 155                 160

Xaa Xaa Leu Asp Xaa Xaa Met Ile Val Ile Leu Asn Asp Asn Xaa Gln
                165                 170                 175

Val Ser Leu Pro Thr Xaa Xaa Xaa Xaa Xaa Xaa Xaa Xaa Pro Val Gly
                180                 185                 190

Ala Xaa Xaa Xaa Xaa Xaa Xaa Xaa Gln Xaa Xaa Xaa Xaa Xaa Leu Arg
        195                 200                 205

Glu Leu Arg Glu Xaa Ala Lys Gly Xaa Thr Lys Gln Xaa Xaa Xaa Xaa
        210                 215                 220

Xaa Xaa Xaa Xaa Xaa Ala Lys Xaa Asp Xaa Tyr Ala Arg Gly Met Ile
225                 230                 235                 240

Ser Gly Xaa Xaa Ser Xaa Leu Phe Glu Glu Leu Gly Leu Tyr Tyr Ile
                245                 250                 255

Gly Pro Xaa Asp Gly His Asn Xaa Asp Asp Leu Xaa Xaa Xaa Leu Xaa
            260                 265                 270

Xaa Val Xaa Xaa Xaa Xaa Thr Xaa Gly Pro Val Leu Xaa His Val Xaa
        275                 280                 285

Thr Glu Lys Gly Xaa Gly Tyr Xaa Xaa Ala Glu Xaa Xaa Xaa Asp Lys
290                 295                 300

Xaa His Gly Val Xaa Lys Phe Asp Pro Xaa Thr Gly Xaa Gln Xaa Xaa
305                 310                 315                 320

Xaa Xaa Xaa Xaa Xaa Xaa Xaa Tyr Thr Xaa Tyr Phe Ala Xaa Xaa Leu
            325                 330                 335

Xaa Xaa Glu Ala Xaa Xaa Asp Xaa Xaa Xaa Xaa Ala Xaa His Ala Ala
            340                 345                 350

Met Xaa Gly Gly Thr Gly Leu Xaa Xaa Phe Xaa Xaa Xaa Pro Xaa
        355                 360                 365

Arg Xaa Phe Asp Val Gly Ile Ala Glu Gln His Ala Val Thr Phe Xaa
        370                 375                 380

Ala Gly Leu Ala Cys Glu Gly Xaa Xaa Pro Phe Cys Xaa Ile Tyr Ser
385                 390                 395                 400

Xaa Phe Xaa Gln Arg Xaa Tyr Asp Gln Xaa Xaa His Asp Val Xaa Leu
        405                 410                 415

Gln Xaa Leu Pro Val Xaa Phe Ala Met Asp Arg Ala Gly Xaa Val Gly
        420                 425                 430

Ala Asp Gly Xaa Thr His Cys Gly Ala Phe Asp Xaa Xaa Xaa Xaa Ala
        435                 440                 445

Xaa Leu Pro Xaa Met Xaa Xaa Met Ala Pro Xaa Asx Glu Ala Xaa Leu
450                 455                 460

Xaa Xaa Met Val Ala Thr Xaa Xaa Ala Ile Asp Asp Xaa Pro Ser Cys
465                 470                 475                 480

Phe Xaa Xaa Pro Arg Gly Asn Gly Xaa Gly Xaa Xaa Leu Xaa Xaa Xaa
        485                 490                 495

Xaa Xaa Xaa Xaa Xaa Lys Gly Xaa Pro Xaa Glu Xaa Gly Xaa Gly
            500                 505                 510

Xaa Xaa Xaa Xaa Xaa Gly Xaa Xaa Val Xaa Leu Xaa Xaa Tyr Gly Xaa
            515                 520                 525

Xaa Val Xaa Xaa Xaa Xaa Ala Xaa Xaa Xaa Leu Glx Xaa Xaa Xaa
        530                 535                 540

Xaa Xaa Xaa Thr Val Xaa Asp Ala Arg Phe Cys Lys Pro Leu Asp Xaa
545                 550                 555                 560

Xaa Leu Xaa Arg Xaa Xaa Ala Xaa Xaa His Xaa Val Xaa Xaa Xaa Xaa
        565                 570                 575

Glu Glu Gly Xaa Xaa Gly Gly Phe Xaa Xaa His Val Xaa Xaa Phe Leu
        580                 585                 590

Xaa Leu Xaa Gly Xaa Leu Asp Gly Xaa Xaa Lys Xaa Xaa Pro Met Xaa
        595                 600                 605

Xaa Pro Asp Xaa Xaa Ile Xaa His Gly Xaa Xaa Xaa Asp Gln Xaa Xaa
        610                 615                 620

Xaa Ala Gly Leu Xaa Xaa Xaa His Ile Ala Xaa Xaa Xaa Xaa Xaa Xaa
625                 630                 635                 640

Xaa Gly Xaa Xaa Xaa Xaa Ala Xaa Xaa Xaa Xaa Xaa Xaa Xaa Xaa
        645                 650                 655

Xaa

<210> SEQ ID NO 24
<211> LENGTH: 72
<212> TYPE: DNA

<213> ORGANISM: Artificial sequence
<220> FEATURE:
<223> OTHER INFORMATION: PCR Primer

<400> SEQUENCE: 24
ggggacaagt ttgtacaaaa aagcaggctt ggttccgcgt ggatcaatga gttttgatat    60
tgccaaatac cc                                                        72

<210> SEQ ID NO 25
<211> LENGTH: 57
<212> TYPE: DNA
<213> ORGANISM: Artificial sequence
<220> FEATURE:
<223> OTHER INFORMATION: PCR Primer

<400> SEQUENCE: 25
ggggaccact ttgtacaaga aagctgggtt cattatgcca gccaggcctt gattttg       57

<210> SEQ ID NO 26
<211> LENGTH: 36
<212> TYPE: DNA
<213> ORGANISM: Artificial sequence
<220> FEATURE:
<223> OTHER INFORMATION: Mutagenic Primer

<400> SEQUENCE: 26
gcgcgaaggc gggaacaaag ttttctctgg cgtgcc                              36

<210> SEQ ID NO 27
<211> LENGTH: 36
<212> TYPE: DNA
<213> ORGANISM: Artificial sequence
<220> FEATURE:
<223> OTHER INFORMATION: Mutagenic Primer

<400> SEQUENCE: 27
ggcacgccag agaaaacttt gttcccgcct tcgcgc                              36

<210> SEQ ID NO 28
<211> LENGTH: 38
<212> TYPE: DNA
<213> ORGANISM: Artificial sequence
<220> FEATURE:
<223> OTHER INFORMATION: Mutagenic Primer

<400> SEQUENCE: 28
cgcaccgaag aacatatttg cggcatggta gtgcctgg                            38

<210> SEQ ID NO 29
<211> LENGTH: 38
<212> TYPE: DNA
<213> ORGANISM: Artificial sequence
<220> FEATURE:
<223> OTHER INFORMATION: Mutagenic Primer

<400> SEQUENCE: 29
ccaggcacta ccatgccgca aatatgttct tcggtgcg                            38